US010913791B2

(12) United States Patent
Lydon

(10) Patent No.: US 10,913,791 B2
(45) Date of Patent: *Feb. 9, 2021

(54) IMMUNOGLOBULINS AND VARIANTS DIRECTED AGAINST PATHOGENIC MICROBES

(71) Applicant: Nicholas B. Lydon, Jackson, WY (US)

(72) Inventor: Nicholas B. Lydon, Jackson, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/666,222

(22) Filed: Oct. 28, 2019

(65) Prior Publication Data

US 2020/0291099 A1 Sep. 17, 2020

Related U.S. Application Data

(63) Continuation of application No. 15/433,963, filed on Feb. 15, 2017, now Pat. No. 10,457,723, which is a continuation of application No. 14/923,221, filed on Oct. 26, 2015, now abandoned, which is a continuation of application No. 14/318,551, filed on Jun. 27, 2014, now Pat. No. 9,988,439, which is a continuation-in-part of application No. 14/312,585, filed on Jun. 23, 2014, now Pat. No. 9,416,171, which is a continuation of application No. PCT/US2012/071556, filed on Dec. 23, 2012.

(60) Provisional application No. 61/580,194, filed on Dec. 23, 2011.

(51) Int. Cl.
*C07K 16/12* (2006.01)

(52) U.S. Cl.
CPC .......... *C07K 16/1271* (2013.01); *C07K 16/12* (2013.01); *C07K 2317/24* (2013.01); *C07K 2317/34* (2013.01); *C07K 2317/52* (2013.01); *C07K 2317/526* (2013.01); *C07K 2317/55* (2013.01); *C07K 2317/56* (2013.01); *C07K 2317/565* (2013.01); *C07K 2317/70* (2013.01); *C07K 2317/71* (2013.01); *C07K 2317/732* (2013.01); *C07K 2317/734* (2013.01); *C07K 2317/76* (2013.01)

(58) Field of Classification Search
CPC ............ C07K 2317/73; C07K 2317/92; C07K 16/32; C07K 2317/21; C07K 2317/76; C07K 2317/52; C07K 2319/30; C07K 16/283; C07K 16/2866; C07K 16/40; C07K 2316/96; C07K 2317/33; C07K 2317/51; C07K 2317/515; C07K 2317/56; C07K 2317/565; C07K 2317/567; C07K 2317/622; C07K 2317/72; C07K 2317/732; C07K 2317/734; C07K 2319/32; C07K 16/00; C07K 16/082; C07K 16/22; C07K 16/2863; C07K 16/2878; C07K 16/2887; C07K 16/2893; C07K 16/2896; C07K 16/30; C07K 2316/52; C07K 2317/24; C07K 2317/41; C07K 2317/524; C07K 2317/526; C07K 2317/77; C07K 2317/90; C07K 2317/94; A61K 2039/505; A61K 39/39558; A61K 45/06; C12P 21/005

See application file for complete search history.

(56) References Cited

U.S. PATENT DOCUMENTS

| | | | |
|---|---|---|---|
| 4,179,337 | A | 12/1979 | Davis et al. |
| 4,301,144 | A | 11/1981 | Iwashita et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 5,530,101 | A | 6/1996 | Queen et al. |
| 5,585,089 | A | 12/1996 | Queen et al. |
| 5,693,761 | A | 12/1997 | Queen et al. |
| 5,693,762 | A | 12/1997 | Queen et al. |
| 5,821,337 | A | 10/1998 | Carter et al. |
| 5,859,205 | A | 1/1999 | Adair et al. |
| 6,054,297 | A | 4/2000 | Carter et al. |
| 6,180,370 | B1 | 1/2001 | Queen et al. |
| 6,322,788 | B1 | 11/2001 | Kim |
| 6,407,213 | B1 | 6/2002 | Carter et al. |
| 6,692,739 | B1 | 2/2004 | Patti et al. |
| 6,797,492 | B2 | 9/2004 | Daugherty et al. |
| 6,979,446 | B2 | 12/2005 | Patti et al. |
| 7,317,091 | B2 | 1/2008 | Lazar et al. |
| 7,488,807 | B2 | 2/2009 | Mach et al. |
| 7,657,380 | B2 | 2/2010 | Lazar et al. |
| 7,704,497 | B2 | 4/2010 | Dall et al. |
| 7,795,402 | B2 | 9/2010 | Kim |
| 8,142,780 | B2 | 3/2012 | Kim |

(Continued)

FOREIGN PATENT DOCUMENTS

| | | |
|---|---|---|
| WO | 1992011018 | 7/1992 |
| WO | 1993011161 | 6/1993 |

(Continued)

OTHER PUBLICATIONS

Acharya, K. Ravi, et al., "Structural basis of superantigen action inferred from crystal structure of toxic-shock syndrome toxic-shock syndrom toxin-1", Nature, 367(6458):94-7 (1994).

(Continued)

*Primary Examiner* — Padmavathi Baskar

(74) *Attorney, Agent, or Firm* — Perkins Coie LLP; Lara J. Dueppen

(57) ABSTRACT

Anti-SpA murine, chimeric and humanized monoclonal antibodies, and variant antibodies having a heavy chain with at least one amino acid substitution are provided. Such antibodies may be used to prevent or treat microbial infections.

6 Claims, 43 Drawing Sheets

Specification includes a Sequence Listing.

(56) References Cited

U.S. PATENT DOCUMENTS

| | | | |
|---|---|---|---|
| 8,188,231 | B2 | 5/2012 | Lazar et al. |
| 9,416,171 | B2 * | 8/2016 | Lydon .................. C07K 16/00 |
| 9,416,172 | B2 | 8/2016 | Simard |
| 9,988,439 | B2 * | 6/2018 | Lydon ................ C07K 16/1271 |
| 10,457,723 | B2 * | 10/2019 | Lydon .................. C07K 16/12 |
| 2002/0119492 | A1 | 8/2002 | Chirino et al. |
| 2003/0022285 | A1 | 1/2003 | Chirino et al. |
| 2004/0132101 | A1 | 7/2004 | Lazar et al. |
| 2004/0230380 | A1 | 11/2004 | Chirino et al. |
| 2005/0114037 | A1 | 5/2005 | Desjarlais et al. |
| 2006/0134105 | A1 | 6/2006 | Lazar et al. |
| 2006/0153857 | A1 | 7/2006 | Horwith et al. |
| 2006/0235208 | A1 | 10/2006 | Lazar et al. |
| 2007/0122403 | A1 | 5/2007 | Dall'Acqua et al. |
| 2008/0019976 | A1 | 1/2008 | Stinson et al. |
| 2008/0242845 | A1 | 10/2008 | Lazar et al. |
| 2008/0311146 | A1 | 12/2008 | Castado et al. |
| 2009/0087478 | A1 | 4/2009 | Hansen et al. |
| 2010/0047252 | A1 | 2/2010 | Mach et al. |
| 2010/0166772 | A1 | 7/2010 | Anderson et al. |
| 2011/0059085 | A1 | 3/2011 | Kim et al. |
| 2014/0170134 | A1 | 6/2014 | Schneewind et al. |
| 2017/0166629 | A1 | 6/2017 | Lydon |
| 2017/0226195 | A1 | 8/2017 | Lydon |

FOREIGN PATENT DOCUMENTS

| | | |
|---|---|---|
| WO | 1994013804 | 6/1994 |
| WO | 1998052976 | 11/1998 |
| WO | 1998059244 | 12/1998 |
| WO | 2000003317 A1 | 1/2000 |
| WO | 2001021823 | 3/2001 |
| WO | 2002000165 | 1/2002 |
| WO | 2002069232 | 9/2002 |
| WO | 2002077187 | 10/2002 |
| WO | 2002079232 | 10/2002 |
| WO | 2003063772 A2 | 8/2003 |
| WO | 2008140487 A2 | 11/2008 |
| WO | 2012109285 A2 | 8/2012 |
| WO | 2013025834 A2 | 2/2013 |
| WO | 2013142349 A1 | 9/2013 |
| WO | 2014074540 A2 | 5/2014 |

OTHER PUBLICATIONS

Almagro, Juan C, et al., "Humanization of antibodies.", Front Biosci, 13:1619-33 (2008).

Al-Shangiti, A. M, et al., "The interaction between staphylococcal superantigen-like proteins and human dendritic cells", Clin Exp Immunol, 140:(3):461-69 (2005).

Arcus, Vickery, "OB-fold domains: a snapshot of the evolution of sequence, structure and function.", Curr Opin Struct Biol, 12(6):794-801 (2002).

Arcus, Vickery L, et al., "The Three-dimensional structure of a superantigen-like protein, SET3, from a pathogenicity island of the Staphylococcus aureus genome.", J Biol Chem, 277(35): 32274-32281 (2002).

Artandi, S.E., et al., "Monoclonal IgM rheumatoid factors bind IgG at a discontinuous epitope comprised of amino acid loops from heavy-chain constant-region domains 2 and 3", Proc. Natl. Acad. Sci. USA 89:94-98 (1992).

Ashkenazi, Avi, et al., "Immunoadhesins as research tools and therapeutic agents.", Curr Opin Immunol, 9:195-200 (1997).

Baba, Tadashi, et al., "Genome and virulence determinants of high virulence community-acquired MRSA.", Lancet, 359(9320):1819-27 (2002).

Baca, Manuel, et al., "Antibody humanization using monovalent phage display.", J Biol Chem, 272(16):10678-10684 (1997).

Bassler, Bonnie L, "How bacteria talk to each other: regulation of gene expression by quorum sensing.", Curr Opin Microbiol, 2(6):582-7 (1999).

Benito, Yvonne, et al., "Probing the structure of RNAIII, the Staphylococcus aureus agr regulatory RNA, and identification of the RNA domain involved in repression of protein A expression.", RNA, 6:668-679 (2000).

Bird, Robert E, et al., "Single-chain antigen-binding proteins.", Science, 242:423-426 (1998).

Bjorck, Lars, "Protein L. A novel bacterial cell wall protein with affinity for Ig L chains.", J Immunol, 140(4):1194-1197 (1988).

Bjorck, Lars, et al., "Purification and some properties of streptococcal protein G, a novel IgG-binding reagent.", J Immunol, 133(2):969-74 (1984).

Blanc, M., et al., "Review of the notation for the allotypic and related markers of human immunoglobins", Eur J Immunol, 6:599-601 (1976).

Blanc, M., et al., "Review of the notation for the allotypic and related markers of human immunoglobulins", J Immunogen, 3:357-362 (1976).

Bohach, Gregory A, et al., "Staphylococcal and streptococcal pyrogenic toxins involved in toxic shock syndrome and related illnesses.", Crit Rev Microbiol, 17(4):251-72 (1990).

Bouma, Barend, et al., "Adhesion mechanism of human beta(2)-glycoprotein I to phospholipids based on its crystal structure.", EMBO J, 18(19):5166-5174 (1999).

Bowers, Peter M, et al., "Coupling mammalian cell surface display with somatic hypermutation for the discovery and maturation of human antibodies.", PNAS, 108(51):20455-60 (2011).

Boyle, Michael D.P, "The type I bacterial immunoglobulin-binding protein: Staphylococcal protein A", Bacterial Immunoglobulin-binding Proteins, 1:17-28 (1990).

Bruggemann, Marianne, et al., "Production of human antibody repertoires in transgenic mice.", Curr Opin Biotechnol, 8(4):455-8 (1997).

Burman, Julia D, et al., "Interaction of human complement with Sbi, a staphylococcal immunoglobulin-binding protein: indications of a novel mechanism of complement evasion by Staphylococcus aureus", J Biol Chem, 283(25):17579-93 (2008).

Burmeister, Wilheim P, et al., "Crystal structure of the complex of rat neonatal Fc receptor with Fc.", Nature, 372(6504):379-83 (1994).

Burton, Dennis R, "Immunoglobulin G: functional sites.", Mol Immunol, 22(3):161-206 (1985).

Carayannopoulos, et al., "Localization of the Binding Site for the Monocyte Immunoglobulin (Ig) A-Fc Receptor (CD89) to the Domain Boundary Between Calpha2 and Calpha3 in Human IgA1", J. Exp. Med. 183, 1579-1586, Apr. 1996.

Carter, et al., "Humanization of an anti-p185HER2 antibody for human cancer therapy.", Proc Natl Acad Sci U S A. May 15, 1992; 89(10): 4285-4289.

Carvalho, Warnessa Araa Jo, et al., "Haplotypes of the bovine IgG2 heavy gamma chain in tick-resistant and tick-susceptible breeds of cattle.", Immunogenetics, 63:319-324 (2011), Feb. 8, 2011.

Cary, Stephen, et al., "The murine clan V(H) III related 7183, J606 and S107 and DNA4 families commonly encode for binding to a bacterial B cell superantigen.", Mol Immunol, 36(11-12):769-76 (1999).

Cary, Stephen P, et al., "Characterization of superantigen-induced clonal deletion with a novel clan III-restricted avian monoclonal antibody: Exploiting evolutionary distance to create antibodies specific for a conserved V(H) region surface.", J Immunol, 164:4730-4741 (2000).

Casadevall, Arturo, et al., "Passive antibody therapy for infectious diseases.", Nature Reviews Microbiology, 2(9):695-703 (2004).

Chamow, Steven M, et al., "Immunoadhesins: principles and applications.", Trends Biotech, 14:52-60 (1996).

Chapman, et al., "Characterization of the interaction between the herpes simplex virus type I Fc receptor and immunoglobulin G.", J Biol Chem. Mar. 12, 1999;274(11):6911-9.

Cheng, Alice G, et al., "Genetic requirements for Staphylococcus aureus abscess formation and persistence in host tissues.", FASEB J, 23:3393-3404 (2009).

Cheung, et al., "Regulation of virulence determinants in vitro and in vivo in Staphylococcus aureus.", FEMS Immunol Med Microbiol. Jan. 15, 2004;40(1):1-9.

(56) References Cited

OTHER PUBLICATIONS

Cheung, Ambrose L, et al., "Cloning and Sequencing fo sarA of *Staphylococcus aureus*, a gene required for the expression of agr.", J Bacteriol, 176(13):4168-4172 (1994).
Chien, Yueh-Tyng, et al., "Molecular interactions between two global regulators, sar and agr, in *Staphylococcus aureus*.", J Biol Chem, 273(5):2645-2652 (1998).
Clark, Elizabeth, et al., "IsaB, a new immunoglobulin-binding protein from *Staphylococcus aureus*.", Mol Immunol,IsaB, 46(14):2834-2835 (2009).
Clark, Michael R, "IgG effector mechanisms.", Chem Immunol, 65:88-110 (1997).
Clark, Mike, "Antibody humanization: a case of the 'Emperor's new clothes'?", Immunol Today, 21(8):397-402 (2000).
Claro, Tania, et al., "*Staphylococcus aureus* protein A binds to osteoblasts and triggers signals that weaken bone in Osteomyelitis. ", PLoS One, 6(4):e18748 (2011).
Dall'Acqua, William F., et al., "Properties of Human IgG1s Engineered for Enhanced Binding to the Neonatal Fc Receptor (FcRn)", J Biol Chem, 281(33): 23514-23524 (2006).
Datta-Mannan, Amita, et al., "Huminized IgG(1) variants with differential binding properties to the neonatal Fc receptor: Relationship to pharmacokinetics in mice and primates.", Drug Metab Disposition, 35(1):86-94 (2007).
Davies, Julian, et al., "Expression of GnTIII in a recombinant anti-CD20 CHO production cell line: Expression of antibodies with altered glycoforms leads to an increase in ADCC through highter affinity for FcyRIII", Biotechnol Bioeng, 74(4):288-294 (2001).
Davis, et al., "Fc receptor homologs: newest members of a remarkably diverse Fc receptor gene family.", Immunol Rev. Dec. 2002;190:123-36.
Davis, Randall, et al., "Fc receptor homologs: newest members of a remarkably diverse Fc receptor gene family", Immunol Reviews, 190:123-136 (2002).
De Pascalis, Roberto, et al., "Grafting of "abbreviated" complementarity-determining regions containing specificity-determining residues essential for ligand contact to engineer a less immunogenic humanized monoclonal antibody.", J Immunol, 169(6):3076-84 (2002).
Deisenhofer, J., "Crystallographic refinement and atomic models of a human Fc fragment and its complex with fragment B of protein A from *Staphylococcus aureus* at 2.9-and 2.8-A resolution.", Biochem, 20(9):2361-2370 (1981).
Dejonge, Mitchell, et al., "Clinical trial of safety and efficacy of INH-A21 for the prevention of nosocomial staphylococcal bloodstream infection the premature infants.", J Pediatr, 151:260-265 (2007).
Delano, Warren L, et al., "Convergent Solutions to Binding at a Protein-Protein Interface.", Science, 287(5456):1279-1283 (2000).
Derrick, Jeremy P, et al., "Crystal structure of a streptococcal protein G domain bound to an Fab fragment.", Nature, 359(6397):752-4 (1992).
Domanski, Paul J, et al., "Adhesion mechanism of human beta(2)-glycoprotein I to phospholipids based on its crystal structure.", Infect Immun, 73(8):5229-32 (2005).
Edelman, et al., "The covalent structure of an entire gammaG immunoglobulin molecule", Proc Natl Acad Sci U S A. May 1969;63(1):78-85.
Emsley, Jonas, et al., "Crystal structure of the von Willebrand Factor Al domain and implications for the binding of platelet glycoprotein lb.", J Biol Chem, 273(17):10396-401 (1998).
European Patent Office, Extended European Search Report, for European Patent Application No. EP12860971, dated Jul. 22, 2015, 3 pgs.
European Patent Office, Examination Report for European Patent Application No. 12860971.6, dated Apr. 8, 2016.
European Patent Office, Examination Report for European Patent Application No. 12860971.6, dated May 30, 2017.
European Patent Office, Examination Report for European Patent Application No. 12860971.6 dated Mar. 20, 2018.
European Patent Office, Examination Report for European Patent Application No. 12860971.6, dated Feb. 14, 2019.
European Patent Office, Examination Report for European Patent Application No. 12860971.6, dated Nov. 15, 2019.
Fagan, K, et al., "Identification and characterization of a novel secreted immunoglobulin binding protein from group A streptococcus. ", Infect Immun, 69(8):4851-7 (2001).
Firan, Mihail, et al., "The MHC class I-related receptor, FcRn, plays an essential role in the maternofetal transfer of gamma-globulin in humans.", Int'l Immunol. 13(8):993-1002 (2001).
Forsgren, Arne, et al., ""Protein A" from *S. aureus*. I. Pseudo-immune reaction with human gamma-globulin.", J Immunol, 97(6):822-7 (1966).
Foster, T. J, et al., "Genetic studies of *Staphylococcus aureus* virulence facts.", Antonie van Leeuwenhoek, 54:475-482 (1988).
Foster, Timothy J, "Immune evasion by *Staphylococci*.", Nature Rev Immunol, 3 948-958 (2005).
Furukawa, Toru, et al., "Demonstration of Immunoglobulin G Receptors Induced by Human Cytomegalovirus", J Clin Microbiol, 2(4): 332-336 (1975).
Garman, Scott, et al., "Structure of teh Fc fragment of human IgE bound to its high-affinity receptor FceRIa", Nature, 406: 259-266 (2000).
Gaspar, et al., "Bacillus anthracis Sortase A (SrtA) Anchors LPXTG Motif-Containing Surface Proteins to the Cell Wall Envelope", J Bacteriol. Jul. 2005; 187(13): 4646-4655.
Gemmell, C.G., et al., "Role of certain virulence factors in a murine model of *Staphylococcus aureus* arthritis", J Med Microbiol, 46:208-213 (1997).
Gemmell, C.G., et al., "Susceptibility to Opsonophagocytosis of Protein A, a-Haemolysin and B-Toxin Deficient Mutants of *S. aureus* Isolated by Allele-Replacement", Zbl Bakt Suppl, 21: 273-277 (1991).
Ghetie, Victor, et al., "Multiple roles for the major histocompatibility complex class I—Related receptor FcRn", Annu Rev immunol, 18:739-766 (2000).
Gomez, Marisa, et al., "*Staphylococcus aureus* protein A activates TACE through EGFR-dependent signaling", EMBO J, 26:701-709 (2007).
Gomez, Marisa, et al., "*Staphylococcus aureus* Protein A Activates TNFR1 Signaling through Conserved IgG Binding Domains", J Biol Chem, 281(29): 20190-20196 (2006).
Gomez, Marisa, et al., "*Staphylococcus aureus* protein A induces airway epithelial inflammatory responses by activating TNFR1", Nature Med, 10(8): 842-848 (2004).
Goodyear, Carl, et al., "Staphylococcal toxin induced preferential and prolonged in vivo deletion of innate-like B lymphocytes", PNAS, 101(31): 11392-11397 (2004).
Gorman, Scott, et al., "Humanisation of monoclonal antibodies for therapy", Semin Immunol 2:457-466 (1990).
Gorman, Scott, et al., "Reshaping a therapeutic CD4 antibody", Proc Natl Acad Sci USA, 88: 4181-4185 (1991).
Gouda, Hiroaki, et al., "NMR Study of the Interaction between the B Domain of Staphylococcal Protein A and the Fc Portion of Immunoglobulin G", Biochem, 37: 129-136 (1998).
Gouda, Hiroaki, et al., "Three-Dimensional Solution Structure of the B Domain of Staphylococcal Protein A: Comparisons of the Solution and Crystal Structures", Biochemistry, 31:9665-9672 (1992).
Goward, Christopher R, et al., "Molecular evolutoin of bacterial cell-surface proteins.", Trends Biochem Sci, 18:136-140 (1993).
Graille, Marc, et al., "Crystal structure of a *Staphylococcus aureus* protein A domain complexed with the Fab fragment of a human IgM antibody: Structural basis for recognition of B-cell receptors and superantigen activity", PNAS, 97(10): 5399-5404 (2000).
Griffiths, Andrew, et al., "Strategies for selection of antibodies by phage display", Curr Opin Biotechnol, 9:102-108 (1998).
Hall, Andrea E., et al., "Characterization of a Protective Monoclonal Antibody Recognizing *Staphylococcus aureus* MSCRAMM Protein Clumping Factor A", Infec Immunol, 6864-6870 (2003).
Hammar, Juergen, et al., "Precise Prediction of Major Histocompatibility Complex Class IT-Peptide Interaction Based on Peptide Side Chain Scanning", J Exp Med, 180: 2353-2358 (1994).

(56) References Cited

OTHER PUBLICATIONS

Haupt, Katrin, et al., "The *Staphylococcus aureus* Protein Sbi Acts as a Complement Inhibitor and Forms a Tripartite Complex with Host Complement Factor H and C3b", PLOS Pathg, 4(12): e1000250 (2008).

Hayhurst, Andrew, et al., "High-throughput antibody isolation", Curr Opin Chem Biol, 5:683-689 (2001).

Haynes, Barton F., et al., "Introduction to the immune system", McGraw Hill, 1907-1930 (2005).

He, Xing-Yue, et al., "Humanization and Pharmacokinetics of a Monoclonal Antibody with Specificity for Both E- and P-Selectin", J Immunol, 160:1029-1035 (1998).

Heden, Lars-Olof, et al., "Molecular characterization of an IgA receptorfrom group B streptococci: sequence of the gene,identification of a proline-rich region with unique structure and isolation of N-terminal fragments with IgA-binding capacity", Eur J Immunol, 21:1481-1490 (1991).

Herr, Andrew B., et al., "Insights into IgA-mediated immune responses from crystal structures of human FcaRI and its complex with IgA1-Fc", Nature, 423:614-620 (2003).

Hillson, Jan, et al., "The structural basis of germaline-encoded Vh3 Immunoglobulin binding to staphylococcal protein A", J Exp Med, 178:331-336 (1993).

Holliger, et al., "Diabodies": small bivalent and bispecific antibody fragments., Proc Natl Acad Sci U S A. Jul. 15, 1993; 90(14): 6444-6448.

Holliger, Philipp, et al., "Engineering bispecific antibodies", Curr Opin Biotechnol, 4:446-449 (1993).

Hoogenboom, Hennie , "Selecting and screening recombinant antibody libraries", Nat Biotechnol, 23: 1105-1116 (2005).

Huizinga, Eric G, et al., "Structures of Glycoprotein Ibalpha and Its Complex with von Willebrand Factor A1 Domain.", Science, 297(5584):1176-1179 (2002).

Hulstein, Janine J.J, et al., "A novel nonobody that detects the gain-of-function phenotype of von Willebrand fact in ADAMTS13 deficiency and von Willebrand disease type 2B.", Blood, 106:3035-42 (2005).

Huston, James S, et al., "Protein engineering of antibody binding sites: Recovery of specific activity in an anti-digoxin single-chain Fv analogue produced in *Escherichia coli*.", PNAS, 85:5879-5883 (1988).

Idusogie, Esohe E, et al., "Mapping of the C1q binding site on Rituxan, a chimeric antibody with a human IgG1 Fc.", J Immunol, 165:4178-84 (2000).

Itoh, S., et al., "Staphylococcal superantigen-like protein 10 (SSL10) binds to human immunoglobulin G (IgG) and inhibits complement activation via the classical pathway.", Mol Immunol, 47(4):932-3 (2010).

James, Leo C, et al., "Structural basis for PRYSPRY-mediated tripartite motif (TRIM) protein function.", PNAS, 104(15):6200-05 (2007).

Jansson, Mathias, et al., "All individual domains of staphlococcal protein A show fab binding", FEMS Immunol Med Microbiol, 20:69-78 (1998).

Jefferis, Roy, et al., "Human immunoglobulin allotypes", mAbs, 1(4):1-7 (2009).

Jefferis, Roy, et al., "Interaction sites on human IgG-Fc for FcγR: current models", Immunol Lett, 82:57-65 (2002).

Jeristrom, P.G., et al., "The IgA-bindingm B antigen of the c protein complex of group B streptococci: sequence determination of its gene and detection of two binding regions", Mol Microbiol, 5(4): 843-849 (1991).

Ji, Guangyong, et al., "Cell density control of staphylococcal virulence mediated by an octapeptide pheromone.", PNAS, 92:12055-12059 (1995).

Jones, Peter, et al., "Replacing the complementary-determining regions in a human antibody with those from a mouse", Nature, 321:522-525 (1986).

Kazeeva, T. N, et al., "IgA-Specific Proteins of Pathogenic Bacteria. ", Biochem (Moscos), 74(1):12-21 (2009).

Keller, Robert, et al., "An IgG-Fc receptor induced in cytomegalovirus-infected human fibroblasts.", J Immunol, 116(3):772-777 (1976).

Kim, Hwan Keun, et al., "Nontoxic protein A vaccine for methicillin-resistant *Staphylococcus aureus* infections in mice", J. Exp. Med. 207:1863-1870 (2010).

Kim, Hwan Keun, et al., "Protein A-Specific Monoclonal Antibodies and Prevention of *Staphylococcus aureus* Disease in Mice", Infect Immun, 80(10):3460-3470 (2012).

Kim, Thomas, et al., "Analysis of FcγRIII and IgG Fc Polymorphism Reveals Functional and Evolutionary Implications of Protein-Protein Interaction", J Mol Evol, 53:1-9 (2001).

Kotzin, Brian, et al., "Superantigens and their potential role in human disease", Adv Immunol, 54:99-166 (1993).

Kozlowski, L.M., et al., "*Staphylococcus aureus* Cowan I-Induced Human immunogunoglobulin Responses:— Preferential IgM Rheumatoid factor production 3;nd VH3 mRNA Expression by Protein A-Binding B cells", J Clin Immunol, 15(3): 145-151 (1995).

Krapp, S., et al., "Structural Analysis. of Human IgG-Fc Glycoforms Reveals a Correlation Between Glycosylation and Structural Integrity", J Mol Biol, 325:979-989 (2003).

Krauss, Jurgen, et al., "Specificity grafting of human antibody frameworks selected from a phage display library: generation of a highly stable humanized anti-CD22 single-chain Fv fragment", Protein Eng, 16(10): 753-759 (2003).

Kristiansen, Sandra, et al., "Staphylococcal Protein A Induces Biased Production of Ig by V HJ-Expressing B Lymphocytes 1", J Immunol, 153: 2974-2982 (1994).

Kroll, Michael, et al., "Platelets and shear stress", Blood, 88(5): 1525-1541 (1996).

Kronvall, Goran , "A surface component in group A, C, and G streptococci with non-immune reactivity for immunoglobin G", J Immunol, 111(5): 1401-1406 (1973).

Langley, Ries, et al., "The Staphylococcal Superantigen-Like Protein 7 Binds IgA and Complement C5 and Inhibits IgA-FcRI Binding and Serum Killing of Bacteria1", J Immunol, 174: 2926-2933 (2005).

Larsson, Anders, et al., "Novel latex agglutination method with chicken anti-protein A for detection of *Staphylococcus aureus* infections.", J Clin Microbiol, 27(12):2856-57 (1989).

Lazar, Greg A., et al., "Engineered antibody Fc variants with enhanced effector function", PNAS, 103(11): 4005-4010 (2006).

Lefranc, G., et al., "Gm, Am and Km Immunoglobulin Allotypes of Two Populations in Tunisia", Hum Genet, 50:199-211 (1979).

Lefranc, M.P. , "Gene conversion in human immunoglobulin γ locus shown by unusual location of IgG allotypes", FEBS, 196(1): 96-102 (1986).

Lehner, T., "Monoclonal antibodies against micro-organisms.", Current Opinion in Immunology, 1(3):462-466, (1989).

Levinson, Arnold, et al., "B-Cell Superantigens: Definition and Potential Impact on the Immune Response", J Clin Immunol, 15(6): 26S-36S (1995).

Levinson, Arnold, et al., "Staphylococcal protein A: Functional properties of a Model B Cell Superantigen", Landes Bioscience, 99-106 (1996).

Lewis, Melanie, et al., "A Common Theme in Interaction of Bacterial Immunoglobulin-binding Proteins with Immunoglobulins Illustrated in the Equine System", J Biol Chem, 283:17615-17623 (2008).

Lewis, Melanie, et al., "Structural Requirements for the Interaction of Human IgA with the Human Polymeric Ig Receptor 1", J Immunol, 175:6694-6701 (2005).

Li, Hongmin, et al., "The structural basis of T cell activation by superantigens", Annu Rev Immunol, 17:435-466 (1999).

Li, Min , "U.S. Appl. No. 60/222,697", filed Aug. 2, 2000, 7 pgs.

Lilley, Brendan N, et al., "Human Cytomegalovirus open reading from TRL11/IRL11 encodes an immunoglobulin G Fc-binding protein.", J Virol, 75(22):11218-11221 (2001).

Lina, Gerard, et al., "Standard Nomenclature for the Superantigens Expressed by *Staphylococcus*", J Infect Dis, 189: 2334-2336 (2004).

Little, M., et al., "Of mice and men: hybridoma and recolllbinant antibodies", Immunol Today, 21:364-370 (2000).

Llewelyn, Martin, et al., "Superantigens: microbial agents that corrupt immunity.", Lancet Infectious Diseases, 2(3):156-162 (2002).

(56) References Cited

OTHER PUBLICATIONS

Lonberg, Nils, "Human antibodies from transgenic animals", Nat Biotechnol, 23(9): 1117-1125 (2005).
Maillard, Patrick, et al., "Fc Receptor-like Activity of Hepatitis C Virus Core Protein", J. Biol Chem, 279(23): 2430-2437 (2004).
Mallios, R. R., "Class II MHC quantitative binding motifs derived from a large molecular database with a versatile iterative stepwise discriminant analysis meta-algorithm", Bioinformatics, 15(6): 432-439 (1999).
Mallios, R. R., "Predicting class II MHC/peptide multi-level binding with an iterative stepwise discriminant analysis meta-algorithm", Bioinformatics, 17(10): 942-948 (2001).
Marasco, Wayne, et al., "The growth and potential of human antiviral monoclonal antibody therapeutics", Nat Biotechnol 25(12): 1421-1434 (2007).
Marshall, Keith W., et al., "Prediction of Peptide Affinity to HLA DRB1 *0401", J Immunol, 154:5927-5933 (1995).
Martin, Francis, et al., "*Staphylococcus aureus* activates type I IFN signaling in mice and humans through the Xr repeated sequences of protein A", J Clin Invest, 119 1931-1939 (2009).
Martin, W. Lance, et al., "Crystal Structure at 2.8 A of an FcRn/Heterodimeric Fc Complex:Mechanism of pH-Dependent Binding", Mol Cell, 7: 867-877 (2001).
Mascari, Lisa, et al., "Quantification of Staphylococcal-Collagen Binding Interactions in Whole Blood by Use of a Confocal Microscopy Shear-Adhesion Assay", J Infec Dis, 188: 98-107 (2003).
Maxwell, Kelly, "Crystal structure of the human leukocyte Fc receptor, FcγRIIa", Nat Struct Biol 6(5): 437-442 (1999).
Maynard, Jennifer, et al., "Antibody Engineering", Annu Rev Biomed Eng 2: 339-376 (2000).
Meehan, Mary, et al., "The fibrinogen-binding protein (FgBP) of *Streptococcus equi* subsp. *equi* additionally binds IgG contributes to virulence in a mouse model", Microbiol 147: 3311-3322 (2001).
Mimura, Yusuke, et al., "Role of Oligosaccharide Residues of IgG1-Fc in FeRIIb Binding", J Biol Chem, 276(49): 45539-45547 (2001).
Moks, Tomas, et al., "Staphylococcal protein A consist of five IgG-binding domains", Eur J Biochem, 156: 637-643 (1986).
Monteiro, Renato C, et al., "IgA Fc Receptors", Annu Rev Immunol, 21:177-204 (2003).
Moore, Gregory, et al., "Engineered Fc variant antibodies with enhanced ability to recruit complement and mediate effector functions", mAbs 2(2): 181-189 (2010).
Morea, Veronica, et al., "Antibody Modeling: Implications for Engineering and design", Methods, 20: 267-279 (2000).
Morea, V., et al., "Antibody structure, prediction and redisign", Biophys Chem, 68: 9-16 (1997).
Morfeldt, Eva, et al., "Activation of alpha-toxin translation in *Staphylococcus aureus* by the trans-encoded antisense RNA, RNAIII", EMBOJ, 14(18): 4569-4577 (1995).
Nardella, Francis, "Fc Intermediate (Fc, a Papain-Generated Fragment of Human IgG, Intermediate in Charge, Molecular Weight and Cleavage Between the Fc and Fc' Fragments of IgG", Mol Immunol, 22(6):705-713 (1985).
Nardella, Francis, et al., "T15 group a streptococcal Fc receptor binds to the same location on IgG as staphylococcal protein A and IgG rheumatoid factors", J Immunol, 138:922-926 (1987).
Nardella, Francis A., et al., "IgG rheumatoid factors and staphylococcal protein A bind to a common molecular site on IgG", J. Exp. Med. 162:1811-1824 (1985).
Natsume, Akito, et al., "Improving effector functions of antibodies for cancer treatment: Enhancing ADCC and CDC", Drug Des Devel Ther, 3: 7-16 (2009).
Nieba, Lars, et al., "Competition BIAcore for Measuring True Affinities: Large Differences from Values Determined from Binding Kinetics", Anal Biochem, 234: 155-165 (1996).
Nilson, Bo H.K., et al., "Purification of antibodies using protein L-binding framework structures in the light chain variable domain", J Immunol Methods, 164: 33-40 (1993).

Nizet, Victor, "Understanding how leading bacterial pathogens subvert innate immunity to reveal novel therapeutic targets", J Allergy Clin Immunol, 120:13-22 (2007).
Novak, Levente, et al., "Shear-dependent morphology of vonWillebrand factor bound to immobilized collagen", Blood, 99:2070-2076 (2002).
Novick, Richard, "Autoinduction and signal transduction in the regulation of staphylococcal virulence", Mol Microbiol, 48(6): 1429-1449 (2003).
Novick, Richard, et al., "Synthesis of staphylococcal virulence factors is controlled by a regulatory RNA molecule", EMBO J, 12(10): 3967-3975 (1993).
O'Seaghda, Maghnus, et al., "*Staphylococcus aureus* protein A binding to von Willebrand factor A1domain is mediated by conserved IgG binding regions", FEBS J, 273:4831-4841 (2006).
O'Toole,, Paul, et al., "Two major classes in the M protein family in group A streptocci", PNAS, 89:8661-8665 (1992).
O'Connor, Shane, et al., "Humanization of an antibody against human protein C and calcium-dependence involving framework residues", Protein Eng, 11(4): 321-328 (1998).
Ogata, Masahiro, et al., "Appearance of immunoglobulin G Fc receptor in cultured human cells infected with Varicella-Zoster virus", Infect Immun, 26(2): 770-774 (1979).
Palmqvist, Niklas, et al., "Protein A is a virulence factor in *Staphylococcus aureus* arthritis and septic death", Microb Pathog, 33(5):239-249 (2002).
Papageorgiou, Anastassios, et al., "Crystal structure of microbial superantigen staphylococcal enterotoxin B at 1.5 A resolution: implications for superantigen recognition by MHC class II Molecules and T-Cell receptors", J Mol Biol Mar, 20;277(1):61-79 (1998).
Papageorgiou, Anastassios, et al., "Microbial superantigens: from structure to function", Trends Microbiol, 8(8):369-75 (2000).
Para, Michael, et al., "Similarities and Differences in the Fc-Binding Glycoprotein (gE) of herpes simplex virus types 1 and 2 tentative mapping of the viral gene for the glycoprotein", J Virol 41:137-44 (1982).
Patel, Arvind H, et al., "Virulence of Protein A-Deficient and Alpha-Toxin-Deficient mutants of *Staphylococcus aureus* isolated by Allele replacement.", Infect Immunity, 55(12):3103-3110 (1987).
Patel, Deepa, et al., "Specificity of Staphylococcal Superantigen-Like Protein 10 toward the Human IgG1 Fc Domain", J Immunol, 84:6283-6292 (2010).
Patti, Joseph M., "A humanized monoclonal antibody targeting *Staphylococcus aureus*", Vaccine 22S:S39-S43 (2004).
Pawar, Parag, et al., "Fluid Shear Regulates the Kinetics and Receptor Specificity of *Staphylococcus aureus* Binding to Activated Platelets1", J Immunol, 173:1258-1265 (2004).
Peng, H.L., et al., "Cloning, characterization, and sequencing of an accessory gene regulator (agr) in *Staphylococcus aureus*", J. Bacteriol, 170:4365-4372 (1988).
Pleass, Richard, et al., "Identification of Residues in the CH2/CH3 Domain Interface of IgA Essential for Interaction with the Human Fc Receptor (FcR) CD89", J Biol Chem, 274:23508-23514 (1999).
Pleass, Richard, et al., "Streptococcal IgA-binding Proteins Bind in the C2-C3 Interdomain Region and Inhibit Binding of IgA to Human CD89*", J Biol Chem, 276:8197-8204 (2001).
Presta, Leonard, et al., "Humanization of an Anti-Vascular endothelial growth factor monoclonal antibody for the therapy of solid tumors and other disorders", Cancer Res, 57(20):4593-4599 (1997).
Presta, Leonard, et al., "Molecular engineering and design of therapeutic antibodies", Curr Opin Immunol, 20(4):460-470 (2008).
Provenza, Giulio, et al., "Functional analysis of a murine monoclonal antibody against the repetitive region of the fibronectin-binding adhesins fibronectin-binding protein A and fibronectin-binding protein B from *Staphylococcus aureus*", FEBS J, 277(21):4490-505 (2010).
Queen, Cary, et al., "A humanized antibody that binds to teh interleukin 2 receptor", Proc Natl Acad Sci, Usa 86:10029-10033 (1989).
Radaev, Sergei, et al., "The Structure of a Human Type III Fc Receptor in Complex with Fc*", J Bioi Chem, 276:16469-16477 (2001).

(56) References Cited

OTHER PUBLICATIONS

Rader, Christoph, et al., "A phage display approach for rapid antibody humanization: Designed combinatorial V gene libraries", Proc Natl Acad Sci USA, 95: 8910-8915 (1998).
Raghavan, Malini, et al., "Fc Receptors and Their Interactions With Immunoglobulins", Annu Rev Cell Dev Bioi, 12:181-220 (1996).
Ramsland, Paul, et al., "Structural basis for evasion of IgA immunity by Staphylococcus aureus revealed in the complex of SSL7 with Fc of human IgA1", Proc. Natl. Aacd. Sci. USA, 104:15051-15056 (2007).
Ravetch, Jeffrey, et al., "IgG Fc receptors", Annu Rev Immunol, 19:275-290 (2001).
Recht, "Structural studies of a human gamma 3 myeloma protein (Goe) that binds staph protein A", J Immunol. Sep. 1981;127(3):917-23.
Recsei, P., "Regulation of exoprotein gene expression in Staphylococcus aureus by agar", Mol Gen Genet, 202(1):58-61 (1986).
Reddy, Sai, et al., "Monoclonal antibodies isolated without screening by analyzing the variable-gene repertoire of plasma cells", Nature Biotechnology, 28: 965-969 (2010).
Reis, Kathleen, et al., "Streptococcal Fc receptors. I. Isolation and partial characterization of the receptor from a group C Streptococcus", J Immunol, 132(6):3091-3097 (1984).
Reiter, Yoram, "Engineering antibody Fv fragments for cancer detection and therapy: disulfide-stabilized Fv fragments", Nat Biotechnol, 14(10):1239-45 (1996).
Riechmann, Lutz, et al., "Reshaping human antibodies for therapy", Nature, 24:332:323-327 (1988).
Roben, Paul, et al., "VH3 family antibodies bind domain D of staphylococcal protein A", J Immunol, 154(12):6437-45 (1995).
Roguska, Michael, et al., "Humanization of murine monoclonal antibodies through variable domain resurfacing", Proc Natl Acad Sci USA 91:969-973 (1994).
Romagnani, Sergio, "Demonstration on protein A of two distinct immunoglobulin-binding sites and their role in the mitogenic activity of Staphylococcus aureus cowan I on human B cells1", J Immunol, 129(2):596-602 (1982).
Roque, A. Cecelia, et al., "Antibodies and genetically engineered related molecules: production and purification", Biotechnol Pro, 20(3):639-654 (2004).
Rosok, Mae Joanne, et al., "A Combinatorial Library Strategy for the Rapid Humanization of Anticarcinoma BR96 Fab*", J Biol Chem, 271(37): 22611-22618 (1996).
Rupp, Mark, et al., "Phase ii, randomized, multicenter, double-blind, placebo-controlled trial of a polyclonal anti-S. aureus capsular polysaccharide immune globulin in treatment of S. aureus bacteremia. Antimicrob Agents Chemother", Antimicrob Agents Chemther 51(12): 4249-4254 (2007).
Sadler, J. Evan, "Biochemistry and genetics of von Willebrand factor", Annu Rev Biochem; 67:395-424 (1998).
Sasano, Minoru, "Molecular selection of human antibodies with an unconventional bacterial B cell antigen", J Immunol,15;151(10):5822-39 (1993).
Sasso, Eric, et al., "Human IgM molecules that bind staphylococcal protein A contain VHIII H chains", J Immunol, 142(8):2778-2783 (1989).
Sauer-Eriksson, E., et al., "Crystal structure of the C2 fragment of streptoccal protein G in complex with the Fc domain of human IgG", Structure 3:265-278 (1995).
Schroder, A.K., et al., "Identification of the site on IgG Fc for interaction with streptococci of gropus A, C and G", Immunology 62:523-527 (1987).
Schroder, Astrid K, et al., "Interaction between streptococcal IgG Fc receptors and human and rebbit IgG domans.", Immunology, 57:305-309 (1986).
Seppala, Ilkka, "Mouse Ig coded by VH families S107 or J606 bind to protein A", J Immunol, 145(9):2989-2993 (1990).

Shields, Robert, et al., "High Resolution Mapping of the Binding Site on Human IgG1 for FcRI, FcRII, FcRIII, and FcRn and Design of IgG1 Variants with Improved Binding to the FcR*", J Bioi Chem, 276:6591-6604 (2001).
Shields, Robert, et al., "Lack of Fucose on Human IgG1 N-Linked Oligosaccharide Improves Binding to Human FcRIII and Antibody-dependent Cellular Toxicity", J Bioi Chem, 277:26733-26740 (2002).
Sidorin, E.V., "IgG-Binding Proteins of bacteria", Biochem (Moscow) 76(3): 295-308 (2011).
Siedlecki, Christopher, et al., "Shear-dependent changes in the three-dimensional structure of humanvon Willebrand factor", Blood; 88: 2939-2950 (1996).
Silverman, Gregg, et al., "A B Cell Superantigen-induced persistent "Hole" in the B-1 repertoire", J Exp Med, 192(1):87-98 (2000).
Silverman, Gregg, "B-cell superantigens", Immunol Today,18(8):379-386 (1997).
Silverman, Gregg, et al., "The Dual Phases of the Response to Neonatal Exposure to a VH Family-Restricted Staphylococcal B Cell Superantigen1", J Immunol, 161: 5720-5732 (1998).
Simmons, Laura, et al., "Expression of full-length immunoglobulins in Escherichia coli: rapid and efficient production of aglycosylated antibodies", J Immunol Methods, 263(12):133-147 (2002).
Smith, Emma Jane, et al., "The Sbi protein is a multifunctional immune evasion factor of Staphylococcus aureus", Infection and Immunity 79(9):3801-3809 (2011).
Sondermann, Peter, et al., "Crystal structure of the soluble form of the human Fcγ-receptor IIb: a new member of the immunoglobulin superfamily at 1.7 Å resolution", The EMBO Journal, 18(5) :1095-1103 (1999).
Sondermann, Peter, et al., "Molecular basis for immune complex recognition: a comparison of Fc-receptor structures", J Mol Biol, 309(3):737-749 (2001).
Sondermann, Peter, et al., "The 3.2-A crystal structure of the human IgG1 Fc fragment—Fc gammaRIII complex", Nature, 406(20):267-273 (2000).
Sprague, Elizabeth, "Crystal Structure of the HSV-1 Fc Receptor Bound to Fc Reveals a Mechanism for Antibody Bipolar Bridging", PLoS Biol 4:e148 (2006).
Sprague, Elizabeth R, et al., "The human Cytomegalovirus Fc receptor gp68 binds the Fc C(H)2-C(H)3 interface of immunoglobiulin G.", J Virol, 82(7):3490-99 (2008).
Starovasnik, Melissa, "Antibody variable region binding by Staphylococcal protein A: Thermodynamic analysis and location of the Fv binding site on E-domain", Protein Sci, 8:1423-1431 (1999).
Starovasnik, Melissa, et al., "Solution structure of the E-domain of staphylococcal protein A", Biochemistry, 35:15558-15569 (1996).
Sturniolo, Tiziana, et al., "Generation of tissue-specific and promiscuous HLA ligand databases using DNA microarrays and virtual HLA class II matrices", Nature Biotech, 17: 555-561 (1999).
Tan, Philip, et al., ""Superhumanized" Antibodies: Reduction of Immunogenic Potential by Complementarity-Determining Region Grafting with Human Germline Sequences: Application to an Anti-CD281", J Immunol, 169:1119-1125 (2002).
Tashiro, Mitsuru, et al., "Structures of bacterial immunoglobulin-binding domains and their complexes with immunoglobulins", Curr Opin Struct Biol, 5(4):471-481 (1995).
Tkaczyk, C., et al., "Identification of anti-alpha toxin mAbs that reduce severity of Staphylococcus aureus dermonecrosis and exhibit a correlation between affinity and potency", Clin. Vaccine Immunol. 2012, CVI Accepts, published online ahead of print on Jan. 11, 2012.
Tomlinson, et al., "Methods for generating multivalent and bispecific antibody fragments.", Methods Enzymol. 2000;326:461-79.
Torpier, G., "Receptor for IgG(Fc) and human beta2-microglobulin on S. mansoni schistosomula", Nature, 278(29): 447-449 (1979).
Tsurushita, Naoya, et al., "Humanization of monoclonal antibodies", Elsevier Sci, 533-545: (2004).
Uff, Sarah, "Crystal Structure of the Platelet Glycoprotein Ib N-terminal Domain Reveals an Unmasking Mechanism for Receptor Activation", J Biol Chem, 277(38): 35657-35663 (2002).
Uhlen, Mathias, "Complete sequence of the Staphylococcal gene encoding protein A", J Biol Chem, 259(3): 1695-1702 (1984).

(56) References Cited

OTHER PUBLICATIONS

Umana, Pablo, et al., "Engineered glycoforms of an antineuroblastoma IgG1 with optimized antibody-dependent cellular cytotoxic activity", Nature Biotechnol (17): 176-180 (1999).
USPTO, International Search Report and Written Opinion, for PCT/US2012/071556 (WO2013/096948), dated Apr. 26, 2013, 11 pgs.
USPTO, Non-Final Office Action for U.S. Appl. No. 15/237,531, dated Oct. 10, 2018.
USPTO, Final Office Action for U.S. Appl. No. 15/237,531, dated Jun. 17, 2019.
USPTO, Notice of Allowance for U.S. Appl. No. 15/237,531, dated Aug. 12, 2020.
Vaccaro, Carlos, et al., "Engineering the Fc region of immunoglobulin G to modulate in vivo antibody levels", Nat Biotechnol 23(10):1283-1288 (2005).
Van Egmond, Marjolein, et al., "FcalphaRI-positive liver Kupffer cells: reappraisal of the function of immunoglobulin A in immunity", Nat Med, 6(6):680-685 (2000).
Van Egmond, Marjolein, et al., "IgA and the IgA Fc receptor", Trends Immunol, 22(4):205-211 (2001).
Van Loghem, Erma, "Allotypic Markers.", Monogr Allergy, 19:40-51 (1986).
Van Loghem, E., "Staphylococcal Protein A and human IgG subclasses and allotypes", Scand J. Immunol, 15: 275-278 (1982).
Verdoliva, et al., "Affinity purification of polyclonal antibodies using a new all-D synthetic peptide ligand: comparison with protein A and protein G.", J Immunological Methods, 271:77-88, 2002, Dec. 20, 2002.
Verhoeyen, Martine, et al., "Reshaping human antibodies: Grafting an antilysozyme activity", Science, 239: 1534-1536 (1988).
Viau, Muriel, et al., "Staphylococcal Protein A Deletes B-1a and Marginal Zone B Lymphocytes Expressing Human Immunoglobulins: An Immune Evasion Mechanism1", J Immunol, 175: 7719-7727 (2005).
Vidarsson, Gestur, et al., "FcRn: an IgG receptor on phagocytes with a novel role in phagocytosis", Blood, 15(108): 3573-3579 (2006).
Ward, et al., "Binding activities of a repertoire of single immunoglobulin variable domains secreted from *Escherichia coli*.", Nature. Oct. 12, 1989;341(6242):544-6.

Watkins., J.F., "Adsorption of sensitized sheep erythrocytes to hela cells infected with herpes simplex virus", Nature 202: 1364-1365 (1964).
Weems, J., John, et al., "Phase II, Randomized, Double-Blind, Multicenter Study Comparing the Safety and Pharmacokinetics of Tefibazumab to Placebo for Treatment of *Staphylococcus aureus* Bacteremia", Antimicrob Agents Chemother, 50(8): 2751-2755 (2006).
Williams, Rachel, et al., "Identification of a Novel Gene Cluster Encoding Staphylococcal Exotoxin-Like Proteins: Characterization of the Prototypic Gene and Its Protein Product, SET1", Infect Immun, 68:4407-4415 (2000).
Wines, Bruce D, et al., "A Competitive Mechanism for Staphylococcal Toxin SSL7 Inhibiting the Leukocyte IgA Receptor, FcRI, Is Revealed by SSL7 Binding at the C2/C3 Interface of IgA.", J Biol Chem, 281(3):1389-1393 (2006).
Wines, Bruce D, et al., "The IgG Fc contains distinct Fc Receptor (FcR) binding site: The leukocyte Receptors FcyRI and FcyRIIa bind to a region in th Fc Distinct from that recoginized by neonatal FcR and protein A.", J Immunol, 164:5513-18 (2000).
Woof, J. M., "The human IgA-Fc alpha receptor interaction and its blockade by streptoccal IgA-binding proteins", Biochem Soc Trans, 30:491-494 (2002).
Wrammert, Jens, et al., "Rapid Cloning of high affinity human monoclonal antibodies against influenza virus", Nature, 29:453(7195): 667-671 (2008).
Wu, Herren, et al., "Humanization of a murine monoclonal antibody by simultaneous optimization of framework and CDR residiudes", J Mol Biol, 294:151-162 (1999).
Xiong, Jian-Ping, et al., "New insights into the structural basis of integrin activation", Blood, 102: 1155-1159 (2003).
Yee, C., et al., "Changes in the expression of Fc receptor produced by induction of Epstein-Barr virus in lymphoma cell lines", Virology, 120(2):376-382 (1982).
Zeitlin, Larry, et al., "Preventing infectious disease with passive immunization", Microbes Infect, 2(6):701-708 (2000).
Zhang, Lihong, et al., "A second IgG-binding protein in *Staphylococcus*", Microbiology, 144, 985-99 (1998).
EPO, "Exam Report" for Application No. EP12860971.6. dated Jul. 23, 2020. 4 pages.

\* cited by examiner

Figure 1
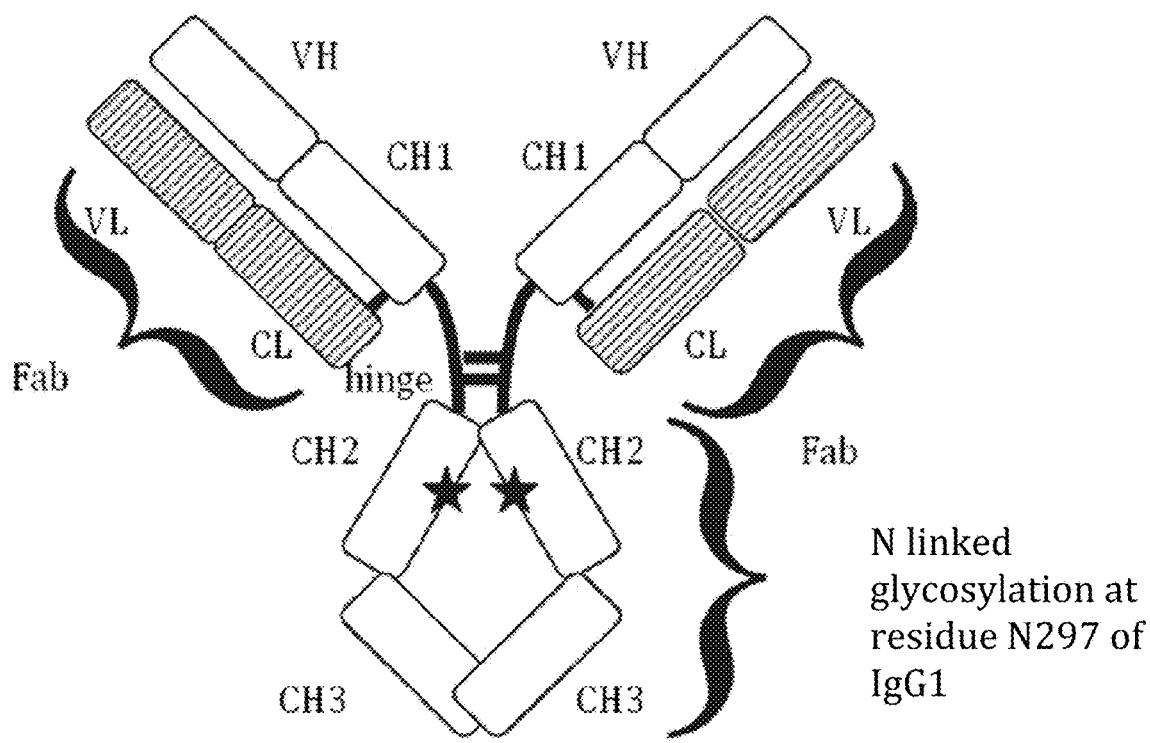
N linked glycosylation at residue N297 of IgG1
▨ Domains of immunoglobulin light chain
☐ Domains of immunoglobulin heavy chain

Figure 5

Human CH1 Sequence

```
IgG1  ASTKGPSVFPLAPSSKSTSGGTAALGCLVKDYFPEPVTVSWNSGALTSGVHTFPAVLQSS    60
IgG2  ASTKGPSVFPLAPCSRSTSESTAALGCLVKDYFPEPVTVSWNSGALTSGVHTFPAVLQSS    60
IgG3  ASTKGPSVFPLAPCSRSTSGGTAALGCLVKDYFPEPVTVSWNSGALTSGVHTFPAVLQSS    60
IgG4  ASTKGPSVFPLAPCSRSTSESTAALGCLVKDYFPEPVTVSWNSGALTSGVHTFPAVLQSS    60

IgG1  GLYSLSSVVTVPSSSLGTQTYICNVNHKPSNTKVDKKV    98   (SEQ ID NO: 68)
IgG2  GLYSLSSVVTVPSSNFGTQTYTCNVDHKPSNTKVDKTV    98   (SEQ ID NO: 69)
IgG3  GLYSLSSVVTVPSSSLGTQTYTCNVNHKPSNTKVDKRV    98   (SEQ ID NO: 70)
IgG4  GLYSLSSVVTVPSSSLGTKTYTCNVDHKPSNTKVDKRV    98   (SEQ ID NO: 71)
```

Human Hinge Sequence

```
IgG1  EPKSCDKTHTCPPCP (SEQ ID NO: 72)
IgG2  ERKCCVECPPCP (SEQ ID NO: 73)
IgG3  ELKTPLGDTTHTCPRCP----EPKSCDTPPPCPRCP----EPKSCDTPPPCPRCP----EPKSCDTPPPCPRCP (SEQ ID NO: 74)
IgG4  SPNMVPHAHHAQ (SEQ ID NO: 75)
```

Human CH2 Sequence

```
IgG1  APELLGGPSVFLFPPKPKDTLMISRTPEVTCVVVDVSHEDPEVKFNWYVDGVEVHNAKTK    60
IgG2  APPVAGPSVFLFPPKPKDTLMISRTPEVTCVVVDVSHEDPEVQFNWYVDGVEVHNAKTK     60
IgG3  APELLGGPSVFLFPPKPKDTLMISRTPEVTCVVVDVSHEDPEVQFKWYVDGVEVHNAKTK    60
IgG4  APEFLGGPSVFLFPPKPKDTLMISRTPEVTCVVVDVSQEDPEVQFNWYVDGVEVHNAKTK    60

IgG1  PREEQYNSTYRVVSVLTVLHQDWLNGKEYKCKVSNKALPAPIEKTISKAK    110   (SEQ ID NO: 76)
IgG2  PREEQFNSTFRVVSVLTVVHQDWLNGKEYKCKVSNKGLPAPIEKTISKTK    110   (SEQ ID NO: 77)
IgG3  PREEQYNSTFRVVSVLTVLHQDWLNGKEYKCKVSNKALPAPIEKTISKTK    110   (SEQ ID NO: 78)
IgG4  PREEQFNSTYRVVSVLTVLHQDWLNGKEYKCKVSNKGLPSSIEKTISKAK    110   (SEQ ID NO: 79)
```

Human CH3 Sequence

```
IgG1  _QPREPQVYTLPPSRDELTKNQVSLTCLVKGFYPSDIAVEWESNGQPENNYKTTPPVLDS    60
IgG2  GQPREPQVYTLPPSREEMTKNQVSLTCLVKGFYPSDIAVEWESNGQPENNYKTTPPMLDS    60
IgG3  GQPREPQVYTLPPSREEMTKNQVSLTCLVKGFYPSDIAVEWESSGQPENNYNTTPPMLDS    60
IgG4  GQPREPQVYTLPPSQEEMTKNQVSLTCLVKGFYPSDIAVEWESNGQPENNYKTTPPVLDS    60

IgG1  DGSFFLYSKLTVDKSRWQQGNVFSCSVMHEALHNHYTQKSLSLSPGK    107   (SEQ ID NO: 80)
IgG2  DGSFFLYSKLTVDKSRWQQGNVFSCSVMHEALHNHYTQKSLSLSPGK    107   (SEQ ID NO: 81)
IgG3  DGSFFLYSKLTVDKSRWQQGNIFSCSVMHEALHNRFTQKSLSLSPGK    107   (SEQ ID NO: 82)
IgG4  DGSFFLYSRLTVDKSRWQEGNVFSCSVMHEALHNHYTQKSLSLSLG_    107   (SEQ ID NO: 83)
```

Figure 6

| | Table 1 Human allotypes | | | |
|---|---|---|---|---|
| Chain | Domain | Allotype | Amino Acid | Position |
| IgG1 | $C_{H1}$ | G1m(f) = (3) | Arg | 214 |
| | $C_{H1}$ | G1m(z) = (17) | Lys | |
| | $C_{H1}$ | G1m(a) = (1) | Arg, Asp, Glu, Leu | 355-358 |
| κ light chain | $C_L$ | Km(1) | Val, Leu | 153, 191 |
| | $C_L$ | Km(3) | Ala, Val | 153, 191 |

Adapted from Stites et al., Basic and Clin. Immunol., 3rd Ed., Table 7-8

Figure 7

| | CH2 | | CH3 | | | | | | | |
|---|---|---|---|---|---|---|---|---|---|---|
| IMGT unique numbering: | 82 | 83 | 39 | 44 | 84 | 88 | 98 | 101 | 115 | 116 |
| EU index positions: | 291 | 292 | 379 | 384 | 397 | 409 | 419 | 422 | 435 | 436 |
| γ1 | Pro | Arg | Val | Asn | Val | Lys | Gln | Val | His | Tyr |
| γ2 | - | - | - | - | Met | - | - | - | - | - |
| γ4 | - | - | - | - | - | Arg | Glu | - | - | - |
| G3m5,10,11,13,14 | - | - | - | Ser | Met | - | - | Ile | Arg | Phe |
| G3m5,6,10,11,14 | - | - | - | Ser | Met | - | Glu | Ile | Arg | Phe |
| G3m5,6,11,24 | - | - | - | Ser | - | Arg | Glu | - | Arg | Phe |
| G3m10,11,13,15 | - | - | Met | Ser | - | - | - | Ile | - | - |
| G3m10,11,13,15,16 | - | Trp | Met | Ser | - | - | - | Ile | - | - |
| G3m21,28 | Leu | - | - | - | Met | - | - | Ile | Arg | - |
| | ↓ | ↓ | ↓ | | | ↓ | ↓ | | ↓ | ↓ |
| G3m allotypes: | 21 | 16 | 15 | | | 6 | 24 | | 28 | 5 |

*Adapted from Roy Jefferis1,\* and Marie-Paule Lefranc2  mAbs 2009; Vol. 1, 1-7*

Figure 8
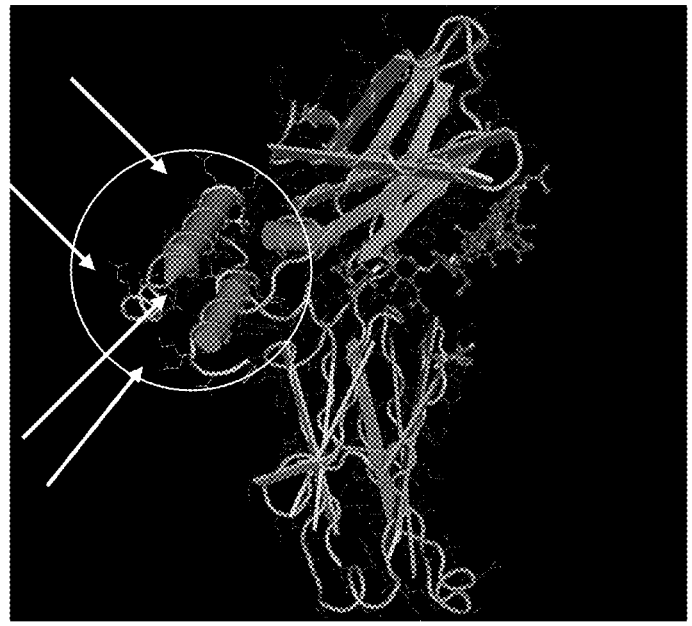
Panel A
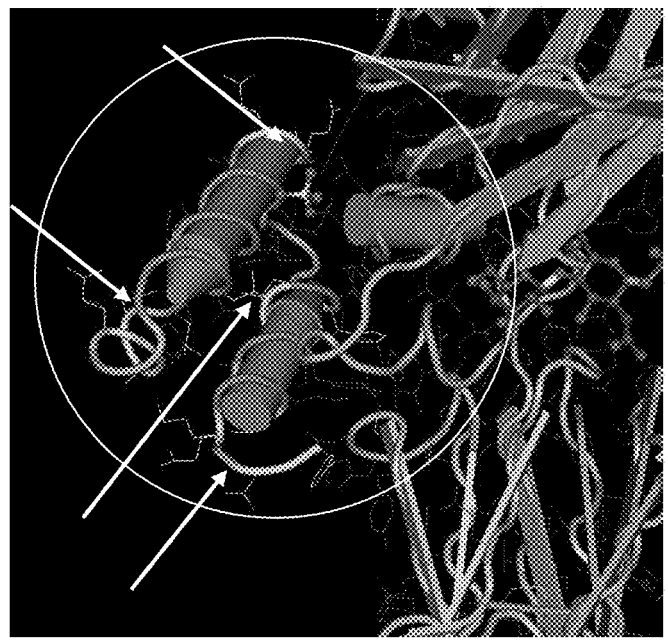
Panel B

| SEQ ID NO | | | |
|---|---|---|---|
| 159 | USA300_FPR3757 | TQNNYVTDQQKAFYQVLHLRGITERQRNQYIKTLRENPERAQEVFSESLRDG | 52 |
| 160 | CC30_M88 | TQNNYVTDQQKAFYQVLHLRGITERQRNQYIKTLRENPERAQEVFSESLRDG | 52 |
| 161 | CC1_TCH70 | TQNNYVTDQQKAFYQVLHLRGITERQRNQYIKTLRENPERAQEVFSESLRDG | 52 |
| 162 | CC38_MRSA252 | TQNNYVTDQQKAFYQVLHLRGITERQRNQYIKTLRENPERAQEVFSESLRDG | 52 |
| 163 | CC7_USA300_TCH959 | TQNNYVTDQQKAFYQVLHLRGITERQRNQYIKTLRENPERAQEVFSESLRDG | 52 |
| 164 | CC66_USA300_TCH1516 | TQNNYVTDQQKAFYQVLHLRGITERQRNQYIKTLRENPERAQEVFSESLRDG | 52 |
| 165 | CC10_H19 | TQNNYVTDQQKAFYQVLHLRGITERQRNQYIKTLRENPERAQEVFSESLRDG | 52 |
| 166 | CC239_JKD6009 | TQNNYVTDQQKAFYQVLHLRGITERQRNQYIKTLRENPERAQEVFSESLRDG | 52 |
| 167 | CC42_C427 | TQNNYVTDQQKAFYQVLHLRGITERQRNQYIKTLRENPERAQEVFSESLRDG | 52 |
| 168 | CC5_A8117 | TQNNYVTDQQKAFYQVLHLRGITERQRNQYIKTLRENPERAQEVFSESLRDG | 52 |
| 169 | CC45_A9635 | TQNNYVTDQQKAFYQVLHLRGITERQRNQYIKTLRENPERAQEVFSESLRDG | 52 |
| | | ************************************************** | |

B

| SEQ ID NO | | | |
|---|---|---|---|
| 170 | USA300_FPR3757 | KNPDRRVAQQNAFYNVLKNDNLTEQENNYIAQIKENPDRSQQVNVESVQSSKA | 54 |
| 171 | CC30_M88 | KNPDRRVAQQNAFYNVLKNDNLTEQENNYIAQIKENPDRSQQVNVESVQSSKA | 54 |
| 172 | CC1_TCH70 | KNPDRRVAQQNAFYNVLKNDNLTEQENNYIAQIKENPDRSQQVNVESVQSSKA | 54 |
| 173 | CC38_MRSA252 | KNPDRRVAQQNAFYNVLKNDNLTEQENNYIAQIKENPDRSQQVNVESVQSSKA | 54 |
| 174 | CC7_USA300_TCH959 | KNPDRRVAQQNAFYNVLKNDNLTEQENNYIAQIKENPDRSQQVNVESVQSSKA | 54 |
| 175 | CC66_USA300_TCH1516 | KNPDRRVAQQNAFYNVLKNDNLTEQENNYIAQIKENPDRSQQVNVESVQSSKA | 54 |
| 176 | CC10_H19 | KNPDRRVAQQNAFYNVLKNDNLTEQENNYIAQIKENPDRSQQVNVESVQSSKA | 54 |
| 177 | CC45_A9635 | KNPDRRVAQQNAFYNVLKNDNLTEQENNYIAQIKENPDRSQQVNVESVQSSKA | 54 |
| 178 | CC5_A8117 | KNPDRRVAQQNAFYNVLKNDNLTEQENNYIAQIKENPDRSQQVNVESVQSSKA | 54 |
| 179 | CC42_C427 | KNPDRRVAQQNAFYNVLKNDNLTEQENNYIAQIKENPDRSQQVNVESVQSSKA | 54 |
| 180 | CC239_JKD6009 | KNPDRRVAQQNAFYSVLKNDNLTEQENNYIAQIKENPDRSQQVNVESVQSSKA | 54 |
| | | ***********,*********************************** | |

Figure 16
MAB1
SDS-PAGE
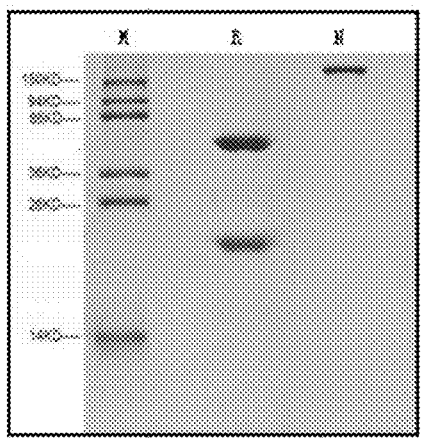
Western blot
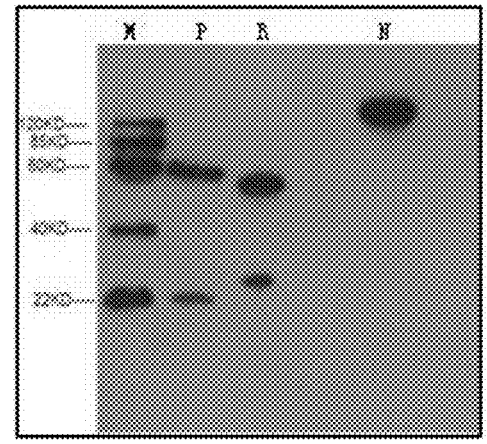
MAB2
SDS-PAGE
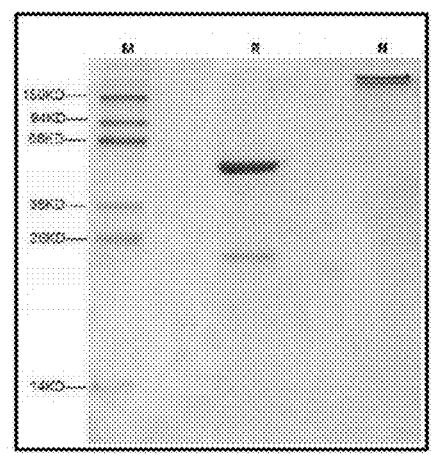
Western blot
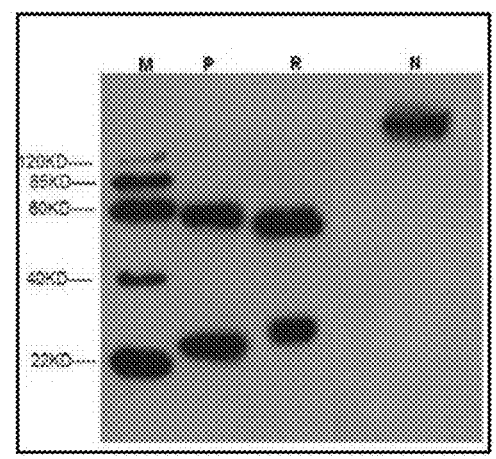
Lane M: Protein marker
Lane R: Purified MAB1 and 2 under reducing condition
Lane N: Purified MAB1 and 2 under non-reducing condition
Lane P: Human IgG1 kappa (Sigma, Cat.No. I5154) as positive control

Figure 17
MAB3
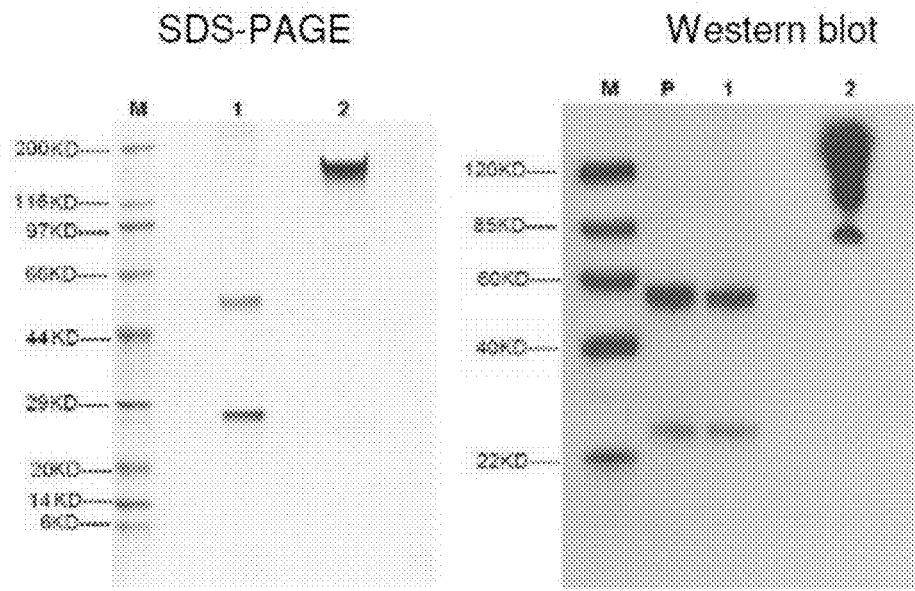
MAB4
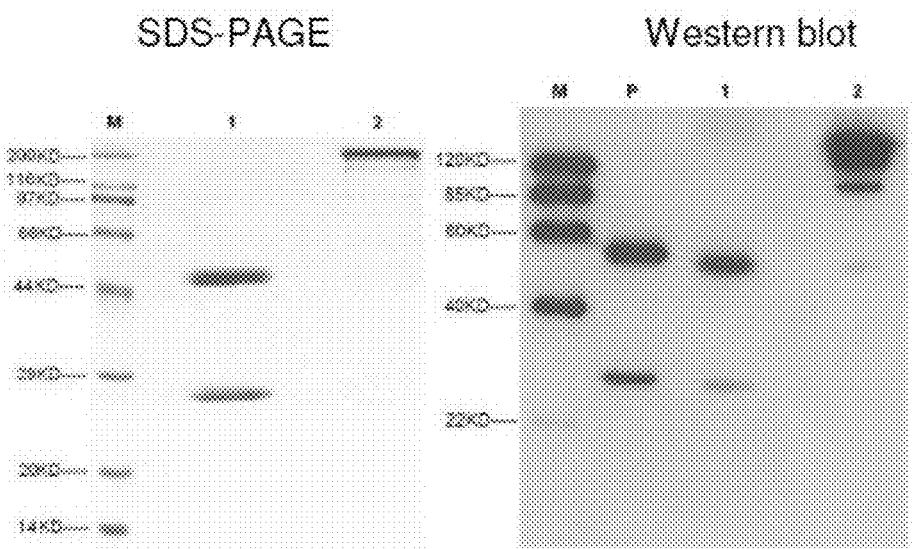
(upper panels) and variant antibody MAB4 (Lower panels)
Lane M: Protein Marker
Lane 1: Reducing conditions
Lane 2: Non-reducing conditions
Lane P: Human IgG1, Kappa (Sigma, Cat.No.I5154) as positive control Lane M: Protein marker
Lane R: Purified MAB5 under reducing condition
Lane N: Purified MAB5 under non-reducing condition
Lane P: Human IgG1 kappa (Sigma, Cat.No. I5154) as positive control Black: No antibody control
Green: MAB2 variant anti-SpA
Red: MAB 1 parental anti-SpA

Figure 36 mAb CS-D7 Light Chain Sequence (SEQ ID NO:58):

| | |
|---|---|
| EIVMTQSPATLSVSPGERAT LSCRASQYVSDNLAWYQQKPGQAPRLLIYG | 51 |
| ASTRATGVPARFSGSGSGTE FTLTISSLQS EDFAVYYCQQYNNWRPVTFG | 101 |
| QGTRLEIKRTVAAPSVFIFP PSDEQLKSGTASVVCLLNNFYPREAKVQWK | 151 |
| VDNALQSGNS QESVTEQDSK DSTYSLSSTLTLSKADYEKHKVYACEVTHQ | 201 |
| GLSSPVTKSFNRGEC | | mAb CS-D7 Heavy Chain Amino Acid Sequence (SEQ ID NO:59):

| | |
|---|---|
| QVQLQESGPGLVKPSETLSLTCTVSGGSIRSSSYYWGWFRQTPGKGLEWL | 51 |
| GNVFFSGSAYYNPSLKNRVT ISIDTSENQSSLKLTSVTAADTAVYYCARP | 101 |
| QAYSHDSSGHSPFDLWGRGTLVTVSSASTKGPSVFPLAPSSKSTSGGTAA | 151 |
| LGCLVKDYFPEPVTVSWNSGALTSGVHTFPAVLQSSGLYS LSSVVTVPSS | 201 |
| SLGTQTYICNVNHKPSNTKVDKRVEPKSCDKTHTCPPCPAPELLGGPSVF | 251 |
| LFPPKPKDTLMISRTPEVTCVVVDVSHEDPEVKFNWYVDGVEVHNAKTKP | 301 |
| REEQYNSTYR VVSVLTVLHQDWLNGKEYKCKVSNKALPAP IEKTISKAKG | 351 |
| QPREPQVYTLPPSREEMTKN QVSLTCLVKGFYPSDIAVEWESNGQPENNY | 401 |
| KTTPPVLDSD GSFFLYSKLTVDKSRWQQGNVFSCSVMHEALHNHYTQKSL | 451 |
| SLSPGK | |

Figure 37 mAb – anti-LTA Light Chain Variable Region Sequences

DIVLSQSPAILSASPGEKVTMTCRASSSVSYMHWYQQKPGSSPKPWIYATSNLASGVP
ARFSGSGSGTSYSLTISRVEAEDAATYYCQQWSSNPPTFGGGTKLEIK (SEQ ID
NO:60)

DIVLSQSPAILSASPGEKVTMTCRASSSVNYMHWYQQKPGSSPKPWISATSNLASGVP
ARFSGSGSGTSYSLTISRVEAEDAATYYCQQWSSNPPTFGGGTMLEIK (SEQ ID
NO:61)

QIVLTQSPAILSAFPGEKVTMTCRASSSVSYMHWYQQKPGSSPKPWIYATSNLASGVP
TRFSGSGSGTSYSLTISRVEAEDVATYYCLQWSSNPPTFGAGTKLELK (SEQ ID
NO:62)

mAb – anti-LTA Heavy Chain Variable Region Sequences

EVMLVESGEGLVQPKGSLKLSCAASGFTFNTYAMNWVRQAPGKGLEWVARIRSKSN
NYATYYADSVKDRFTISRDDSQSMLYLQMNNLKTEDTAMYYCVRRGGKETDYAMDY
WGQGTSVTVSS (SEQ ID NO:63)

EVMLVESGGGLVQPKGSLKLSCAASGFTFNNYAMNWVRQAPGKGLEWVARIRSKSN
NYATFYADSVKDRFTISRDDSQSMLYLQMNNLKTEDTAMYYCVRRGASGIDYAMDYW
GQGTSLTVSS (SEQ ID NO:64)

EVKLHESGGGFVQPKGSLKLSCAASGFTFNAYAMNWVRQAPGKGLEWVARIRSKSN
NYETYYADSVKDFTISRDDSQYMVYLQMNNLKSEDTAMYYCVRRGSMRSYYYAMDY
WGQGTSVTVSS (SEQ ID NO:65)

SEQUENCE LISTING

<160> NUMBER OF SEQ ID NOS: 242

<210> SEQ ID NO 1
<211> LENGTH: 122
<212> TYPE: PRT
<213> ORGANISM: Artificial Sequence
<220> FEATURE:
<223> OTHER INFORMATION: Synthetic peptide: VH chimeric

<400> SEQUENCE: 1

```
Glu Val Lys Leu Val Glu Ser Gly Gly Gly Leu Val Gln Pro Gly Gly
1               5                   10                  15

Ser Arg Arg Leu Ser Cys Thr Thr Ser Gly Phe Thr Phe Thr Glu Ser
            20                  25                  30

Phe Met Thr Trp Val Arg Gln Pro Pro Gly Lys Ala Leu Asp Trp Leu
            35                  40                  45

Ala Phe Ile Arg Asn Lys Ala Asn Gly Tyr Thr Thr Glu Tyr Ser Ala
        50                  55                  60

Ser Val Lys Gly Arg Phe Thr Ile Ala Arg Asp Asn Ser Gln Ser Ile
65                  70                  75                  80

Leu Tyr Leu Gln Met Asn Ala Leu Arg Ala Glu Asp Ser Ala Thr Tyr
                85                  90                  95

Tyr Cys Val Arg Gly Gly Glu Tyr Pro Leu Tyr Val Met Asp Tyr Trp
            100                 105                 110

Gly Lys Gly Thr Ser Val Thr Val Ser Ser
            115                 120
```

<210> SEQ ID NO 2
<211> LENGTH: 122
<212> TYPE: PRT
<213> ORGANISM: Artificial Sequence
<220> FEATURE:
<223> OTHER INFORMATION: Synthetic peptide: VH1

<400> SEQUENCE: 2

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Glu Ser
            20                  25                  30

Phe Met Ser Trp Phe Arg Gln Ala Pro Gly Lys Gly Leu Glu Trp Val
            35                  40                  45

Gly Phe Ile Arg Asn Lys Ala Asn Gly Tyr Thr Thr Glu Tyr Ala Ala
        50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Val Arg Gly Gly Glu Tyr Pro Leu Tyr Val Met Asp Tyr Trp
            100                 105                 110

Gly Gln Gly Thr Leu Val Thr Val Ser Ser
            115                 120
```

<210> SEQ ID NO 3
<211> LENGTH: 122
<212> TYPE: PRT
<213> ORGANISM: Artificial Sequence
<220> FEATURE:
<223> OTHER INFORMATION: Synthetic peptide: VH2

<400> SEQUENCE: 3

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Glu Ser
            20                  25                  30

Phe Met Ser Trp Ile Arg Gln Pro Pro Gly Lys Ala Leu Glu Trp Leu
            35                  40                  45

Ala Phe Ile Arg Asn Lys Ala Asn Gly Tyr Thr Thr Glu Tyr Ala Ala
        50                  55                  60
```

```
Ser Val Lys Gly Arg Phe Thr Ile Ser Arg Asp Asp Ser Lys Ser Ile
 65                  70                  75                  80

Ala Tyr Leu Gln Met Asn Ser Leu Lys Thr Glu Asp Thr Ala Val Tyr
                 85                  90                  95

Tyr Cys Val Arg Gly Gly Glu Tyr Pro Leu Tyr Val Met Asp Tyr Trp
                100                 105                 110

Gly Gln Gly Thr Leu Val Thr Val Ser Ser
            115                 120

<210> SEQ ID NO 4
<211> LENGTH: 122
<212> TYPE: PRT
<213> ORGANISM: Artificial Sequence
<220> FEATURE:
<223> OTHER INFORMATION: Synthetic peptide: VH3

<400> SEQUENCE: 4

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Glu Ser
                 20                  25                  30

Phe Met Asp Trp Val Arg Gln Ala Pro Gly Lys Gly Leu Glu Trp Val
                 35                  40                  45

Gly Arg Ile Arg Asn Lys Ala Asn Gly Tyr Thr Thr Glu Tyr Ala Ala
             50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg Gly Gly Glu Tyr Pro Leu Tyr Val Met Asp Tyr Trp
                100                 105                 110

Gly Gln Gly Thr Leu Val Thr Val Ser Ser
            115                 120

<210> SEQ ID NO 5
<211> LENGTH: 122
<212> TYPE: PRT
<213> ORGANISM: Artificial Sequence
<220> FEATURE:
<223> OTHER INFORMATION: Synthetic peptide: VH4

<400> SEQUENCE: 5

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Glu Ser
                 20                  25                  30

Phe Met Asp Trp Ile Arg Gln Pro Pro Gly Lys Ala Leu Glu Trp Leu
                 35                  40                  45

Ala Phe Ile Arg Asn Lys Ala Asn Gly Tyr Thr Thr Glu Tyr Ala Ala
             50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg Gly Gly Glu Tyr Pro Leu Tyr Val Met Asp Tyr Trp
                100                 105                 110

Gly Gln Gly Thr Leu Val Thr Val Ser Ser
```

```
              115                 120

<210> SEQ ID NO 6
<211> LENGTH: 111
<212> TYPE: PRT
<213> ORGANISM: Artificial Sequence
<220> FEATURE:
<223> OTHER INFORMATION: Synthetic peptide: VL chimeric

<400> SEQUENCE: 6

Asp Ile Val Leu Thr Gln Ser Pro Val Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Asp Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Phe Ala Thr Tyr Phe Cys Gln Gln Ser Arg
                85                  90                  95

Lys Val Pro Trp Thr Phe Gly Gly Gly Thr Lys Leu Glu Ile Lys
            100                 105                 110

<210> SEQ ID NO 7
<211> LENGTH: 111
<212> TYPE: PRT
<213> ORGANISM: Artificial Sequence
<220> FEATURE:
<223> OTHER INFORMATION: Synthetic peptide: VL1

<400> SEQUENCE: 7

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Glu Tyr Tyr
            20                  25                  30

Asp Thr Ser Leu Leu Ala Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Val Pro Trp Thr Phe Gly Gln Gly Thr Lys Leu Glu Ile Lys
            100                 105                 110

<210> SEQ ID NO 8
<211> LENGTH: 111
<212> TYPE: PRT
<213> ORGANISM: Artificial Sequence
<220> FEATURE:
<223> OTHER INFORMATION: Synthetic peptide: VL2

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Glu Tyr Tyr
            20                  25                  30
```

```
Asp Thr Ser Leu Leu Ala Trp Tyr Gln Gln Lys Pro Gly Gln Pro Pro
            35                  40                  45

Lys Leu Leu Ile Tyr Ala Ala Ser Asn Val Glu Ser Gly Val Pro Ala
     50                  55                  60

Arg Phe Ser Gly Ser Gly Ser Gly Thr Asp Phe Thr Leu Thr Ile Ser
 65                  70                  75                  80

Ser Leu Gln Glu Glu Asp Val Ala Val Tyr Tyr Cys Gln Gln Ser Arg
                 85                  90                  95

Lys Val Pro Trp Thr Phe Gly Gln Gly Thr Lys Leu Glu Ile Lys
            100                 105                 110

<210> SEQ ID NO 9
<211> LENGTH: 111
<212> TYPE: PRT
<213> ORGANISM: Artificial Sequence
<220> FEATURE:
<223> OTHER INFORMATION: Synthetic peptide: VL3

<400> SEQUENCE: 9

Asp Ile Val Met Thr Gln Ser Pro Asp Ser Leu Ala Val Ser Leu Gly
 1               5                  10                  15

Glu Arg Ala Thr Ile Asn Cys Lys Ser Ser Glu Ser Val Glu Tyr Tyr
             20                  25                  30

Asp Thr Ser Leu Leu Ala Trp Tyr Gln Gln Lys Pro Gly Gln Pro Pro
            35                  40                  45

Lys Leu Leu Ile Tyr Ala Ala Ser Asn Val Glu Ser Gly Val Pro Ser
     50                  55                  60

Arg Phe Ser Gly Ser Gly Ser Gly Thr Asp Phe Thr Leu Thr Ile Ser
 65                  70                  75                  80

Ser Leu Gln Pro Glu Asp Val Ala Val Tyr Tyr Cys Gln Gln Ser Arg
                 85                  90                  95

Lys Val Pro Trp Thr Phe Gly Gln Gly Thr Lys Leu Glu Ile Lys
            100                 105                 110

<210> SEQ ID NO 10
<211> LENGTH: 111
<212> TYPE: PRT
<213> ORGANISM: Artificial Sequence
<220> FEATURE:
<223> OTHER INFORMATION: Synthetic peptide: VL4

<400> SEQUENCE: 10

Asp Ile Val Met Thr Gln Ser Pro Asp Ser Leu Ala Val Ser Leu Gly
 1               5                  10                  15

Glu Arg Ala Thr Ile Asn Cys Lys Ser Ser Glu Ser Val Glu Tyr Tyr
             20                  25                  30

Asp Thr Ser Leu Leu Ala Trp Tyr Gln Gln Lys Pro Gly Gln Pro Pro
            35                  40                  45

Lys Leu Leu Ile Tyr Ala Ala Ser Asn Val Glu Ser Gly Val Pro Ala
     50                  55                  60

Arg Phe Ser Gly Ser Gly Ser Gly Thr Asp Phe Thr Leu Thr Ile Ser
 65                  70                  75                  80

Ser Leu Gln Pro Glu Asp Val Ala Val Tyr Tyr Cys Gln Gln Ser Arg
                 85                  90                  95

Lys Val Pro Trp Thr Phe Gly Gln Gly Thr Lys Leu Glu Ile Lys
            100                 105                 110
```

```
<210> SEQ ID NO 11
<211> LENGTH: 111
<212> TYPE: PRT
<213> ORGANISM: Artificial Sequence
<220> FEATURE:
<223> OTHER INFORMATION: Synthetic peptide: VL5

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Asp Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Val Pro Trp Thr Phe Gly Gln Gly Thr Lys Leu Glu Ile Lys
            100                 105                 110

<210> SEQ ID NO 12
<211> LENGTH: 111
<212> TYPE: PRT
<213> ORGANISM: Artificial Sequence
<220> FEATURE:
<223> OTHER INFORMATION: Synthetic peptide: VL6

<400> SEQUENCE: 12

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Asp Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Glu Glu Asp Val Ala Val Tyr Tyr Cys Gln Gln Ser Arg
                85                  90                  95

Lys Val Pro Trp Thr Phe Gly Gln Gly Thr Lys Leu Glu Ile Lys
            100                 105                 110

<210> SEQ ID NO 13
<211> LENGTH: 111
<212> TYPE: PRT
<213> ORGANISM: Artificial Sequence
<220> FEATURE:
<223> OTHER INFORMATION: Synthetic peptide: VL7

<400> SEQUENCE: 13

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Asp Thr Ser Leu Met Gln Trp Tyr Gln Gln Lys Pro Gly Gln Pro Pro
        35                  40                  45
```

Lys Leu Leu Ile Tyr Ala Ala Ser Asn Val Glu Ser Gly Val Pro Ser
            50                  55                  60

Arg Phe Ser Gly Ser Gly Ser Gly Thr Asp Phe Thr Leu Thr Ile Ser
 65                  70                  75                  80

Ser Leu Gln Glu Glu Asp Val Ala Val Tyr Tyr Cys Gln Gln Ser Arg
                85                  90                  95

Lys Val Pro Trp Thr Phe Gly Gln Gly Thr Lys Leu Glu Ile Lys
            100                 105                 110

<210> SEQ ID NO 14
<211> LENGTH: 111
<212> TYPE: PRT
<213> ORGANISM: Artificial Sequence
<220> FEATURE:
<223> OTHER INFORMATION: Synthetic peptide: VL8

<400> SEQUENCE: 14

Asp Ile Val Met Thr Gln Ser Pro Asp Ser Leu Ala Val Ser Leu Gly
 1               5                  10                  15

Glu Arg Ala Thr Ile Asn Cys Arg Ala Ser Glu Ser Val Glu Tyr Tyr
                20                  25                  30

Asp Thr Ser Leu Met Gln Trp Tyr Gln Gln Lys Pro Gly Gln Pro Pro
                35                  40                  45

Lys Leu Leu Ile Tyr Ala Ala Ser Asn Val Glu Ser Gly Val Pro Ala
            50                  55                  60

Arg Phe Ser Gly Ser Gly Ser Gly Thr Asp Phe Thr Leu Thr Ile Ser
 65                  70                  75                  80

Ser Leu Gln Pro Glu Asp Val Ala Val Tyr Tyr Cys Gln Gln Ser Arg
                85                  90                  95

Lys Val Pro Trp Thr Phe Gly Gln Gly Thr Lys Leu Glu Ile Lys
            100                 105                 110

<210> SEQ ID NO 15
<211> LENGTH: 111
<212> TYPE: PRT
<213> ORGANISM: Artificial Sequence
<220> FEATURE:
<223> OTHER INFORMATION: Synthetic peptide: VL9

<400> SEQUENCE: 15

Asp Ile Val Met Thr Gln Ser Pro Asp Ser Leu Ala Val Ser Leu Gly
 1               5                  10                  15

Glu Arg Ala Thr Ile Asn Cys Arg Ala Ser Glu Ser Val Glu Tyr Tyr
                20                  25                  30

Asp Thr Ser Leu Met Gln Trp Tyr Gln Gln Lys Pro Gly Gln Pro Pro
                35                  40                  45

Lys Leu Leu Ile Tyr Ala Ala Ser Asn Val Glu Ser Gly Val Pro Asp
            50                  55                  60

Arg Phe Ser Gly Ser Gly Ser Gly Thr Asp Phe Thr Leu Thr Ile Ser
 65                  70                  75                  80

Ser Leu Gln Glu Glu Asp Phe Ala Thr Tyr Phe Cys Gln Gln Ser Arg
                85                  90                  95

Lys Val Pro Trp Thr Phe Gly Gln Gly Thr Lys Leu Glu Ile Lys
            100                 105                 110

<210> SEQ ID NO 16
<211> LENGTH: 111
<212> TYPE: PRT

```
<213> ORGANISM: Artificial Sequence
<220> FEATURE:
<223> OTHER INFORMATION: Synthetic peptide: VL10

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Asp Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Glu Glu Asp Phe Ala Thr Tyr Phe Cys Gln Gln Ser Arg
                85                  90                  95

Lys Val Pro Trp Thr Phe Gly Gln Gly Thr Lys Leu Glu Ile Lys
            100                 105                 110

<210> SEQ ID NO 17
<211> LENGTH: 111
<212> TYPE: PRT
<213> ORGANISM: Artificial Sequence
<220> FEATURE:
<223> OTHER INFORMATION: Synthetic peptide: VL11

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Asp Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Glu Glu Asp Phe Ala Thr Tyr Phe Cys Gln Gln Ser Arg
                85                  90                  95

Lys Val Pro Trp Thr Phe Gly Gln Gly Thr Lys Leu Glu Ile Lys
            100                 105                 110

<210> SEQ ID NO 18
<211> LENGTH: 111
<212> TYPE: PRT
<213> ORGANISM: Artificial Sequence
<220> FEATURE:
<223> OTHER INFORMATION: Synthetic peptide: VL12

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Asp Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60
```

```
Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Phe Cys Gln Gln Ser Arg
             85                  90                  95

Lys Val Pro Trp Thr Phe Gly Gln Gly Thr Lys Leu Glu Ile Lys
            100                 105                 110

<210> SEQ ID NO 19
<211> LENGTH: 452
<212> TYPE: PRT
<213> ORGANISM: Artificial Sequence
<220> FEATURE:
<223> OTHER INFORMATION: Synthetic peptide: HC 1, Anti SpA Chimeric HC
      G1M17

<400> SEQUENCE: 19

Glu Val Lys Leu Val Glu Ser Gly Gly Gly Leu Val Gln Pro Gly Gly
  1               5                  10                  15

Ser Arg Arg Leu Ser Cys Thr Thr Ser Gly Phe Thr Phe Thr Glu Ser
             20                  25                  30

Phe Met Thr Trp Val Arg Gln Pro Pro Gly Lys Ala Leu Asp Trp Leu
             35                  40                  45

Ala Phe Ile Arg Asn Lys Ala Asn Gly Tyr Thr Thr Glu Tyr Ser Ala
 50                  55                  60

Ser Val Lys Gly Arg Phe Thr Ile Ala Arg Asp Asn Ser Gln Ser Ile
 65                  70                  75                  80

Leu Tyr Leu Gln Met Asn Ala Leu Arg Ala Glu Asp Ser Ala Thr Tyr
             85                  90                  95

Tyr Cys Val Arg Gly Gly Glu Tyr Pro Leu Tyr Val Met Asp Tyr Trp
            100                 105                 110

Gly Lys Gly Thr Ser Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
```

```
              305                 310                 315                 320
    Gly Lys Glu Tyr Lys Cys Lys Val Ser Asn Lys Ala Leu Pro Ala Pro
                    325                 330                 335

Ile Glu Lys Thr Ile Ser Lys Ala Lys Gly Gln Pro Arg Glu Pro Gln
                    340                 345                 350

Val Tyr Thr Leu Pro Pro Ser Arg Glu Met Thr Lys Asn Gln Val
                    355                 360                 365

Ser Leu Thr Cys Leu Val Lys Gly Phe Tyr Pro Ser Asp Ile Ala Val
                    370                 375                 380

Glu Trp Glu Ser Asn Gly Gln Pro Glu Asn Asn Tyr Lys Thr Thr Pro
    385                 390                 395                 400

Pro Val Leu Asp Ser Asp Gly Ser Phe Phe Leu Tyr Ser Lys Leu Thr
                    405                 410                 415

Val Asp Lys Ser Arg Trp Gln Gln Gly Asn Val Phe Ser Cys Ser Val
                    420                 425                 430

Met His Glu Ala Leu His Asn His Tyr Thr Gln Lys Ser Leu Ser Leu
                    435                 440                 445

Ser Pro Gly Lys
            450

<210> SEQ ID NO 20
<211> LENGTH: 452
<212> TYPE: PRT
<213> ORGANISM: Artificial Sequence
<220> FEATURE:
<223> OTHER INFORMATION: Synthetic peptide: HC 2, Anti SpA Chimeric
      variant HC G1M17

<400> SEQUENCE: 20

Glu Val Lys Leu Val Glu Ser Gly Gly Gly Leu Val Gln Pro Gly Gly
    1               5                   10                  15

Ser Arg Arg Leu Ser Cys Thr Thr Ser Gly Phe Thr Phe Thr Glu Ser
                    20                  25                  30

Phe Met Thr Trp Val Arg Gln Pro Pro Gly Lys Ala Leu Asp Trp Leu
                    35                  40                  45

Ala Phe Ile Arg Asn Lys Ala Asn Gly Tyr Thr Thr Glu Tyr Ser Ala
                    50                  55                  60

Ser Val Lys Gly Arg Phe Thr Ile Ala Arg Asp Asn Ser Gln Ser Ile
    65                  70                  75                  80

Leu Tyr Leu Gln Met Asn Ala Leu Arg Ala Glu Asp Ser Ala Thr Tyr
                    85                  90                  95

Tyr Cys Val Arg Gly Gly Glu Tyr Pro Leu Tyr Val Met Asp Tyr Trp
                    100                 105                 110

Gly Lys Gly Thr Ser Val Thr Val Ser Ser Ala Ser Thr Lys Gly Pro
                    115                 120                 125

Ser Val Phe Pro Leu Ala Pro Ser Ser Lys Ser Thr Ser Gly Gly Thr
                    130                 135                 140

Ala Ala Leu Gly Cys Leu Val Lys Asp Tyr Phe Pro Glu Pro Val Thr
    145                 150                 155                 160

Val Ser Trp Asn Ser Gly Ala Leu Thr Ser Gly Val His Thr Phe Pro
                    165                 170                 175

Ala Val Leu Gln Ser Ser Gly Leu Tyr Ser Leu Ser Ser Val Val Thr
                    180                 185                 190

Val Pro Ser Ser Ser Leu Gly Thr Gln Thr Tyr Ile Cys Asn Val Asn
                    195                 200                 205
```

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
            275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn Arg Phe Thr Gln Lys Ser Leu Ser Leu
            435                 440                 445

Ser Pro Gly Lys
    450

<210> SEQ ID NO 21
<211> LENGTH: 220
<212> TYPE: PRT
<213> ORGANISM: Artificial Sequence
<220> FEATURE:
<223> OTHER INFORMATION: Synthetic peptide: LC 1, Anti SpA Chimeric LC

<400> SEQUENCE: 21

Lys Met Asp Ile Val Leu Thr Gln Ser Pro Val Ser Leu Ala Val Ser
1               5                   10                  15

Leu Gly Gln Arg Ala Thr Ile Ser Cys Arg Ala Ser Glu Ser Val Glu
            20                  25                  30

Tyr Tyr Asp Thr Ser Leu Met Gln Trp Tyr Gln Gln Lys Pro Gly Gln
            35                  40                  45

Pro Pro Lys Leu Leu Ile Tyr Ala Ala Ser Asn Val Glu Ser Gly Val
        50                  55                  60

Pro Ala Arg Phe Ser Gly Ser Gly Ser Gly Thr Asp Phe Ser Leu Asn
65                  70                  75                  80

Ile His Pro Val Glu Glu Asp Asp Phe Ala Thr Tyr Phe Cys Gln Gln
            85                  90                  95

Ser Arg Lys Val Pro Trp Thr Phe Gly Gly Gly Thr Lys Leu Glu Ile
            100                 105                 110

Lys Arg Thr Val Ala Ala Pro Ser Val Phe Ile Phe Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
    195                 200                 205

Ser Pro Val Thr Lys Ser Phe Asn Arg Gly Glu Cys
    210                 215                 220

<210> SEQ ID NO 22
<211> LENGTH: 450
<212> TYPE: PRT
<213> ORGANISM: Artificial Sequence
<220> FEATURE:
<223> OTHER INFORMATION: Synthetic peptide: HC3, Anti RSV HC parental
      IgG1 of allotype G1m17

<400> SEQUENCE: 22

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

```
Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 23
<211> LENGTH: 450
<212> TYPE: PRT
<213> ORGANISM: Artificial Sequence
<220> FEATURE:
<223> OTHER INFORMATION: Synthetic peptide: HC4, Anti RSV variant HC of
      allotype G1m17

<400> SEQUENCE: 23

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
                145             150             155             160
        Trp Asn Ser Gly Ala Leu Thr Ser Gly Val His Thr Phe Pro Ala Val
                    165             170             175

Leu Gln Ser Ser Gly Leu Tyr Ser Leu Ser Ser Val Val Thr Val Pro
                    180             185             190

Ser Ser Ser Leu Gly Thr Gln Thr Tyr Ile Cys Asn Val Asn His Lys
                    195             200             205

Pro Ser Asn Thr Lys Val Asp Lys Lys Val Glu Pro Lys Ser Cys Asp
                210             215             220

Lys Thr His Thr Cys Pro Pro Cys Pro Ala Pro Glu Leu Leu Gly Gly
        225             230             235             240

Pro Ser Val Phe Leu Phe Pro Pro Lys Pro Lys Asp Thr Leu Met Ile
                        245             250             255

Ser Arg Thr Pro Glu Val Thr Cys Val Val Val Asp Val Ser His Glu
                        260             265             270

Asp Pro Glu Val Gln Phe Asn Trp Tyr Val Asp Gly Val Glu Val His
                    275             280             285

Asn Ala Lys Thr Lys Pro Arg Glu Glu Gln Tyr Asn Ser Thr Tyr Arg
                290             295             300

Val Val Ser Val Leu Thr Val Leu His Gln Asp Trp Leu Asn Gly Lys
        305             310             315             320

Glu Tyr Lys Cys Lys Val Ser Asn Lys Ala Leu Pro Ala Pro Ile Glu
                        325             330             335

Lys Thr Ile Ser Lys Ala Lys Gly Gln Pro Arg Glu Pro Gln Val Tyr
                        340             345             350

Thr Leu Pro Pro Ser Arg Glu Glu Met Thr Lys Asn Gln Val Ser Leu
                    355             360             365

Thr Cys Leu Val Lys Gly Phe Tyr Pro Ser Asp Ile Ala Val Glu Trp
                370             375             380

Glu Ser Asn Gly Gln Pro Glu Asn Asn Tyr Lys Thr Thr Pro Pro Val
        385             390             395             400

Leu Asp Ser Asp Gly Ser Phe Phe Leu Tyr Ser Lys Leu Thr Val Asp
                        405             410             415

Lys Ser Arg Trp Gln Gln Gly Asn Val Phe Ser Cys Ser Val Met His
                        420             425             430

Glu Ala Leu His Asn Arg Phe Thr Gln Lys Ser Leu Ser Leu Ser Pro
                    435             440             445

Gly Lys
            450

<210> SEQ ID NO 24
<211> LENGTH: 213
<212> TYPE: PRT
<213> ORGANISM: Artificial Sequence
<220> FEATURE:
<223> OTHER INFORMATION: Synthetic peptide: LC 2, Anti RSV LC

<400> SEQUENCE: 24

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
                20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
```

```
                    50                  55                  60
Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                     85                  90                  95

Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 25
<211> LENGTH: 451
<212> TYPE: PRT
<213> ORGANISM: Artificial Sequence
<220> FEATURE:
<223> OTHER INFORMATION: Synthetic peptide: HC 5, Humanized anti-ClfA HC
      in G1m17 heavy chain background

<400> SEQUENCE: 25

Gln Val Gln Leu Lys Glu Ser Gly Pro Gly Leu Val Lys Pro Ser Gln
 1               5                  10                  15

Thr Leu Ser Ile Thr Cys Thr Ile Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Gly Asn Thr Asp Tyr Asn Ser Ala Leu Lys
    50                  55                  60

Ser Arg Leu Ser Ile Ser Lys Asp Asn Ser Lys Asn Gln Val Phe Leu
 65                  70                  75                  80

Lys Met Asn Ser Leu Thr Ala Ala Asp Thr Ala Val Tyr Tyr Cys Ala
                 85                  90                  95

Arg Lys Gly Glu Phe Tyr Tyr Gly Tyr Asp Gly Phe Val Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 26
<211> LENGTH: 451
<212> TYPE: PRT
<213> ORGANISM: Artificial Sequence
<220> FEATURE:
<223> OTHER INFORMATION: Synthetic peptide: HC 6, Humanized anti-ClfA HC
      in variant G1M17 heavy chain background

<400> SEQUENCE: 26

Gln Val Gln Leu Lys Glu Ser Gly Pro Gly Leu Val Lys Pro Ser Gln
1               5                   10                  15

Thr Leu Ser Ile Thr Cys Thr Ile Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Gly Asn Thr Asp Tyr Asn Ser Ala Leu Lys
    50                  55                  60

Ser Arg Leu Ser Ile Ser Lys Asp Asn Ser Lys Asn Gln Val Phe Leu
65                  70                  75                  80

Lys Met Asn Ser Leu Thr Ala Ala Asp Thr Ala Val Tyr Tyr Cys Ala
                85                  90                  95
```

-continued

```
Arg Lys Gly Glu Phe Tyr Tyr Gly Tyr Asp Gly Phe Val Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn Arg Phe Thr Gln Lys Ser Leu Ser Leu Ser
        435                 440                 445

Pro Gly Lys
    450

<210> SEQ ID NO 27
<211> LENGTH: 219
<212> TYPE: PRT
<213> ORGANISM: Artificial Sequence
<220> FEATURE:
<223> OTHER INFORMATION: Synthetic peptide: LC 3, Humanized ClfA LC KM3

<400> SEQUENCE: 27
```

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Val Leu Tyr Ser
            20                  25                  30

Ser Asn Gln Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser Ser Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
210                 215

<210> SEQ ID NO 28
<211> LENGTH: 121
<212> TYPE: PRT
<213> ORGANISM: Artificial Sequence
<220> FEATURE:
<223> OTHER INFORMATION: Synthetic peptide: VH 5, ClfA Humanized 12-9 VH
      sequence

<400> SEQUENCE: 28

Gln Val Gln Leu Lys Glu Ser Gly Pro Gly Leu Val Lys Pro Ser Gln
1               5                   10                  15

Thr Leu Ser Ile Thr Cys Thr Ile Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Gly Asn Thr Asp Tyr Asn Ser Ala Leu Lys
50                  55                  60

Ser Arg Leu Ser Ile Ser Lys Asp Asn Ser Lys Asn Gln Val Phe Leu
65                  70                  75                  80

Lys Met Asn Ser Leu Thr Ala Ala Asp Thr Ala Val Tyr Tyr Cys Ala
                85                  90                  95

Arg Lys Gly Glu Phe Tyr Tyr Gly Tyr Asp Gly Phe Val Tyr Trp Gly
            100                 105                 110

Gln Gly Thr Leu Val Thr Val Ser Ser
        115                 120

```
<210> SEQ ID NO 29
<211> LENGTH: 112
<212> TYPE: PRT
<213> ORGANISM: Artificial Sequence
<220> FEATURE:
<223> OTHER INFORMATION: Synthetic peptide: VL 13, ClfA Humanized 12-9
      VL sequence

<400> SEQUENCE: 29

Asp Ile Val Met Thr Gln Ser Pro Asp Ser Leu Ala Val Ser Leu Gly
1               5                   10                  15

Glu Arg Val Thr Met Asn Cys Lys Ser Ser Gln Ser Val Leu Tyr Ser
            20                  25                  30

Ser Asn Gln Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser Ser Tyr Thr Phe Gly Gly Gly Thr Lys Leu Glu Ile Lys
            100                 105                 110

<210> SEQ ID NO 30
<211> LENGTH: 447
<212> TYPE: PRT
<213> ORGANISM: Artificial Sequence
<220> FEATURE:
<223> OTHER INFORMATION: Synthetic peptide: Heavy chain constant region
      1
<220> FEATURE:
<221> NAME/KEY: misc_feature
<222> LOCATION: (1)..(117)
<223> OTHER INFORMATION: Xaa can be any naturally occurring amino acid

<400> SEQUENCE: 30

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 31
<211> LENGTH: 447
<212> TYPE: PRT
<213> ORGANISM: Artificial Sequence
<220> FEATURE:
<223> OTHER INFORMATION: Synthetic peptide: Heavy chain constant region
      2
<220> FEATURE:
<221> NAME/KEY: misc_feature
<222> LOCATION: (1)..(117)
<223> OTHER INFORMATION: Xaa can be any naturally occurring amino acid

<400> SEQUENCE: 31

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
```

```
                65                  70                  75                  80
Xaa Xaa Xaa Xaa Xaa Xaa Xaa Xaa Xaa Xaa Xaa Xaa Xaa Xaa
                    85                  90                  95

Xaa Xaa Xaa Xaa Xaa Xaa Xaa Xaa Xaa Xaa Xaa Xaa Xaa Xaa
                    100                 105                 110

Xaa Xaa Xaa Xaa Xaa Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn Arg Tyr Thr Gln Lys Ser Leu Ser Leu Ser Pro Gly Lys
                435                 440                 445

<210> SEQ ID NO 32
<211> LENGTH: 447
<212> TYPE: PRT
<213> ORGANISM: Artificial Sequence
<220> FEATURE:
<223> OTHER INFORMATION: Synthetic peptide: Heavy chain constant region
      3
```

<220> FEATURE:
<221> NAME/KEY: misc_feature
<222> LOCATION: (1)..(117)
<223> OTHER INFORMATION: Xaa can be any naturally occurring amino acid

<400> SEQUENCE: 32

Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa
            100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

-continued

```
Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn Arg Tyr Thr Gln Lys Ser Leu Ser Leu Ser Pro Gly Lys
    435                 440                 445

<210> SEQ ID NO 33
<211> LENGTH: 447
<212> TYPE: PRT
<213> ORGANISM: Artificial Sequence
<220> FEATURE:
<223> OTHER INFORMATION: Synthetic peptide: Heavy chain constant region
      4
<220> FEATURE:
<221> NAME/KEY: misc_feature
<222> LOCATION: (1)..(117)
<223> OTHER INFORMATION: Xaa can be any naturally occurring amino acid

<400> SEQUENCE: 33

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
```

```
                275                 280                 285
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Ile Phe Ser Cys Ser Val Met His Glu Ala Leu
            420                 425                 430

His Asn Arg Tyr Thr Gln Lys Ser Leu Ser Leu Ser Pro Gly Lys
        435                 440                 445
```

<210> SEQ ID NO 34
<211> LENGTH: 447
<212> TYPE: PRT
<213> ORGANISM: Artificial Sequence
<220> FEATURE:
<223> OTHER INFORMATION: Synthetic peptide: Heavy chain constant region 5
<220> FEATURE:
<221> NAME/KEY: misc_feature
<222> LOCATION: (1)..(117)
<223> OTHER INFORMATION: Xaa can be any naturally occurring amino acid

<400> SEQUENCE: 34

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Ile Phe Ser Cys Ser Val Met His Glu Ala Leu
            420                 425                 430

His Asn Arg Tyr Thr Gln Lys Ser Leu Ser Leu Ser Pro Gly Lys
            435                 440                 445

<210> SEQ ID NO 35
<211> LENGTH: 447
<212> TYPE: PRT
<213> ORGANISM: Artificial Sequence
<220> FEATURE:
<223> OTHER INFORMATION: Synthetic peptide: Heavy chain constant region
      6
<220> FEATURE:
<221> NAME/KEY: misc_feature
<222> LOCATION: (1)..(117)
<223> OTHER INFORMATION: Xaa can be any naturally occurring amino acid

<400> SEQUENCE: 35

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60
```

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn Arg Tyr Thr Gln Lys Ser Leu Ser Leu Ser Pro Gly Lys
        435                 440                 445

<210> SEQ ID NO 36
<211> LENGTH: 448
<212> TYPE: PRT
<213> ORGANISM: Artificial Sequence
<220> FEATURE:
<223> OTHER INFORMATION: Synthetic peptide: Heavy chain constant region 7
<220> FEATURE:
<221> NAME/KEY: misc_feature
<222> LOCATION: (1)..(117)
<223> OTHER INFORMATION: Xaa can be any naturally occurring amino acid

<400> SEQUENCE: 36

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

```
Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Glu Gly Asn Val Phe Ser Cys Ser Val Met His Glu Ala Ala
        420                 425                 430

Leu His Asn Arg Tyr Thr Gln Lys Ser Leu Ser Leu Ser Pro Gly Lys
            435                 440                 445

<210> SEQ ID NO 37
<211> LENGTH: 447
<212> TYPE: PRT
<213> ORGANISM: Artificial Sequence
<220> FEATURE:
<223> OTHER INFORMATION: Synthetic peptide: Heavy chain constant region
      8
<220> FEATURE:
<221> NAME/KEY: misc_feature
<222> LOCATION: (1)..(117)
<223> OTHER INFORMATION: Xaa can be any naturally occurring amino acid

<400> SEQUENCE: 37

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Ile Phe Ser Cys Ser Val Met His Glu Ala Leu
            420                 425                 430

His Asn Arg Tyr Thr Gln Lys Ser Leu Ser Leu Ser Pro Gly Lys
            435                 440                 445

<210> SEQ ID NO 38
<211> LENGTH: 447
<212> TYPE: PRT
<213> ORGANISM: Artificial Sequence
<220> FEATURE:
<223> OTHER INFORMATION: Synthetic peptide: Heavy chain constant region
      9
<220> FEATURE:
<221> NAME/KEY: misc_feature
<222> LOCATION: (1)..(117)
<223> OTHER INFORMATION: Xaa can be any naturally occurring amino acid

<400> SEQUENCE: 38

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser

```
                    165                 170                 175
Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Ile Phe Ser Cys Ser Val Met His Glu Ala Leu
            420                 425                 430

His Asn Arg Tyr Thr Gln Lys Ser Leu Ser Leu Ser Pro Gly Lys
        435                 440                 445

<210> SEQ ID NO 39
<211> LENGTH: 447
<212> TYPE: PRT
<213> ORGANISM: Artificial Sequence
<220> FEATURE:
<223> OTHER INFORMATION: Synthetic peptide: Heavy chain constant region
      10
<220> FEATURE:
<221> NAME/KEY: misc_feature
<222> LOCATION: (1)..(117)
<223> OTHER INFORMATION: Xaa can be any naturally occurring amino acid

<400> SEQUENCE: 39

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60
```

```
Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn Arg Phe Thr Gln Lys Ser Leu Ser Leu Ser Pro Gly Lys
                435                 440                 445

<210> SEQ ID NO 40
<211> LENGTH: 447
<212> TYPE: PRT
<213> ORGANISM: Artificial Sequence
<220> FEATURE:
```

<223> OTHER INFORMATION: Synthetic peptide: Heavy chain constant region 11
<220> FEATURE:
<221> NAME/KEY: misc_feature
<222> LOCATION: (1)..(117)
<223> OTHER INFORMATION: Xaa can be any naturally occurring amino acid

<400> SEQUENCE: 40

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
```

-continued

```
                    370                 375                 380
Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                    405                 410                 415

Trp Gln Gln Gly Asn Val Phe Ser Cys Ser Val Met His Glu Ala Leu
                    420                 425                 430

His Asn Arg Phe Thr Gln Lys Ser Leu Ser Leu Ser Pro Gly Lys
                    435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic peptide: Heavy chain constant region
      12
<220> FEATURE:
<221> NAME/KEY: misc_feature
<222> LOCATION: (1)..(117)
<223> OTHER INFORMATION: Xaa can be any naturally occurring amino acid

<400> SEQUENCE: 41

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
                210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270
```

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Ile Phe Ser Cys Ser Val Met His Glu Ala Leu
            420                 425                 430

His Asn Arg Phe Thr Gln Lys Ser Leu Ser Leu Ser Pro Gly Lys
            435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic peptide: Heavy chain constant region
      13
<220> FEATURE:
<221> NAME/KEY: misc_feature
<222> LOCATION: (1)..(117)
<223> OTHER INFORMATION: Xaa can be any naturally occurring amino acid

<400> SEQUENCE: 42

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Ile Phe Ser Cys Ser Val Met His Glu Ala Leu
            420                 425                 430

His Asn Arg Phe Thr Gln Lys Ser Leu Ser Leu Ser Pro Gly Lys
        435                 440                 445

<210> SEQ ID NO 43
<211> LENGTH: 447
<212> TYPE: PRT
<213> ORGANISM: Artificial Sequence
<220> FEATURE:
<223> OTHER INFORMATION: Synthetic peptide: Heavy chain constant region
      14
<220> FEATURE:
<221> NAME/KEY: misc_feature
<222> LOCATION: (1)..(117)
<223> OTHER INFORMATION: Xaa can be any naturally occurring amino acid

<400> SEQUENCE: 43

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa

```
            50                  55                  60
Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn Arg Phe Thr Gln Lys Ser Leu Ser Leu Ser Pro Gly Lys
        435                 440                 445

<210> SEQ ID NO 44
<211> LENGTH: 447
<212> TYPE: PRT
<213> ORGANISM: Artificial Sequence
```

<220> FEATURE:
<223> OTHER INFORMATION: Synthetic peptide: Heavy chain constant region 15
<220> FEATURE:
<221> NAME/KEY: misc_feature
<222> LOCATION: (1)..(117)
<223> OTHER INFORMATION: Xaa can be any naturally occurring amino acid

<400> SEQUENCE: 44

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365
```

-continued

```
Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
                420                 425                 430

His Asn Arg Phe Thr Gln Lys Ser Leu Ser Leu Ser Pro Gly Lys
                435                 440                 445

<210> SEQ ID NO 45
<211> LENGTH: 447
<212> TYPE: PRT
<213> ORGANISM: Artificial Sequence
<220> FEATURE:
<223> OTHER INFORMATION: Synthetic peptide: Heavy chain constant region
      16
<220> FEATURE:
<221> NAME/KEY: misc_feature
<222> LOCATION: (1)..(117)
<223> OTHER INFORMATION: Xaa can be any naturally occurring amino acid

<400> SEQUENCE: 45

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
                210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
```

```
                    260                 265                 270
Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Ile Phe Ser Cys Ser Val Met His Glu Ala Leu
            420                 425                 430

His Asn Arg Phe Thr Gln Lys Ser Leu Ser Leu Ser Pro Gly Lys
        435                 440                 445

<210> SEQ ID NO 46
<211> LENGTH: 447
<212> TYPE: PRT
<213> ORGANISM: Artificial Sequence
<220> FEATURE:
<223> OTHER INFORMATION: Synthetic peptide: Heavy chain constant region
      17
<220> FEATURE:
<221> NAME/KEY: misc_feature
<222> LOCATION: (1)..(117)
<223> OTHER INFORMATION: Xaa can be any naturally occurring amino acid

<400> SEQUENCE: 46

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160
```

-continued

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Glu Gly Asn Ile Phe Ser Cys Ser Val Met His Glu Ala Leu
            420                 425                 430

His Asn Arg Phe Thr Gln Lys Ser Leu Ser Leu Ser Pro Gly Lys
            435                 440                 445

<210> SEQ ID NO 47
<211> LENGTH: 447
<212> TYPE: PRT
<213> ORGANISM: Artificial Sequence
<220> FEATURE:
<223> OTHER INFORMATION: Synthetic peptide: Heavy chain constant region
      18
<220> FEATURE:
<221> NAME/KEY: misc_feature
<222> LOCATION: (1)..(117)
<223> OTHER INFORMATION: Xaa can be any naturally occurring amino acid

<400> SEQUENCE: 47

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa
            50                  55                      60

Xaa Xaa Xaa Xaa Xaa Xaa Xaa Xaa Xaa Xaa Xaa Xaa
 65                  70                      75                  80

Xaa Xaa Xaa Xaa Xaa Xaa Xaa Xaa Xaa Xaa Xaa Xaa
                85                  90                      95

Xaa Xaa Xaa Xaa Xaa Xaa Xaa Xaa Xaa Xaa Xaa Xaa
            100                 105                     110

Xaa Xaa Xaa Xaa Xaa Ala Ser Thr Lys Gly Pro Ser Val Phe Pro Leu
            115                 120                     125

Ala Pro Ser Ser Lys Ser Thr Ser Gly Gly Thr Ala Ala Leu Gly Cys
130                 135                     140

Leu Val Lys Asp Tyr Phe Pro Glu Pro Val Thr Val Ser Trp Asn Ser
145                 150                     155                 160

Gly Ala Leu Thr Ser Gly Val His Thr Phe Pro Ala Val Leu Gln Ser
                165                 170                     175

Ser Gly Leu Tyr Ser Leu Ser Ser Val Val Thr Val Pro Ser Ser Ser
            180                 185                     190

Leu Gly Thr Gln Thr Tyr Ile Cys Asn Val Asn His Lys Pro Ser Asn
        195                 200                     205

Thr Lys Val Asp Lys Lys Val Glu Pro Lys Ser Cys Asp Lys Thr His
    210                 215                     220

Thr Cys Pro Pro Cys Pro Ala Pro Glu Leu Leu Gly Gly Pro Ser Val
225                 230                     235                 240

Phe Leu Phe Pro Pro Lys Pro Lys Asp Thr Leu Met Ile Ser Arg Thr
                245                 250                     255

Pro Glu Val Thr Cys Val Val Val Asp Val Ser His Glu Asp Pro Glu
            260                 265                     270

Val Lys Phe Asn Trp Tyr Val Asp Gly Val Glu Val His Asn Ala Lys
        275                 280                     285

Thr Lys Pro Arg Glu Glu Gln Tyr Asn Ser Thr Tyr Arg Val Val Ser
    290                 295                     300

Val Leu Thr Val Leu His Gln Asp Trp Leu Asn Gly Lys Glu Tyr Lys
305                 310                     315                 320

Cys Lys Val Ser Asn Lys Ala Leu Pro Ala Pro Ile Glu Lys Thr Ile
                325                 330                     335

Ser Lys Ala Lys Gly Gln Pro Arg Glu Pro Gln Val Tyr Thr Leu Pro
            340                 345                     350

Pro Ser Arg Glu Glu Met Thr Lys Asn Gln Val Ser Leu Thr Cys Leu
        355                 360                     365

Val Lys Gly Phe Tyr Pro Ser Asp Ile Ala Val Glu Trp Glu Ser Asn
370                 375                     380

Gly Gln Pro Glu Asn Asn Tyr Lys Thr Thr Pro Pro Val Leu Asp Ser
385                 390                     395                 400

Asp Gly Ser Phe Phe Leu Tyr Ser Lys Leu Thr Val Asp Lys Ser Arg
                405                 410                     415

Trp Gln Gln Gly Asn Val Phe Ser Cys Ser Val Met His Glu Ala Leu
            420                 425                     430

His Asn His Phe Thr Gln Lys Ser Leu Ser Leu Ser Pro Gly Lys
        435                 440                     445

<210> SEQ ID NO 48
<211> LENGTH: 447
<212> TYPE: PRT

```
<213> ORGANISM: Artificial Sequence
<220> FEATURE:
<223> OTHER INFORMATION: Synthetic peptide: Heavy chain constant region
      19
<220> FEATURE:
<221> NAME/KEY: misc_feature
<222> LOCATION: (1)..(117)
<223> OTHER INFORMATION: Xaa can be any naturally occurring amino acid

<400> SEQUENCE: 48

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Phe Thr Gln Lys Ser Leu Ser Leu Ser Pro Gly Lys
                435                 440                 445

<210> SEQ ID NO 49
<211> LENGTH: 447
<212> TYPE: PRT
<213> ORGANISM: Artificial Sequence
<220> FEATURE:
<223> OTHER INFORMATION: Synthetic peptide: Heavy chain constant region
      20
<220> FEATURE:
<221> NAME/KEY: misc_feature
<222> LOCATION: (1)..(117)
<223> OTHER INFORMATION: Xaa can be any naturally occurring amino acid

<400> SEQUENCE: 49

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Thr Arg Thr
                245                 250                 255
```

```
Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 50
<211> LENGTH: 447
<212> TYPE: PRT
<213> ORGANISM: Artificial Sequence
<220> FEATURE:
<223> OTHER INFORMATION: Synthetic peptide: Heavy chain constant region
      21
<220> FEATURE:
<221> NAME/KEY: misc_feature
<222> LOCATION: (1)..(117)
<223> OTHER INFORMATION: Xaa can be any naturally occurring amino acid

<400> SEQUENCE: 50

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
```

-continued

```
            145                 150                 155                 160
        Gly Ala Leu Thr Ser Gly Val His Thr Phe Pro Ala Val Leu Gln Ser
                        165                 170                 175
        Ser Gly Leu Tyr Ser Leu Ser Ser Val Val Thr Val Pro Ser Ser Ser
                        180                 185                 190
        Leu Gly Thr Gln Thr Tyr Ile Cys Asn Val Asn His Lys Pro Ser Asn
                        195                 200                 205
        Thr Lys Val Asp Lys Lys Val Glu Pro Lys Ser Cys Asp Lys Thr His
                    210                 215                 220
        Thr Cys Pro Pro Cys Pro Ala Pro Glu Leu Leu Gly Gly Pro Ser Val
        225                 230                 235                 240
        Phe Leu Phe Pro Pro Lys Pro Lys Asp Thr Leu Met Ile Thr Arg Thr
                        245                 250                 255
        Pro Glu Val Thr Cys Val Val Val Asp Val Ser His Glu Asp Pro Glu
                        260                 265                 270
        Val Gln Phe Asn Trp Tyr Val Asp Gly Val Glu Val His Asn Ala Lys
                        275                 280                 285
        Thr Lys Pro Arg Glu Glu Gln Tyr Asn Ser Thr Tyr Arg Val Val Ser
                    290                 295                 300
        Val Leu Thr Val Leu His Gln Asp Trp Leu Asn Gly Lys Glu Tyr Lys
        305                 310                 315                 320
        Cys Lys Val Ser Asn Lys Ala Leu Pro Ala Pro Ile Glu Lys Thr Ile
                        325                 330                 335
        Ser Lys Ala Lys Gly Gln Pro Arg Glu Pro Gln Val Tyr Thr Leu Pro
                        340                 345                 350
        Pro Ser Arg Glu Glu Met Thr Lys Asn Gln Val Ser Leu Thr Cys Leu
                        355                 360                 365
        Val Lys Gly Phe Tyr Pro Ser Asp Ile Ala Val Glu Trp Glu Ser Asn
                    370                 375                 380
        Gly Gln Pro Glu Asn Asn Tyr Lys Thr Thr Pro Pro Val Leu Asp Ser
        385                 390                 395                 400
        Asp Gly Ser Phe Phe Leu Tyr Ser Lys Leu Thr Val Asp Lys Ser Arg
                        405                 410                 415
        Trp Gln Gln Gly Asn Val Phe Ser Cys Ser Val Met His Glu Ala Leu
                        420                 425                 430
        His Asn His Tyr Thr Gln Lys Ser Leu Ser Leu Ser Pro Gly Lys
                    435                 440                 445

<210> SEQ ID NO 51
<211> LENGTH: 447
<212> TYPE: PRT
<213> ORGANISM: Artificial Sequence
<220> FEATURE:
<223> OTHER INFORMATION: Synthetic peptide: Heavy chain constant region
      22
<220> FEATURE:
<221> NAME/KEY: misc_feature
<222> LOCATION: (1)..(117)
<223> OTHER INFORMATION: Xaa can be any naturally occurring amino acid

<400> SEQUENCE: 51

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45
```

Xaa Xaa Xaa Xaa Xaa Xaa Xaa Xaa Xaa Xaa Xaa Xaa Xaa Xaa
    50                  55                      60
Xaa Xaa Xaa Xaa Xaa Xaa Xaa Xaa Xaa Xaa Xaa Xaa Xaa Xaa Xaa Xaa
65                  70                  75                  80
Xaa Xaa Xaa Xaa Xaa Xaa Xaa Xaa Xaa Xaa Xaa Xaa
                85                  90                  95
Xaa Xaa Xaa Xaa Xaa Xaa Xaa Xaa Xaa Xaa Xaa Xaa
                100                 105                 110
Xaa Xaa Xaa Xaa Xaa Ala Ser Thr Lys Gly Pro Ser Val Phe Pro Leu
                115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Gln Thr Tyr Ile Cys Asn Val Asn His Lys Pro Ser Asn
                195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Thr Ile Thr Arg Thr
                245                 250                 255
Pro Glu Val Thr Cys Val Val Val Asp Val Ser His Glu Asp Pro Glu
                260                 265                 270
Val Lys Phe Asn Trp Tyr Val Asp Gly Val Glu Val His Asn Ala Lys
                275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Arg Glu Glu Met Thr Lys Asn Gln Val Ser Leu Thr Cys Leu
                355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly Lys
                435                 440                 445

<210> SEQ ID NO 52
<211> LENGTH: 447

```
<212> TYPE: PRT
<213> ORGANISM: Artificial Sequence
<220> FEATURE:
<223> OTHER INFORMATION: Synthetic peptide: Heavy chain constant region
      23
<220> FEATURE:
<221> NAME/KEY: misc_feature
<222> LOCATION: (1)..(117)
<223> OTHER INFORMATION: Xaa can be any naturally occurring amino acid

<400> SEQUENCE: 52

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Thr Ile Thr Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
```

```
                355                 360                 365
Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 53
<211> LENGTH: 447
<212> TYPE: PRT
<213> ORGANISM: Artificial Sequence
<220> FEATURE:
<223> OTHER INFORMATION: Synthetic peptide: Heavy chain constant region
      24
<220> FEATURE:
<221> NAME/KEY: misc_feature
<222> LOCATION: (1)..(117)
<223> OTHER INFORMATION: Xaa can be any naturally occurring amino acid

<400> SEQUENCE: 53

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Thr Arg Thr
                245                 250                 255
```

```
Pro Glu Val Thr Cys Val Val Asp Val Ser His Glu Asp Pro Glu
        260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Phe Thr Gln Lys Ser Leu Ser Leu Ser Pro Gly Lys
        435                 440                 445

<210> SEQ ID NO 54
<211> LENGTH: 448
<212> TYPE: PRT
<213> ORGANISM: Artificial Sequence
<220> FEATURE:
<223> OTHER INFORMATION: Synthetic peptide: Heavy chain constant region
      25
<220> FEATURE:
<221> NAME/KEY: misc_feature
<222> LOCATION: (1)..(117)
<223> OTHER INFORMATION: Xaa can be any naturally occurring amino acid

<400> SEQUENCE: 54

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
        130                 135                 140
```

-continued

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Thr Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Ala
            420                 425                 430

Leu His Asn His Phe Thr Gln Lys Ser Leu Ser Leu Ser Pro Gly Lys
        435                 440                 445

<210> SEQ ID NO 55
<211> LENGTH: 447
<212> TYPE: PRT
<213> ORGANISM: Artificial Sequence
<220> FEATURE:
<223> OTHER INFORMATION: Synthetic peptide: Heavy chain constant region
      26
<220> FEATURE:
<221> NAME/KEY: misc_feature
<222> LOCATION: (1)..(117)
<223> OTHER INFORMATION: Xaa can be any naturally occurring amino acid

<400> SEQUENCE: 55

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa

```
                35                  40                  45
Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Thr Ile Thr Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Phe Thr Gln Lys Ser Leu Ser Leu Ser Pro Gly Lys
        435                 440                 445

<210> SEQ ID NO 56
```

```
<211> LENGTH: 447
<212> TYPE: PRT
<213> ORGANISM: Artificial Sequence
<220> FEATURE:
<223> OTHER INFORMATION: Synthetic peptide: Heavy chain constant region
      27
<220> FEATURE:
<221> NAME/KEY: misc_feature
<222> LOCATION: (1)..(117)
<223> OTHER INFORMATION: Xaa can be any naturally occurring amino acid

<400> SEQUENCE: 56
```

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Thr Ile Thr Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

```
Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Phe Thr Gln Lys Ser Leu Ser Leu Ser Pro Gly Lys
            435                 440                 445

<210> SEQ ID NO 57
<211> LENGTH: 94
<212> TYPE: PRT
<213> ORGANISM: Artificial Sequence
<220> FEATURE:
<223> OTHER INFORMATION: Synthetic peptide: EcoR1, Kozak Sequence,
      Leader signal peptide
<220> FEATURE:
<221> NAME/KEY: misc_feature
<222> LOCATION: (73)..(84)
<223> OTHER INFORMATION: Xaa can be any naturally occurring amino acid

<400> SEQUENCE: 57

Gly Ala Ala Thr Thr Cys Gly Cys Cys Gly Cys Ala Cys Cys Ala
1               5                   10                  15

Thr Gly Gly Gly Ala Thr Gly Gly Ala Gly Cys Thr Gly Thr Ala Thr
            20                  25                  30

Cys Ala Thr Cys Cys Thr Cys Thr Thr Cys Thr Thr Gly Gly Thr Ala
        35                  40                  45

Gly Cys Ala Ala Cys Ala Gly Cys Thr Ala Cys Ala Gly Gly Thr Gly
    50                  55                  60

Thr Cys Cys Ala Cys Thr Cys Cys Xaa Xaa Xaa Xaa Xaa Xaa Xaa Xaa
65                  70                  75                  80

Xaa Xaa Xaa Xaa Thr Gly Ala Thr Ala Ala Gly Cys Thr Thr
            85                  90

<210> SEQ ID NO 58
<211> LENGTH: 215
<212> TYPE: PRT
<213> ORGANISM: Artificial Sequence
<220> FEATURE:
<223> OTHER INFORMATION: Synthetic peptide: mAb CS-D7 Light Chain
      Sequence

<400> SEQUENCE: 58

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Tyr Val Ser Asp Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Arg Pro
            85                  90                  95
```

```
Val Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                    165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 59
<211> LENGTH: 456
<212> TYPE: PRT
<213> ORGANISM: Artificial Sequence
<220> FEATURE:
<223> OTHER INFORMATION: Synthetic peptide: mAb CS-D7 Heavy Chain Amino
      Acid Sequence

<400> SEQUENCE: 59

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Ser
            20                  25                  30

Ser Tyr Tyr Trp Gly Trp Phe Arg Gln Thr Pro Gly Lys Gly Leu Glu
            35                  40                  45

Trp Leu Gly Asn Val Phe Phe Ser Gly Ser Ala Tyr Tyr Asn Pro Ser
    50                  55                  60

Leu Lys Asn Arg Val Thr Ile Ser Ile Asp Thr Ser Glu Asn Gln Ser
65                  70                  75                  80

Ser Leu Lys Leu Thr Ser Val Thr Ala Ala Asp Thr Ala Val Tyr Tyr
                85                  90                  95

Cys Ala Arg Pro Gln Ala Tyr Ser His Asp Ser Ser Gly His Ser Pro
            100                 105                 110

Phe Asp Leu Trp Gly Arg Gly Thr Leu Val Thr Val Ser Ser Ala Ser
            115                 120                 125

Thr Lys Gly Pro Ser Val Phe Pro Leu Ala Pro Ser Ser Lys Ser Thr
            130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
            195                 200                 205

Cys Asn Val Asn His Lys Pro Ser Asn Thr Lys Val Asp Lys Arg Val
            210                 215                 220

Glu Pro Lys Ser Cys Asp Lys Thr His Thr Cys Pro Pro Cys Pro Ala
```

```
                225                 230                 235                 240
Pro Glu Leu Leu Gly Gly Pro Ser Val Phe Leu Phe Pro Pro Lys Pro
                    245                 250                 255

Lys Asp Thr Leu Met Ile Ser Arg Thr Pro Glu Val Thr Cys Val Val
                    260                 265                 270

Val Asp Val Ser His Glu Asp Pro Glu Val Lys Phe Asn Trp Tyr Val
                    275                 280                 285

Asp Gly Val Glu Val His Asn Ala Lys Thr Lys Pro Arg Glu Glu Gln
                    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                    325                 330                 335

Leu Pro Ala Pro Ile Glu Lys Thr Ile Ser Lys Ala Lys Gly Gln Pro
                    340                 345                 350

Arg Glu Pro Gln Val Tyr Thr Leu Pro Pro Ser Arg Glu Glu Met Thr
                    355                 360                 365

Lys Asn Gln Val Ser Leu Thr Cys Leu Val Lys Gly Phe Tyr Pro Ser
                    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                    405                 410                 415

Ser Lys Leu Thr Val Asp Lys Ser Arg Trp Gln Gln Gly Asn Val Phe
                    420                 425                 430

Ser Cys Ser Val Met His Glu Ala Leu His Asn His Tyr Thr Gln Lys
                    435                 440                 445

Ser Leu Ser Leu Ser Pro Gly Lys
                    450                 455

<210> SEQ ID NO 60
<211> LENGTH: 106
<212> TYPE: PRT
<213> ORGANISM: Artificial Sequence
<220> FEATURE:
<223> OTHER INFORMATION: Synthetic peptide: mAb - anti-LTA Light Chain
      Variable Region Sequence

<400> SEQUENCE: 60

Asp Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
                    20                  25                  30

His Trp Tyr Gln Gln Lys Pro Gly Ser Ser Pro Lys Pro Trp Ile Tyr
                    35                  40                  45

Ala Thr Ser Asn Leu Ala Ser Gly Val Pro Ala Arg Phe Ser Gly Ser
                    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Pro Thr
                    85                  90                  95

Phe Gly Gly Gly Thr Lys Leu Glu Ile Lys
                    100                 105

<210> SEQ ID NO 61
<211> LENGTH: 106
```

```
<212> TYPE: PRT
<213> ORGANISM: Artificial Sequence
<220> FEATURE:
<223> OTHER INFORMATION: Synthetic peptide: mAb - anti-LTA Light Chain
      Variable Region Sequence

<400> SEQUENCE: 61

Asp Ile Val Leu Ser Gln Ser Pro Ala Ile Leu Ser Ala Ser Pro Gly
1               5                   10                  15

Glu Lys Val Thr Met Thr Cys Arg Ala Ser Ser Val Asn Tyr Met
            20                  25                  30

His Trp Tyr Gln Gln Lys Pro Gly Ser Ser Pro Lys Pro Trp Ile Ser
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Met Leu Glu Ile Lys
            100                 105

<210> SEQ ID NO 62
<211> LENGTH: 106
<212> TYPE: PRT
<213> ORGANISM: Artificial Sequence
<220> FEATURE:
<223> OTHER INFORMATION: Synthetic peptide: mAb - anti-LTA Light Chain
      Variable Region Sequence

<400> SEQUENCE: 62

Gln Ile Val Leu Thr Gln Ser Pro Ala Ile Leu Ser Ala Phe Pro Gly
1               5                   10                  15

Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Thr Arg Phe Ser Gly Ser
    50                  55                  60

Gly Ser Gly Thr Ser Tyr Ser Leu Thr Ile Ser Arg Val Glu Ala Glu
65                  70                  75                  80

Asp Val Ala Thr Tyr Tyr Cys Leu Gln Trp Ser Ser Asn Pro Pro Thr
                85                  90                  95

Phe Gly Ala Gly Thr Lys Leu Glu Leu Lys
            100                 105

<210> SEQ ID NO 63
<211> LENGTH: 123
<212> TYPE: PRT
<213> ORGANISM: Artificial Sequence
<220> FEATURE:
<223> OTHER INFORMATION: Synthetic peptide: mAb - anti-LTA Heavy Chain
      Variable Region Sequence

<400> SEQUENCE: 63

Glu Val Met Leu Val Glu Ser Gly Glu Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
```

```
                35                  40                  45
Ala Arg Ile Arg Ser Lys Ser Asn Asn Tyr Ala Thr Tyr Tyr Ala Asp
        50                  55                  60
Ser Val Lys Asp Arg Phe Thr Ile Ser Arg Asp Asp Ser Gln Ser Met
65                  70                  75                  80
Leu Tyr Leu Gln Met Asn Asn Leu Lys Thr Glu Asp Thr Ala Met Tyr
                85                  90                  95
Tyr Cys Val Arg Arg Gly Gly Lys Glu Thr Asp Tyr Ala Met Asp Tyr
                100                 105                 110
Trp Gly Gln Gly Thr Ser Val Thr Val Ser Ser
            115                 120

<210> SEQ ID NO 64
<211> LENGTH: 123
<212> TYPE: PRT
<213> ORGANISM: Artificial Sequence
<220> FEATURE:
<223> OTHER INFORMATION: Synthetic peptide: mAb - anti-LTA Heavy Chain
      Variable Region Sequence

<400> SEQUENCE: 64

Glu Val Met Leu Val Glu Ser Gly Gly Gly Leu Val Gln Pro Lys Gly
1               5                   10                  15
Ser Leu Lys Leu Ser Cys Ala Ala Ser Gly Phe Thr Phe Asn Asn Tyr
                20                  25                  30
Ala Met Asn Trp Val Arg Gln Ala Pro Gly Lys Gly Leu Glu Trp Val
            35                  40                  45
Ala Arg Ile Arg Ser Lys Ser Asn Asn Tyr Ala Thr Phe Tyr Ala Asp
        50                  55                  60
Ser Val Lys Asp Arg Phe Thr Ile Ser Arg Asp Asp Ser Gln Ser Met
65                  70                  75                  80
Leu Tyr Leu Gln Met Asn Asn Leu Lys Thr Glu Asp Thr Ala Met Tyr
                85                  90                  95
Tyr Cys Val Arg Arg Gly Ala Ser Gly Ile Asp Tyr Ala Met Asp Tyr
                100                 105                 110
Trp Gly Gln Gly Thr Ser Leu Thr Val Ser Ser
            115                 120

<210> SEQ ID NO 65
<211> LENGTH: 123
<212> TYPE: PRT
<213> ORGANISM: Artificial Sequence
<220> FEATURE:
<223> OTHER INFORMATION: Synthetic peptide: mAb - anti-LTA Heavy Chain
      Variable Region Sequence

<400> SEQUENCE: 65

Glu Val Lys Leu His Glu Ser Gly Gly Gly Phe Val Gln Pro Lys Gly
1               5                   10                  15
Ser Leu Lys Leu Ser Cys Ala Ala Ser Gly Phe Thr Phe Asn Ala Tyr
                20                  25                  30
Ala Met Asn Trp Val Arg Gln Ala Pro Gly Lys Gly Leu Glu Trp Val
            35                  40                  45
Ala Arg Ile Arg Ser Lys Ser Asn Asn Tyr Glu Thr Tyr Tyr Ala Asp
        50                  55                  60
Ser Val Lys Asp Phe Thr Ile Ser Arg Asp Asp Ser Gln Tyr Met Val
65                  70                  75                  80
Tyr Leu Gln Met Asn Asn Leu Lys Ser Glu Asp Thr Ala Met Tyr Tyr
```

```
                    85                  90                  95

Cys Val Arg Arg Gly Ser Met Arg Ser Tyr Tyr Tyr Ala Met Asp Tyr
            100                 105                 110

Trp Gly Gln Gly Thr Ser Val Thr Val Ser Ser
        115                 120
```

<210> SEQ ID NO 66
<211> LENGTH: 61
<212> TYPE: PRT
<213> ORGANISM: S. aureus

<400> SEQUENCE: 66

```
Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60
```

<210> SEQ ID NO 67
<211> LENGTH: 5
<212> TYPE: PRT
<213> ORGANISM: S. aureus

<400> SEQUENCE: 67

```
Gln His Asp Glu Ala
1               5
```

<210> SEQ ID NO 68
<211> LENGTH: 98
<212> TYPE: PRT
<213> ORGANISM: Homo sapiens
<220> FEATURE:
<221> NAME/KEY: misc_feature
<222> LOCATION: (1)..(98)
<223> OTHER INFORMATION: Human CH1 Sequence, IgG1

<400> SEQUENCE: 68

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

<210> SEQ ID NO 69
<211> LENGTH: 98
<212> TYPE: PRT
<213> ORGANISM: Homo sapiens
<220> FEATURE:
<221> NAME/KEY: misc_feature
<222> LOCATION: (1)..(98)

<223> OTHER INFORMATION: Human CH1 Sequence, IgG2

<400> SEQUENCE: 69

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val
```

<210> SEQ ID NO 70
<211> LENGTH: 98
<212> TYPE: PRT
<213> ORGANISM: Homo sapiens
<220> FEATURE:
<221> NAME/KEY: misc_feature
<222> LOCATION: (1)..(98)
<223> OTHER INFORMATION: Human CH1 Sequence, IgG3

<400> SEQUENCE: 70

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val
```

<210> SEQ ID NO 71
<211> LENGTH: 98
<212> TYPE: PRT
<213> ORGANISM: Homo sapiens
<220> FEATURE:
<221> NAME/KEY: misc_feature
<222> LOCATION: (1)..(98)
<223> OTHER INFORMATION: Human CH1 Sequence, IgG4

<400> SEQUENCE: 71

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val

<210> SEQ ID NO 72
<211> LENGTH: 15
<212> TYPE: PRT
<213> ORGANISM: Homo sapiens
<220> FEATURE:
<221> NAME/KEY: misc_feature
<222> LOCATION: (1)..(15)
<223> OTHER INFORMATION: Human Hinge Sequence, IgG1

<400> SEQUENCE: 72

Glu Pro Lys Ser Cys Asp Lys Thr His Thr Cys Pro Pro Cys Pro
1               5                   10                  15

<210> SEQ ID NO 73
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: Human Hinge Sequence, IgG2

<400> SEQUENCE: 73

Glu Arg Lys Cys Cys Val Glu Cys Pro Pro Cys Pro
1               5                   10

<210> SEQ ID NO 74
<211> LENGTH: 62
<212> TYPE: PRT
<213> ORGANISM: Homo sapiens
<220> FEATURE:
<221> NAME/KEY: misc_feature
<222> LOCATION: (1)..(62)
<223> OTHER INFORMATION: Human Hinge Sequence, IgG3

<400> SEQUENCE: 74

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
                20                  25                  30

Glu Pro Lys Ser Cys Asp Thr Pro Pro Pro Cys Pro Arg Cys Pro Glu
            35                  40                  45

Pro Lys Ser Cys Asp Thr Pro Pro Pro Cys Pro Arg Cys Pro
        50                  55                  60

<210> SEQ ID NO 75
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: Human Hinge Sequence, IgG4

<400> SEQUENCE: 75

Ser Pro Asn Met Val Pro His Ala His His Ala Gln
1               5                   10
```

-continued

```
<210> SEQ ID NO 76
<211> LENGTH: 110
<212> TYPE: PRT
<213> ORGANISM: Homo sapiens
<220> FEATURE:
<221> NAME/KEY: misc_feature
<222> LOCATION: (1)..(110)
<223> OTHER INFORMATION: Human CH2 Sequence, IgG1

<400> SEQUENCE: 76

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 77
<211> LENGTH: 109
<212> TYPE: PRT
<213> ORGANISM: Homo sapiens
<220> FEATURE:
<221> NAME/KEY: misc_feature
<222> LOCATION: (1)..(109)
<223> OTHER INFORMATION: Human CH2 Sequence, IgG2

<400> SEQUENCE: 77

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
            100                 105

<210> SEQ ID NO 78
<211> LENGTH: 110
<212> TYPE: PRT
<213> ORGANISM: Homo sapiens
<220> FEATURE:
<221> NAME/KEY: misc_feature
<222> LOCATION: (1)..(110)
<223> OTHER INFORMATION: Human CH2 Sequence, IgG3

<400> SEQUENCE: 78

Ala Pro Glu Leu Leu Gly Gly Pro Ser Val Phe Leu Phe Pro Pro Lys
1               5                   10                  15
```

```
Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
            35                  40                  45

Val Asp Gly Val Glu Val His Asn Ala Lys Thr Lys Pro Arg Glu Glu
 50                      55                  60

Gln Tyr Asn Ser Thr Phe Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Thr Lys
            100                 105                 110

<210> SEQ ID NO 79
<211> LENGTH: 110
<212> TYPE: PRT
<213> ORGANISM: Homo sapiens
<220> FEATURE:
<221> NAME/KEY: misc_feature
<222> LOCATION: (1)..(110)
<223> OTHER INFORMATION: Human CH2 Sequence, IgG4

<400> SEQUENCE: 79

Ala Pro Glu Phe Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
 50                      55                  60

Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys
            100                 105                 110

<210> SEQ ID NO 80
<211> LENGTH: 106
<212> TYPE: PRT
<213> ORGANISM: Homo sapiens
<220> FEATURE:
<221> NAME/KEY: misc_feature
<222> LOCATION: (1)..(106)
<223> OTHER INFORMATION: Human CH3 Sequence, IgG1

<400> SEQUENCE: 80

Gln Pro Arg Glu Pro Gln Val Tyr Thr Leu Pro Pro Ser Arg Asp Glu
 1               5                  10                  15

Leu Thr Lys Asn Gln Val Ser Leu Thr Cys Leu Val Lys Gly Phe Tyr
            20                  25                  30

Pro Ser Asp Ile Ala Val Glu Trp Glu Ser Asn Gly Gln Pro Glu Asn
            35                  40                  45

Asn Tyr Lys Thr Thr Pro Pro Val Leu Asp Ser Asp Gly Ser Phe Phe
 50                  55                  60

Leu Tyr Ser Lys Leu Thr Val Asp Lys Ser Arg Trp Gln Gln Gly Asn
 65                  70                  75                  80
```

Val Phe Ser Cys Ser Val Met His Glu Ala Leu His Asn His Tyr Thr
                85                  90                  95

Gln Lys Ser Leu Ser Leu Ser Pro Gly Lys
        100                 105

<210> SEQ ID NO 81
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: Human CH3 Sequence, IgG2

<400> SEQUENCE: 81

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 82
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: Human CH3 Sequence, IgG3

<400> SEQUENCE: 82

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Ser Gly Gln Pro Glu
            35                  40                  45

Asn Asn Tyr Asn Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 83
<211> LENGTH: 106
<212> TYPE: PRT
<213> ORGANISM: Homo sapiens
<220> FEATURE:
<221> NAME/KEY: misc_feature
<222> LOCATION: (1)..(106)
<223> OTHER INFORMATION: Human CH3 Sequence, IgG4

<400> SEQUENCE: 83

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly
            100                 105

<210> SEQ ID NO 84
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC8a_USA300_FPR3757

<400> SEQUENCE: 84

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro
    50                  55

<210> SEQ ID NO 85
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC8b_USA300_TCH1516

<400> SEQUENCE: 85

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro
    50                  55

<210> SEQ ID NO 86
<211> LENGTH: 57
<212> TYPE: PRT
<213> ORGANISM: S. aureus

```
<220> FEATURE:
<221> NAME/KEY: misc_feature
<222> LOCATION: (1)..(57)
<223> OTHER INFORMATION: CC1_TCH70

<400> SEQUENCE: 86

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro
    50                  55

<210> SEQ ID NO 87
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC5_A8117

<400> SEQUENCE: 87

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro
    50                  55

<210> SEQ ID NO 88
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC42_C427

<400> SEQUENCE: 88

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro
    50                  55

<210> SEQ ID NO 89
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC36_MRSA252

<400> SEQUENCE: 89
```

-continued

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro
    50                  55

<210> SEQ ID NO 90
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC30_MN8

<400> SEQUENCE: 90

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro
    50                  55

<210> SEQ ID NO 91
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC7_USA300_TCH959

<400> SEQUENCE: 91

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro
    50                  55

<210> SEQ ID NO 92
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: EMRSA16

<400> SEQUENCE: 92

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala

Lys Lys Leu Asn Glu Ser Gln Ala Pro
    50                  55

<210> SEQ ID NO 93
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: ST398

<400> SEQUENCE: 93

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro
    50                  55

<210> SEQ ID NO 94
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC45_A9635

<400> SEQUENCE: 94

Ala Asp Asn Asn Phe Asn Lys Asp Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro
    50                  55

<210> SEQ ID NO 95
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: spa_A

<400> SEQUENCE: 95

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro
    50                  55

<210> SEQ ID NO 96

```
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC10_H19

<400> SEQUENCE: 96

Ala Asp Asn Asn Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro
    50                  55

<210> SEQ ID NO 97
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC239_JKD6009

<400> SEQUENCE: 97

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro
    50                  55

<210> SEQ ID NO 98
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC8A_USA300_FPR3757

<400> SEQUENCE: 98

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro
    50                  55

<210> SEQ ID NO 99
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: ST398
```

-continued

```
<400> SEQUENCE: 99

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro
    50                  55

<210> SEQ ID NO 100
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC45_A9635

<400> SEQUENCE: 100

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro
    50                  55

<210> SEQ ID NO 101
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC239_JKD6009

<400> SEQUENCE: 101

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro
    50                  55

<210> SEQ ID NO 102
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC42_C427

<400> SEQUENCE: 102

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
```

```
                20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro
    50                  55

<210> SEQ ID NO 103
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC30_MN8

<400> SEQUENCE: 103

Ala Asp Asn Lys Phe Asn Lys Glu Gln Gln Asn Ala Phe Tyr Glu Ile
1               5                  10                  15

Leu His Leu Pro Asn Leu Asn Glu Glu Gln Arg Asn Gly Phe Ile Gln
                20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro
    50                  55

<210> SEQ ID NO 104
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC36_MRSA252

<400> SEQUENCE: 104

Ala Asp Asn Lys Phe Asn Lys Glu Gln Gln Asn Ala Phe Tyr Glu Ile
1               5                  10                  15

Leu His Leu Pro Asn Leu Asn Glu Glu Gln Arg Asn Gly Phe Ile Gln
                20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro
    50                  55

<210> SEQ ID NO 105
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: EMRSA16

<400> SEQUENCE: 105

Ala Asp Asn Lys Phe Asn Lys Glu Gln Gln Asn Ala Phe Tyr Glu Ile
1               5                  10                  15

Leu His Leu Pro Asn Leu Asn Glu Glu Gln Arg Asn Gly Phe Ile Gln
                20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro
    50                  55
```

<210> SEQ ID NO 106
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC7_USA300_TCH959

<400> SEQUENCE: 106

Ala Asp Asn Asn Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro
    50                  55

<210> SEQ ID NO 107
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: spa_B

<400> SEQUENCE: 107

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro
    50                  55

<210> SEQ ID NO 108
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC8b_USA300_TCH1516

<400> SEQUENCE: 108

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro
    50                  55

<210> SEQ ID NO 109
<211> LENGTH: 57
<212> TYPE: PRT
<213> ORGANISM: S. aureus
<220> FEATURE:

-continued

```
<221> NAME/KEY: misc_feature
<222> LOCATION: (1)..(57)
<223> OTHER INFORMATION: CC1_TCH70

<400> SEQUENCE: 109
```

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro
    50                  55

```
<210> SEQ ID NO 110
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC5_A8117

<400> SEQUENCE: 110
```

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro
    50                  55

```
<210> SEQ ID NO 111
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC10 H19

<400> SEQUENCE: 111
```

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro
    50                  55

```
<210> SEQ ID NO 112
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC8a_USA300_FPR3757

<400> SEQUENCE: 112
```

Ala Asp Asn Lys Phe Asn Lys Glu Gln Gln Asn Ala Phe Tyr Glu Ile

```
                 1               5                   10                  15
Leu His Leu Pro Asn Leu Thr Glu Glu Gln Arg Asn Gly Phe Ile Gln
             20                  25                  30

Ser Leu Lys Asp Asp Pro Ser Val Ser Lys Glu Ile Leu Ala Glu Ala
         35                  40                  45

Lys Lys Leu Asn Asp Ala Gln Ala Pro
     50                  55

<210> SEQ ID NO 113
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: ST398

<400> SEQUENCE: 113

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
             20                  25                  30

Ser Leu Lys Asp Asp Pro Ser Val Ser Lys Glu Ile Leu Ala Glu Ala
         35                  40                  45

Lys Lys Leu Asn Asp Ala Gln Ala Pro
     50                  55

<210> SEQ ID NO 114
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: spa_C

<400> SEQUENCE: 114

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
             20                  25                  30

Ser Leu Lys Asp Asp Pro Ser Val Ser Lys Glu Ile Leu Ala Glu Ala
         35                  40                  45

Lys Lys Leu Asn Asp Ala Gln Ala Pro
     50                  55

<210> SEQ ID NO 115
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: EMRSA16

<400> SEQUENCE: 115

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
             20                  25                  30

Ser Leu Lys Asp Asp Pro Ser Val Ser Lys Glu Ile Leu Ala Glu Ala
         35                  40                  45
```

-continued

```
Lys Lys Leu Asn Asp Ala Gln Ala Pro
    50                  55

<210> SEQ ID NO 116
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC8b_USA300_TCH1516

<400> SEQUENCE: 116

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro
    50                  55

<210> SEQ ID NO 117
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC1_TCH70

<400> SEQUENCE: 117

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro
    50                  55

<210> SEQ ID NO 118
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC5_A8117

<400> SEQUENCE: 118

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro
    50                  55

<210> SEQ ID NO 119
<211> LENGTH: 57
```

```
<212> TYPE: PRT
<213> ORGANISM: S. aureus
<220> FEATURE:
<221> NAME/KEY: misc_feature
<222> LOCATION: (1)..(57)
<223> OTHER INFORMATION: CC7_USA300_TCH959

<400> SEQUENCE: 119
```

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro
    50                  55

```
<210> SEQ ID NO 120
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC10_H19

<400> SEQUENCE: 120
```

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro
    50                  55

```
<210> SEQ ID NO 121
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC36_MRSA252

<400> SEQUENCE: 121
```

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro
    50                  55

```
<210> SEQ ID NO 122
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC30_MN8
```

<400> SEQUENCE: 122

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro
    50                  55

<210> SEQ ID NO 123
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC42_C427

<400> SEQUENCE: 123

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro
    50                  55

<210> SEQ ID NO 124
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC239_JKD6009

<400> SEQUENCE: 124

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro
    50                  55

<210> SEQ ID NO 125
<211> LENGTH: 57
<212> TYPE: PRT
<213> ORGANISM: S. aureus
<220> FEATURE:
<221> NAME/KEY: misc_feature
<222> LOCATION: (1)..(57)
<223> OTHER INFORMATION: CC45_A9635

<400> SEQUENCE: 125

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

```
Ser Leu Lys Asp Asp Pro Ser Val Ser Lys Glu Ile Leu Ala Glu Ala
        35                  40                  45

Lys Lys Leu Asn Asp Ala Gln Ala Pro
 50                  55

<210> SEQ ID NO 126
<211> LENGTH: 60
<212> TYPE: PRT
<213> ORGANISM: S. aureus
<220> FEATURE:
<221> NAME/KEY: misc_feature
<222> LOCATION: (1)..(60)
<223> OTHER INFORMATION: CC8b_USA300_TCH1516

<400> SEQUENCE: 126

Ala Asp Ala Gln Gln Asn Asn Phe Asn Lys Asp Gln Gln Ser Ala Phe
 1               5                  10                  15

Tyr Glu Ile Leu Asn Met Pro Asn Leu Asn Glu Ala Gln Arg Asn Gly
             20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro
 50                  55                  60

<210> SEQ ID NO 127
<211> LENGTH: 60
<212> TYPE: PRT
<213> ORGANISM: S. aureus
<220> FEATURE:
<221> NAME/KEY: misc_feature
<222> LOCATION: (1)..(60)
<223> OTHER INFORMATION: CC45_A9635

<400> SEQUENCE: 127

Ala Glu Ala Gln Gln Asn Asn Phe Asn Lys Asp Gln Gln Ser Ala Phe
 1               5                  10                  15

Tyr Glu Ile Leu Asn Met Pro Asn Leu Asn Glu Ala Gln Arg Asn Gly
             20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro
 50                  55                  60

<210> SEQ ID NO 128
<211> LENGTH: 60
<212> TYPE: PRT
<213> ORGANISM: S. aureus
<220> FEATURE:
<221> NAME/KEY: misc_feature
<222> LOCATION: (1)..(60)
<223> OTHER INFORMATION: CC8a_USA300_FPR3757

<400> SEQUENCE: 128

Ala Asp Ala Gln Gln Asn Asn Phe Asn Lys Asp Gln Gln Ser Ala Phe
 1               5                  10                  15

Tyr Glu Ile Leu Asn Met Pro Asn Leu Asn Glu Ala Gln Arg Asn Gly
             20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro
 50                  55                  60
```

<210> SEQ ID NO 129
<211> LENGTH: 60
<212> TYPE: PRT
<213> ORGANISM: S. aureus
<220> FEATURE:
<221> NAME/KEY: misc_feature
<222> LOCATION: (1)..(60)
<223> OTHER INFORMATION: CC7_USA300_TCH959

<400> SEQUENCE: 129

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro
    50                  55                  60

<210> SEQ ID NO 130
<211> LENGTH: 60
<212> TYPE: PRT
<213> ORGANISM: S. aureus
<220> FEATURE:
<221> NAME/KEY: misc_feature
<222> LOCATION: (1)..(60)
<223> OTHER INFORMATION: CC6_A8117

<400> SEQUENCE: 130

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro
    50                  55                  60

<210> SEQ ID NO 131
<211> LENGTH: 60
<212> TYPE: PRT
<213> ORGANISM: S. aureus
<220> FEATURE:
<221> NAME/KEY: misc_feature
<222> LOCATION: (1)..(60)
<223> OTHER INFORMATION: CC1_TCH70

<400> SEQUENCE: 131

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro
    50                  55                  60

<210> SEQ ID NO 132
<211> LENGTH: 60
<212> TYPE: PRT
<213> ORGANISM: S. aureus
<220> FEATURE:
<221> NAME/KEY: misc_feature
<222> LOCATION: (1)..(60)
<223> OTHER INFORMATION: spa_D

<400> SEQUENCE: 132

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro
    50                  55                  60

<210> SEQ ID NO 133
<211> LENGTH: 60
<212> TYPE: PRT
<213> ORGANISM: S. aureus
<220> FEATURE:
<221> NAME/KEY: misc_feature
<222> LOCATION: (1)..(60)
<223> OTHER INFORMATION: CC42_C427

<400> SEQUENCE: 133

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Glu Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro
    50                  55                  60

<210> SEQ ID NO 134
<211> LENGTH: 60
<212> TYPE: PRT
<213> ORGANISM: S. aureus
<220> FEATURE:
<221> NAME/KEY: misc_feature
<222> LOCATION: (1)..(60)
<223> OTHER INFORMATION: CC10_H19

<400> SEQUENCE: 134

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Glu Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro
    50                  55                  60

<210> SEQ ID NO 135
<211> LENGTH: 60
<212> TYPE: PRT
<213> ORGANISM: S. aureus
<220> FEATURE:
<221> NAME/KEY: misc_feature
<222> LOCATION: (1)..(60)
<223> OTHER INFORMATION: CC36_MRSA252

<400> SEQUENCE: 135

Ala Asp Ala Gln Gln Asn Lys Phe Asn Lys Asp Gln Gln Ser Ala Phe
1               5                   10                  15

```
Tyr Glu Ile Leu Asn Met Pro Asn Leu Asn Glu Glu Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro
    50                  55                  60
```

<210> SEQ ID NO 136
<211> LENGTH: 60
<212> TYPE: PRT
<213> ORGANISM: S. aureus
<220> FEATURE:
<221> NAME/KEY: misc_feature
<222> LOCATION: (1)..(60)
<223> OTHER INFORMATION: CC30_MN8

<400> SEQUENCE: 136

```
Ala Asp Ala Gln Gln Asn Lys Phe Asn Lys Asp Gln Gln Ser Ala Phe
1               5                   10                  15

Tyr Glu Ile Leu Asn Met Pro Asn Leu Asn Glu Glu Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro
    50                  55                  60
```

<210> SEQ ID NO 137
<211> LENGTH: 60
<212> TYPE: PRT
<213> ORGANISM: S. aureus
<220> FEATURE:
<221> NAME/KEY: misc_feature
<222> LOCATION: (1)..(60)
<223> OTHER INFORMATION: CC239_JKD6009

<400> SEQUENCE: 137

```
Ala Asp Ala Gln Gln Asn Lys Phe Asn Lys Asp Arg Gln Ser Ala Phe
1               5                   10                  15

Tyr Glu Ile Leu Asn Met Pro Asn Leu Asn Glu Glu Gln Arg Asn Gly
            20                  25                  30

Phe Ile Gln Ser Leu Lys Asp Asp Pro Ser Gln Ser Ala Asn Leu Leu
        35                  40                  45

Ala Glu Ala Lys Lys Leu Asn Glu Ser Gln Ala Pro
    50                  55                  60
```

<210> SEQ ID NO 138
<211> LENGTH: 56
<212> TYPE: PRT
<213> ORGANISM: S. aureus
<220> FEATURE:
<221> NAME/KEY: misc_feature
<222> LOCATION: (1)..(56)
<223> OTHER INFORMATION: CC8a_USA300_FPR3757

<400> SEQUENCE: 138

```
Ala Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Asp Asp Pro Ser Gln Ser Ala Asn Val Leu Gly Glu Ala Gln
        35                  40                  45
```

Lys Leu Asn Asp Ser Gln Ala Pro
 50                  55

<210> SEQ ID NO 139
<211> LENGTH: 56
<212> TYPE: PRT
<213> ORGANISM: S. aureus
<220> FEATURE:
<221> NAME/KEY: misc_feature
<222> LOCATION: (1)..(56)
<223> OTHER INFORMATION: ST398

<400> SEQUENCE: 139

Ala Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Asp Asp Pro Ser Gln Ser Ala Asn Val Leu Gly Glu Ala Gln
        35                  40                  45

Lys Leu Asn Asp Ser Gln Ala Pro
 50                  55

<210> SEQ ID NO 140
<211> LENGTH: 56
<212> TYPE: PRT
<213> ORGANISM: S. aureus
<220> FEATURE:
<221> NAME/KEY: misc_feature
<222> LOCATION: (1)..(56)
<223> OTHER INFORMATION: spa_E

<400> SEQUENCE: 140

Ala Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Asp Asp Pro Ser Gln Ser Ala Asn Val Leu Gly Glu Ala Gln
        35                  40                  45

Lys Leu Asn Asp Ser Gln Ala Pro
 50                  55

<210> SEQ ID NO 141
<211> LENGTH: 56
<212> TYPE: PRT
<213> ORGANISM: S. aureus
<220> FEATURE:
<221> NAME/KEY: misc_feature
<222> LOCATION: (1)..(56)
<223> OTHER INFORMATION: EMRSA16

<400> SEQUENCE: 141

Ala Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Asp Asp Pro Ser Gln Ser Ala Asn Val Leu Gly Glu Ala Gln
        35                  40                  45

Lys Leu Asn Asp Ser Gln Ala Pro
 50                  55

<210> SEQ ID NO 142
<211> LENGTH: 56
<212> TYPE: PRT

```
<213> ORGANISM: S. aureus
<220> FEATURE:
<221> NAME/KEY: misc_feature
<222> LOCATION: (1)..(56)
<223> OTHER INFORMATION: CC8b_USA300_TCH1516

<400> SEQUENCE: 142
```

Ala Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Asp Asp Pro Ser Gln Ser Ala Asn Val Leu Gly Glu Ala Gln
        35                  40                  45

Lys Leu Asn Asp Ser Gln Ala Pro
    50                  55

```
<210> SEQ ID NO 143
<211> LENGTH: 56
<212> TYPE: PRT
<213> ORGANISM: S. aureus
<220> FEATURE:
<221> NAME/KEY: misc_feature
<222> LOCATION: (1)..(56)
<223> OTHER INFORMATION: CC1_TCH70

<400> SEQUENCE: 143
```

Ala Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Asp Asp Pro Ser Gln Ser Ala Asn Val Leu Gly Glu Ala Gln
        35                  40                  45

Lys Leu Asn Asp Ser Gln Ala Pro
    50                  55

```
<210> SEQ ID NO 144
<211> LENGTH: 56
<212> TYPE: PRT
<213> ORGANISM: S. aureus
<220> FEATURE:
<221> NAME/KEY: misc_feature
<222> LOCATION: (1)..(56)
<223> OTHER INFORMATION: CC5_A8117

<400> SEQUENCE: 144
```

Ala Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Asp Asp Pro Ser Gln Ser Ala Asn Val Leu Gly Glu Ala Gln
        35                  40                  45

Lys Leu Asn Asp Ser Gln Ala Pro
    50                  55

```
<210> SEQ ID NO 145
<211> LENGTH: 56
<212> TYPE: PRT
<213> ORGANISM: S. aureus
<220> FEATURE:
<221> NAME/KEY: misc_feature
<222> LOCATION: (1)..(56)
<223> OTHER INFORMATION: CC7_USA300_TCH959

<400> SEQUENCE: 145
```

Ala Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Asp Asp Pro Ser Gln Ser Ala Asn Val Leu Gly Glu Ala Gln
        35                  40                  45

Lys Leu Asn Asp Ser Gln Ala Pro
    50                  55

<210> SEQ ID NO 146
<211> LENGTH: 56
<212> TYPE: PRT
<213> ORGANISM: S. aureus
<220> FEATURE:
<221> NAME/KEY: misc_feature
<222> LOCATION: (1)..(56)
<223> OTHER INFORMATION: CC30_MN8

<400> SEQUENCE: 146

Ala Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Asp Asp Pro Ser Gln Ser Ala Asn Val Leu Gly Glu Ala Gln
        35                  40                  45

Lys Leu Asn Asp Ser Gln Ala Pro
    50                  55

<210> SEQ ID NO 147
<211> LENGTH: 56
<212> TYPE: PRT
<213> ORGANISM: S. aureus
<220> FEATURE:
<221> NAME/KEY: misc_feature
<222> LOCATION: (1)..(56)
<223> OTHER INFORMATION: CC239_JKD6009

<400> SEQUENCE: 147

Ala Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Asp Asp Pro Ser Gln Ser Ala Asn Val Leu Gly Glu Ala Gln
        35                  40                  45

Lys Leu Asn Asp Ser Gln Ala Pro
    50                  55

<210> SEQ ID NO 148
<211> LENGTH: 56
<212> TYPE: PRT
<213> ORGANISM: S. aureus
<220> FEATURE:
<221> NAME/KEY: misc_feature
<222> LOCATION: (1)..(56)
<223> OTHER INFORMATION: CC36_MRSA252

<400> SEQUENCE: 148

Ala Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
            20                  25                  30

-continued

Leu Lys Asp Asp Pro Ser Gln Ser Ala Asn Val Leu Gly Glu Ala Gln
         35                  40                  45

Lys Leu Asn Asp Ser Gln Ala Pro
 50                  55

<210> SEQ ID NO 149
<211> LENGTH: 56
<212> TYPE: PRT
<213> ORGANISM: S. aureus
<220> FEATURE:
<221> NAME/KEY: misc_feature
<222> LOCATION: (1)..(56)
<223> OTHER INFORMATION: CC10_H19

<400> SEQUENCE: 149

Ala Ala Gln His Asp Glu Ala Gln Gln Asn Ala Phe Tyr Gln Val Leu
 1               5                  10                  15

Asn Met Pro Asn Leu Asn Ala Asp Gln Arg Asn Gly Phe Ile Gln Ser
             20                  25                  30

Leu Lys Asp Asp Pro Ser Gln Ser Ala Asn Val Leu Gly Glu Ala Lys
         35                  40                  45

Lys Leu Asn Asp Ser Gln Ala Pro
 50                  55

<210> SEQ ID NO 150
<211> LENGTH: 56
<212> TYPE: PRT
<213> ORGANISM: S. aureus
<220> FEATURE:
<221> NAME/KEY: misc_feature
<222> LOCATION: (1)..(56)
<223> OTHER INFORMATION: CC42_C427

<400> SEQUENCE: 150

Ala Ala Gln His Asp Glu Ala Gln Gln Asn Ala Phe Tyr Gln Val Leu
 1               5                  10                  15

Asn Met Pro Asn Leu Asn Ala Asp Gln Arg Asn Gly Phe Ile Gln Ser
             20                  25                  30

Leu Lys Asp Asp Pro Ser Gln Ser Ala Asn Val Leu Gly Glu Ala Lys
         35                  40                  45

Lys Leu Asn Asp Ser Gln Ala Pro
 50                  55

<210> SEQ ID NO 151
<211> LENGTH: 56
<212> TYPE: PRT
<213> ORGANISM: S. aureus
<220> FEATURE:
<221> NAME/KEY: misc_feature
<222> LOCATION: (1)..(56)
<223> OTHER INFORMATION: CC45_A9635

<400> SEQUENCE: 151

Ala Ala Gln His Asp Glu Ala Gln Gln Asn Ala Phe Tyr Gln Val Leu
 1               5                  10                  15

Asn Met Pro Asn Leu Asn Ala Asp Gln Arg Asn Gly Phe Ile Gln Ser
             20                  25                  30

Leu Lys Asp Asp Pro Ser Gln Ser Ala Asn Val Leu Gly Glu Ala Lys
         35                  40                  45

Lys Leu Asn Asp Ser Gln Ala Pro
 50                  55

```
<210> SEQ ID NO 152
<211> LENGTH: 61
<212> TYPE: PRT
<213> ORGANISM: S. aureus

<400> SEQUENCE: 152

Ala Asp Ala Gln Gln Asn Gln His Asp Glu Ala Gln Gln Asn Ala Phe
1               5                   10                  15

Tyr Gln Val Leu Asn Met Pro Asn Leu Asn Ala Asp Gln Arg Asn Gly
            20                  25                  30

Phe Ile Gln Ser Leu Lys Asp Asp Pro Ser Gln Ser Ala Asn Val Leu
        35                  40                  45

Gly Glu Ala Gln Lys Leu Asn Asp Ser Gln Ala Pro Lys
50                  55                  60

<210> SEQ ID NO 153
<211> LENGTH: 5
<212> TYPE: PRT
<213> ORGANISM: S. aureus

<400> SEQUENCE: 153

Asn Phe Asn Lys Asp
1               5

<210> SEQ ID NO 154
<211> LENGTH: 5
<212> TYPE: PRT
<213> ORGANISM: S. aureus

<400> SEQUENCE: 154

Asn Phe Asn Lys Glu
1               5

<210> SEQ ID NO 155
<211> LENGTH: 5
<212> TYPE: PRT
<213> ORGANISM: S. aureus

<400> SEQUENCE: 155

Lys Phe Asn Lys Glu
1               5

<210> SEQ ID NO 156
<211> LENGTH: 5
<212> TYPE: PRT
<213> ORGANISM: S. aureus

<400> SEQUENCE: 156

Lys Phe Asn Lys Glu
1               5

<210> SEQ ID NO 157
<211> LENGTH: 52
<212> TYPE: PRT
<213> ORGANISM: S. aureus
<220> FEATURE:
<221> NAME/KEY: misc_feature
<222> LOCATION: (1)..(52)
<223> OTHER INFORMATION: Sbi domain I

<400> SEQUENCE: 157

Thr Gln Asn Asn Tyr Val Thr Asp Gln Gln Lys Ala Phe Tyr Gln Val
1               5                   10                  15

Leu His Leu Lys Gly Ile Thr Glu Glu Gln Arg Asn Gln Tyr Ile Lys
```

```
                20                  25                  30

Thr Leu Arg Glu His Pro Glu Arg Ala Gln Glu Val Phe Ser Glu Ser
            35                  40                  45

Leu Lys Asp Ser
        50

<210> SEQ ID NO 158
<211> LENGTH: 54
<212> TYPE: PRT
<213> ORGANISM: S. aureus
<220> FEATURE:
<221> NAME/KEY: misc_feature
<222> LOCATION: (1)..(54)
<223> OTHER INFORMATION: Sbi domain II

<400> SEQUENCE: 158

Lys Asn Pro Asp Arg Arg Val Ala Gln Gln Asn Ala Phe Tyr Asn Val
1               5                   10                  15

Leu Lys Asn Asp Asn Leu Thr Glu Gln Glu Lys Asn Asn Tyr Ile Ala
            20                  25                  30

Gln Ile Lys Glu Asn Pro Asp Arg Ser Gln Gln Val Trp Val Glu Ser
        35                  40                  45

Val Gln Ser Ser Lys Ala
        50

<210> SEQ ID NO 159
<211> LENGTH: 52
<212> TYPE: PRT
<213> ORGANISM: S. aureus
<220> FEATURE:
<221> NAME/KEY: misc_feature
<222> LOCATION: (1)..(52)
<223> OTHER INFORMATION: USA300_FPR3757

<400> SEQUENCE: 159

Thr Gln Asn Asn Tyr Val Thr Asp Gln Gln Lys Ala Phe Tyr Gln Val
1               5                   10                  15

Leu His Leu Lys Gly Ile Thr Glu Glu Gln Arg Asn Gln Tyr Ile Lys
            20                  25                  30

Thr Leu Arg Glu His Pro Glu Arg Ala Gln Glu Val Phe Ser Glu Ser
        35                  40                  45

Leu Lys Asp Ser
        50

<210> SEQ ID NO 160
<211> LENGTH: 52
<212> TYPE: PRT
<213> ORGANISM: S. aureus
<220> FEATURE:
<221> NAME/KEY: misc_feature
<222> LOCATION: (1)..(52)
<223> OTHER INFORMATION: CC30_MN8

<400> SEQUENCE: 160

Thr Gln Asn Asn Tyr Val Thr Asp Gln Gln Lys Ala Phe Tyr Gln Val
1               5                   10                  15

Leu His Leu Lys Gly Ile Thr Glu Glu Gln Arg Asn Gln Tyr Ile Lys
            20                  25                  30

Thr Leu Arg Glu His Pro Glu Arg Ala Gln Glu Val Phe Ser Glu Ser
        35                  40                  45

Leu Lys Asp Ser
        50
```

<210> SEQ ID NO 161
<211> LENGTH: 52
<212> TYPE: PRT
<213> ORGANISM: S. aureus
<220> FEATURE:
<221> NAME/KEY: misc_feature
<222> LOCATION: (1)..(52)
<223> OTHER INFORMATION: CC1_TCH70

<400> SEQUENCE: 161

Thr Gln Asn Asn Tyr Val Thr Asp Gln Gln Lys Ala Phe Tyr Gln Val
1               5                   10                  15

Leu His Leu Lys Gly Ile Thr Glu Glu Gln Arg Asn Gln Tyr Ile Lys
            20                  25                  30

Thr Leu Arg Glu His Pro Glu Arg Ala Gln Glu Val Phe Ser Glu Ser
        35                  40                  45

Leu Lys Asp Ser
    50

<210> SEQ ID NO 162
<211> LENGTH: 52
<212> TYPE: PRT
<213> ORGANISM: S. aureus
<220> FEATURE:
<221> NAME/KEY: misc_feature
<222> LOCATION: (1)..(52)
<223> OTHER INFORMATION: CC36_MRSA252

<400> SEQUENCE: 162

Thr Gln Asn Asn Tyr Val Thr Asp Gln Gln Lys Ala Phe Tyr Gln Val
1               5                   10                  15

Leu His Leu Lys Gly Ile Thr Glu Glu Gln Arg Asn Gln Tyr Ile Lys
            20                  25                  30

Thr Leu Arg Glu His Pro Glu Arg Ala Gln Glu Val Phe Ser Glu Ser
        35                  40                  45

Leu Lys Asp Ser
    50

<210> SEQ ID NO 163
<211> LENGTH: 52
<212> TYPE: PRT
<213> ORGANISM: S. aureus
<220> FEATURE:
<221> NAME/KEY: misc_feature
<222> LOCATION: (1)..(52)
<223> OTHER INFORMATION: CC7_USA300_TCH959

<400> SEQUENCE: 163

Thr Gln Asn Asn Tyr Val Thr Asp Gln Gln Lys Ala Phe Tyr Gln Val
1               5                   10                  15

Leu His Leu Lys Gly Ile Thr Glu Glu Gln Arg Asn Gln Tyr Ile Lys
            20                  25                  30

Thr Leu Arg Glu His Pro Glu Arg Ala Gln Glu Val Phe Ser Glu Ser
        35                  40                  45

Leu Lys Asp Ser
    50

<210> SEQ ID NO 164
<211> LENGTH: 52
<212> TYPE: PRT
<213> ORGANISM: S. aureus
<220> FEATURE:

```
<221> NAME/KEY: misc_feature
<222> LOCATION: (1)..(52)
<223> OTHER INFORMATION: CCbb_USA300_TCH1516

<400> SEQUENCE: 164

Thr Gln Asn Asn Tyr Val Thr Asp Gln Gln Lys Ala Phe Tyr Gln Val
1               5                   10                  15

Leu His Leu Lys Gly Ile Thr Glu Glu Gln Arg Asn Gln Tyr Ile Lys
            20                  25                  30

Thr Leu Arg Glu His Pro Glu Arg Ala Gln Glu Val Phe Ser Glu Ser
        35                  40                  45

Leu Lys Asp Ser
    50

<210> SEQ ID NO 165
<211> LENGTH: 52
<212> TYPE: PRT
<213> ORGANISM: S. aureus
<220> FEATURE:
<221> NAME/KEY: misc_feature
<222> LOCATION: (1)..(52)
<223> OTHER INFORMATION: CC10_H19

<400> SEQUENCE: 165

Thr Gln Asn Asn Tyr Val Thr Asp Gln Gln Lys Ala Phe Tyr Gln Val
1               5                   10                  15

Leu His Leu Lys Gly Ile Thr Glu Glu Gln Arg Asn Gln Tyr Ile Lys
            20                  25                  30

Thr Leu Arg Glu His Pro Glu Arg Ala Gln Glu Val Phe Ser Glu Ser
        35                  40                  45

Leu Lys Asp Ser
    50

<210> SEQ ID NO 166
<211> LENGTH: 52
<212> TYPE: PRT
<213> ORGANISM: S. aureus
<220> FEATURE:
<221> NAME/KEY: misc_feature
<222> LOCATION: (1)..(52)
<223> OTHER INFORMATION: CC239_JKD6009

<400> SEQUENCE: 166

Thr Gln Asn Asn Tyr Val Thr Asp Gln Gln Lys Ala Phe Tyr Gln Val
1               5                   10                  15

Leu His Leu Lys Gly Ile Thr Glu Glu Gln Arg Asn Gln Tyr Ile Lys
            20                  25                  30

Thr Leu Arg Glu His Pro Glu Arg Ala Gln Glu Val Phe Ser Glu Ser
        35                  40                  45

Leu Lys Asp Ser
    50

<210> SEQ ID NO 167
<211> LENGTH: 52
<212> TYPE: PRT
<213> ORGANISM: S. aureus
<220> FEATURE:
<221> NAME/KEY: misc_feature
<222> LOCATION: (1)..(52)
<223> OTHER INFORMATION: CC42_C427

<400> SEQUENCE: 167

Thr Gln Asn Asn Tyr Val Thr Asp Gln Gln Lys Ala Phe Tyr Gln Val
```

```
                1               5                  10                  15
Leu His Leu Lys Gly Ile Thr Glu Glu Gln Arg Asn Gln Tyr Ile Lys
                20                  25                  30

Thr Leu Arg Glu His Pro Glu Arg Ala Gln Glu Val Phe Ser Glu Ser
        35                  40                  45

Leu Lys Asp Ser
    50

<210> SEQ ID NO 168
<211> LENGTH: 52
<212> TYPE: PRT
<213> ORGANISM: S. aureus
<220> FEATURE:
<221> NAME/KEY: misc_feature
<222> LOCATION: (1)..(52)
<223> OTHER INFORMATION: CC5_A8117

<400> SEQUENCE: 168

Thr Gln Asn Asn Tyr Val Thr Asp Gln Gln Lys Ala Phe Tyr Gln Val
1               5                   10                  15

Leu His Leu Lys Gly Ile Thr Glu Glu Gln Arg Asn Gln Tyr Ile Lys
                20                  25                  30

Thr Leu Arg Glu His Pro Glu Arg Ala Gln Glu Val Phe Ser Glu Ser
        35                  40                  45

Leu Lys Asp Ser
    50

<210> SEQ ID NO 169
<211> LENGTH: 52
<212> TYPE: PRT
<213> ORGANISM: S. aureus
<220> FEATURE:
<221> NAME/KEY: misc_feature
<222> LOCATION: (1)..(52)
<223> OTHER INFORMATION: CC45_A9635

<400> SEQUENCE: 169

Thr Gln Asn Asn Tyr Val Thr Asp Gln Gln Lys Ala Phe Tyr Gln Val
1               5                   10                  15

Leu His Leu Lys Gly Ile Thr Glu Glu Gln Arg Asn Gln Tyr Ile Lys
                20                  25                  30

Thr Leu Arg Glu His Pro Glu Arg Ala Gln Glu Val Phe Ser Glu Ser
        35                  40                  45

Leu Lys Asp Ser
    50

<210> SEQ ID NO 170
<211> LENGTH: 54
<212> TYPE: PRT
<213> ORGANISM: S. aureus
<220> FEATURE:
<221> NAME/KEY: misc_feature
<222> LOCATION: (1)..(54)
<223> OTHER INFORMATION: USA300_FPR3757

<400> SEQUENCE: 170

Lys Asn Pro Asp Arg Arg Val Ala Gln Gln Asn Ala Phe Tyr Asn Val
1               5                   10                  15

Leu Lys Asn Asp Asn Leu Thr Glu Gly Glu Lys Asn Asn Tyr Ile Ala
                20                  25                  30

Gln Ile Lys Glu Asn Pro Asp Arg Ser Gln Gln Val Trp Val Glu Ser
        35                  40                  45
```

Val Gln Ser Ser Lys Ala
    50

<210> SEQ ID NO 171
<211> LENGTH: 54
<212> TYPE: PRT
<213> ORGANISM: S. aureus
<220> FEATURE:
<221> NAME/KEY: misc_feature
<222> LOCATION: (1)..(54)
<223> OTHER INFORMATION: CC30_MN8

<400> SEQUENCE: 171

Lys Asn Pro Asp Arg Arg Val Ala Gln Gln Asn Ala Phe Tyr Asn Val
1               5                   10                  15

Leu Lys Asn Asp Asn Leu Thr Glu Gln Glu Lys Asn Asn Tyr Ile Ala
            20                  25                  30

Gln Ile Lys Glu Asn Pro Asp Arg Ser Gln Gln Val Trp Val Glu Ser
        35                  40                  45

Val Gln Ser Ser Lys Ala
    50

<210> SEQ ID NO 172
<211> LENGTH: 54
<212> TYPE: PRT
<213> ORGANISM: S. aureus
<220> FEATURE:
<221> NAME/KEY: misc_feature
<222> LOCATION: (1)..(54)
<223> OTHER INFORMATION: CC1_TCH70

<400> SEQUENCE: 172

Lys Asn Pro Asp Arg Arg Val Ala Gln Gln Asn Ala Phe Tyr Asn Val
1               5                   10                  15

Leu Lys Asn Asp Asn Leu Thr Glu Gln Glu Lys Asn Asn Tyr Ile Ala
            20                  25                  30

Gln Ile Lys Glu Asn Pro Asp Arg Ser Gln Gln Val Trp Val Glu Ser
        35                  40                  45

Val Gln Ser Ser Lys Ala
    50

<210> SEQ ID NO 173
<211> LENGTH: 54
<212> TYPE: PRT
<213> ORGANISM: S. aureus
<220> FEATURE:
<221> NAME/KEY: misc_feature
<222> LOCATION: (1)..(54)
<223> OTHER INFORMATION: CC36_MRSA252

<400> SEQUENCE: 173

Lys Asn Pro Asp Arg Arg Val Ala Gln Gln Asn Ala Phe Tyr Asn Val
1               5                   10                  15

Leu Lys Asn Asp Asn Leu Thr Glu Gln Glu Lys Asn Asn Tyr Ile Ala
            20                  25                  30

Gln Ile Lys Glu Asn Pro Asp Arg Ser Gln Gln Val Trp Val Glu Ser
        35                  40                  45

Val Gln Ser Ser Lys Ala
    50

<210> SEQ ID NO 174
<211> LENGTH: 54

```
<212> TYPE: PRT
<213> ORGANISM: S. aureus
<220> FEATURE:
<221> NAME/KEY: misc_feature
<222> LOCATION: (1)..(54)
<223> OTHER INFORMATION: CC7_USA300_TCH959

<400> SEQUENCE: 174
```

Lys Asn Pro Asp Arg Arg Val Ala Gln Gln Asn Ala Phe Tyr Asn Val
1               5                   10                  15

Leu Lys Asn Asp Asn Leu Thr Glu Gln Glu Lys Asn Asn Tyr Ile Ala
            20                  25                  30

Gln Ile Lys Glu Asn Pro Asp Arg Ser Gln Gln Val Trp Val Glu Ser
        35                  40                  45

Val Gln Ser Ser Lys Ala
    50

```
<210> SEQ ID NO 175
<211> LENGTH: 54
<212> TYPE: PRT
<213> ORGANISM: S. aureus
<220> FEATURE:
<221> NAME/KEY: misc_feature
<222> LOCATION: (1)..(54)
<223> OTHER INFORMATION: CCbb_USA300_TCH1516

<400> SEQUENCE: 175
```

Lys Asn Pro Asp Arg Arg Val Ala Gln Gln Asn Ala Phe Tyr Asn Val
1               5                   10                  15

Leu Lys Asn Asp Asn Leu Thr Glu Gln Glu Lys Asn Asn Tyr Ile Ala
            20                  25                  30

Gln Ile Lys Glu Asn Pro Asp Arg Ser Gln Gln Val Trp Val Glu Ser
        35                  40                  45

Val Gln Ser Ser Lys Ala
    50

```
<210> SEQ ID NO 176
<211> LENGTH: 54
<212> TYPE: PRT
<213> ORGANISM: S. aureus
<220> FEATURE:
<221> NAME/KEY: misc_feature
<222> LOCATION: (1)..(54)
<223> OTHER INFORMATION: CC10_H19

<400> SEQUENCE: 176
```

Lys Asn Pro Asp Arg Arg Val Ala Gln Gln Asn Ala Phe Tyr Asn Val
1               5                   10                  15

Leu Lys Asn Asp Asn Leu Thr Glu Gln Glu Lys Asn Asn Tyr Ile Ala
            20                  25                  30

Gln Ile Lys Glu Asn Pro Asp Arg Ser Gln Gln Val Trp Val Glu Ser
        35                  40                  45

Val Gln Ser Ser Lys Ala
    50

```
<210> SEQ ID NO 177
<211> LENGTH: 54
<212> TYPE: PRT
<213> ORGANISM: S. aureus
<220> FEATURE:
<221> NAME/KEY: misc_feature
<222> LOCATION: (1)..(54)
<223> OTHER INFORMATION: CC45_A9635
```

-continued

<400> SEQUENCE: 177

Lys Asn Pro Asp Arg Arg Val Ala Gln Gln Asn Ala Phe Tyr Asn Val
1               5                   10                  15

Leu Lys Asn Asp Asn Leu Thr Glu Gln Glu Lys Asn Asn Tyr Ile Ala
            20                  25                  30

Gln Ile Lys Glu Asn Pro Asp Arg Ser Gln Gln Val Trp Val Glu Ser
        35                  40                  45

Val Gln Ser Ser Lys Ala
    50

<210> SEQ ID NO 178
<211> LENGTH: 54
<212> TYPE: PRT
<213> ORGANISM: S. aureus
<220> FEATURE:
<221> NAME/KEY: misc_feature
<222> LOCATION: (1)..(54)
<223> OTHER INFORMATION: CC5_A8117

<400> SEQUENCE: 178

Lys Asn Pro Asp Arg Arg Val Ala Gln Gln Asn Ala Phe Tyr Asn Val
1               5                   10                  15

Leu Lys Asn Asp Asn Leu Thr Glu Gln Glu Lys Asn Asn Tyr Ile Ala
            20                  25                  30

Gln Ile Lys Glu Asn Pro Asp Arg Ser Gln Gln Val Trp Val Glu Ser
        35                  40                  45

Val Gln Ser Ser Lys Ala
    50

<210> SEQ ID NO 179
<211> LENGTH: 54
<212> TYPE: PRT
<213> ORGANISM: S. aureus
<220> FEATURE:
<221> NAME/KEY: misc_feature
<222> LOCATION: (1)..(54)
<223> OTHER INFORMATION: CC42_C427

<400> SEQUENCE: 179

Lys Asn Pro Asp Arg Arg Val Ala Gln Gln Asn Ala Phe Tyr Asn Val
1               5                   10                  15

Leu Lys Asn Asp Asn Leu Thr Glu Gln Glu Lys Asn Asn Tyr Ile Ala
            20                  25                  30

Gln Ile Lys Glu Asn Pro Asp Arg Ser Gln Gln Val Trp Val Glu Ser
        35                  40                  45

Val Gln Ser Ser Lys Ala
    50

<210> SEQ ID NO 180
<211> LENGTH: 54
<212> TYPE: PRT
<213> ORGANISM: S. aureus
<220> FEATURE:
<221> NAME/KEY: misc_feature
<222> LOCATION: (1)..(54)
<223> OTHER INFORMATION: CC239_JKD6009

<400> SEQUENCE: 180

Lys Asn Pro Asp Arg Arg Val Ala Gln Gln Asn Ala Phe Tyr Ser Val
1               5                   10                  15

Leu Lys Asn Asp Asn Leu Thr Glu Gln Glu Lys Asn Asn Tyr Ile Ala
            20                  25                  30

```
Gln Ile Lys Glu Asn Pro Asp Arg Ser Gln Gln Val Trp Val Glu Ser
        35                  40                  45

Val Gln Ser Ser Lys Ala
    50
```

<210> SEQ ID NO 181
<211> LENGTH: 106
<212> TYPE: PRT
<213> ORGANISM: Artificial Sequence
<220> FEATURE:
<223> OTHER INFORMATION: Synthetic: LC CDR murine graft-
      GKV4-55*01-IGKJ1

<400> SEQUENCE: 181

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Tyr Pro Pro Thr
                85                  90                  95

Phe Gly Gly Gly Thr Lys Leu Glu Ile Lys
            100                 105
```

<210> SEQ ID NO 182
<211> LENGTH: 125
<212> TYPE: PRT
<213> ORGANISM: Artificial Sequence
<220> FEATURE:
<223> OTHER INFORMATION: Synthetic: HC CDR murine
      graf-IGHV5-9-4*01-IGHJ4
<220> FEATURE:
<221> NAME/KEY: misc_feature
<222> LOCATION: (98)..(99)
<223> OTHER INFORMATION: Xaa, if present, can be any naturally occurring
      amino acid

<400> SEQUENCE: 182

```
Glu Val Gln Leu Val Glu Ser Gly Gly Leu Val Lys Pro Gly Gly
1               5                   10                  15

Ser Leu Lys Leu Ser Cys Ala Ala Ser Gly Phe Ala Phe Ser Asn Tyr
            20                  25                  30

Asp Met Ser Trp Val Arg Gln Ser Pro Glu Lys Arg Leu Glu Trp Val
        35                  40                  45

Ala Glu Ile Ser Ser Gly Gly Thr Tyr Pro Tyr Pro Asp Thr Val Thr
    50                  55                  60

Gly Arg Phe Thr Ile Ser Arg Asp Asn Ala Lys Asn Thr Leu Tyr Leu
65                  70                  75                  80

Glu Met Ser Ser Leu Arg Ser Glu Asp Thr Ala Met Tyr Tyr Cys Ala
                85                  90                  95

Arg Xaa Xaa Gly Gly Phe Leu Ile Thr Thr Arg Asp Tyr Tyr Ala Met
            100                 105                 110

Asp Tyr Trp Gly Gln Gly Thr Ser Val Thr Val Ser Ser
        115                 120                 125
```

<210> SEQ ID NO 183
<211> LENGTH: 111
<212> TYPE: PRT
<213> ORGANISM: Artificial Sequence
<220> FEATURE:
<223> OTHER INFORMATION: Synthetic: LC CDR murine
      graft-IGKV3-1*01-IGKJ1

<400> SEQUENCE: 183

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Ser
            20                  25                  30

Gly Ala Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Ser Thr Phe Gly Gly Gly Thr Lys Leu Glu Ile Lys
            100                 105                 110

<210> SEQ ID NO 184
<211> LENGTH: 125
<212> TYPE: PRT
<213> ORGANISM: Artificial Sequence
<220> FEATURE:
<223> OTHER INFORMATION: Synthetic: HC CDR murine
      graft -IGHV10S3*01-IGHJ4
<220> FEATURE:
<221> NAME/KEY: misc_feature
<222> LOCATION: (99)..(100)
<223> OTHER INFORMATION: Xaa, if present, can be any naturally occurring
      amino acid

<400> SEQUENCE: 184

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Xaa Xaa Val Thr Glu His Tyr Asp Tyr Asp Tyr Tyr Val Met
            100                 105                 110

Asp Tyr Trp Gly Gln Gly Thr Ser Val Thr Val Ser Ser
        115                 120                 125

<210> SEQ ID NO 185
<211> LENGTH: 105
<212> TYPE: PRT
<213> ORGANISM: Artificial Sequence
<220> FEATURE:
<223> OTHER INFORMATION: Synthetic: LC CDR murine graft-IGKV4-86*01-IGKJ1

<400> SEQUENCE: 185

```
Glu Ile Val Leu Thr Gln Ser Pro Ala Ile Thr Ala Ala Ser Leu Gly
1               5                   10                  15

Gln Lys Val Thr Ile Thr Cys Ser Ala Ser Ser Val Ser Tyr Met
            20                  25                  30

His Trp Tyr Gln Gln Lys Ser Gly Thr Ser Pro Lys Pro Trp Ile Tyr
            35                  40                  45

Glu Ile Ser Lys Leu Ala Ser Gly Val Pro Ala Arg Phe Ser Gly Ser
        50                  55                  60

Gly Ser Gly Thr Ser Tyr Ser Leu Thr Ile Ser Met Glu Ala Glu
65                  70                  75                  80

Asp Ala Ala Ile Tyr Tyr Cys Gln Gln Trp Ser Tyr Pro Phe Thr Phe
                85                  90                  95

Gly Ser Gly Thr Lys Leu Glu Ile Lys
            100                 105
```

<210> SEQ ID NO 186
<211> LENGTH: 123
<212> TYPE: PRT
<213> ORGANISM: Artificial Sequence
<220> FEATURE:
<223> OTHER INFORMATION: Synthetic: HC CDR murine graft
      -IGHV1S30*01-IGHJ4
<220> FEATURE:
<221> NAME/KEY: misc_feature
<222> LOCATION: (99)..(100)
<223> OTHER INFORMATION: Xaa, if present, can be any naturally occurring
      amino acid

<400> SEQUENCE: 186

```
Glu Val Gln Leu Gln Gln Ser Gly Pro Glu Leu Val Lys Leu Gly Pro
1               5                   10                  15

Ser Val Lys Ile Ser Cys Lys Ala Ser Gly Tyr Ser Phe Thr Ser Tyr
            20                  25                  30

Tyr Met His Trp Val Lys Gln Ser His Gly Lys Ser Leu Glu Trp Ile
        35                  40                  45

Gly Glu Ile Asp Pro Phe Asn Gly Gly Thr Ser Tyr Asn Gln Lys Phe
    50                  55                  60

Lys Gly Lys Ala Thr Leu Thr Val Asp Thr Ser Ser Ser Thr Ala Tyr
65                  70                  75                  80

Met Glu Leu His Ser Leu Thr Ser Glu Asp Ser Leu Val Tyr Tyr Cys
                85                  90                  95

Ala Arg Xaa Xaa Tyr Gly Tyr Asp Gly Thr Phe Tyr Ala Met Asp Tyr
            100                 105                 110

Trp Gly Gln Gly Thr Ser Val Thr Val Ser Ser
        115                 120
```

<210> SEQ ID NO 187
<211> LENGTH: 90
<212> TYPE: PRT
<213> ORGANISM: Artificial Sequence
<220> FEATURE:
<223> OTHER INFORMATION: Synthetic: murine VL sequence mIGKV3-1

<400> SEQUENCE: 187

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
```

20                  25                  30
Gly Thr Ser Leu Met Gln Trp Tyr Gln Gln Lys Pro Gly Gln Pro Pro
            35                  40                  45

Lys Leu Leu Ile Tyr Ala Ala Ser Asn Val Glu Ser Gly Val Pro Ala
 50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr
                85                  90

<210> SEQ ID NO 188
<211> LENGTH: 218
<212> TYPE: PRT
<213> ORGANISM: Artificial Sequence
<220> FEATURE:
<223> OTHER INFORMATION: Synthetic: Chimeric light chain amino acid
      sequence mIGKV3-cdr graft

<400> SEQUENCE: 188

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Ser
            20                  25                  30

Gly Ala Ser Leu Met Gln Trp Tyr Gln Gln Lys Pro Gly Gln Pro Pro
            35                  40                  45

Lys Leu Leu Ile Tyr Ala Ala Ser Asn Val Glu Ser Gly Val Pro Ala
 50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 189
<211> LENGTH: 95
<212> TYPE: PRT
<213> ORGANISM: Artificial Sequence
<220> FEATURE:
<223> OTHER INFORMATION: Synthetic: Human VL sequence IGKV1D-39*1

<400> SEQUENCE: 189

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro
                 85                  90                  95

<210> SEQ ID NO 190
<211> LENGTH: 101
<212> TYPE: PRT
<213> ORGANISM: Artificial Sequence
<220> FEATURE:
<223> OTHER INFORMATION: Synthetic: Human VL sequence IGKV4-1*1

<400> SEQUENCE: 190

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 191
<211> LENGTH: 218
<212> TYPE: PRT
<213> ORGANISM: Artificial Sequence
<220> FEATURE:
<223> OTHER INFORMATION: Synthetic: Humanized light chain amino acid
      sequence hIGKV1D-39-cdr graft-IGKJ1-hIgKC

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr Ser
            20                  25                  30

Gly Ala Ser Leu Met Gln Trp Tyr Gln Gln Lys Pro Gly Lys Ala Pro
        35                  40                  45

Lys Leu Leu Ile Tyr Ala Ala Ser Asn Val Glu Ser Gly Val Pro Ser
 50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Arg
                85                  90                  95

Lys Val Pro Ser Thr Phe Gly Gly Gly Thr Lys Val Glu Ile Lys Arg
            100                 105                 110
```

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 192
<211> LENGTH: 218
<212> TYPE: PRT
<213> ORGANISM: Artificial Sequence
<220> FEATURE:
<223> OTHER INFORMATION: Synthetic: Humanized light chain amino acid
      sequence hIGKV4-1-cdr graft-IGKJ1-hIgKC

<400> SEQUENCE: 192

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Ser
            20                  25                  30

Gly Ala Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Val Pro Ser Thr Phe Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 193
<211> LENGTH: 100
<212> TYPE: PRT
<213> ORGANISM: Artificial Sequence

```
<220> FEATURE:
<223> OTHER INFORMATION: Synthetic: murine VH sequence IGHV10-1

<400> SEQUENCE: 193

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Ser Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Thr Tyr Tyr Ala Asp
        50                  55                  60

Ser Val Lys Asp Arg Phe Thr Ile Ser Arg Asp Asp Ser Glu Ser Met
65                  70                  75                  80

Leu Tyr Leu Gln Met Asn Asn Leu Lys Thr Glu Asp Thr Ala Met Tyr
                85                  90                  95

Tyr Cys Val Arg
            100

<210> SEQ ID NO 194
<211> LENGTH: 453
<212> TYPE: PRT
<213> ORGANISM: Artificial Sequence
<220> FEATURE:
<223> OTHER INFORMATION: Synthetic: Chimeric heavy chain amino acid
      sequence mIGHV10-IGHJ4-hIgG1

<400> SEQUENCE: 194

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Asn
                20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Thr Tyr Tyr Ala Asp
        50                  55                  60

Ser Val Lys Asp Arg Phe Thr Ile Ser Arg Asp Asp Ser Glu Ser Met
65                  70                  75                  80

Leu Tyr Leu Gln Met Asn Asn Leu Lys Thr Glu Asp Thr Ala Met Tyr
                85                  90                  95

Tyr Cys Val Thr Glu His Tyr Asp Tyr Asp Tyr Val Met Asp Tyr
            100                 105                 110

Trp Gly Gln Gly Thr Ser Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220
```

```
Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Lys
    450

<210> SEQ ID NO 195
<211> LENGTH: 455
<212> TYPE: PRT
<213> ORGANISM: Artificial Sequence
<220> FEATURE:
<223> OTHER INFORMATION: Synthetic: Chimeric heavy chain amino acid
      sequence mIGHV10-IGHJ4-hIgG1

<400> SEQUENCE: 195

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Glu Ser Met
65                  70                  75                  80

Leu Tyr Leu Gln Met Asn Asn Leu Lys Thr Glu Asp Thr Ala Met Tyr
            85                  90                  95

Tyr Cys Ala Arg Val Thr Glu His Tyr Asp Tyr Asp Tyr Tyr Val Met
        100                 105                 110

Asp Tyr Trp Gly Gln Gly Thr Ser Val Thr Val Ser Ser Ala Ser Thr
    115                 120                 125
```

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 196
<211> LENGTH: 453
<212> TYPE: PRT
<213> ORGANISM: Artificial Sequence
<220> FEATURE:
<223> OTHER INFORMATION: Synthetic: Chimeric heavy chain variant amino
      acid sequence mIGHV10-IGHJ4-hIgG1

<400> SEQUENCE: 196

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Asn

```
                  20                  25                  30
Ala Met Asn Trp Val Arg Gln Ala Pro Gly Lys Gly Leu Glu Trp Val
             35                  40                  45
Ala Arg Ile Arg Ser Lys Ser Asn Asn Tyr Ala Thr Tyr Tyr Ala Asp
 50                  55                  60
Ser Val Lys Asp Arg Phe Thr Ile Ser Arg Asp Asp Ser Glu Ser Met
 65                  70                  75                  80
Leu Tyr Leu Gln Met Asn Asn Leu Lys Thr Glu Asp Thr Ala Met Tyr
                 85                  90                  95
Tyr Cys Val Thr Glu His Tyr Asp Tyr Asp Tyr Val Met Asp Tyr
                100                 105                 110
Trp Gly Gln Gly Thr Ser Val Thr Val Ser Ser Ala Ser Thr Lys Gly
             115                 120                 125
Pro Ser Val Phe Pro Leu Ala Pro Ser Ser Lys Ser Thr Ser Gly Gly
             130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
             180                 185                 190
Thr Val Pro Ser Ser Ser Leu Gly Thr Gln Thr Tyr Ile Cys Asn Val
             195                 200                 205
Asn His Lys Pro Ser Asn Thr Lys Val Asp Lys Lys Val Glu Pro Lys
         210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
             260                 265                 270
Ser His Glu Asp Pro Glu Val Gln Phe Asn Trp Tyr Val Asp Gly Val
         275                 280                 285
Glu Val His Asn Ala Lys Thr Lys Pro Arg Glu Glu Gln Tyr Asn Ser
     290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
             340                 345                 350
Gln Val Tyr Thr Leu Pro Pro Ser Arg Glu Glu Met Thr Lys Asn Gln
             355                 360                 365
Val Ser Leu Thr Cys Leu Val Lys Gly Phe Tyr Pro Ser Asp Ile Ala
         370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
             420                 425                 430
Val Met His Glu Ala Leu His Asn Arg Phe Thr Gln Lys Ser Leu Ser
         435                 440                 445
```

Leu Ser Pro Gly Lys
    450

<210> SEQ ID NO 197
<211> LENGTH: 455
<212> TYPE: PRT
<213> ORGANISM: Artificial Sequence
<220> FEATURE:
<223> OTHER INFORMATION: Synthetic: Chimeric heavy chain variant amino
      acid sequence mIGHV10-IGHJ4-hIgG1

<400> SEQUENCE: 197

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Glu Ser Met
65                  70                  75                  80

Leu Tyr Leu Gln Met Asn Asn Leu Lys Thr Glu Asp Thr Ala Met Tyr
                85                  90                  95

Tyr Cys Ala Arg Val Thr Glu His Tyr Asp Tyr Asp Tyr Val Met
            100                 105                 110

Asp Tyr Trp Gly Gln Gly Thr Ser Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Gln Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg

```
                    340                 345                 350
Glu Pro Gln Val Tyr Thr Leu Pro Pro Ser Arg Glu Glu Met Thr Lys
                355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn Arg Phe Thr Gln Lys Ser
                435                 440                 445

Leu Ser Leu Ser Pro Gly Lys
            450                 455

<210> SEQ ID NO 198
<211> LENGTH: 100
<212> TYPE: PRT
<213> ORGANISM: Artificial Sequence
<220> FEATURE:
<223> OTHER INFORMATION: Synthetic: Human VH sequence IGHV3-73

<400> SEQUENCE: 198

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Pro Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Arg
            100

<210> SEQ ID NO 199
<211> LENGTH: 98
<212> TYPE: PRT
<213> ORGANISM: Artificial Sequence
<220> FEATURE:
<223> OTHER INFORMATION: Synthetic: Human VH sequence IGHV3-23_1

<400> SEQUENCE: 199

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys

<210> SEQ ID NO 200
<211> LENGTH: 453
<212> TYPE: PRT
<213> ORGANISM: Artificial Sequence
<220> FEATURE:
<223> OTHER INFORMATION: Synthetic: Humanized heavy chain amino acid
      sequence: hIGHV3-73graft-IGHJ4-hIgG1

<400> SEQUENCE: 200

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu His Tyr Asp Tyr Asp Tyr Val Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335
```

```
Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 201
<211> LENGTH: 455
<212> TYPE: PRT
<213> ORGANISM: Artificial Sequence
<220> FEATURE:
<223> OTHER INFORMATION: Synthetic: Humanized heavy chain amino acid
      sequence: hIGHV3-73graft-IGHJ4-hIgG1

<400> SEQUENCE: 201

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Val Thr Glu His Tyr Asp Tyr Asp Tyr Val Met
            100                 105                 110

Asp Tyr Trp Gly Gln Gly Thr Ser Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240
```

```
Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 202
<211> LENGTH: 453
<212> TYPE: PRT
<213> ORGANISM: Artificial Sequence
<220> FEATURE:
<223> OTHER INFORMATION: Synthetic: Humanized heavy chain amino acid
      sequence: hIGHV3-23graft-IGHJ4-hIgG1

<400> SEQUENCE: 202

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ser Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Glu His Tyr Asp Tyr Asp Tyr Val Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
```

```
                    130                 135                 140
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
                210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
                450
```

<210> SEQ ID NO 203
<211> LENGTH: 455
<212> TYPE: PRT
<213> ORGANISM: Artificial Sequence
<220> FEATURE:
<223> OTHER INFORMATION: Synthetic: Humanized heavy chain amino acid
      sequence: hIGHV3-23graft-IGHJ4-hIgG1

<400> SEQUENCE: 203

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Asn
                20                  25                  30
```

```
Ala Met Asn Trp Val Arg Gln Ala Pro Gly Lys Gly Leu Glu Trp Val
         35                  40                  45
Ser Arg Ile Arg Ser Lys Ser Asn Asn Tyr Ala Thr Tyr Tyr Ala Asp
 50                  55                  60
Ser Val Lys Asp Arg Phe Thr Ile Ser Arg Asp Asn Ser Lys Asn Thr
 65                  70                  75                  80
Leu Tyr Leu Gln Met Asn Ser Leu Arg Ala Glu Asp Thr Ala Val Tyr
                 85                  90                  95
Tyr Cys Ala Lys Val Thr Glu His Tyr Asp Tyr Asp Tyr Val Met
                100                 105                 110
Asp Tyr Trp Gly Gln Gly Thr Ser Val Thr Val Ser Ser Ala Ser Thr
            115                 120                 125
Lys Gly Pro Ser Val Phe Pro Leu Ala Pro Ser Ser Lys Ser Thr Ser
        130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Gln Thr Tyr Ile Cys
        195                 200                 205
Asn Val Asn His Lys Pro Ser Asn Thr Lys Val Asp Lys Lys Val Glu
    210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Glu Glu Met Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys
```

```
            450                 455

<210> SEQ ID NO 204
<211> LENGTH: 453
<212> TYPE: PRT
<213> ORGANISM: Artificial Sequence
<220> FEATURE:
<223> OTHER INFORMATION: Synthetic: Humanized variant heavy chain amino
      acid sequence: hIGHV3-73graft-IGHJ4-hIgG1

<400> SEQUENCE: 204

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu His Tyr Asp Tyr Asp Tyr Tyr Val Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350
```

```
Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn Arg Phe Thr Gln Lys Ser Leu Ser
    435                 440                 445

Leu Ser Pro Gly Lys
    450

<210> SEQ ID NO 205
<211> LENGTH: 455
<212> TYPE: PRT
<213> ORGANISM: Artificial Sequence
<220> FEATURE:
<223> OTHER INFORMATION: Synthetic: Humanized variant heavy chain amino
      acid sequence: hIGHV3-73graft-IGHJ4-hIgG1

<400> SEQUENCE: 205

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Val Thr Glu His Tyr Asp Tyr Asp Tyr Tyr Val Met
            100                 105                 110

Asp Tyr Trp Gly Gln Gly Thr Ser Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255
```

```
Asp Thr Leu Met Ile Ser Arg Thr Pro Glu Val Thr Cys Val Val
            260                 265                 270
Asp Val Ser His Glu Asp Pro Glu Val Gln Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Glu Glu Met Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn Arg Phe Thr Gln Lys Ser
        435                 440                 445
Leu Ser Leu Ser Pro Gly Lys
    450                 455

<210> SEQ ID NO 206
<211> LENGTH: 453
<212> TYPE: PRT
<213> ORGANISM: Artificial Sequence
<220> FEATURE:
<223> OTHER INFORMATION: Synthetic: Humanized variant heavy chain amino
      acid sequence: hIGHV3-23graft-IGHJ4-hIgG1

<400> SEQUENCE: 206

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Asn Thr Asn
            20                  25                  30
Ala Met Asn Trp Val Arg Gln Ala Pro Gly Lys Gly Leu Glu Trp Val
        35                  40                  45
Ser Arg Ile Arg Ser Lys Ser Asn Asn Tyr Ala Thr Tyr Tyr Ala Asp
    50                  55                  60
Ser Val Lys Asp Arg Phe Thr Ile Ser Arg Asp Asn Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Ala Lys Glu His Tyr Asp Tyr Asp Tyr Tyr Val Met Asp Tyr
            100                 105                 110
Trp Gly Gln Gly Thr Ser Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
```

```
                145                 150                 155                 160
        Thr Val Ser Trp Asn Ser Gly Ala Leu Thr Ser Gly Val His Thr Phe
                        165                 170                 175

Pro Ala Val Leu Gln Ser Ser Gly Leu Tyr Ser Leu Ser Ser Val Val
                        180                 185                 190

Thr Val Pro Ser Ser Ser Leu Gly Thr Gln Thr Tyr Ile Cys Asn Val
                        195                 200                 205

Asn His Lys Pro Ser Asn Thr Lys Val Asp Lys Lys Val Glu Pro Lys
                        210                 215                 220

Ser Cys Asp Lys Thr His Thr Cys Pro Pro Cys Pro Ala Pro Glu Leu
        225                 230                 235                 240

Leu Gly Gly Pro Ser Val Phe Leu Phe Pro Pro Lys Pro Lys Asp Thr
                        245                 250                 255

Leu Met Ile Ser Arg Thr Pro Glu Val Thr Cys Val Val Val Asp Val
                        260                 265                 270

Ser His Glu Asp Pro Glu Val Gln Phe Asn Trp Tyr Val Asp Gly Val
                        275                 280                 285

Glu Val His Asn Ala Lys Thr Lys Pro Arg Glu Glu Gln Tyr Asn Ser
                        290                 295                 300

Thr Tyr Arg Val Val Ser Val Leu Thr Val Leu His Gln Asp Trp Leu
        305                 310                 315                 320

Asn Gly Lys Glu Tyr Lys Cys Lys Val Ser Asn Lys Ala Leu Pro Ala
                        325                 330                 335

Pro Ile Glu Lys Thr Ile Ser Lys Ala Lys Gly Gln Pro Arg Glu Pro
                        340                 345                 350

Gln Val Tyr Thr Leu Pro Pro Ser Arg Glu Glu Met Thr Lys Asn Gln
                        355                 360                 365

Val Ser Leu Thr Cys Leu Val Lys Gly Phe Tyr Pro Ser Asp Ile Ala
                        370                 375                 380

Val Glu Trp Glu Ser Asn Gly Gln Pro Glu Asn Asn Tyr Lys Thr Thr
        385                 390                 395                 400

Pro Pro Val Leu Asp Ser Asp Gly Ser Phe Phe Leu Tyr Ser Lys Leu
                        405                 410                 415

Thr Val Asp Lys Ser Arg Trp Gln Gln Gly Asn Val Phe Ser Cys Ser
                        420                 425                 430

Val Met His Glu Ala Leu His Asn Arg Phe Thr Gln Lys Ser Leu Ser
                        435                 440                 445

Leu Ser Pro Gly Lys
            450

<210> SEQ ID NO 207
<211> LENGTH: 455
<212> TYPE: PRT
<213> ORGANISM: Artificial Sequence
<220> FEATURE:
<223> OTHER INFORMATION: Synthetic: Humanized variant heavy chain amino
      acid sequence: hIGHV3-23graft-IGHJ4-hIgG1

<400> SEQUENCE: 207

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Asn
                20                  25                  30

Ala Met Asn Trp Val Arg Gln Ala Pro Gly Lys Gly Leu Glu Trp Val
            35                  40                  45
```

```
Ser Arg Ile Arg Ser Lys Ser Asn Asn Tyr Ala Thr Tyr Tyr Ala Asp
 50              55                  60

Ser Val Lys Asp Arg Phe Thr Ile Ser Arg Asp Asn Ser Lys Asn Thr
 65              70                  75                  80

Leu Tyr Leu Gln Met Asn Ser Leu Arg Ala Glu Asp Thr Ala Val Tyr
                 85                  90                  95

Tyr Cys Ala Lys Val Thr Glu His Tyr Asp Tyr Asp Tyr Tyr Val Met
                100                 105                 110

Asp Tyr Trp Gly Gln Gly Thr Ser Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Gln Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn Arg Phe Thr Gln Lys Ser
        435                 440                 445

Leu Ser Leu Ser Pro Gly Lys
450                 455
```

```
<210> SEQ ID NO 208
<211> LENGTH: 214
<212> TYPE: PRT
<213> ORGANISM: Artificial Sequence
<220> FEATURE:
<223> OTHER INFORMATION: Synthetic: Humanized light chain amino acid
      sequence IGKV3-11*-1-cdr graft-IGKJ1-hIgKC

<400> SEQUENCE: 208

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ser Val Ser Tyr
                20                  25                  30

Leu Ala Trp Tyr Gln Gln Lys Pro Gly Gln Ala Pro Arg Leu Leu Ile
            35                  40                  45

Tyr Asp Thr Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Trp Ser Ser Tyr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 209
<211> LENGTH: 455
<212> TYPE: PRT
<213> ORGANISM: Artificial Sequence
<220> FEATURE:
<223> OTHER INFORMATION: Synthetic: Humanized heavy chain amino acid
      sequence: hIGHV3-66*4 graft-IGHJ4-hIgG1

<400> SEQUENCE: 209

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Asn Tyr
                20                  25                  30

Asp Met Ser Trp Val Arg Gln Ala Pro Gly Lys Gly Leu Glu Trp Val
            35                  40                  45

Ser Val Ile Ser Ser Gly Gly Thr Tyr Pro Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
```

```
                85                  90                  95
Arg Ala Arg Gly Gly Phe Leu Ile Thr Thr Arg Asp Tyr Tyr Ala Met
            100                 105                 110
Asp Tyr Trp Gly Gln Gly Thr Ser Val Thr Val Ser Ser Ala Ser Thr
            115                 120                 125
Lys Gly Pro Ser Val Phe Pro Leu Ala Pro Ser Ser Lys Ser Thr Ser
130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Gln Thr Tyr Ile Cys
            195                 200                 205
Asn Val Asn His Lys Pro Ser Asn Thr Lys Val Asp Lys Lys Val Glu
210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
            275                 280                 285
Gly Val Glu Val His Asn Ala Lys Thr Lys Pro Arg Glu Glu Gln Tyr
            290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Glu Met Thr Lys
            355                 360                 365
Asn Gln Val Ser Leu Thr Cys Leu Val Lys Gly Phe Tyr Pro Ser Asp
            370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
            435                 440                 445
Leu Ser Leu Ser Pro Gly Lys
450                 455

<210> SEQ ID NO 210
<211> LENGTH: 453
<212> TYPE: PRT
<213> ORGANISM: Artificial Sequence
<220> FEATURE:
<223> OTHER INFORMATION: Synthetic: Humanized heavy chain amino acid
      sequence: hIGHV3-66*4 graft-IGHJ4-hIgG1
```

<400> SEQUENCE: 210

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Asn Tyr
            20                  25                  30

Asp Met Ser Trp Val Arg Gln Ala Pro Gly Lys Gly Leu Glu Trp Val
        35                  40                  45

Ser Val Ile Ser Ser Gly Thr Tyr Pro Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Leu Ile Thr Thr Arg Asp Tyr Tyr Ala Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu

```
                         405                 410                 415
Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 211
<211> LENGTH: 455
<212> TYPE: PRT
<213> ORGANISM: Artificial Sequence
<220> FEATURE:
<223> OTHER INFORMATION: Synthetic: Humanized variant heavy chain amino
      acid sequence: hIGHV3-66*4 -23graft-IGHJ4-hIgG1

<400> SEQUENCE: 211

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Asn Tyr
            20                  25                  30

Asp Met Ser Trp Val Arg Gln Ala Pro Gly Lys Gly Leu Glu Trp Val
        35                  40                  45

Ser Val Ile Ser Ser Gly Gly Thr Tyr Pro Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Arg Gly Gly Phe Leu Ile Thr Thr Arg Asp Tyr Tyr Ala Met
            100                 105                 110

Asp Tyr Trp Gly Gln Gly Thr Ser Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Gln Phe Asn Trp Tyr Val Asp
        275                 280                 285

Gly Val Glu Val His Asn Ala Lys Thr Lys Pro Arg Glu Glu Gln Tyr
    290                 295                 300
```

```
Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
        340                 345                 350

Glu Pro Gln Val Tyr Thr Leu Pro Pro Ser Arg Glu Glu Met Thr Lys
    355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn Arg Phe Thr Gln Lys Ser
    435                 440                 445

Leu Ser Leu Ser Pro Gly Lys
450                 455

<210> SEQ ID NO 212
<211> LENGTH: 453
<212> TYPE: PRT
<213> ORGANISM: Artificial Sequence
<220> FEATURE:
<223> OTHER INFORMATION: Synthetic: Humanized variant heavy chain amino
      acid sequence: hIGHV3-66*4 graft-IGHJ4-hIgG1

<400> SEQUENCE: 212

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Asn Tyr
            20                  25                  30

Asp Met Ser Trp Val Arg Gln Ala Pro Gly Lys Gly Leu Glu Trp Val
        35                  40                  45

Ser Val Ile Ser Ser Gly Gly Thr Tyr Pro Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Gly Gly Phe Leu Ile Thr Thr Arg Asp Tyr Tyr Ala Met Asp Tyr
        100                 105                 110

Trp Gly Gln Gly Thr Ser Val Thr Val Ser Ser Ala Ser Thr Lys Gly
    115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205
```

```
Asn His Lys Pro Ser Asn Thr Lys Val Asp Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn Arg Phe Thr Gln Lys Ser Leu Ser
        435                 440                 445

Leu Ser Pro Gly Lys
    450

<210> SEQ ID NO 213
<211> LENGTH: 8
<212> TYPE: PRT
<213> ORGANISM: Artificial Sequence
<220> FEATURE:
<223> OTHER INFORMATION: Synthetic: Heavy chain CDR1

<400> SEQUENCE: 213

Gly Phe Ala Phe Ser Asn Tyr Asp
1               5

<210> SEQ ID NO 214
<211> LENGTH: 8
<212> TYPE: PRT
<213> ORGANISM: Artificial Sequence
<220> FEATURE:
<223> OTHER INFORMATION: Synthetic: Heavy chain CDR1

<400> SEQUENCE: 214

Gly Phe Thr Phe Asn Thr Asn Ala
1               5

<210> SEQ ID NO 215
<211> LENGTH: 8
<212> TYPE: PRT
```

```
<213> ORGANISM: Artificial Sequence
<220> FEATURE:
<223> OTHER INFORMATION: Synthetic: Heavy chain CDR1

<400> SEQUENCE: 215

Gly Tyr Ser Phe Thr Ser Tyr Tyr
1               5

<210> SEQ ID NO 216
<211> LENGTH: 8
<212> TYPE: PRT
<213> ORGANISM: Artificial Sequence
<220> FEATURE:
<223> OTHER INFORMATION: Synthetic: Heavy chain CDR2

<400> SEQUENCE: 216

Ile Ser Ser Gly Gly Thr Tyr Pro
1               5

<210> SEQ ID NO 217
<211> LENGTH: 10
<212> TYPE: PRT
<213> ORGANISM: Artificial Sequence
<220> FEATURE:
<223> OTHER INFORMATION: Synthetic: Heavy chain CDR2

<400> SEQUENCE: 217

Ile Arg Ser Lys Ser Asn Asn Tyr Ala Thr
1               5                   10

<210> SEQ ID NO 218
<211> LENGTH: 8
<212> TYPE: PRT
<213> ORGANISM: Artificial Sequence
<220> FEATURE:
<223> OTHER INFORMATION: Synthetic: Heavy chain CDR2

<400> SEQUENCE: 218

Ile Asp Pro Phe Asn Gly Gly Thr
1               5

<210> SEQ ID NO 219
<211> LENGTH: 17
<212> TYPE: PRT
<213> ORGANISM: Artificial Sequence
<220> FEATURE:
<223> OTHER INFORMATION: Synthetic: Heavy chain CDR3
<220> FEATURE:
<221> NAME/KEY: misc_feature
<222> LOCATION: (1)..(2)
<223> OTHER INFORMATION: Xaa, if present, can be any naturally occurring
      amino acid

<400> SEQUENCE: 219

Xaa Xaa Gly Gly Phe Leu Ile Thr Thr Arg Asp Tyr Tyr Ala Met Asp
1               5                   10                  15

Tyr

<210> SEQ ID NO 220
<211> LENGTH: 14
<212> TYPE: PRT
<213> ORGANISM: Artificial Sequence
<220> FEATURE:
<223> OTHER INFORMATION: Synthetic: Heavy chain CDR3
<220> FEATURE:
<221> NAME/KEY: misc_feature
<222> LOCATION: (1)..(2)
<223> OTHER INFORMATION: Xaa, if present, can be any naturally occurring
``` amino acid

<400> SEQUENCE: 220

Xaa Xaa Tyr Gly Tyr Asp Gly Thr Phe Tyr Ala Met Asp Tyr
1               5                   10

<210> SEQ ID NO 221
<211> LENGTH: 14
<212> TYPE: PRT
<213> ORGANISM: Artificial Sequence
<220> FEATURE:
<223> OTHER INFORMATION: Synthetic: Heavy chain CDR3
<220> FEATURE:
<221> NAME/KEY: misc_feature
<222> LOCATION: (1)..(2)
<223> OTHER INFORMATION: Xaa, if present, can be any naturally occurring
      amino acid

<400> SEQUENCE: 221

Xaa Xaa Glu His Tyr Asp Tyr Asp Tyr Tyr Val Met Asp Tyr
1               5                   10

<210> SEQ ID NO 222
<211> LENGTH: 5
<212> TYPE: PRT
<213> ORGANISM: Artificial Sequence
<220> FEATURE:
<223> OTHER INFORMATION: Synthetic: Light chain CDR1

<400> SEQUENCE: 222

Ser Ser Val Ser Tyr
1               5

<210> SEQ ID NO 223
<211> LENGTH: 10
<212> TYPE: PRT
<213> ORGANISM: Artificial Sequence
<220> FEATURE:
<223> OTHER INFORMATION: Synthetic: Light chain CDR1

<400> SEQUENCE: 223

Glu Ser Val Glu Tyr Ser Gly Ala Ser Leu
1               5                   10

<210> SEQ ID NO 224
<211> LENGTH: 3
<212> TYPE: PRT
<213> ORGANISM: Artificial Sequence
<220> FEATURE:
<223> OTHER INFORMATION: Synthetic: Light chain CDR2

<400> SEQUENCE: 224

Asp Thr Ser
1

<210> SEQ ID NO 225
<211> LENGTH: 3
<212> TYPE: PRT
<213> ORGANISM: Artificial Sequence
<220> FEATURE:
<223> OTHER INFORMATION: Synthetic: Light chain CDR2

<400> SEQUENCE: 225

Ala Ala Ser
1

<210> SEQ ID NO 226

```
<211> LENGTH: 3
<212> TYPE: PRT
<213> ORGANISM: Artificial Sequence
<220> FEATURE:
<223> OTHER INFORMATION: Synthetic: Light chain CDR2

<400> SEQUENCE: 226

Glu Ile Ser
1

<210> SEQ ID NO 227
<211> LENGTH: 9
<212> TYPE: PRT
<213> ORGANISM: Artificial Sequence
<220> FEATURE:
<223> OTHER INFORMATION: Synthetic: Light chain CDR3

<400> SEQUENCE: 227

Gln Gln Trp Ser Ser Tyr Pro Pro Thr
1               5

<210> SEQ ID NO 228
<211> LENGTH: 9
<212> TYPE: PRT
<213> ORGANISM: Artificial Sequence
<220> FEATURE:
<223> OTHER INFORMATION: Synthetic: Light chain CDR3

<400> SEQUENCE: 228

Gln Gln Ser Arg Lys Val Pro Ser Thr
1               5

<210> SEQ ID NO 229
<211> LENGTH: 8
<212> TYPE: PRT
<213> ORGANISM: Artificial Sequence
<220> FEATURE:
<223> OTHER INFORMATION: Synthetic: Light chain CDR3

<400> SEQUENCE: 229

Gln Gln Trp Ser Tyr Pro Phe Thr
1               5

<210> SEQ ID NO 230
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: X is Q or V
<220> FEATURE:
<221> NAME/KEY: misc_feature
<222> LOCATION: (9)..(9)
<223> OTHER INFORMATION: X is A, S, or D
<220> FEATURE:
<221> NAME/KEY: misc_feature
<222> LOCATION: (17)..(17)
<223> OTHER INFORMATION: X is E or D
<220> FEATURE:
<221> NAME/KEY: misc_feature
<222> LOCATION: (22)..(22)
<223> OTHER INFORMATION: X is T, N, or S
<220> FEATURE:
<221> NAME/KEY: misc_feature
<222> LOCATION: (24)..(24)
<223> OTHER INFORMATION: X is K or R
<220> FEATURE:
<221> NAME/KEY: misc_feature
```

```
<222> LOCATION: (25)..(25)
<223> OTHER INFORMATION: X is S or A
<220> FEATURE:
<221> NAME/KEY: misc_feature
<222> LOCATION: (27)..(27)
<223> OTHER INFORMATION: X is L or M
<220> FEATURE:
<221> NAME/KEY: misc_feature
<222> LOCATION: (28)..(37)
<223> OTHER INFORMATION: XXXXXXXXXX, if present, can be ESVEYYDTSL (SEQ
      ID NO:231), ESVEYSGASL (SEQ ID NO:223),or SSVSY (SEQ ID NO:222)
<220> FEATURE:
<221> NAME/KEY: misc_feature
<222> LOCATION: (38)..(38)
<223> OTHER INFORMATION: X is Q or is absent
<220> FEATURE:
<221> NAME/KEY: misc_feature
<222> LOCATION: (39)..(39)
<223> OTHER INFORMATION: X is A or Q
<220> FEATURE:
<221> NAME/KEY: misc_feature
<222> LOCATION: (47)..(47)
<223> OTHER INFORMATION: X is K or Q
<220> FEATURE:
<221> NAME/KEY: misc_feature
<222> LOCATION: (48)..(48)
<223> OTHER INFORMATION: X is P or A
<220> FEATURE:
<221> NAME/KEY: misc_feature
<222> LOCATION: (55)..(57)
<223> OTHER INFORMATION: XXX can be AAS (SEQ ID NO:225) or DTS
      (SEQ ID NO:224)
<220> FEATURE:
<221> NAME/KEY: misc_feature
<222> LOCATION: (59)..(59)
<223> OTHER INFORMATION: X is V or R
<220> FEATURE:
<221> NAME/KEY: misc_feature
<222> LOCATION: (60)..(60)
<223> OTHER INFORMATION: X is E or A
<220> FEATURE:
<221> NAME/KEY: misc_feature
<222> LOCATION: (61)..(61)
<223> OTHER INFORMATION: X is S or T
<220> FEATURE:
<221> NAME/KEY: misc_feature
<222> LOCATION: (63)..(63)
<223> OTHER INFORMATION: X is V or I
<220> FEATURE:
<221> NAME/KEY: misc_feature
<222> LOCATION: (65)..(65)
<223> OTHER INFORMATION: X is D, A, or S
<220> FEATURE:
<221> NAME/KEY: misc_feature
<222> LOCATION: (84)..(84)
<223> OTHER INFORMATION: X is Q or E
<220> FEATURE:
<221> NAME/KEY: misc_feature
<222> LOCATION: (85)..(85)
<223> OTHER INFORMATION: X is A, E, or P
<220> FEATURE:
<221> NAME/KEY: misc_feature
<222> LOCATION: (88)..(88)
<223> OTHER INFORMATION: X is V or F
<220> FEATURE:
<221> NAME/KEY: misc_feature
<222> LOCATION: (90)..(90)
<223> OTHER INFORMATION: X is V or T
<220> FEATURE:
<221> NAME/KEY: misc_feature
<222> LOCATION: (92)..(92)
<223> OTHER INFORMATION: X is Y or F
<220> FEATURE:
<221> NAME/KEY: misc_feature
<222> LOCATION: (94)..(102)
<223> OTHER INFORMATION: XXXXXXXXX is QQSRKVPWT (SEQ ID NO:232),
      QQSRKVPST (SEQ ID NO:228), or QQWSSYPPT (SEQ ID NO:227)
<220> FEATURE:
<221> NAME/KEY: misc_feature
```

<222> LOCATION: (105)..(105)
<223> OTHER INFORMATION: X is Q or G
<220> FEATURE:
<221> NAME/KEY: misc_feature
<222> LOCATION: (109)..(109)
<223> OTHER INFORMATION: X is L or V

<400> SEQUENCE: 230

Asp Ile Xaa Met Thr Gln Ser Pro Xaa Ser Leu Ala Val Ser Leu Gly
1               5                   10                  15

Xaa Arg Ala Thr Ile Xaa Cys Xaa Xaa Ser Xaa Xaa Xaa Xaa Xaa Xaa
            20                  25                  30

Xaa Xaa Xaa Xaa Xaa Xaa Xaa Trp Tyr Gln Gln Lys Pro Gly Xaa Xaa
        35                  40                  45

Pro Lys Leu Leu Ile Tyr Xaa Xaa Xaa Asn Xaa Xaa Xaa Gly Xaa Pro
    50                  55                  60

Xaa Arg Phe Ser Gly Ser Gly Ser Gly Thr Asp Phe Thr Leu Thr Ile
65              70                  75                  80

Ser Ser Leu Xaa Xaa Glu Asp Xaa Ala Xaa Tyr Xaa Cys Xaa Xaa Xaa
                85                  90                  95

Xaa Xaa Xaa Xaa Xaa Xaa Phe Gly Xaa Gly Thr Lys Xaa Glu Ile Lys
            100                 105                 110

<210> SEQ ID NO 231
<211> LENGTH: 10
<212> TYPE: PRT
<213> ORGANISM: Artificial Sequence
<220> FEATURE:
<223> OTHER INFORMATION: Synthetic

<400> SEQUENCE: 231

Glu Ser Val Glu Tyr Tyr Asp Thr Ser Leu
1               5                   10

<210> SEQ ID NO 232
<211> LENGTH: 9
<212> TYPE: PRT
<213> ORGANISM: Artificial Sequence
<220> FEATURE:
<223> OTHER INFORMATION: Synthetic

<400> SEQUENCE: 232

Gln Gln Ser Arg Lys Val Pro Trp Thr
1               5

<210> SEQ ID NO 233
<211> LENGTH: 126
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: X is A or T
<220> FEATURE:
<221> NAME/KEY: misc_feature
<222> LOCATION: (26)..(33)
<223> OTHER INFORMATION: XXXXXXX can be GFTFTESF (SEQ ID NO:234),
     GFTFNTNA (SEQ ID NO:214), or GFAFSNYD (SEQ ID NO:213)
<220> FEATURE:
<221> NAME/KEY: misc_feature
<222> LOCATION: (35)..(35)
<223> OTHER INFORMATION: X is S, D, or N
<220> FEATURE:
<221> NAME/KEY: misc_feature
<222> LOCATION: (37)..(37)

```
<223> OTHER INFORMATION: X is F, I, or V
<220> FEATURE:
<221> NAME/KEY: misc_feature
<222> LOCATION: (40)..(40)
<223> OTHER INFORMATION: X is P or A
<220> FEATURE:
<221> NAME/KEY: misc_feature
<222> LOCATION: (44)..(44)
<223> OTHER INFORMATION: X is G or A
<220> FEATURE:
<221> NAME/KEY: misc_feature
<222> LOCATION: (48)..(48)
<223> OTHER INFORMATION: X is L or V
<220> FEATURE:
<221> NAME/KEY: misc_feature
<222> LOCATION: (49)..(49)
<223> OTHER INFORMATION: X is S, G, or A
<220> FEATURE:
<221> NAME/KEY: misc_feature
<222> LOCATION: (50)..(50)
<223> OTHER INFORMATION: X is F, R, or V
<220> FEATURE:
<221> NAME/KEY: misc_feature
<222> LOCATION: (51)..(60)
<223> OTHER INFORMATION: XXXXXXXXXX, if present, can be IRNKANGYTT (SEQ
      ID NO:235), IRSKSNNYAT (SEQ ID NO:217), or ISSGGTYP
      (SEQ ID NO:216)
<220> FEATURE:
<221> NAME/KEY: misc_feature
<222> LOCATION: (61)..(61)
<223> OTHER INFORMATION: X is E, Y, or is absent
<220> FEATURE:
<221> NAME/KEY: misc_feature
<222> LOCATION: (64)..(64)
<223> OTHER INFORMATION: X is A or D
<220> FEATURE:
<221> NAME/KEY: misc_feature
<222> LOCATION: (68)..(68)
<223> OTHER INFORMATION: X is G or D
<220> FEATURE:
<221> NAME/KEY: misc_feature
<222> LOCATION: (76)..(76)
<223> OTHER INFORMATION: X is D or N
<220> FEATURE:
<221> NAME/KEY: misc_feature
<222> LOCATION: (79)..(79)
<223> OTHER INFORMATION: X is S or N
<220> FEATURE:
<221> NAME/KEY: misc_feature
<222> LOCATION: (80)..(80)
<223> OTHER INFORMATION: X is I, S, or T
<220> FEATURE:
<221> NAME/KEY: misc_feature
<222> LOCATION: (81)..(81)
<223> OTHER INFORMATION: X is A or L
<220> FEATURE:
<221> NAME/KEY: misc_feature
<222> LOCATION: (89)..(89)
<223> OTHER INFORMATION: X is K or R
<220> FEATURE:
<221> NAME/KEY: misc_feature
<222> LOCATION: (90)..(90)
<223> OTHER INFORMATION: X is T or A
<220> FEATURE:
<221> NAME/KEY: misc_feature
<222> LOCATION: (99)..(99)
<223> OTHER INFORMATION: X is A or V
<220> FEATURE:
<221> NAME/KEY: misc_feature
<222> LOCATION: (100)..(100)
<223> OTHER INFORMATION: X is R, T, or K
<220> FEATURE:
<221> NAME/KEY: misc_feature
<222> LOCATION: (101)..(115)
<223> OTHER INFORMATION: XXXXXXXXXXXXXXX, if present, can be GGEYPLYVMDY
      (SEQ ID NO:236), EHYDYDYYVMDY (SEQ ID NO:221), or GGFLITTRDYYAMDY
      (SEQ ID NO:219)
<220> FEATURE:
<221> NAME/KEY: misc_feature
```

<222> LOCATION: (121)..(121)
<223> OTHER INFORMATION: X is L or S

<400> SEQUENCE: 233

Glu Val Gln Leu Val Glu Ser Gly Gly Gly Leu Val Gln Pro Gly Arg
1               5                   10                  15

Ser Leu Arg Leu Ser Cys Xaa Ala Ser Xaa Xaa Xaa Xaa Xaa Xaa
            20                  25                  30

Xaa Met Xaa Trp Xaa Arg Gln Xaa Pro Gly Lys Xaa Leu Glu Trp Xaa
        35                  40                  45

Xaa Xaa Xaa Xaa Xaa Xaa Xaa Xaa Xaa Xaa Xaa Xaa Tyr Ala Xaa
    50                  55                  60

Ser Val Lys Xaa Arg Phe Thr Ile Ser Arg Asp Xaa Ser Lys Xaa Xaa
65              70                  75                  80

Xaa Tyr Leu Gln Met Asn Ser Leu Xaa Xaa Glu Asp Thr Ala Val Tyr
            85                  90                  95

Tyr Cys Xaa Xaa Xaa Xaa Xaa Xaa Xaa Xaa Xaa Xaa Xaa Xaa
        100                 105                 110

Xaa Xaa Xaa Trp Gly Gln Gly Thr Xaa Val Thr Val Ser Ser
        115                 120                 125

<210> SEQ ID NO 234
<211> LENGTH: 8
<212> TYPE: PRT
<213> ORGANISM: Artificial Sequence
<220> FEATURE:
<223> OTHER INFORMATION: Synthetic

<400> SEQUENCE: 234

Gly Phe Thr Phe Thr Glu Ser Phe
1               5

<210> SEQ ID NO 235
<211> LENGTH: 10
<212> TYPE: PRT
<213> ORGANISM: Artificial Sequence
<220> FEATURE:
<223> OTHER INFORMATION: Synthetic

<400> SEQUENCE: 235

Ile Arg Asn Lys Ala Asn Gly Tyr Thr Thr
1               5                   10

<210> SEQ ID NO 236
<211> LENGTH: 11
<212> TYPE: PRT
<213> ORGANISM: Artificial Sequence
<220> FEATURE:
<223> OTHER INFORMATION: Synthetic

<400> SEQUENCE: 236

Gly Gly Glu Tyr Pro Leu Tyr Val Met Asp Tyr
1               5                   10

<210> SEQ ID NO 237
<211> LENGTH: 453
<212> TYPE: PRT
<213> ORGANISM: Artificial Sequence
<220> FEATURE:
<223> OTHER INFORMATION: Synthetic: hIGHV3-73graft 3F6

<400> SEQUENCE: 237

Glu Val Gln Leu Val Glu Ser Gly Gly Gly Leu Val Gln Pro Gly Gly

-continued

```
1               5                   10                  15
Ser Leu Arg Leu Ser Cys Ala Ala Ser Gly Phe Thr Phe Asn Thr Asn
                20                  25                  30
Ala Met Asn Trp Val Arg Gln Ala Pro Gly Lys Gly Leu Glu Trp Val
                35                  40                  45
Gly Arg Ile Arg Ser Lys Ser Asn Asn Tyr Ala Thr Tyr Tyr Ala Asp
                50                  55                  60
Ser Val Lys Asp Arg Phe Thr Ile Ser Arg Asp Asp Ser Lys Asn Ser
65                  70                  75                  80
Leu Tyr Leu Gln Met Asn Ser Leu Lys Thr Glu Asp Thr Ala Val Tyr
                85                  90                  95
Tyr Cys Val Thr Glu His Tyr Asp Tyr Asp Tyr Val Met Asp Tyr
                100                 105                 110
Trp Gly Gln Gly Thr Ser Val Thr Val Ser Ser Ala Ser Thr Lys Gly
                115                 120                 125
Pro Ser Val Phe Pro Leu Ala Pro Ser Ser Lys Ser Thr Ser Gly Gly
                130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
                195                 200                 205
Asn His Lys Pro Ser Asn Thr Lys Val Asp Lys Lys Val Glu Pro Lys
        210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
                260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
        290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Glu Glu Met Thr Lys Asn Gln
                355                 360                 365
Val Ser Leu Thr Cys Leu Val Lys Gly Phe Tyr Pro Ser Asp Ile Ala
                370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
                420                 425                 430
```

Val Met His Glu Ala Leu His Asn His Tyr Thr Gln Lys Ser Leu Ser
        435                 440                 445

Leu Ser Pro Gly Lys
    450

<210> SEQ ID NO 238
<211> LENGTH: 453
<212> TYPE: PRT
<213> ORGANISM: Artificial Sequence
<220> FEATURE:
<223> OTHER INFORMATION: Synthetic: hIGHV3-23graft 3F6

<400> SEQUENCE: 238

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ser Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Thr Glu His Tyr Asp Tyr Asp Tyr Tyr Val Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

```
Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 239
<211> LENGTH: 453
<212> TYPE: PRT
<213> ORGANISM: Artificial Sequence
<220> FEATURE:
<223> OTHER INFORMATION: Synthetic: Fc variant 40 of 78

<400> SEQUENCE: 239

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Gly Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Thr Glu His Tyr Asp Tyr Asp Tyr Val Met Asp Tyr
            100                 105                 110

Trp Gly Gln Gly Thr Ser Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240
```

```
Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
        260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn Arg Phe Thr Gln Lys Ser Leu Ser
            435                 440                 445

Leu Ser Pro Gly Lys
        450

<210> SEQ ID NO 240
<211> LENGTH: 453
<212> TYPE: PRT
<213> ORGANISM: Artificial Sequence
<220> FEATURE:
<223> OTHER INFORMATION: Synthetic: Fc variant 40 of 80

<400> SEQUENCE: 240

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ser Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Thr Glu His Tyr Asp Tyr Asp Tyr Val Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140
```

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Gln Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn Arg Phe Thr Gln Lys Ser Leu Ser
            435                 440                 445

Leu Ser Pro Gly Lys
        450

<210> SEQ ID NO 241
<211> LENGTH: 453
<212> TYPE: PRT
<213> ORGANISM: Artificial Sequence
<220> FEATURE:
<223> OTHER INFORMATION: Synthetic: hIGHV3-66* graft 5A10

<400> SEQUENCE: 241

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Asn Tyr
            20                  25                  30

Asp Met Ser Trp Val Arg Gln Ala Pro Gly Lys Gly Leu Glu Trp Val
        35                  40                  45

-continued

```
Ser Val Ile Ser Ser Gly Gly Thr Tyr Pro Tyr Ala Asp Ser Val Lys
         50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Gly Phe Leu Ile Thr Thr Arg Asp Tyr Tyr Ala Met Asp Tyr
                100                 105                 110

Trp Gly Gln Gly Thr Ser Val Thr Val Ser Ser Ala Ser Thr Lys Gly
                115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
        450
```

<210> SEQ ID NO 242
<211> LENGTH: 453
<212> TYPE: PRT
<213> ORGANISM: Artificial Sequence
<220> FEATURE:
<223> OTHER INFORMATION: Synthetic: Fc variant 40 of 86

<400> SEQUENCE: 242

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Asn Tyr
            20                  25                  30

Asp Met Ser Trp Val Arg Gln Ala Pro Gly Lys Gly Leu Glu Trp Val
        35                  40                  45

Ser Val Ile Ser Ser Gly Gly Thr Tyr Pro Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Phe Leu Ile Thr Thr Arg Asp Tyr Tyr Ala Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365
```

```
Val Ser Leu Thr Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu His Asn Arg Phe Thr Gln Lys Ser Leu Ser
        435             440             445

Leu Ser Pro Gly Lys
    450
```

IMMUNOGLOBULINS AND VARIANTS DIRECTED AGAINST PATHOGENIC MICROBES

PRIORITY CLAIM

This application is a continuation of U.S. patent application Ser. No. 15/433,963, filed Feb. 15, 2017 and now pending, which is a continuation of U.S. patent application Ser. No. 14/923,221, filed Oct. 26, 2015 and now abandoned, which is a continuation of U.S. patent application Ser. No. 14/318,551, filed Jun. 27, 2014 and now U.S. Pat. No. 9,988,439 and is also a continuation in part of U.S. patent application Ser. No. 14/312,585, filed Jun. 23, 2014 and now U.S. Pat. No. 9,416,171, which is a continuation of International Patent Application No. PCT/US2012/071556, filed Dec. 23, 2012, which claims the benefit of U.S. Provisional Application No. 61/580,194, filed Dec. 23, 2011, the subject matter of all of which is hereby incorporated by reference as if fully set forth herein.

BACKGROUND

Pathogenic microbes, such as gram-positive cocci, can produce an array of secreted or cell surface-associated virulence factors, which are capable of interfering with the host immune responses. A number of such virulence factors are binding proteins, which contain one or more domains that bind to host immunoglobulins. Such Immunoglobulin binding virulence factors which bind to the heavy chain constant region of the immunoglobulin are referred to at Immunoglobulin Binding Proteins (IgBPs). A subset of Immunoglobulin Binding Proteins, which interact with the Fc region of immunoglobulins, are referred to as Fc Binding proteins (FcBPs). This non-immune binding of immunoglobulins by IgBPs involves regions of the immunoglobulin outside of the antigen-antibody combining site. Such non-immune binding of host immunoglobulins by microbial virulence factors is thought to subvert the host anti-microbial immune response. Functionally, this can occurs through immuno-shielding by coating of the bacteria with Fc bound antibody, by blocking immunoglobulin Fc-mediated effector functions such as complement activation or Fc-receptor mediated binding to effector cells, or by expression of superantigens which interact with immune cell surface receptors.

In the case of *Staphylococcus aureus* (*S. aureus*), a number of immunoglobulin binding proteins are expressed, including Protein A (SpA), Sbi, SSL7 and SSL10.

There is some evidence that it is possible to generate an antibody response to highly purified surface components of *S. aureus* such as capsular polysaccharide, the collagen-binding protein Cna and the fibrinogen-binding protein ClfA. This has led to the discovery and clinical testing of a number of antibodies based therapies directed against such *S. aureus* antigens.

Despite promising preclinical activity, clinical trials of such agents have been met with little success. Infants with very low birth weights (<1500 g; <32 weeks gestation) are at a particular risk for nosocomial bacterial infection, as they have not benefited from trans-placental transfer of maternal antibodies. Many of these infections are caused by *S. aureus*. Altastaph® is a vaccine-induced hyperimmune polyclonal antibody with specificity for *S. aureus* serotype 5 and 8, developed by Nabi Biopharmaceuticals (US20060153857 A1). In spite of reaching target serum antibody levels, no decrease in *S. aureus* infection rates was observed in treatment groups in two clinical trials (Rupp et al., 2007; DeJonge et al., 2007). A second anti-*S. aureus* human immune sera, INH-A21 (Veronate®) was prepared by first screening donors for high titres against MSCRAMM (microbial surface components recognizing adhesion matrix molecules), (Inhibitex—U.S. Pat. No. 6,692,739). Although Phase II trials appeared promising at the highest antibody dose, Phase III of the trial did not observe any effect of antibody treatment in reducing the frequency of *S. aureus* infection.

Additional antibodies or antibody derived molecules which have been under development include Aurograb, an antibody that targets the immunodominant ABC transporter in MRSA (Weems et al., 2006), which was designed to blocks the multi-drug efflux pump, allowing antibiotics to retain effectivity; tefibazumab (Aurexis®) (U.S. Pat. No. 6,979,446), which targets Clumping Factor A (ClfA) and pagibaximab (BYSX-A110, US20080019976 A1), a chimeric antibody which binds lipoteichoic acid (LTA) present in the membrane of gram-positive bacteria. Elusys Therapeutics has also attempted to developed a bispecific heteropolymer antibody by cross-linking an antibody directed against SpA with a second antibody the recognizes the CR1 receptors (WO 2008/140487 A2).

Currently, none of the approaches described above have shown significant activity in clinical trials. The development of new antibody based agents which overcome microbial immune evasion for the treatment or prevention of microbial infections, including *S. aureus*, is an important goal that would be of great clinical benefit.

SUMMARY

The embodiments described herein provide for anti-microbial variant antibodies, which have attenuated non-immune binding (binding to residues outside of the antigen-antibody combining site) to one or more microbial immunoglobulin binding proteins (IgBPs).

According to the embodiments described herein, the disclosure provides anti-microbial monoclonal antibodies. In one embodiment, an anti-microbial variant antibody is provided that includes an immunoglobulin heavy chain (e.g., an IgG heavy chain) that differs from that of its unmodified parent anti-microbial antibody by at least one amino acid substitution, wherein the variant immunoglobulin heavy chain has attenuated non-immune binding to one or more microbial virulence factors as compared to that of the unmodified parent antibody. In one aspect, the variant anti-microbial IgG antibody includes a variant heavy chain, in which at least one amino acid from the IgG heavy chain constant region is substituted with another amino acid which is different from that present in the parent antibody.

In some embodiments, the monoclonal antibody is a chimeric, humanized of human anti-microbial IgG variant antibody, in which at least one amino acid from the IgG heavy chain constant region, is substituted with another amino acid which is different from that present in the parent antibody. Such variant anti-microbial antibodies have attenuated heavy chain constant region binding to one or more microbial IgBPs or IgBP domains expressed by the target microbe.

The variant immunoglobulin IgG heavy chain constant regions described herein can be combined with immunoglobulin variable heavy and light chain regions which bind antigens produced by microbes that express one or more microbial IgBP.

In some embodiments, the variable domain of the antibody binds to a microbial protein that is a microbial immunoglobulin binding protein, and the heavy chain constant region of the antibody is a variant which has attenuated binding to one or more microbial IgBPs or IgBP domains expressed by the target microbe.

In other embodiments, the variable domain of the antibody binds to a microbial protein that is not an microbial immunoglobulin binding protein, and the heavy chain constant region of the antibody is a variant which has attenuated binding to one or more microbial IgBPs or IgBP domains expressed by the target microbe.

The anti-microbial heavy chain constant region variant IgG immunoglobulins claimed herein have enhanced antimicrobial activity relative to their parental antibodies. For example, in the case of S. aureus, an important human pathogen for which there is an urgent unmet therapeutic need, a number of IgBPs can be expressed, including SpA, Sbi, SSL7 and SSL10.

In some embodiments the target microbe is S. aureus. Heavy chain constant region variant IgG immunoglobulins are described, which have attenuated binding to one or more S. aureus IgBPs due to the introduction of one or more amino acid substitutions in the heavy chain constant region domain relative to the parental IgG.

In some embodiments in which the target microbe is S. aureus, such heavy chain constant region variant IgG polypeptide sequences are combined with immunoglobulin heavy chain variable polypeptide sequences and light chains polypeptide sequences, which bind one or more cell surface or secreted S. aureus antigen.

In some embodiments, the S. aureus antigen recognized by the variable domain of variant antibodies are cell surface or secreted antigens selected from the list which includes but is not limited to: ClfA, ClfB, Cna, Eap, Ebh, EbpS, FnBPA, FnBPB, IsaA, IsaB, IsdA, IsdB, IsdH, SasB, SasC, SasD, SasF, SasG, SasH, SasK, SdrC, SdrD, SdrE, Spa, SraP, Coa, Ecb, Efb, Emp, EsaC, EsxA, EssC, FLIPr, FLIPr like, Sbi, SCIN-B, SCIN-C, VWbp, SpA, LTA, CP5, CP8, PNAG, dPNAG, alpha toxin, CHIPS, PVL leukocidin, α, β and γ-hemolysins, SAK, Sea, Sep, Seb, Epa, Efb, SCIN, Exfoliatins ETB and ETA, Staphylococcal Enterotoxins SEA, SEB, SECn, SED, SEG, SHE, and SEI, Toxic-shock syndrome toxin TSST-1, Alpha Toxin, Beta toxin, Delta toxin.

In some embodiments, the antigen recognized by the variable domain of the antibody or its heavy chain constant region variants is *S. aureus* SpA. In such embodiments, the microbial antigen recognized by the variable domain of the variant IgG antibody is an epitope found in one or more of the repeat homology IgBP domains of *S. aureus* SpA (referred to as SpA domains E, D, A, B, and C).

In some embodiments, the antigen recognized by the variable domain of the antibody or its heavy chain constant region variants is *S. aureus* Sbi. In such embodiments, the antigen epitope recognized by the variable domain of the antibody or its variants is located in one or more of the Sbi IgBP binding domains I and II.

In some embodiments, the antigen epitope recognized by the variable domain of the antibody or its heavy chain constant region variants is found in two or more of the repeat IgBP homology domains of SpA or Sbi, selected from the list SpA domains E, D, A, B, and C, and Sbi domains I and II.

In some embodiments, the antigen epitope recognized by the variable domain of the antibody or its heavy chain constant region variants is found in one more of the repeat IgBP homology domains of both SpA and Sbi, selected from the list SpA domains E, D, A, B, and C, and Sbi domains I and II.

Described herein are methods of producing monoclonal antibodies that recognize SpA and/or Sbi, methods for selecting antibodies that cross react with multiple SpA IgBP domains (selected from SpA domains E, D, A, B, and C) and/or Sbi (selected from Sbi domains I and II), methods of selecting antibodies that cross react with one or more SpA IgG binding domains and Sbi domains I and/or II, methods of assaying for antigen binding to SpA or Sbi using variant IgG1 antibodies, having one or more amino acid substitutions in the heavy chain constant region which prevent heavy chain constant region binding to SpA, Sbi or SSL10. In some aspects, the variant Fc domain used for antibody selection is of human isotype IgG1 having one or more of the following amino acid substitutions: a His to Arg substitution at position 435, a Tyr to Phe substitution at position 436 and a Arg to Gln at position 274. In one aspect, the variant Fc domain used for antibody selection is of human isotype IgG1 and has a His to Arg substitution at position 435, a Tyr to Phe substitution at position 436 and a Arg to Gln at position 274. In another aspect, the variant Fc domain used for antibody selection is of human isotype IgG1 and has a His to Arg substitution at position 435. The uses of such Fc variants are important so as to differentiate antigen specific binding of the antibody from Fc mediated binding to Sbi and or SpA (positions refer to EU numbering).

In an additional embodiment, modification of human or humanized VH3 family derived anti-*S. aureus* IgG variable heavy domain residues are claimed which abrogate super-antigen type binding of SpA to anti *S. aureus* immunoglobulins or their heavy chain constant region variants.

In an additional embodiment, the antigen recognized by the variable domain of the claimed heavy chain constant region variant immunoglobulins is *S. aureus* Clumping factor A (ClfA).

In additional embodiments, heavy chain constant region variant anti-*S. aureus* antibodies are provided in which the human, humanized, or chimeric variable domain, or variable domain CDRs of the antibody are derived from an anti-*S. aureus* antibodies selected from the list: Pagibaximab (a chimeric anti-LTA antibody; Biosynexus/Medimmune), Tefibazumab (a humanized IgG1 anti-ClfA; Aurexis, Inhibitex/BMS), CS-D7 (human anti-IsdB IgG1, Merck), Aurograb (scFv fragment anti ABC transporter; NeuTec/Novartis), anti-Alpha toxin (Medimmune patent application WO/2012/109285).

In other embodiments, affinity matured heavy chain constant region variant anti-*S. aureus* antibodies are provided in which human, humanized, or chimeric variable domain of the antibody are derived from an anti-*S. aureus* antibodies selected from the list including, but not limited to: Pagibaximab (a chimeric anti-LTA; Biosynexus/Medimmune), Tefibazumab (a humanized IgG1 anti-ClfA, Inhibitex/BMS), CS-D7 (a humanized anti-IsdB IgG1, Merck), Aurograb (an scFv fragment anti-ABC transporter; NeuTec/Novartis), anti-Alpha toxin (Medimmune patent application WO/2012/109285). Such claimed affinity matured Heavy chain constant region variant antibodies have at least one amino acid substitution, deletion or insertion relative to the parental heavy or light chain variable domain sequences.

In additional embodiments, the disclosure also relates to the prophylactic or therapeutic use of such anti-microbial immunoglobulins and their heavy chain constant region variants, and their use in combinations with additional antimicrobial chemotherapy or anti-infective agents or in combination with one or more additional antimicrobial immunoglobulins or variant immunoglobulins.

The disclosure also relates to the prophylactic or therapeutic use of such anti-microbial immunoglobulins and their heavy chain constant region variants, and their use in combinations with additional antimicrobial chemotherapy or anti-infective agents or in combination with one or more additional antimicrobial immunoglobulins or variant immunoglobulins for use in veterinary or animal use.

The anti-microbial heavy chain constant region variants immunoglobulins described herein, which have enhanced anti-microbial activity relative to their parental antibodies, may be used for the prophylactic or therapeutic treatment of a number of important infectious diseases.

BRIEF DESCRIPTION OF THE DRAWINGS

FIG. 1 is a schematic diagram showing the domain organization of an IgG polypeptide according to some embodiments.

FIG. 5 shows a sequence alignment of human IgG sequences IgG1, IgG2, IgG3 and IgG4 for the CH1 region (SEQ ID NOs: 68-71), the Hinge Sequence (SEQ ID NOs: 72-75), the CH2 sequence (SEQ ID NOs: 76-79) and the CH3 sequence (SEQ ID NOs: 80-83).

FIG. 6 is a table showing Human IgG1 allotypes.

FIG. 7 illustrates the allotypes of the gamma chain of human IgG3. The positions of amino acid substitutions in the gamma chain of IgG 1, 2 and 4 are compared to IgG3 allotypes.

FIG. 8 illustrates domain B of Spa with inter-domain substitutions. Panel A shows domain B of SpA interacting with an IgG Fc domain. Inter-domain substitution positions are shown in yellow and by arrows. Panel B shows a close up of the interaction of SpA domain B with the IgG constant region. The structure encompasses the IgG CH2-CH3 interface. Alpha Helices are shown as cylinders (within the circle). SpA Helix I and II (Helix III is not shown), which form the binding interface with residues within the IgG CH2-CH3 region, are shown. Amino acids of the backbone (worm representation) and side chains which vary between domains B and domains E, D, A and C (FIG. 2) are shown in yellow and by arrows. Diagram made using Cn3D using and PDB ID 1FC2).

FIG. 9A shows Domain D of SpA interacting with the Fab domain of a human IgM. The diagram is adapted from Grille, et al., 2000 using Cn3D (PDB ID: 1DEE). Helix II and III, which form the binding interface with residues within the VH3 Fab, are shown. Amino acid backbone (worm representation) and side chains are shown. The position of amino acids which vary between domains E, D, A, B, and C (FIG. 2) are shown in yellow (inter-domain substitutions). The contact residues which form the binding interface are conserved among all SpA Ig-binding domains, suggesting that each could bind in a similar manner. FIGS. 9B and 9C show close ups of the interactions from different angles.

FIG. 12) were analyzed. Amino acids within Helix I are highly conserved between Sbi domains I and II. Conservation is also found between Sbi domains I and II and SpA Fc binding domains within SpA helix I, and a number of amino acids in SpA Helix II (* in FIG. 12B). Invariant residues (conserved in SpA domains and Sbi domains I and II) were mapped onto the model of Spa domain B (Helix I and II shown) binding to the Fc region of IgG. Important residues (yellow residues and arrows) that interact with Fc domain are conserved between SpA domains and Sbi domains. In addition to these invariant residues, a number of residues are found in Sbi domains I and II that are present in some SpA domains (FIG. 12). Thus, the Fc binding interface of Sbi and SpA has a high degree of conservation.

FIG. 14 (SEQ ID NOs: 159-180) shows the amino acid sequence of the individual Sbi IgBP domains from sequenced stains of S. aureus. Panel A illustrates multiple sequence alignment of Sbi domain I. Panel B illustrates multiple sequence alignment of Sbi domain II.

FIG. 14), using the structure of SpA domain B. Sbi was analyzed for inter-strain substitutions within domains I and II. One Sbi amino acids within Domain I of strain CC239_JKD6009 was found to differ. This substitution (yellow residue and arrow in FIG. 15) is located in the predicted Helix I of Sbi. This position is not conserved between Sbi domains I and II. The position of this substitution (amino acid N to S substitution) was mapped onto the model of SpA domain B (Helix I and II shown) binding to the Fc region of IgG. As shown, the residue (yellow residue and arrow) is not predicted to form an interaction with the Fc domain.

FIG. 16 is an SDS-PAGE and Western blot of anti-SpA parental antibody MAB1 (upper panels) and anti-SpA-variant antibody MAB2 (Lower panels).

FIG. 17 is an SDS-PAGE and Western blot of anti-ClfA parental antibody MAB3 (upper panels) and variant antibody MAB4 (Lower panels).

FIG. 36 shows the amino acid sequence of the light chain (SEQ ID NO:58) and heavy chain SEQ ID NO:59) of a CS-D7 parental monoclonal antibody.

FIG. 37 shows the amino acid sequence of three light chains (SEQ ID NOs:60-62) and three heavy chains (SEQ ID NOs:63-65) of an anti-LTA parental monoclonal antibody.

DETAILED DESCRIPTION

Figure 2:
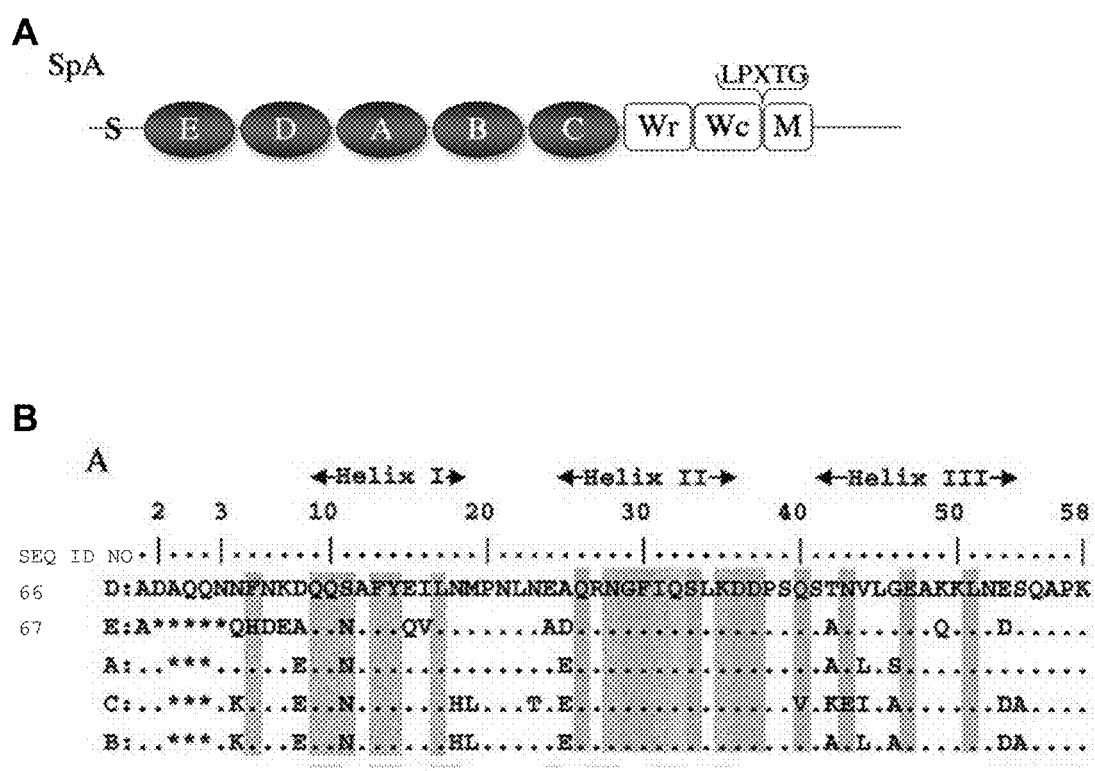
FIG. 2 is a schematic diagram illustrates the domain organization of the SpA (SpA) polypeptide (Panel A) and shows the sequence alignment of the five highly homologous extracellular Ig-binding domains of SpA in tandem, designated domains E (SEQ ID NO: 67), D (SEQ ID NO: 66), A, B, and C (Panel B).

Antibodies and variant antibodies that may be used to reduce, treat or eliminate pathogenic microbes and/or associated virulence factors are provided herein. The variant antibodies described herein have enhanced antimicrobial activity relative to their parent antibody. In some embodiments, the enhanced antimicrobial activity is due to at least one amino acid substitution—as compared to the parent antibody—that gives rise to a variant heavy chain constant region, a variant variable region, or both. As described below, such variant constant and variable regions may result in attenuated non-immune binding to one or more virulence factors produced by a targeted pathogenic microbe. Virulence factor binding that may be affected by the variant heavy chain constant and heavy chain variable regions described herein include virulence factors that involve non-immune binding to an antibody (e.g., immunoglobulin binding proteins (IgBPs), Fc binding proteins (FcBPs) and superantigens which interact with the Fab domain). Variant antibodies of the invention are directed against microbial antigens, including virulence factors and IgBPs. Antibodies and variant antibodies described herein can be affinity matured, resulting in enhanced antigen specific immune binding.

Microbial Targets

The antibodies and variant antibodies described herein may be designed to target the effector function of any pathogenic microbe including, but not limited to, bacteria (e.g., bacteria from the following genare: *Bordetella, Borrelia, Brucilla, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio, Yersinia*), viruses (e.g. Adenovirus, Coxsackievirus, Epstein-Barr virus, Hepatitis A virus, Hepatitis B virus, Hepatitis C virus, Herpes simplex virus, type 1, Herpes simplex virus, type 2, cytomegalovirus, Human herpesvirus, type 8, HIV, Influenza virus, measles virus, Mumps virus, Human papillomavirus, Parainfluenza virus, Poliovirus, Rabies virus, Respiratory syncytial virus, Rubella virus, Varicella-zoster virus), and parasites (e.g., *Acanthamoeba, Anisakis, Balantidium coli, Entamoeba histolytica, Giardia lamblia, Leishmania, Plasmodium falciparum, Schistosoma, Toxoplasma gondii, Trypanosoma*).

In certain embodiments, the antibodies and variant antibodies may be designed to target the pathogenic gram positive bacteria, such as Staphylococci *aureus* (*S. aureus*) and group A *Streptococcus* (GAS). *S. aureus* and GAS are prominent Gram-positive human pathogens responsible for a wide spectrum of superficial and invasive disease conditions (Nizet, 2007). *S. aureus* accounts for >10 million skin and soft tissue infections annually in the United States alone1 and is the single leading cause of hospital acquired infections. Each year worldwide, GAS is responsible for more than 700 million cases of pharyngitis or skin infection and more than 650,000 invasive infections. Both pathogens can produce infections in essentially every human organ or tissue, including severe life-threatening conditions such as necrotizing fascitis, endocarditis, sepsis, and toxic shock syndrome. The propensity of *S. aureus* and GAS to produce systemic infections, often in otherwise healthy children and adults, defines a capacity of each pathogen to resist host immune clearance mechanisms that normally function to prevent microbial dissemination beyond epithelial surfaces. *S. aureus* and GAS systemic disease reflects diverse abilities of these pathogens to resist clearance by the multifaceted defenses of the human immune system. The mechanisms by which *S. aureus* and GAS avoid the bactericidal activities of cationic antimicrobial peptides, delay phagocyte recruitment, escape neutrophil extracellular traps, inhibit complement and antibody opsonization functions, impair phagocytotic uptake, resist oxidative burst killing, and promote phagocyte lysis or apoptosis have been reviewed by Nizet (Nizet, 2007).

*S. aureus* causes a variety of suppurative (pus-forming) infections and toxinoses in humans. It causes superficial skin lesions such as boils, styes and furuncules; more serious infections such as pneumonia, mastitis, phlebitis, meningitis, and urinary tract infections; and deep-seated infections, such as osteomyelitis and endocarditis. *S. aureus* is a major cause of hospital acquired (nosocomial) infection of surgical wounds and infections associated with in dwelling medical devices. *S. aureus* causes food poisoning by releasing enterotoxins into food, and toxic shock syndrome by release of superantigens into the blood stream. Although methicillin-resistant *S. aureus* (MRSA) have been entrenched in hospital settings for several decades, MRSA strains have recently emerged outside the hospital becoming known as community associated-MRSA (CA-MRSA) or superbug strains of the organism, which now account for the majority of staphylococcal infections seen in the ER or clinic. *S. aureus* permanently colonizes the moist squamous epithelium of the anterior nares of 20% of the population, and is transiently associated with another 60%. Occasionally, the organism can cause superficial skin infections such as abscesses and impetigo, or serious invasive infections such as septic arthritis, osteomyelitis and endocarditis. Colonization is a known risk factor for invasive disease both in the hospital and the community. Hospital patients who have been catheterized or who have undergone surgery are at increased risk of infection. Treatment of infections with antibiotics has become increasingly difficult owing to the widespread occurrence of strains that are resistant to multiple antibiotics, known as meticillin (formerly methicillin)-resistant *S. aureus* (MRSA). Furthermore, the isolation of MRSA strains that have also become resistant to vancomycin, the last drug to which the organism had been uniformly sensitive, raises the spectre of a return to the pre-antibiotic era.

The pathogenicity of *S. aureus* is a complex process involving a diverse array of extracellular and cell wall components that are also coordinately expressed during different stages of infection (i.e. colonization, avoidance of host defense, growth and cell division, bacterial spread). The coordinated expression of diverse virulence factors in response to environmental cues during infections (e.g. expression of adhesins early during colonization vs. production of toxins late in infection to facilitate tissue spread) suggests the existence of global regulators in which a single regulatory determinant controls the expression of many unlinked target genes (FEMS Immunol Med Microbiol. 2004 Jan. 15; 40(1):1-9). Bacteria use quorum sensing to synchronize release of these molecules. Individual bacteria secrete small molecules termed "auto-inducers" (AI), including N-acyl homo-serine lactones (gram-negative bacteria) and oligopeptides (gram-positive bacteria), at a constant, low level as a means of detecting the local concentration of bacteria.

An individual who has suffered from a *S. aureus* infection is usually not protected from a subsequent infection. This is because the host is prevented from mounting a strong antibody response, and immunological memory is compromised by the immunosuppressive activities of Vβ binding superantigens (Enterotoxin B, TSST-1, SAC1-3) and by nonspecific polyclonal B cell receptor activation resulting from binding of SpA to the B cell receptor Ig heavy-chain gene products of the VH3 family. In one such embodiment, the antibodies may be designed to target *Staphylococci aureus* (*S. aureus*).

Virulence Factors and their Effect on the Immune Response

The antimicrobial effector functions of antibodies are the target of a number of microbial immune evasion strategies, which have evolved to evade the immune response to the pathogen. These molecules, which are responsible for immune evasion, belong to the family of microbial virulence factors.

An immune response to a foreign antigen includes the production of antibodies by B-cells of the immune system against the foreign antigens that are detected within the body. Pathogenic microbes are one source of foreign antigens, which can stimulate the production of antibodies. A successful humoral immune response against such a pathogen results in the production of high affinity antibodies against the microbe, which are able to contribute to the elimination of the infection due to the effector function of the antibody. However, as described in detail below, a variety of pathogenic microbes (e.g., Staphylococci and Streptococci) produce a variety of virulence factors, which, among other functions, are able to attenuate the immune response against the microbe.

Virulence factors refer to microbial proteins or molecules (i.e., gene products) that enable a pathogen to establish itself on or within a host of a particular species and enhance its potential to cause disease. Most bacterial virulence genes involved in pathogenesis encode proteins that are either displayed on the bacterial surface (e.g. cell surface proteins) or are released into the surroundings (e.g. toxins and enzymes) and confers resistance to antimicrobials, which may strengthen its virulence and confer resistance to all families of antibiotics. These enable the organism to evade host defenses, to adhere to cells and the tissue matrix, to spread within the host and to degrade cells and tissues, for both nutrition and protection. These accessory genes are collectively known as the virulon (Novick 2003).

In one embodiment, a variant antibody has attenuated binding to a virulence factor when it binds the virulence factor in a non-immune fashion, i.e., the antibody binds the one or more virulence factor via a portion of the antibody that is not involved in antigen-dependent binding to the variable region of the antibody (e.g., Fc region binding or superantigen type Fab binding). In another embodiment, an antibody or variant antibody has enhanced antigen dependent immune-binding to a virulence factor when it binds the virulence factor in an immune fashion, i.e., the antibody or variant antibody binds a virulence factor in an antigen-dependent manner, via binding to the variable region of the antibody. Such antibodies and their variants can undergo affinity maturation when their antigen-dependent binding is enhanced by one or more amino acid substitution within the variable domain. These altered binding properties of the variant antibodies are not mutually exclusive. In other words, a variant antibody may have one or more amino acid substitutions (described below) that result in both attenuated non-immune binding to one or more IgBP virulence factors, and enhanced immune-binding to one or more virulence factors or microbial antigens.

Microbial proteins that contribute to the virulence of microbes such as *S. aureus* can be divided into at least five major families (described below): immune response inhibitors, superantigens, adhesion proteins, toxins, and enzymes. These virulence factor families are described below.

Immune Response Inhibitors.

Many bacteria produce virulence factors that inhibit the host's immune system defenses. For example, a common bacterial strategy is to produce IgBPs that bind to the Fc region of host immunoglobulin. Such IgBPs bind to the Fc region via non-immune binding. The best studies examples of FcBPs are SpA and Protein G (Goward et al., 1993; Bjorck et al., 1984, Reis et al., 1984), which are described in detail below. Additionally, the polysaccharide capsule coating the microbe can prevent effective elimination by host immune system effector cells.

Microbial IgBPs.

The non-immune binding of antibodies by bacterial or viral immunoglobulin IgBPs and FcBPs is a common strategy employed by pathogens to subvert the host immune response. The capacity of microorganisms to bind IgG or IgA via the Fc region has emerged as a widespread biological phenomenon. Immunoglobulin FcBPs are expressed on the cell surface of many Gram-positive pathogenic bacteria and are able to bind to Igs in a non-immune manner. In many cases, the Fc binding function has been incorporated into a larger multifunctional protein, which can have a number of virulence functions. The role of these proteins is almost certainly to help the bacteria adhere to host surfaces and to evade the immune response by allowing host proteins to cover the bacterial cell surface. Two of the first such proteins to be recognized were SpA (also referred to as Protein A), a cell-wall component of *S. aureus*, and Protein G, a protein associated with the cell walls of certain Streptococci. The Fc Binding Protein, SpA of *S. aureus*, serves to block Fc-receptor mediated effector functions such as opsonophagocytosis and contributes to virulence (Palmqvist et al., 2002). SpA binds the Fc region of IgG (Uhlen et al., 1984) and prevents both opsonophagocytosis and complement fixation (Gemmell et al., 1991).

Such FcBP proteins are also found among bacteria including streptococci of groups A, C, and G (Kronvall, 1973; Schroder et al., 1986), and Staphylococci (Forsgren & Sjouist, J Immunol. 1966). Furthermore, IgG FcBPs have been demonstrated on cells infected with Herpes simplex virus (Watkins, 1964; Chapman et al., 1999) of both serotypes I and 2 (Para, 1982), Varicellazoster (Ogata & Shigeta, 1974), Epstein-Barr virus (Yee et al., 1982) and Cytomegalovirus (Furatawa et al., 1975; Keller et al., 1976; Sprague et al., 2008; Lilley et al., 2001), Hepatitis C virus (Maillard et al., 2004), as well as on cells infected with schistosomes (Torpier, 1979).

Examples of such Fc Binding proteins (reviewed in Sidorin and Solov'eva, 2011) include, but are not limited to, Protein G from group C and group G streptococci (Derrick, 1992; Bjorck, 1984; Reis et al., 1984); β protein and M or M like family FcBPs such as Protein H, Arp4, Arp 60, Mrp4, Sir22, Enn4, FgBP (Kazeeval & Shevelev, 2009; Pleass et al., 2001; O'Toole et al., 1992; Heden et al., 1991; Jerlstro et al., 1991; Lewis et al., 2008; Meehan et al., 2001); SibA from GAS (Fagan et al., 1991); SpA from *S. aureus* (Boyle 1990 in Bacterial Immunoglobulin-Binding Proteins, ed. Boyle, M. P. D. (Academic, San Diego), Vol. 1, pp. 17-28, Gouda et al., Biochemistry. 1992 31:9665-7; Goward et al., 1993); SSL family members including SSL 7 and SSL10 from *S. aureus* (Ramsland et al., 2007; Kazeeval & Shevelev 2009; Ramsland et al., 2007); Sbi from *S. aureus* (Burman et al., 2008, Itoh et al., 2010); IsaB from *S. aureus* (Clark et al., 1999); PsaA from *Y. Pestis*; Eib-proteins from *E. Coli* (Sidorin. and Solov'eva, 2011).

It has been demonstrated that there is a striking overlap of the Ig Fc regions recognized by distinct bacterial IgBPs proteins, despite the fact that they derive from very different microbes (e.g. streptococcal and staphylococcal strains) and these microbes are pathogenic in different mammalian species. Even more remarkably, the fact that unrelated IgG binding proteins (e.g. SpA, Protein G) bind to similar sites in the IgG interdomain region parallels the situation for the unrelated bacterial IgA binding proteins (e.g. Sir22 from *S. pyogenes*, β-protein from group B *streptococcus*, and SSL7 from *S. aureus*), which all bind to the Fc domain interface in human IgA (Pleass et al., 2001; Wines et al., 2006; Ramsland et al., 2007). Although a different immunoglobulin class is involved, FcBP proteins produced by very different bacterial pathogens target the equivalent Fc region. Thus, it seems that convergent evolution may have favored the appearance of bacterial proteins that bind to the CH2/CH3 interface in IgG and IgA. This interdomain region in IgG, has been recognized as one of only a limited number of regions on the Ig surface that is particularly suited to protein-protein interactions (Burton, 1985; DeLano et al., 2000). For example, purified IgG Fc binding protein (FcBP) from the M15 strain of group A streptococci binds to the same site in the interface between the CH2 and CH3 domains as SpA, Protein G (SPA) (Nardella et al., 1985; Nardella et al., 1987) and IgG rheumatoid factors. His 435 and Tyr 436 on the IgG heavy chain, and possibly one or both of His 433 and 310, were demonstrated to be involved in the binding. The importance of His 435 in binding of many FcBPs to IgG originated with the findings on the specificity of IgG isotypes and allotypes for SpA. It was found that human IgG3 allotypes with Arg at position 435 lack the ability to bind SpA (Recht et al., 1982; van Loghem et al., 1982). IgG3 allotypes and IgG isotypes capable of binding SpA possess a His residue at position 435 within the interaction site for SpA. However, allotypes, which carry an Arg at this important CH3 domain residue, are unable to bind SpA (Recht et al., 1982; van Loghem et al., 1982).

Lack of Fc binding of antibodies to SpA has been used to develop a number of applications, including antibody based diagnostic tests for *S. aureus* Infection (Larsson & Sjoquist, 1989). In such cases, chicken or mouse immunoglobulin of non-binding isotypes can be used for the selective testing for *S. aureus* SpA by immune-assays.

The evolutionary reasons why such sites of relative vulnerability have been retained on the surface of Ig Fc regions probably relate to their role as interaction sites for important host receptors. In IgG, for example, the Fc interdomain region forms the interaction site for FcRn, the so-called neonatal Fc receptor that mediates a number of processes fundamental to IgG function, including regulation of IgG turnover and transepithelial transfer of IgG. It has been shown that the same residue at position 435 is important for FcRn binding. Its mutation (H435A) results in loss of binding of the antibody to both human and mouse FcRn.

Superantigens.

Superantigens (SAgs) are a class of antigens, which cause non-specific activation of T-cells or B-cells, resulting in polyclonal T or B cell activation. SAgs can be produced by pathogenic microbes (including viruses, mycoplasma and bacteria) (Llewely, 2002) as a defense mechanism against the immune system, and bind to antibodies via non-immune binding.

Superantigens are microbial or viral toxins that comprise a class of disease-associated, immunostimulatory molecules and act as Vβ-restricted extremely potent polyclonal T cell mitogens. They bind major histocompatibility complex (MHC) class-II molecules without any prior processing and stimulate large number of T cells (up to 20% of all T cells) on the basis of epitope specified by this receptor (Papageorgiou & Acharya, 2000; Acharya et al., 1994; Haynes & Fauci 2005). These properties are attributable to their unique ability to cross-link MHC class II and the T cell receptor (TCR), forming a trimolecular complex. The large number of activated T-cells generates a massive immune response, which is not specific to any particular epitope on the SAg thus undermining one of the fundamental strengths of the adaptive immune system, that is, its ability to target antigens with high specificity. More importantly, the large numbers of activated T-cells secrete large amounts of cytokines, which can cause severe and life-threatening symptoms, including shock and multiple organ failure.

Figure 3:
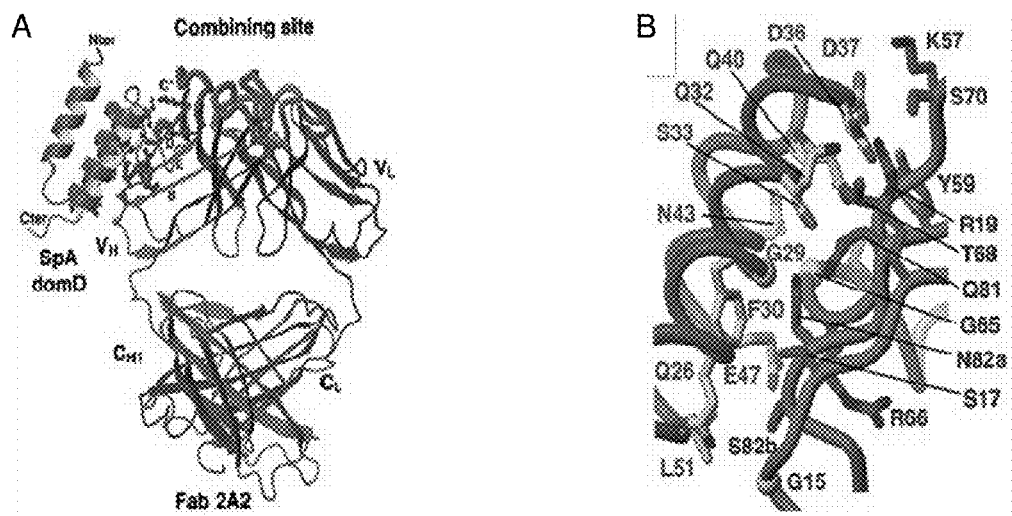
FIG. 3 is a schematic representation of a complex between SpA domain D and Fab 2A2 from a human IgM. (Panel A) shows a side view of SpA domain D bound to the framework region of the Fab heavy chain. The VL domain, which is not involved in this interaction, is shown on the right. The CDR loops as defined by Chothia and Lesk are highlighted at the top. (Panel B) shows a schematic diagram detailing the residues of SpA domain D and Fab 2A2 involved in the interaction. Kabat numbering is used for the VH residues; domain D is numbered with the convention used for SpA domains.

In contrast, B cell-directed superantigens target the B cell compartment. By definition, these agents (1) stimulate a high frequency of B cells, (2) target B cells that have restricted usage of VH or VL family genes, and (3) bind to immunoglobulins outside the sites that bind conventional antigens. A B-cell superantigen that has received considerable attention is staphylococcal SpA (Silverman et al., 2000; Graille et al., 2000). This agent has the ability to bind to the Fc fragment of IgG. This binding has been localized to a region contains α-helical 1 and 2 (helix I and II) structures on each of four or five homologous regions that comprise the extracellular domain of SpA (FIG. 2). However, it is now clear that SpA repeat IgG binding domains contain a second site, located in a region containing helix II and helix III, (FIG. 2) that binds to determinants on the Fab regions of certain immunoglobulins independently of their heavy-chain isotype (Graille et al., 2000). In humans, this so-called alternative site appears to bind only to immunoglobulins that utilize heavy-chain genes of the VH3 subfamily. The x-ray structure of this interaction has been solved, explaining the basis for this interaction (FIG. 3). In the mouse this type of binding is restricted to immunoglobulins using heavy chains belonging to the S107 and J606 VH families.

A number of microbial immunoglobulin binding proteins (IgBP) can bind to regions of immunoglobulin outside the Fc region. Examples of such proteins include SpA, which is also able to bind to the Fab region of Most VH3 sequences. This binding uses a separate binding site to that used for Fc binding. The ability to bind to Fab sequences enables SpA to act as a B cell superantigen. The L protein from the surface of bacterial species *Peptostreptococcus magnus* was found to bind Ig through L chain interaction, from which the name was suggested (Bjorck, 1988). Unlike SpA and Protein G, which bind to the Fc region of immunoglobulins (antibodies), Protein L binds antibodies through light chain interactions. Since no part of the heavy chain is involved in the binding interaction, Protein L binds a wider range of antibody classes than SpA or G. Protein L binds to representatives of all antibody classes, including IgG, IgM, IgA, IgE and IgD. Single chain variable fragments (ScFv) and Fab fragments also bind to Protein L.

Despite this wide binding range, Protein L is not a universal antibody-binding protein. Protein L binding is restricted to those antibodies that contain kappa light chains. In humans and mice, most antibody molecules contain kappa (κ) light chains and the remainder have lambda (ι) light chains. Protein L is only effective in binding certain subtypes of kappa light chains. For example, it binds human VκI, VκIII and VκIV subtypes but does not bind the VκII subtype. Binding of mouse immunoglobulins is restricted to those having VκI light chains (Nilson et al., 1993).

Adhesion Proteins.

Many bacteria must first bind to host cell surfaces. Many bacterial and host molecules that are involved in the adhesion of bacteria to host cells have been identified. Often, the host cell receptors for bacteria are essential proteins for other functions. Members of the MSCRAMM (microbial surface component recognizing adhesive matrix molecule) family of adhesion proteins bind ECM ligands such as collagen, fibronectin, and fibrinogen, Toxins.

Many virulence factors are proteins made by bacteria that poison host cells and cause tissue damage. For example, there are many food poisoning toxins produced by bacteria that can contaminate human foods. Some of these can remain in "spoiled" food even after cooking and cause illness when the contaminated food is consumed Enzymes.

A number of virulence factors encode proteases or microbial activators of host protease, which are able to interfere with antibody and complement mediated microbial killing. For example, S. aureus can express a number of proteases or zymogens, and additional virulence factors, which encode enzymes such as lipases, deoxyribonucleases (DNase) and a fatty acid modifying enzymes.

Microbial Antigenic Surface Proteins

Surface proteins of S. aureus are linked to the cell wall by sortase, an enzyme that cleaves polypeptides at a conserved LPXTG motif. SpA, a surface protein of S. aureus synthesized as a precursor bearing an N-terminal signal peptide, which is cleaved during secretion, and a C-terminal sorting signal with an LPXTG motif. After signal peptide-mediated initiation of the precursor into the secretory pathway, the sorting signal directs SpA to the cell wall envelope. The polypeptide is then cleaved between the threonine and the glycine of the LPXTG motif. The liberated carboxyl group of threonine forms an amide bond with the amino group of the pentaglycine crossbridge, thereby tethering the C terminus of SpA to the bacterial peptidoglycan. The genome of S. aureus encodes at least 10 different surface proteins bearing C-terminal sorting signals with an LPXTG motif. Many of these polypeptides are known to interact with various human tissues, serum proteins, or polypeptides of the extracellular matrix. For example, SpA binds to the Fc portion of immunoglobulins, a mechanism that is thought to prevent opsonophagocytosis of staphylococci after their entry into the human host. Binding of the clumping factors, ClfA and ClfB, to fibrinogen promotes bacterial adhesion to vascular and endocardic lesions. The FnbA and FnbB surface proteins bind to fibronectin. This interaction allows staphylococci to adhere to various tissues and, similar to fibronectin-binding proteins of Streptococcus pyogenes, presumably provides for the invasion and apoptotic death of infected epithelial cells.

According to the embodiments described herein, antimicrobial monoclonal antibodies and variant monoclonal antibodies that have variable domains that recognize one or more microbial cell surface or secreted antigens are provided.

In some embodiments, IgG antibodies, such as a human IgG antibody, a humanized or a chimeric IgG class antibody or their variants are provided. In such embodiments, the antigen recognition region of the antibody is directed against one or more microbial cell surface or secreted antigens (i.e., antigen specific immune binding). In some embodiments, the one or more microbial cell surface or secreted antigens include ClfA, SpA and Sbi.

In other embodiments, IgG antibodies, such as a non-human IgG antibody, or their variants are claimed for use in veterinary medicine. In such embodiments, the antigen recognition region of the antibody is directed against one or more microbial cell surface or secreted antigen.

Virulence Factors of a Target Microbe, S. aureus

In some embodiments, the antibodies and variant antibodies described herein may be designed to target one or more virulence factors produced by the target microbe, which according to some aspects, is S. aureus. S. aureus produces an array of virulence factors (Foster, 2005), examples of which include (1) cell surface proteins that promote colonization of host tissues (e.g. SpA (Protein A), Clumping Factor A (ClfA); (2) invasins that promote bacterial spread in tissues (e.g. leukocidin, hyaluronidase); (3) cell surface factors that inhibit phagocytic engulfment and complement mediated killing (SpA, Sbi, Capsular Polysaccharide Serotypes 5 and 8 (Cps 5 and 8); (4) biochemical properties that enhance their survival in phagocytes (proteases, and protease activators: among the array of secreted staphylococcal factors, a number of proteases, including the serine proteases V8 (SspA/V8) and SplA-SplF, the cysteine proteases ScpA (staphopain A) and SspB (staphopain B), the metalloprotease aureolysin and, staphylokinase which can activate host zymogens; (5) immunoglobulin binding proteins (SpA, Sbi, SSL10, SSL7); (6) membrane-damaging toxins that lyse eukaryotic cell membranes (e.g. γ-hemolysins, leukotoxin E-D, Panton-Valentin leukocidin; (7) exotoxins that damage host tissues or otherwise provoke symptoms of disease (e.g. Enterotoxins A, B, C, D, G, H); (8) superantigens which compromise the T cell or B cell response (e.g. SpA, Enterotoxin B, TSST-1,SAC1-3); and (9) inherent and acquired resistance to antimicrobial agents. Several of the virulence factors that may be affected by the variant antibodies described herein are described below.

SpA.

SpA (Protein A), which exists in both secreted and membrane-associated forms, possesses two distinct Ig-binding activities: each domain can bind Fcγ (the constant region of IgG involved in effector functions, as described above) and Fab (the Ig fragment responsible for antigen recognition) (Boyle, 1990). SpA is a 42-kDa protein covalently anchored in the staphylococcal cell wall through its carboxyl terminal end. The protein is comprised of five repeated domains (E, D, A, B, C) of ~58 residues linked to the cell surface by region Xr, which contains a variable number of short 8-residue repeats (FIG. 2). Each SpA domain can bind with high affinity to the Fc region of immunoglobulin G and to the Fab region of immunoglobulin of the VH3 subclass (Jansson et al., 1998, Moks et al., 1986; Roben et al., 1995; Sasso et al., 1989). The interaction with IgG Fc hinders phagocytosis because bacteria become coated with IgG in an inappropriate conformation not recognized by the Fc receptor on neutrophils. Moreover, SpA-bound IgG cannot stimulate complement fixation by the classical pathway. An additional consequence of the ability of SpA to bind to B lymphocytes displaying IgM bearing VH3 heavy chains is the induction of proliferation resulting in depletion of a significant part of the B cell repertoire (Goodyear et al., 2004; Viau et al., 2005).

Both the SpA-Fc and SpA-Fab interactions have been analyzed at the molecular level with co-crystallized complexes (Deisenhofer 1981; Gouda et al., 1998; Graille et al., 2000). The SpA domains adopt three-helix bundles. One face includes residues from helices I and II binds IgG Fc, whereas residues from helices II and III on the other face bind VH3 Ig (Graille et al., 2000). The residues from helix II that bind Fc are different from those that bind Fab, with the exception of a single glutamine (Gln-32 in SpA domain D) (Deisenhofer 1981; Graille et al., 2000). SpA also binding strongly to a number of other proteins including von Willebrand factor (vWF) (O'Seaghdha et al., 2006), the TNF receptor I (TNFRI) (Gomez et al., 2006), the Epidermal growth factor receptor (EGFR) (Gomez et al., 2007) and also binds to an undefined target on osteoblasts (Claro et al., 2011).

The SpA Fcγ binding site has been localized to the elbow region at the CH2 and CH3 interface of most IgG subclasses, and this binding property has been extensively used for the labeling and purification of antibodies (Deisenhofer, 1981; Tashiro & Montelione, 1995). The X-ray structure of the SpA IgG-binding domains in complex with the Fc region of IgG have been solved and residues from helix I and II that are involved in the interaction have been identified and verified by site-directed mutagenesis, and by the existence of allotypes of IgG3 (with an Arg435 residue) that do not bind SpA. The consequence of the interaction between SpA and IgG-Fc is to coat the surface of the cell with IgG molecules that are in the incorrect orientation to be recognized by Fc receptors on effector cells. This could explain the anti-phagocytic effect of SpA and its role in the pathogenesis of S. aureus infections. Protein-A-deficient mutants of S. aureus are phagocytosed more efficiently by neutrophils in vitro and show decreased virulence in several animal infection models (Gemmell et al., 1997; Palmqvist et al., 2002).

SpA (Protein A) also acts as a B-cell superantigen through interactions with the heavy-chain variable part of Fab fragments, and sequesters immunoglobulins by forming insoluble immune complexes with human IgG. It has been shown that the formation of insoluble immune complexes is mediated by the binding of (VH3+) Fab fragments in addition to Fc. B-cell superantigens, unlike conventional antigens, bind to the Fab regions of immunoglobulin (Ig) molecules outside their complementarity-determining regions (CDRs) reviewed in references (Levinson et al., 1995; Silverman, 1997). These unconventional antigens can react with a substantial amount of a host's peripheral B-cell repertoire and serum Igs by virtue of their ability to interact with many members of an entire variable region heavy (VH) or variable region light (VL) gene family (Levinson & Kozlowski, 1996).

S. aureus SpA (Protein A) is one of the most studied B-cell SAg. Although it had long been known that this microbial product binds to the Fc region of IgG, it became clear that SpA also binds, via an alternative site, to determinants outside the CDRs in the Fab region of Igs. SpA reacts with the Fabs of most VH3 Igs, which are expressed on 30 to 60% of human peripheral B cells. The crystal structure of an S. aureus SpA domain complexed with a Fab fragment of human IgM has been solved, showing the molecular basis for B-Cell receptor recognition and superantigen activity. The interactions of SpA with the Fab region of membrane-anchored Igs can stimulate a large fraction of B cells, contributing to lymphocyte clonal selection. The crystal structure of the complex between domain D of SpA and the Fab fragment of a human IgM antibody to 2.7-Å resolution has been solved (Graille et al., 2000). In the complex, helices II and III of domain D interact with the variable region of the Fab heavy chain ($V_H$) through framework residues, without the involvement of the hypervariable regions implicated in antigen recognition. The contact residues are highly conserved in human $V_H$3 antibodies but not in other families. The contact residues from domain D also are conserved among all SpA Ig-binding domains, suggesting that each could bind in a similar manner. Correlation with antibody sequence usage indicates that the Fab binding specificity is restricted to products of the human variable region of the Fab heavy chain $V_H$3 family that represent nearly half of inherited $V_H$ genes (Sasso et al., 1989; Sasso et al., 1991; Sasano et al., 1993; Hillson et al., 1993) and their homologues in other mammalian species (Seppala et al., 1990; Cary et al., 1999). Presumably through interactions with surface membrane-associated $V_H$3-encoded B-cell antigen receptors (Romagnani et al., 1982), in vitro stimulation with SpA can contribute to selection of these B cells and promote their production of antibodies that may include rheumatoid factor autoantibodies (Kristiansen et al., 1994); Kozlowski et al., 1995). In vivo exposure to recombinant SpA can result in supraclonal suppression and deletion of B-lymphocytes that are susceptible based on their $V_H$ usage (Silverman et al., 1998; Cary et al., 2000).

Although the mechanism(s) are not defined, experimental models indicate that SpA enhances staphylococcal virulence (Foster et al., 1988; Patel et al., 1987). Many features of the interactions of SpA with host B lymphocytes are akin to those of superantigens for T lymphocytes that cause a variety of inflammatory diseases including toxic shock syndrome, food poisoning, and exfoliative syndromes (Kotzin et al., 1993; Bohach et al., 1990; Papageorgiou et al., 1998) and T-cell superantigens also have been postulated to contribute to the pathogenesis of autoimmune disease (Li et al., 1999). These superantigens target T-cell receptors (TcRs) from particular variable β chain ($V_β$) families and induce global changes in T lymphocyte repertoires (Kotzin et al., 1993). The site responsible for Fab binding is structurally separate from the domain surface that mediates Fcγ binding. As first demonstrated in a crystallographic complex and recently reinvestigated in NMR studies the interaction of Fcγ with domain B primarily involves residues in helix I with lesser involvement of helix II (Graille et al., 2000). With the exception of the Gln-32, a minor contact in both complexes, none of the residues that mediate the Fcγ interaction are involved in Fab binding. The area buried in the Fcγ-domain B interface is 1,320 Å$^2$, which is comparable to the 1,220 Å$^2$ buried in the current complex with Fab. However, the nature of these buried SpA residues differs significantly, as the Fab binding is dominated by polar contacts whereas the Fcγ interaction is predominantly hydrophobic. To examine the spatial relationship between these different Ig-binding sites, the SpA domains in these complexes were superposed (Graille et al., 2000) to construct a model of a complex between a Fab, a SpA domain, and an Fcγ molecule. Fab and Fcγ form a sandwich about opposite faces of the helix II without evidence of steric hindrance of either interaction. These findings illustrate how, despite its small size (i.e., 56-61 aa), SpA domains can simultaneously display both activities, explaining experimental evidence that the interactions of Fcγ and Fab with an individual domain are noncompetitive (Starovasnik et al., 1999).

SpA has also been found to activates tumor necrosis factor receptor 1 (TNFR1) (Gomez et al., 2004) Staphylococci frequently cause pneumonia, and these clinical isolates often have increased expression of SpA, suggesting that this protein may have a role in virulence. It has been found that TNFR1, a receptor for tumor-necrosis factor-α (TNF-α) that is widely distributed on the airway epithelium, is a receptor for SpA (Gomez et al., 2004).

SpA can also act directly as an immune effector itself through its ability to bind and activate tumor necrosis factor α (TNF-α) receptor 1 (TNFR1) (Gomez et al., 2004, 2006). This interaction is particularly important at sites of infection where TNF-α signaling is important, as in the lung. SpA-TNFR1 interaction is essential for the pathogenesis of pneumonia as TNFR1 null mice are not susceptible to S. aureus pneumonia and SpA-defective mutants of S. aureus do not cause infection in wild-type animals. SpA activates proinflammatory signaling through binding to TNFR1 and activation of TRAF2, the p38/c-Jun NH2-terminal kinase MAPKs, and NF-κB (Gomez et al., 2004). TNFR1 ectodomain shedding is induced by SpA (Gomez et al., 2004), presumably by activating the TNF-converting enzyme (TACE or ADAM17) through a signaling pathway not yet elucidated. As there is no apparent homology between the trimeric TNFR1 and IgG, both of which function as receptors for SpA, we were interested in defining the molecular basis for the SpA-TNFR1 interaction.

Each SpA binding domain includes a triple helical bundle (Deisenhofer 1981). By analyzing a series of amino acid substitutions in the SpA D domain, Gomez et al (2006) showed that the residues important in the interaction between SpA D and the Fc region of IgG are also involved in binding to and activating TNFR1. SpA residues that are on the opposite face of the protein that are involved in IgM Fab binding are not involved in the interaction with TNFR1 (Gomez et al., 2006). The IgG Fc region binds to residues exposed on the face formed by helices I and II. TNFR-1 also binds to this face but there are some differences in the residues of SpA that are involved. In particular, leucine 17 is crucial for binding to IgG but not for TNFR-1 binding.

SpA is known to bind human von Willebrand factor (VWF), a protein that is essential for haemostasis, with an affinity of 15 nM as measured by surface plasmon resonance using full length recombinant SpA and VWF that had been purified from plasma. This interaction was shown to occur in the presence of physiological IgG concentrations. Heritable defects in VWF result in von Willebrand's disease, a common bleeding disorder, symptoms of which can mirror severe hemophilia. The main function of VWF is to capture platelets by binding to the platelet receptor GPIb-a and immobilize them at the site of damage to a blood vessel and to stimulate the formation of a blood clot. The VWF protein consists of four types of repeat domain A, B, C and D. Domains are arranged in the sequence D'-D3-A1-A2-A3-D4-B1-B2-B3-C1-C2-CK in the mature protein (for review, see Sadler J. E, 1998). The crystal structure of the recombinant A1 domain in complex with platelet glycoprotein Gibe has been solved (Emsley et al., 1998; Huizinga et al., 2002; Uff et al., 2002). Binding of circulating VWF to the ligands such as collagen in exposed subendothelial matrix of damaged blood vessels under high shear-stress stimulates a conformational change which promotes immobilized VWF binding to Gplba on platelets (Siedlecki et al., 1996; Novak et al., 2002; Hulstein et al., 2005). Circulating platelets are captured and activated, stimulating the formation of a thrombus (Kroll et al., 1996; Xiong et al., 2003). The ability of S. aureus to bind VWF could contribute to the adherence of the bacterium to platelets or to damaged blood vessels. By studying a Spa-deficient mutant of S. aureus it was shown that the Spa-VWF interaction is necessary for efficient recruitment of S. aureus by platelets under high shear stress in whole blood (Pawar et al., 2004). Also fluid-shear adhesion experiments suggested that VWF binding to Spa can promote adherence of circulating S. aureus cells to immobilized collagen (Mascara et al., 2003). In a recent study, it was shown that Spa is sufficient for adherence of bacteria to immobilized VWF under low shear conditions. Recombinant Spa and VWF truncates were used to identify and characterize the domain(s) in each protein that are involved in binding and to refined the VWF binding domain in SpA by site-directed mutagenesis (O'Seaghdha et al., 2006).

Previous studies have suggested that the SpA-VWF interaction is important in S. aureus adherence to platelets under conditions of shear stress and that Spa expression is sufficient for adherence of bacteria to immobilized VWF under low fluid shear (Pawar et al., 2004). The full-length recombinant Ig-binding region of SpA, Spa-EDABC, fused to glutathione-S-transferase (GST), bound recombinant VWF in a dose-dependent and saturable fashion with half maximal binding of about 30 nM in immunosorbent assays. Full-length (FL)-Spa did not bind recombinant VWF A3 domain but displayed binding to recombinant VWF domains A1 and D'-D3 (half-maximal binding at 100 nM and 250 nM, respectively). Each recombinant SpA Ig-binding domain bound to the A1 domain in a similar manner to the FL-Spa molecule (half-maximal binding 100 nM). Amino acid substitutions were introduced in the GST-SpaD protein at sites known to be involved in IgG Fc or in VH3-Fab binding. Mutants altered in residues that recognized IgG Fc but not those that recognized VH3 Fab had reduced binding to VWF-A1 and D'-D3. This indicated that both VWF regions recognized a region on helices I and II that overlapped the IgG Fc binding site (O'Seaghdha et al., 2006).

Osteomyelitis is a debilitating infectious disease of the bone. It is predominantly caused by S. aureus and is associated with significant morbidity and mortality. It is characterized by weakened bones associated with progressive bone loss. Currently the mechanism through which either bone loss or bone destruction occurs in osteomyelitis patients is poorly understood (Claro et al., 2011). S. aureus SpA (Protein A) has recently been shown to binds directly to osteoblasts (Claro et al., 2011). This interaction prevents proliferation, induces apoptosis and inhibits mineralization of cultured osteoblasts. Infected osteoblasts also increase the expression of RANKL, an important protein involved in initiating bone desorption. None of these effects was seen in a mutant of S. aureus lacking SpA. Complementing the SpA-defective mutant with a plasmid expressing spa or using purified SpA resulted in attachment to osteoblasts, inhibited proliferation and induced apoptosis to a similar extent as wildtype S. aureus. These events demonstrate mechanisms through which loss of bone formation and bone weakening may occur in osteomyelitis patients.

Staphylococcal SpA is a conserved surface component of all S. aureus strains, consisting of an N-terminal IgG-binding domain, an Xr or short sequence-repeat region (SSR) encoded by variable numbers of 24-bp repeated DNA sequences, and a C-terminal anchor to the bacterial cell wall. Resent studies have shown that the Xr domain of SpA, activates known components of the type I IFN cascade and that this contributes to the virulence of the organism as a respiratory pathogen (Martin et al., 2009).

Sbi.

Figure 4:
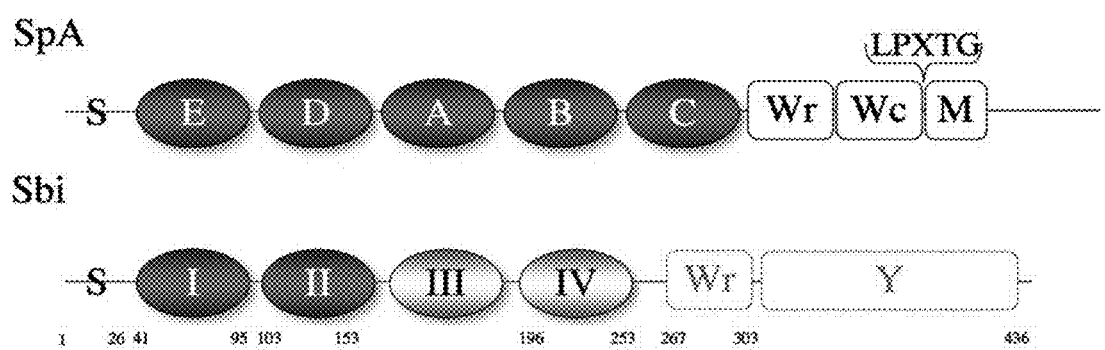
FIG. 4 is a schematic diagram illustrating the SpA (top) and Sbi (bottom) polypeptide domain organization.
Figure 9A:
FIGS. 9A-9C are a series of diagrams showing domain D of SpA interacting with the Fab domain of a human IgM.
Figure 9B:
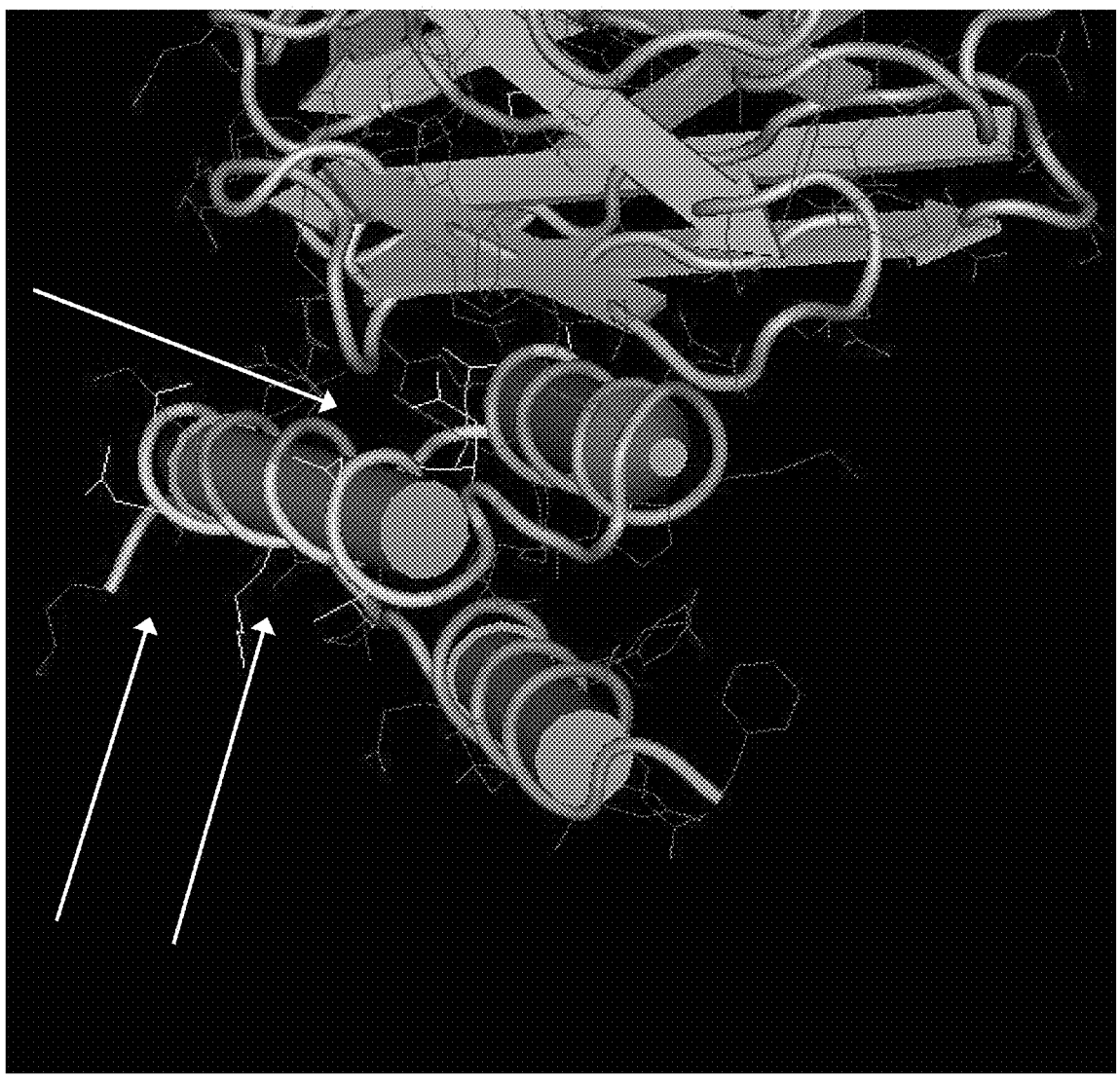
Figure 9C:
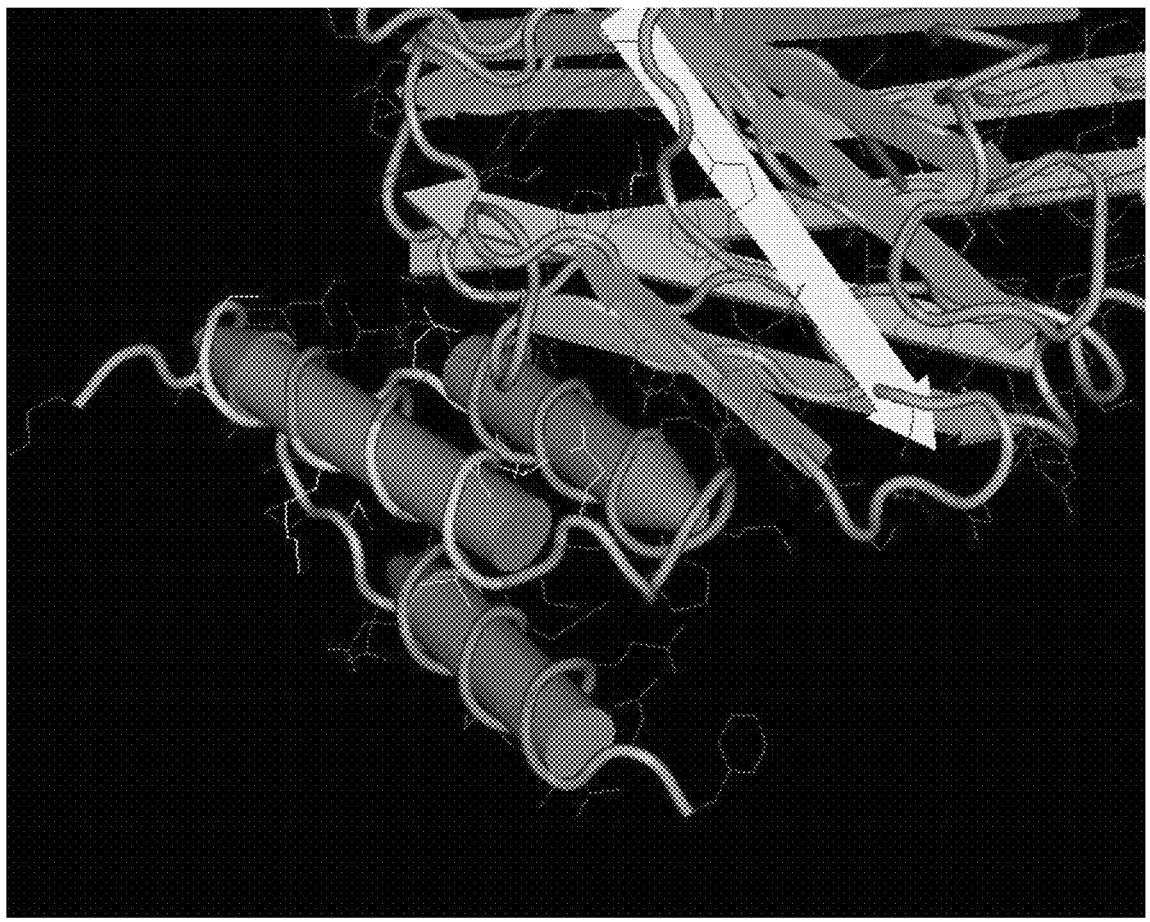
Figure 10:
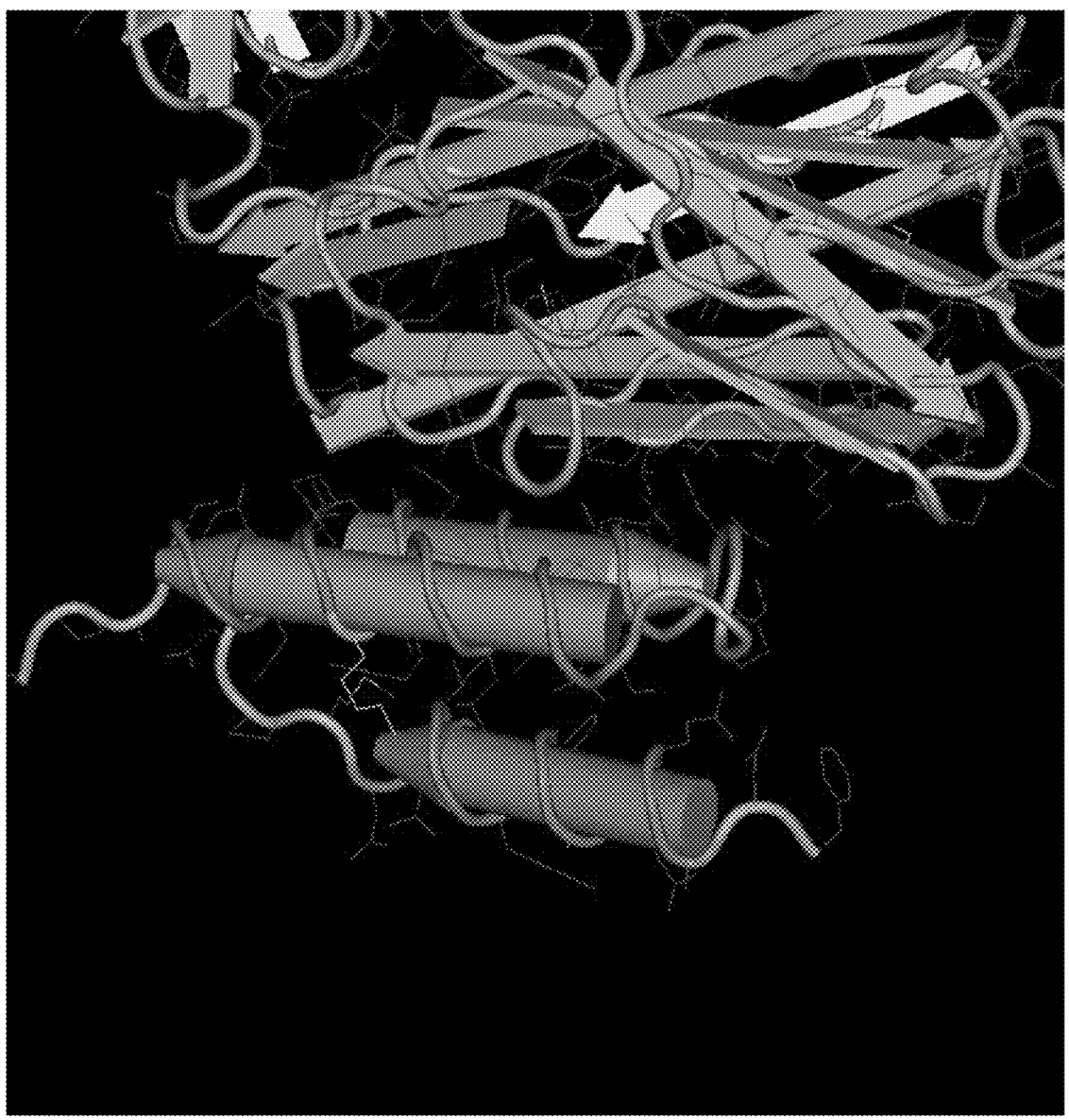
FIG. 10 models a Q to K substitution at amino acid 45 of SpA domain E. Amino acid K is found at the same position in all sequenced stains of S. aureus domains D, A, B and C that were analyzed (FIG. 11). The position of the Q to K substitution in domain E (yellow), is located on the face of Helix II that does not interact with the VH3 Fab from human IgM.
Figure 11A:
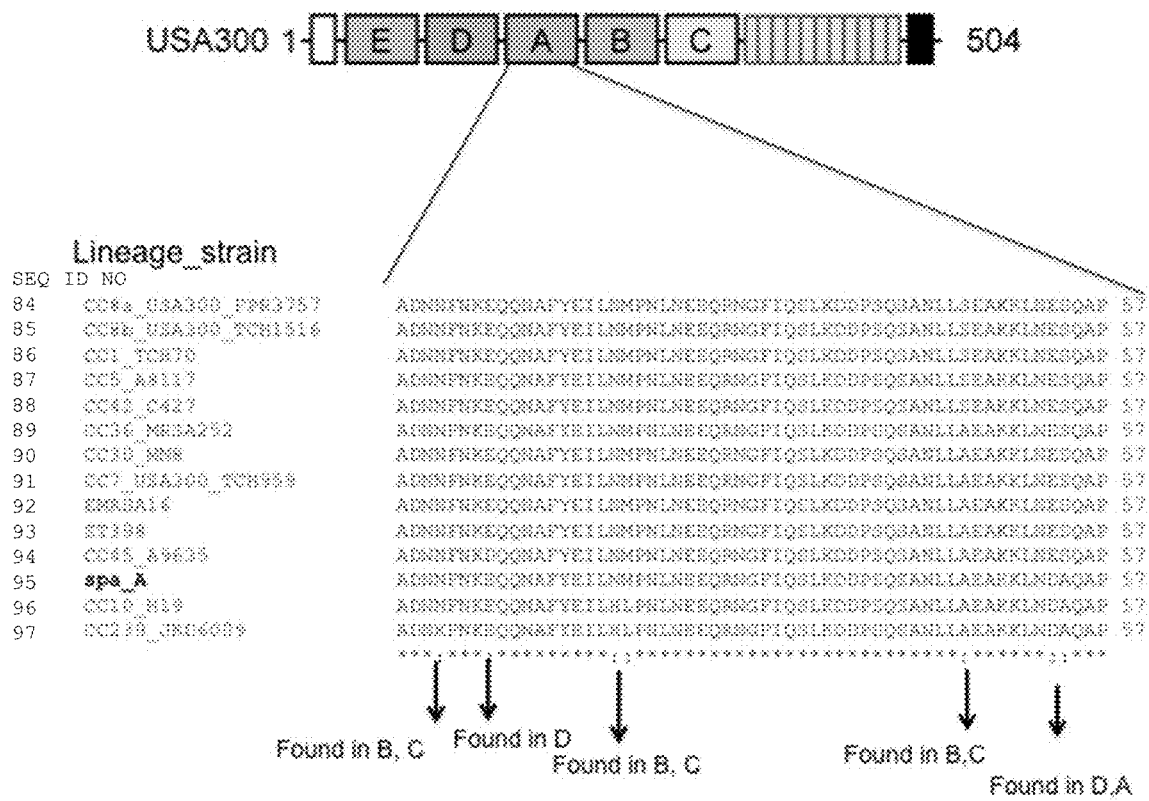
FIGS. 11A-11E (SEQ ID NOs: 84-151) show the amino acid sequence alignment of individual SpA IgBP domains A-E, respectively, from sequenced stains of S. aureus. The position of intra-SpA domain substitutions found in different S. aureus stains are indicated with an arrow. If the substitution is found in one or more of the other SpA domains, it is indicated under the arrow. For example, the SpA A domain of S. aureus stain CC45_A9635 has and E to D substitution at residue #8 (FIG. 11A). Residue D is found at the homologous position of SpA domain D in all sequenced stains of S. aureus (amino acid position 11 in domain D).
Figure 11B:
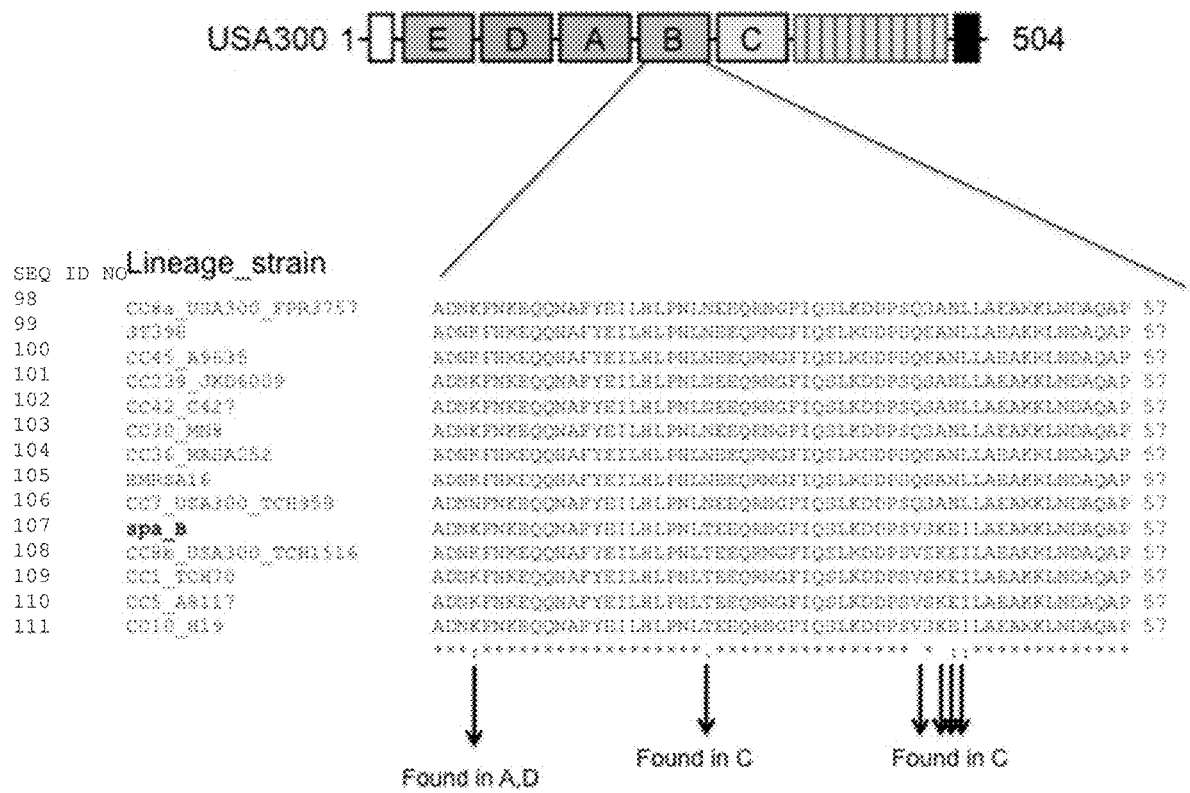
Figure 11C:
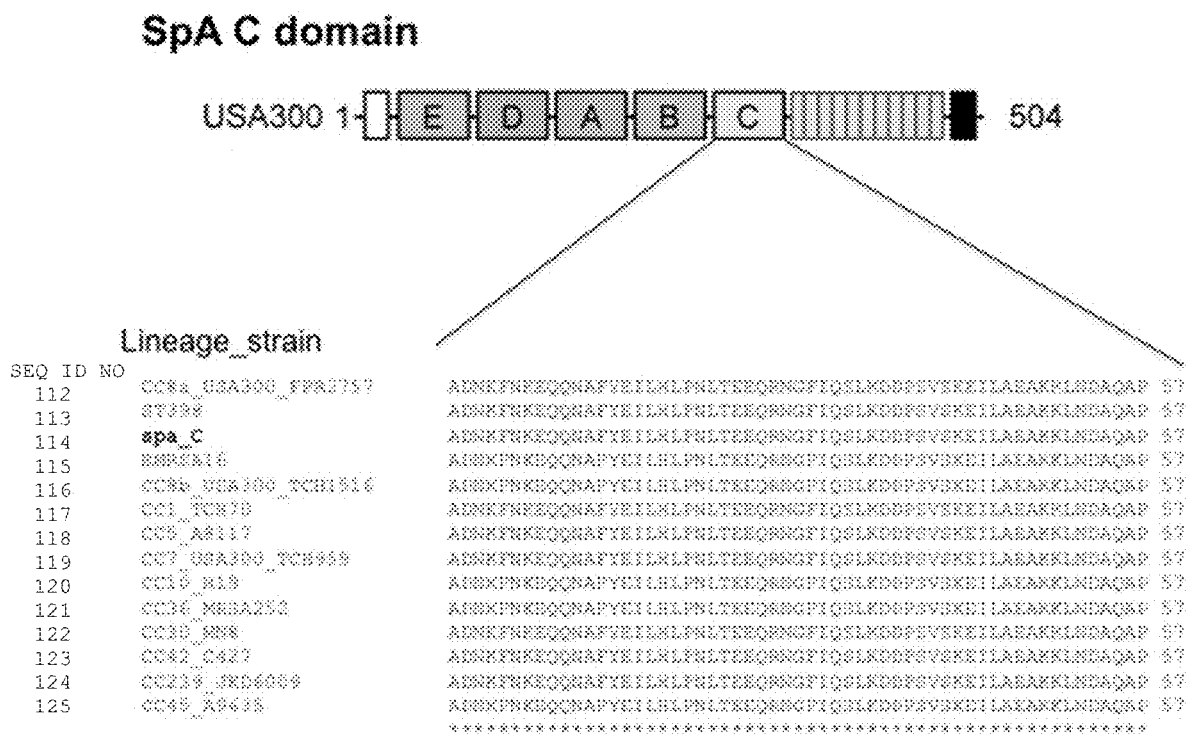
Figure 11D:
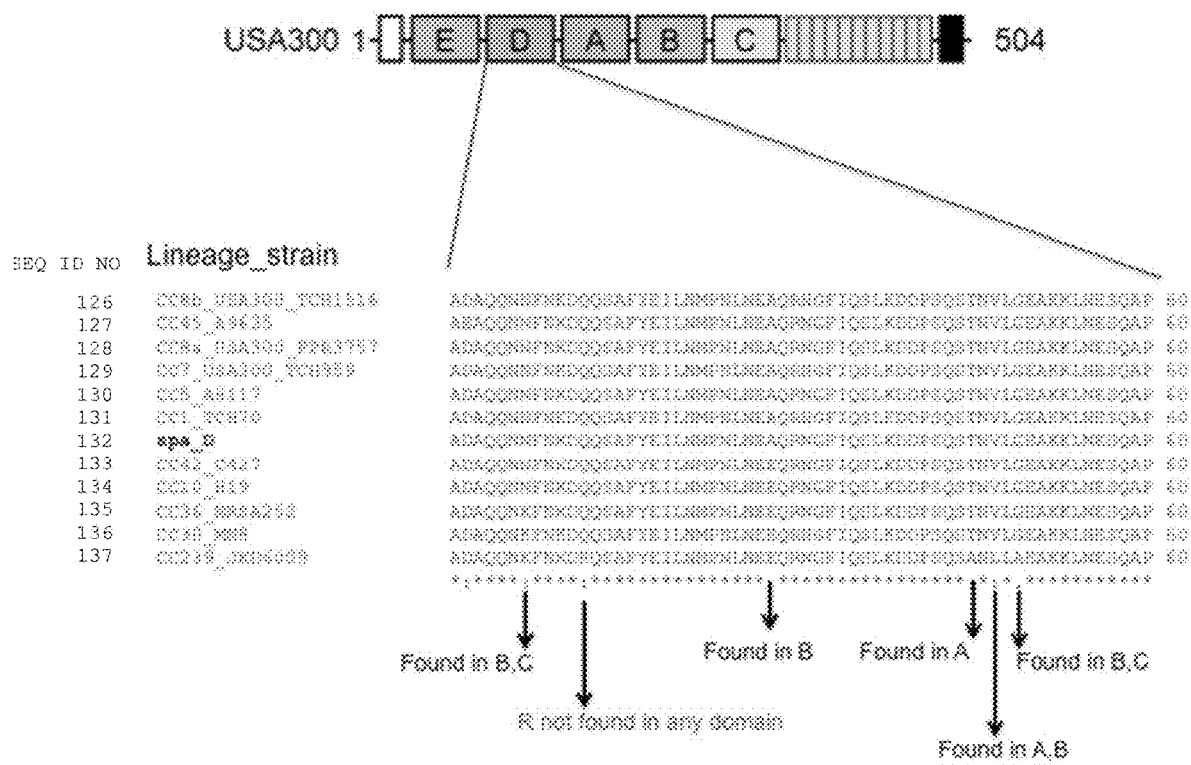
Figure 11E:
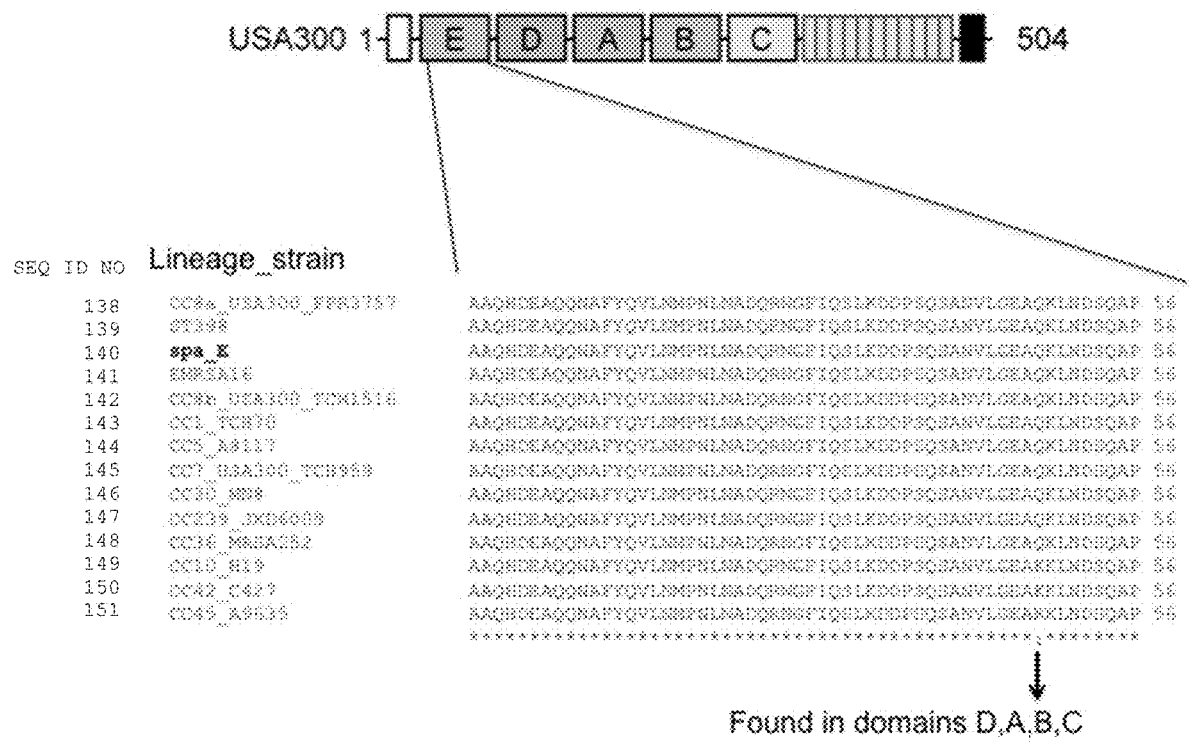

In addition to SpA, many stains of S. aureus also produce Sbi, a second protein with Fc binding activity. Sbi is a multidomain protein, which was originally identified as an IgG-binding, and 132 glycoprotein-I binding protein (Zhang et al., 1998). Sbi is a 436-amino acid protein that occurs in many S. aureus strains, including methicillin-sensitive (MSSA) and methicillin-resistant (MRSA) strains. From its N terminus, Sbi includes four small domains up to residue 266 followed by eight copies of a PXXXX repeat motif with a high concentration of glutamine, lysine, aspartate, valine, and isoleucine and then a C-terminal tyrosine-rich 130-residue region (FIG. 4). Unlike SpA, Sbi lacks the typical Gram-positive cell wall anchoring sequence LPXTG, but it does have a predicted proline-rich cell wall-spanning segment (Zhang et al., 1998). Evidence from Western blots of fractionated cells from several S. aureus strains, including Newman, indicates that most Sbi is secreted into the medium. It has also been suggested that Sbi is associates with the bacterial surface through electrostatic interactions (Zhang et al., 1998). Sbi has also been shown to bind a plasma component, adhesion protein β2-glycoprotein I (β2-GPI), a protein that has been implicated in blood coagulation (Zhang et al., 1999; Bouma et al., 1999). It has been demonstrated that Sbi interferes directly with the adaptive immune system through its two N-terminal IgG binding domains (Sbi-I and Sbi-II) (Zhang, L, 1998), and also modulates the innate immune system through its third and fourth domains (Sbi-III and Sbi-IV) (Burman et al., 2008). Specifically, Sbi binds complement protein C3 through Sbi-IV interaction with C3 subunits and induces a futile consumption of complement predominantly via fluid phase activation of the alternative pathway. Sbi fragments containing domains I-II-III-IV (Sbi-E) and III-IV induce this futile consumption of complement, whereas isolated Sbi-IV does not. Sbi-IV is nevertheless strongly inhibitory in an assay measuring alternative pathway activation (Burman et al., 2008).

SSL7 and SSL10.

SSL7 (formerly named SET1) and SSL10 are members of the staphylococcal superantigen-like (SSL) proteins family (Lina et al., 2004; Williams et al., 2000), related to the staphylococcal enterotoxins (SEs) or superantigens. The SSL proteins have 30% sequence identity with toxic shock syndrome 1 (TSST-1) and 25% or less identity with other SEs. Despite the sequence differences, the SSL proteins have a typical SE tertiary structure consisting of a distinct oligonucleotide/oligosaccharide binding (OB-fold) linked to a β-grasp domain (Arcus et al., 2002a; Arcus, 2002b). Similar to the se genes, the ssl genes are located in a pathogenicity island (SaPIn2) and are likely to be significant virulence factors. Most healthy individuals have antibodies to SSL proteins (Al-Shangiti et al., 2005), and the ssl genes exhibit marked allelic variance consistent with selective pressure from the host immune system (Baba et al., 2002). However, unlike SE, the SSL proteins do not have superantigen activity, but some have been shown to inhibit important molecules of the host immune system. SSL10 (Staphylococcus Super antigen like protein 10) bind IgG1 not IgG2/3/4. The dissociation equilibrium constant for the interaction between human IgG and recombinant SSL10 was estimated to be 220 nM. Recombinant SSL10 inhibited the binding of complement component C1q to IgG. The binding site of SSL10 to IgG1 has been located by site directed mutagenesis to residues within the CH2 domain. Specifically, mutation of IgG1 at residues 274 and 276 to the residues found in IgG3 (which does not bind SSL 10) abolish binding to the variant IgG1 (Patel et al., 2010). In contrast to SSL10, SSL7 bind to the Fc domain interface in human IgA.

Antibody Structure and Interactions with Immunoglobulin Binding Proteins

Antibodies are immunological proteins that bind a specific antigen. In most mammals, including humans and mice, antibodies are constructed from paired heavy and light polypeptide chains. Each chain is made up of individual immunoglobulin (Ig) domains, and thus the generic term immunoglobulin is used for such proteins. Each chain is made up of two distinct regions, referred to as the variable and constant regions. The light and heavy chain variable regions show significant sequence diversity between antibodies, and are responsible for binding the target antigen. The constant regions show less sequence diversity, and are responsible for binding a number of natural proteins to elicit important biochemical events. In humans there are five different classes of antibodies including IgA (which includes subclasses IgAI and IgA2), IgD, IgE, IgG (which includes subclasses IgG1, IgG2, IgG3, and IgG4), and IgM. The distinguishing features between these antibody classes are their constant regions, although subtler differences may exist in the Variable or V region. FIG. 1 shows an IgG antibody, used here as an example to describe the general structural features of immunoglobulins. IgG antibodies are tetrameric proteins that include two heavy chains and two light chains. Each IgG heavy chain includes four immunoglobulin domains linked from N- to C-terminus in the following order: heavy chain variable domain (VH), heavy chain constant domain 1 (CH1), heavy chain constant domain 2 (CH2), and heavy chain constant domain 3 (CH3) (VH-CH1-CH2-CH3; also referred to as VH-Cγ1-Cγ2-Cγ3, referring to the heavy chain variable domain, constant gamma I domain, constant gamma 2 domain, and constant gamma 3 domain respectively). The CH1-CH2-CH3 or Cγ1-Cγ2-Cγ3 domains are also referred to collectively as the heavy chain constant region. The IgG light chain is composed of two immunoglobulin domains linked from N- to C-terminus in the following order light chain variable domain (VL) and light chain constant domain (CL) (VL-CL).

Each variable region of an antibody (VH and VL) contains the antigen binding determinants of the molecule, and thus determines the specificity of an antibody for its target antigen. The variable region is so named because it is the most distinct in sequence from other antibodies within the same class. The majority of sequence variability occurs in the complementarity determining regions (CDRs). There are 6 CDRs total, three in each variable domain (VH and VL), designated VH CDRI, VH CDR2, VH CDR3, VL CDRI, VL CDR2, and VL CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens.

A number of high-resolution structures are available for a variety of variable region fragments from different organisms, some unbound and some in complex with antigen. The sequence and structural features of antibody variable regions are well characterized (Morea et al., 1997; Morea et al., 2000), and the conserved features of antibodies have enabled the development of a wealth of antibody engineering techniques (Maynard et al., 2000). For example, it is possible to graft the CDRs from one antibody, for example a murine antibody, onto the framework region of another antibody, for example a human antibody. This process, referred to in the art as "humanization," enables generation of antibody therapeutics that have a lower immunogenicity as compared to nonhuman antibodies. Fragments including the variable region can exist in the absence of other regions of the antibody, including for example, the antigen binding fragment (Fab) which includes VH-CH1 and VH-CL, the variable fragment (Fv) which includes VH and Vu, the single chain variable fragment (scFv) which includes VH and VL linked together in the same chain, as well as a variety of other variable region fragments (Little et al., 2000).

Part of the heavy chain constant region is referred to as the Fc domain or region. The Fc region of an antibody interacts with a number of Fc receptors and ligands, imparting an array of important functional capabilities referred to as effector functions. For IgG the Fc region, as shown in FIG. 1, includes Ig domains CH2 and CH3 and the N-terminal hinge leading into CH2. An important family of Fc receptors for the IgG class is the Fc gamma receptors (FcγRs). These receptors mediate communication between antibodies and the cellular arm of the immune system (Raghavan et al., 1996; Ravetch et al., 2001). In humans this protein family includes Fcγ RI (CD64), including isoforms FcγRIa, FcγRIb, and FcγRIc; FcγRII (CD32), including isoforms FcγRIIa (including allotypes H131 and R131), Fcγ RIIb (including Fcγ RIIb-1 and FcγRIIb-2), and FcγRIIc; and FcγRIII (CD16), including isoforms FcγRIIa (including allotypes VI58 and F158) and FcγRIIIb (including allotypes Fcγ RIIIb-NAI and Fcγ RIIIbNA2) (Jefferis et al., 2002). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and γγ T cells.

Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996; Ghetie et al., 2000; Ravetch et al., 2001). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP). In the case of antimicrobial activity, the cell mediated anti-microbial reaction is generally referred to as opsono phagocytosis. Opsonization involves the binding of an opsonin, e.g., antibody, to a receptor on the pathogen's cell membrane. After opsonin binds to the membrane, phagocytes are attracted to the pathogen. The Fab portion of the antibody binds to the antigen, whereas the Fc portion of the antibody binds to an Fc receptor on the phagocyte, facilitating phagocytosis. The receptor-opsonin complex can also create byproducts like C3b and C4b which are important components of the complement system. These components are deposited on the cell surface of the pathogen and aid in its destruction. A number of structures have been solved of the extracellular domains of human FcγRs, including FcγRIIa (protein data bank (pdb) accession code IH9V) (Sondermann et al., 2001) (pdb accession code IFCG) (Maxwell et al., 1999), FcγRIIb (pdb accession code 2FCB) (Sondermann et al., 1999) and FcγRIIIb (pdb accession code IE4J) (Sondermann et al., 2000). All FcγRs bind the same region on Fc, at the N-terminal end of the Cγ2 domain and the preceding hinge. This interaction is well characterized structurally (Sondermann et al., 2001), and several structures of the human Fc bound to the extracellular domain of human FcγRIIIb have been solved (pdb accession code IE4K) (Sondermann et al., 2000), (pdb accession codes HIS and IIIX) (Radaev et al., 2001), as well as has the structure of the human IgE Fc/FcERIa complex (pdb accession code IF6A) (Garman et al., 2000).

The different IgG subclasses have different affinities for the FcγRs, with IgG1 and IgG3 typically binding substantially better to the receptors than IgG2 and IgG4 (Jefferis et al., 2002). All FcγRs bind the same region on IgG Fc, yet with different affinities: the high affinity binder FcγRI has a Kd for IgG1 of $10^{-8}$ M whereas the low affinity receptors FcγRII and FcγRIII generally bind at $10^{-6}$ M and $10^{-5}$ M, respectively. The extracellular domains of FcγRIIa and FcγRIIIb are 96% identical; however FcγRIIIb does not have an intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. An overlapping but separate site on Fc, serves as the interface for the complement protein C1q. Antibodies can also destroy pathogens or cancerous cells by complement-dependent cytotoxicity (CDC) whereby antibodies bound to the cell-surface initiate deposition and activation of early complement components. In the same way that Fc/FcγR binding mediates opsonophagocytosis, ADCC and ADCP, Fc/C1q binding mediates complement dependent cytotoxicity (CDC) or complement deposition on the target cell surface. C1q forms a complex with the serine proteases C1r and C1s to form the C1 complex. C1q is capable of binding six antibodies, although binding to two IgGs is sufficient to activate the complement cascade. Similar to Fc interaction with FcγRs, different IgG subclasses have different affinity for C1q, with IgG1 and IgG3 typically binding substantially better to the FcγRs than IgG2 and IgG4 (Jefferis et al., 2002). There is currently no structure available for the Fc/C1q complex; however, mutagenesis studies have mapped the binding site on human IgG for C1q to a region involving residues D270, K322, K326, P329, and P331, and E333 (Idusogie et al., 2000; Idusogie et al., 2001).

A site on Fc between the CH2 and CH3 domains of IgG, mediates interaction with the neonatal receptor FcRn, the binding of which recycles endocytosed antibody from the endosome back to the bloodstream (Raghavan et al., 1996; Ghetie et al., 2000). This process, coupled with preclusion of kidney filtration due to the large size of the full-length molecule, results in favorable antibody serum half-lives ranging from one to three weeks. Binding of Fc to FcRn also plays an important role in antibody transport.

The binding site for FcRn on Fc overlaps with the site at which S. aureus SpA, streptococcal Protein G and a variety of other microbial Fc Binding Proteins (FcBP) bind. The tight binding by these proteins has been exploited as a means to purify antibodies by employing SpA or Protein G affinity chromatography during protein purification. Thus, the fidelity of this region on Fc is important for both the clinical properties of antibodies and their purification. Available structures of the rat Fc/FcRn complex (Martin et al., 2001), and of the complexes of Fc with Proteins A and G (Deisenhofer, 1981; Sauer-Eriksson et al., 1995; Tashiro et al., 1995) provide insight into the interaction of Fc with these proteins.

An important feature of the Fc region is the conserved N-linked glycosylation that occurs at N297, shown in FIG. 1. This carbohydrate, or oligosaccharide as it is sometimes referred, plays an important structural and functional role for the antibody, and is one of the principle reasons that antibodies must be produced using mammalian expression systems. While not wanting to be limited to one theory, it is believed that the structural purpose of this carbohydrate may be to stabilize or solubilize Fc, determine a specific angle or level of flexibility between the Cγ3 and Cγ2 domains, keep the two Cγ2 domains from aggregating with one another across the central axis, or a combination of these. Efficient Fc binding to FcγR and C1q requires this modification and alterations in the composition of the N297 carbohydrate or its elimination affect binding to these proteins (Umaiia et al., 1999; Davies et al., 2001; Mimura et al., 2001; Radaev et al., 2001; Shields et al., 2001; Shields et al., 2002; Simmons et al., 2002). Yet the carbohydrate makes little if any specific contact with FcγRs (Radaev et al., 2001), indicating that the functional role of the N297 carbohydrate in mediating Fc/Fcγ R binding may be via the structural role it plays in determining the Fc conformation. This is supported by a collection of crystal structures of four different Fc glycoforms, which show that the composition of the oligosaccharide impacts the conformation of Cγ2 and as a result the Fc/Fcγ R interface (Krapp et al., 2003).

The features of antibodies discussed above, specificity for its target, ability to mediate immune effector functions, and good half-lifes in serum-make antibodies powerful therapeutics. Monoclonal antibodies are used therapeutically for the treatment of a variety of conditions including cancer, inflammation, cardiovascular disease and infectious diseases. There are currently several antibody products on the market and hundreds in development. In addition to antibodies, an antibody-like protein that is finding an expanding role in research and therapy is the Fc fusion (Chamow et al., 1996; Ashkenazi et al., 1997). An Fc fusion is a protein wherein one or more polypeptides are operably linked to Fc. An Fc fusion combines the Fc region of an antibody, and thus its favorable effector function and pharmacokinetics, with the target-binding region of a receptor, ligand, or some other protein or protein domain. The role of the latter is to mediate target recognition, and thus it is functionally analogous to the antibody variable region. Because of the structural and functional overlap of Fc fusions with antibodies, the discussion on antibodies herein is also applicable to Fc fusions.

The mechanisms by which an antibody neutralizes pathogenic material can be diverse, including antibody dependent cellular cytotoxicity (ADCC), antibody-dependent cellular phagocytosis, complement-dependent cytotoxicity (CDC), opsonization, and steric hindrance, almost all of which require the antibody Fc region to interact with cellular receptors (Marasco & Sui, 2007; Lehner 1989; Lazar et al. 2006). For instance, ADCC depends upon the Fc interaction with the activating FcγRIIIa receptor, present on natural killer cells and other leukocytes. Increasing the affinity and selectivity of this interaction through three Fc amino acid substitutions increased ADCC by two orders of magnitude in vitro (Lazar et al., U.S. Patent Publication No. 20080242845). Additionally, heavy chain constant region variants with increased ability to recruit complement have been described. Variants demonstrated enhanced potency in a cell-based CDC assay and improved binding affinity to C1q. (Moore et al., 2010)

Antibodies have been used to bind and inactivate pathogenic material for many years, originally being isolated as polyclonal antibody mixtures from immunized horse serum. This "passive immunotherapy" was used successfully to treat many viral and bacterial infections but due to numerous problems, including product heterogeneity and low specific titer, coupled with risks of immunogenicity and viral contamination, lost favor after the introduction of antibiotics (Casadevall et al., 2004).

The emergence of antibiotic-resistant microorganisms, emerging viruses and the threat of engineered microorganisms coupled with advances in understanding pathogenic mechanisms and antibody technology leaves this class of therapeutics poised for a comeback (Casadevall et al., 2004; Zeitlin et al., 2000). Antibodies are attractive anti-infective therapeutics for their ability to recognize pathogen-associated ligand molecules with exquisite specificity and to recruit additional immune system components such as complement and natural killer cells, facilitating pathogen inactivation and removal. When properly designed, an antibody can effectively eliminate or control the infection. Unfortunately, efforts to develop recombinant monoclonal antibodies that recapitulate polyclonal anti-sera has not been straightforward, largely due to challenges in identifying appropriate target epitopes, microbial evasion of the humeral immune response and interactions with the rest of the immune system. In the cases of RSV and anthrax, important neutralizing epitopes have been identified, resulting in a remarkably successful drug in the first case and several promising candidates in the second. Several approaches to treating infection involve antibodies that directly bind surface-exposed or associated molecules on whole pathogen cells. These antibodies (depending on the isotype selected) can act by (1) recruiting immune system components to eliminate the pathogen through antibody effector functionalities (e.g., complement, CDC, ADCC, ADCP and opsonophagocytosis); (2) blocking cell associated pathogenic mechanisms, i.e., type III secretion of virulence factors; and (3) directly killing pathogens by targeted delivery of chemotherapeutic agents. These approaches are less developed than those for antiviral or anti-toxin therapies in that none have been approved for use and several promising candidates for treatment of *Staphylococcus* infections reached Phase III trials, only to miss their efficacy targets.

Variant Immunoglobulins Having Attenuated Binding to Virulence Factors

According to the embodiments described herein, variant antibodies having attenuated non-immune binding to one or more IgBP virulence factors are provided. In some embodiments, the antibodies have a variant heavy chain constant region (i.e., a variant CH1-CH2-CH3 domain or variant Cγ1-Cγ2-Cγ3 domain) having attenuated binding to one or more microbial immunoglobulin binding proteins (IgBPs).

According to the embodiments described herein, the disclosure provides anti-microbial monoclonal immunoglobulins, such as variant IgG immunoglobulins, in which at least one amino acid from the IgG heavy chain constant region is substituted with another amino acid which is different from that present in the parent antibody. The amino acid substitution or substitutions may be in any one or more of the heavy chain constant domains, CH1, CH2 or CH3.

In some embodiments, the monoclonal antibody is a mammalian, chimeric, humanized of human anti-microbial IgG variant antibody in which at least one amino acid from an IgG heavy chain constant region, is substituted with at least one amino acid that differs from that present in the parent antibody. Such variant anti-microbial antibodies have attenuated Fc binding to one or more microbial Fc Binding proteins or Fc binding protein domains expressed by the target microbe.

In other embodiments, the monoclonal antibody is a animal anti-microbial Ig variant antibody for veterinary use, in which at least one amino acid from the IgG heavy chain constant region is substituted with another amino acid which is different from that present in the parent antibody. Such variant anti-microbial antibodies have attenuated Fc binding to one or more microbial Fc Binding proteins or Fc binding protein domains expressed by the target microbe.

The variant immunoglobulin IgG heavy chain and light chain constant regions described herein can be combined with immunoglobulin variable heavy and light chain regions (the variable domain), which bind antigens produced by microbes that express one or more microbial immunoglobulin binding protein.

In some embodiments, the variable domain of the antibody binds to a microbial protein that is a microbial immunoglobulin binding protein, and the heavy chain constant regions of the antibody is a variant IgG Fc which has attenuated binding to one or more microbial Ig Binding Protein or Fc Binding Protein domain expressed by the target microbe.

In other embodiments, the variable domain of the antibody binds to a microbial protein that is not an microbial immunoglobulin binding protein, and the heavy chain constant region of the antibody is a variant IgG Fc which has attenuated binding to one or more microbial Ig Binding Proteins or Fc Binding Protein domains expressed by the target microbe.

The heavy chain constant region variant IgG immunoglobulins claimed herein have enhanced antimicrobial activity relative to their parental antibodies.

In some embodiments such variant IgG heavy chain constant polypeptide sequences are combined with immunoglobulin heavy chain variable polypeptide sequences and light chains polypeptide sequences, which bind one or more cell surface or secreted microbial antigen.

In some embodiments, immunoglobulins with variant heavy chain constant regions having altered (i.e., decreased) non-immune binding to one or more microbial IgBP are provided. The embodiments described herein provide modified antibodies having altered non-immune IgBP binding relative to the corresponding unmodified antibody. More particularly, the embodiments described herein are directed to variant human or humanized monoclonal antibodies directed against microbial surface antigens or surface associated antigens, which have attenuated Fc binding to one or more microbial IgBPs.

The embodiments described herein are directed to variant IgG immunoglobulin heavy chain constant region-containing polypeptides that have attenuated heavy chain constant regions binding to one or more microbial IgBPs as a consequence of the introduction of amino acid changes within the immunoglobulin heavy chain region.

According to the embodiments described herein, the variant anti-microbial antibodies of the disclosure may include one or more sequences derived from at least 4 regions of the IgG antibody. These regions include, but are not limited to:

The heavy chain constant region, which includes domains CH1, the hinge region, CH2 and CH3. This region of the antibody is responsible for the effector function of the antibody. In some embodiments, this region is derived from human IgG1. In alternative embodiments, the Fc region is of mixed isotype in which the CH3 domain of IgG1, or the CH2 and CH3 domains of IgG1, are exchanged with their homologous domains from IgG3 of any human allotype. The EU numbering of the heavy chain constant region corresponds to approximate positions of H118-H446

The heavy chain variable domain, which contains the antigen recognition region of the heavy chain, including the CDR1, CDR2 and CDR3 and framework regions. This region can be derived from a human antibody, from a chimeric or humanized antibody, or by humanization of a non-human antibody.

The light chain constant regions: In one embodiment, the light chain constant region is a kappa light chain. In other embodiments the light chain constant region is a lambda light chain. The EU numbering positions for a light chain correspond to approximate positions of L108-L214

The light chain variable domain, which includes the antigen recognition region of the light chain, including the CDR1, CDR2 and CDR3 and framework regions. This region can be derived from a human antibody, from a chimeric or humanized antibody, or by humanization of a non-human antibody.

In some embodiments, the heavy chain constant region variant antibody is of IgG immunoglobulin, in which at least one amino acid from the heavy chain constant region selected from, but not limited to amino acid residues (i.e., EU positions) 214, 251, 252, 253, 254, 274, 276, 311, 314, 356, 358, 380, 382, 384, 419, 422, 428, 431, 432, 433, 434, 435, 436 and 438 is substituted with an amino acid residue different from that present in the unmodified IgG1 antibody. The substitutions described herein are not limiting and in some aspect, additional substitution residues may be made. Further, at least one amino acid from the heavy chain constant region may be a single amino acid substitution alone, or a combination of at least two amino acids selected from any combination of one or more of the amino acid substitutions described herein, combined with one or more second amino acid substitution describe herein, or alternatively, may be combined with another substitution not disclosed herein. Substitutions, either alone or in combinations, attenuates the binding of one or more microbial Ig Binding Protein to the heavy chain constant region of the variant antibody In some embodiments, the heavy chain constant region variant antibody is of isotype IgG1, in which at least one amino acid from the heavy chain constant region selected from, but not limited to amino acid residues (i.e., EU positions) 214, 251, 252, 253, 254, 274, 276, 311, 314, 356, 358, 380, 382, 384, 419, 422, 428, 431, 432, 433, 434, 435, 436 and 438 is substituted with an amino acid residue different from that present in the unmodified IgG1 antibody. The substitutions described herein are not limiting and in some aspect, additional substitution residues may be made. Further, at least one amino acid from the heavy chain constant region may be a single amino acid substitution alone, or a combination of at least two amino acids selected from any combination of one or more of the amino acid substitutions described herein, combined with one or more second amino acid substitution describe herein, or alternatively, may be combined with another substitution not disclosed herein. Substitutions, either alone or in combinations, attenuates the binding of one or more microbial Ig Binding Protein to the heavy chain constant region of the variant antibody In embodiments in which the heavy chain constant region variant anti-microbial antibody is directed against *S. aureus*, amino acid changes can be introduced into the heavy chain constant CH2 domain to attenuate SSL10 binding to the variant immunoglobulin. Separate mutations can be introduced into the CH2 or CH3 domain to attenuate Sbi and/or SpA binding to the Fc domain. Mutations can also be introduced into the heavy chain variable FW region to attenuate superantigen type SpA binding to the Fab domain of VH3 derived antibodies.

In some embodiments, amino acid residue (i.e., EU position) 435 from the heavy chain constant region is substituted with Arg, resulting in attenuated binding of the Fc domain of the variant antibody to Sbi and/or SpA (Including but not limited to SEQ ID: 31-46).

In some embodiments, amino acid residue (i.e., EU position) 435 from the heavy chain constant region is substituted with Arg and amino acid residue (i.e., EU position) 274 from the heavy chain constant region is substituted with Gln resulting in attenuated binding of the Fc domain of the variant antibody to Sbi and SSL 10 or SpA (Including but not limited to SEQ ID: 32, 34, 36, 38, 40, 42, 44, 46, 48, 50, 52, 54, 56)

In some embodiments, amino acid residue (i.e., EU position) 435 from the heavy chain constant region is substituted with Arg and amino acid residue (i.e., EU position) 436 from the heavy chain constant region is substituted with Phe resulting in attenuated binding of the Fc domain of the variant antibody to Sbi and/or SpA (Including but not limited to SEQ ID: 39-46).

In some embodiments, amino acid residue (i.e., EU position) 435 from the heavy chain constant region is substituted with Arg, amino acid residue (i.e., EU position) 436 from the heavy chain constant region is substituted with Phe and amino acid residue (i.e., EU position) 274 from the heavy chain constant region is substituted with Gln resulting in attenuated binding of the Fc domain of the variant antibody to Sbi and SSL 10 and/or SpA (Including but not limited to SEQ ID: 40, 42, 44, 46)

In some embodiments, amino acid residue (i.e., EU position) 422 from the heavy chain constant region is substituted with Ile and amino acid residue (i.e., EU position) 435 from the heavy chain constant region is substituted with Arg resulting in attenuated binding of the variant antibody to Sbi and/or SpA (Including but not limited to SEQ ID 33, 34, 37, 38, 41, 42, 45, 46).

In some embodiments, amino acid residue (i.e., EU position) 422 from the heavy chain constant region is substituted with Ile, amino acid residue (i.e., EU position) 274 from the heavy chain constant region is substituted with Gln and amino acid residue (i.e., EU position) 435 from the heavy chain constant region is substituted with Arg resulting in attenuated binding of the variant antibody to Sbi and SSL 10 and/or SpA (Including but not limited to SEQ ID 34, 38, 42, 46).

In some embodiments, amino acid residue (i.e., EU position) 422 from the heavy chain constant region is substituted with Ile, amino acid residue (i.e., EU position) 435 from the heavy chain constant region is substituted with Arg and amino acid residue (i.e., EU position) 436 from the heavy chain constant region is substituted with Phe resulting in attenuated binding of the variant antibody to Sbi and/or SpA (Including but not limited to SEQ ID: 41, 42, 45, 46).

In some embodiments, amino acid residue (i.e., EU position) 422 from the heavy chain constant region is substituted with Ile, amino acid residue (i.e., EU position) 274 from the heavy chain constant region is substituted with Gln, amino acid residue (i.e., EU position) 435 from the heavy chain constant region is substituted with Arg and amino acid residue (i.e., EU position) 436 from the heavy chain constant region is substituted with Phe resulting in attenuated binding of the variant antibody to Sbi and/or SpA (Including but not limited to SEQ ID:42, 46).

In some embodiments, amino acid residue (i.e., EU position) 419 from the heavy chain constant region is substituted with Glu and amino acid residue (i.e., EU position) 435 from the heavy chain constant region is substituted with Arg resulting in attenuated binding of the variant antibody to Sbi and/or SpA (Including but not limited to SEQ ID: 35-38, 43-46)

In some embodiments, amino acid residue (i.e., EU position) 419 from the heavy chain constant region is substituted with Glu, amino acid residue (i.e., EU position) 435 from the heavy chain constant region is substituted with Arg and amino acid residue (i.e., EU position) 274 from the heavy chain constant region is substituted with Gln resulting in attenuated binding of the variant antibody to Sbi and SSL10 and/or SpA (Including but not limited to SEQ ID: 36, 38 44, 46).

In some embodiments, amino acid residue (i.e., EU position) 419 from the heavy chain constant region is substituted with Glu, amino acid residue (i.e., EU position) 435 from the heavy chain constant region is substituted with Arg and amino acid residue (i.e., EU position) 436 from the heavy chain constant region is substituted with Phe, resulting in attenuated binding of the variant antibody to Sbi and/or SpA (Including but not limited to SEQ ID: 43-46).

In some embodiments, amino acid residue (i.e., EU position) 419 from the heavy chain constant region is substituted with Glu, amino acid residue (i.e., EU position) 435 from the heavy chain constant region is substituted with Arg, amino acid residue (i.e., EU position) 274 from the heavy chain constant region is substituted with Gln and amino acid residue (i.e., EU position) 436 from the heavy chain constant region is substituted with Phe, resulting in attenuated binding of the variant antibody to Sbi and/or SpA (Including but not limited to SEQ ID: 44, 46).

In some embodiments, amino acid residue (i.e., EU position) 419 from the heavy chain constant region is substituted with Glu, amino acid residue (i.e., EU position) 422 from the heavy chain constant region is substituted with Ile and amino acid residue (i.e., EU position) 435 from the heavy chain constant region is substituted with Arg resulting in attenuated binding of the variant antibody to Sbi and/or SpA (Including but not limited to SEQ ID: 37, 38, 45, 46).

In some embodiments, amino acid residue (i.e., EU position) 419 from the heavy chain constant region is substituted with Glu, amino acid residue (i.e., EU position) 422 from the heavy chain constant region is substituted with Ile, amino acid residue (i.e., EU position) 274 from the heavy chain constant region is substituted with Gln and amino acid residue (i.e., EU position) 435 from the heavy chain constant region is substituted with Arg resulting in attenuated binding of the variant antibody to Sbi and SSL10 and/or SpA (Including but not limited to SEQ ID: 38, 46).

In some embodiments, amino acid residue (i.e., EU position) 419 from the heavy chain constant region is substituted with Glu, amino acid residue (i.e., EU position) 422 from the heavy chain constant region is substituted with Ile, amino acid residue (i.e., EU position) 435 from the heavy chain constant region is substituted with Arg and amino acid residue (i.e., EU position) 436 from the heavy chain constant region is substituted with Phe, resulting in attenuated binding of the variant antibody to Sbi and/or SpA (Including but not limited to SEQ ID: 45, 46).

In some embodiments, amino acid residue (i.e., EU position) 419 from the heavy chain constant region is substituted with Glu, amino acid residue (i.e., EU position) 422 from the heavy chain constant region is substituted with Ile, amino acid residue (i.e., EU position) 435 from the heavy chain constant region is substituted with Arg, amino acid residue (i.e., EU position) 274 from the heavy chain constant region is substituted with Gln and amino acid residue (i.e., EU position) 436 from the heavy chain constant region is substituted with Phe, resulting in attenuated binding of the variant antibody to Sbi and SSL10 and/or SpA (Including but not limited to SEQ ID: 46).

In some embodiments, amino acid residue (i.e., EU position) 436 from the heavy chain constant region is substituted with Phe resulting in attenuated binding of the Fc domain of the variant antibody to Sbi and/or SpA (Including but not limited to SEQ ID: 39-48, 53-56).

In some embodiments, amino acid residue (i.e., EU position) 436 from the heavy chain constant region is substituted with Phe and amino acid residue (i.e., EU position) 274 from the heavy chain constant region is substituted with Gln resulting in attenuated binding of the Fc domain of the variant antibody to Sbi and SSL 10 and/or SpA (Including but not limited to SEQ ID: 40, 42, 44, 46, 48, 54, 56).

In some embodiments, amino acid residue (i.e., EU position) 254 from the heavy chain constant region is substituted with Thr resulting in attenuated binding of the variant antibody to Sbi and/or SpA (Including but not limited to SEQ ID: 49-56).

In some embodiments, amino acid residue (i.e., EU position) 254 from the heavy chain constant region is substituted with Thr and amino acid residue (i.e., EU position) 274 from the heavy chain constant region is substituted with Gln resulting in attenuated binding of the variant antibody to Sbi and SSL10 and/or SpA (Including but not limited to SEQ ID: 50, 52, 54, 56).

In some embodiments, amino acid residue (i.e., EU position) 252 and 254 from the heavy chain constant region are substituted with Thr resulting in attenuated binding of the variant antibody to Sbi and/or SpA (Including but not limited to SEQ ID: 51, 52, 55, 56)

In some embodiments, amino acid residue (i.e., EU position) 252 and 254 from the heavy chain constant region are substituted with Thr, and amino acid residue (i.e., EU position) 274 from the heavy chain constant region is substituted with Gln resulting in attenuated binding of the variant antibody to Sbi and SSL10 and/or SpA (Including but not limited to SEQ ID: 52, 56)

In some embodiments, amino acid residue (i.e., EU position) 254 from the heavy chain constant region is substituted with Thr and amino acid residue (i.e., EU position) 456 from the heavy chain constant region is substituted with Phe resulting in attenuated binding of the variant antibody to Sbi and/or SpA (Including but not limited to SEQ ID: 53-56).

In some embodiments, amino acid residue (i.e., EU position) 254 from the heavy chain constant region is substituted with Thr, amino acid residue (i.e., EU position) 274 from the heavy chain constant region is substituted with Gln and amino acid residue (i.e., EU position) 456 from the heavy chain constant region is substituted with Phe resulting in attenuated binding of the variant antibody to SSL10 and Sbi and/or SpA (Including but not limited to SEQ ID: 54, 56).

In some embodiments, amino acid residue (i.e., EU position) 252 and 254 from the heavy chain constant region are substituted with Thr and amino acid residue (i.e., EU position) 456 from the heavy chain constant region is substituted with Phe resulting in attenuated binding of the variant antibody to Sbi and/or SpA (Including but not limited to SEQ ID: 55, 56).

In some embodiments, amino acid residue (i.e., EU position) 252 and 254 from the heavy chain constant region are substituted with Thr, amino acid residue (i.e., EU position) 456 from the heavy chain constant region is substituted with Phe and amino acid residue (i.e., EU position) 274 from the heavy chain constant region is substituted with Gln resulting in attenuated binding of the variant antibody to Sbi and SSL10 and/or SpA (Including but not limited to SEQ ID: 56).

In some embodiments, amino acid residue (i.e., EU position) 274 and/or 276 from the heavy chain constant region are substituted with another amino acid, which is different from that present in an unmodified parental antibody. The resulting variant antibody variant antibody has attenuated binding to the SSL10 IgBPs compared with the unmodified antibody.

In some embodiments, amino acid residue (i.e., EU position) 274 from the heavy chain constant region is substituted with Gln, which is different from that present in an unmodified parental antibody. The resulting variant antibody has attenuated binding to SSL10 IgBPs compared with the unmodified antibody (Including but not limited to SEQ ID: 32, 34, 36, 38, 40, 42, 44, 46, 48, 50, 52, 54, 56).

In some embodiments, amino acid residue (i.e., EU position) 276 from the heavy chain constant region is substituted with Lys, which is different from that present in an unmodified parental antibody. The resulting variant antibody has attenuated binding to SSL10 IgBPs compared with the unmodified antibody.

In some embodiments, amino acid residue (i.e., EU position) 274 and 276 from the heavy chain constant region is substituted with Gln and Lys respectively, which is different from the residues present in an unmodified parental antibody. The resulting variant antibody has attenuated binding affinity for SSL10 IgBPs compared with the unmodified antibody.

In some embodiments, where the immunoglobulin is directed against a staphylococcal antigen, a variant IgG1 antibody having attenuated binding to S. aureus SSL 10 as compared with the parental antibody is provided, wherein either one of both of amino acid residues (i.e., EU position) 274 and 276 from the heavy chain constant region are substituted with Gln and Lys respectively.

In some embodiments, antibodies having a heavy chain constant region substantially identical to a naturally occurring class IgG1 antibody constant region are provided, wherein at least two amino acid residue selected from residues (i.e., EU positions) 214, 251, 252, 253, 254, 274, 276, 311, 314, 356, 358, 380, 382, 384, 419, 422, 428, 431, 432, 433, 434, 435, 436 and 438 are different from that present in the parental antibody, thereby attenuating binding of the variant heavy chain constant region (relative to the parental antibody) to one or more FcBP selected from the list: S. aureus SSL10, Sbi and Protein.

In some embodiments, antibodies having a heavy chain constant region substantially identical to a naturally occurring class IgG1 antibody heavy chain constant region are provided, wherein at least three amino acid residue selected from residues (i.e., EU positions) 214, 251, 252, 253, 254, 274, 276, 311, 314, 356, 358, 380, 382, 384, 419, 422, 428, 431, 432, 433, 434, 435, 436 and 438 are different from that present in the naturally occurring class IgG1 antibody, thereby attenuating binding of the variant heavy chain constant region (relative to the parental antibody) to one or more FcBP selected from the list: *S. aureus* SSL10, Sbi and Protein.

In some embodiments, antibodies having a heavy chain constant region substantially identical to a naturally occurring class IgG1 antibody heavy chain constant region are provided, wherein at least three amino acid residue selected from residues (i.e., EU positions) 274, 276, 419, 422, 435 and 436 are different from that present in the naturally occurring class IgG1 antibody, thereby attenuating binding of the variant heavy chain constant region (relative to the parental antibody) to one or more FcBP selected from the list: *S. aureus* SSL10, Sbi and Protein.

In some embodiments, antibodies having a heavy chain constant region substantially identical to a naturally occurring class IgG1 antibody constant region are provided, wherein at least three amino acid residue selected from residues (i.e., EU positions) 214, 252, 254, 274, 276, 356, 358, 419, 422, 431, 435 and 436 are different from that present in the parental antibody, thereby attenuating binding of the variant heavy chain constant region (relative to the parental antibody) to one or more FcBP selected from the list: *S. aureus* SSL10, Sbi and Protein.

In some embodiments, allotypic versions of variant IgG1 antibodies with attenuated microbial FcBP binding to the variant Fc domain of the antibody are provided, wherein at least one heavy chain amino acid residue selected from residues (i.e., EU positions) 214, 356, 358 and 431 of the heavy chain are different from that present in the parental antibody.

In some embodiments, iso-allotypic versions of variant IgG1 antibodies with attenuated FcBP binding to the variant heavy chain constant region of the antibody are claimed, wherein at least one heavy chain amino acid residue selected from residues (i.e., EU positions) 214, 251, 252, 253, 254, 274, 276, 311, 314, 356, 358, 380, 382, 384, 419, 422, 428, 431, 432, 433, 434, 435, 436 and 438 of the heavy chain are different from that present in the parental antibody.

In some embodiments, iso-allotypic version of variant IgG1 antibodies with attenuated microbial FcBP binding to the variant heavy chain constant region of the antibody are claimed, wherein at least one heavy chain amino acid residue selected from residues (i.e., EU positions) 214, 251, 252, 253, 254, 274, 276, 311, 314, 356, 358, 380, 382, 384, 419, 422, 428, 431, 432, 433, 434, 435, 436 and 438 of the heavy chain are different from that present in the parental antibody. In embodiments amino acid 365 is Glu, 358 is Met, 431 is Ala and 214 is Lys.

In some embodiments, the heavy chain constant region of the variant IgG1 antibody has decreased binding to one or more microbial FcBPs selected from the list including, but not limited to *S. aureus* Sbi, SpA and SSL10 compared with the parental antibody, in which at least two heavy chain constant region amino acids selected from residues (i.e., EU positions) 214, 251, 252, 253, 254, 274, 276, 311, 314, 356, 358, 380, 382, 384, 419, 422, 428, 431, 432, 433, 434, 435, 436 and 438 are substituted with amino acid residues different from that present in the parental IgG1 antibody.

In some embodiments the heavy chain constant region of the variant IgG1 antibody has decreased binding to one or more microbial FcBPs selected from the group including, but not limited to *S. aureus* Sbi, SpA and SSL10 compared with the parental antibody, in which at least three heavy chain constant region amino acids selected from residues (i.e., EU positions) 214, 251, 252, 253, 254, 274, 276, 311, 314, 356, 358, 380, 382, 384, 419, 422, 428, 431, 432, 433, 434, 435, 436 and 438 are substituted with amino acid residues different from that present in the parental IgG1 antibody.

In some embodiments, the heavy chain constant region of the antibody, or variant antibody, contains a heavy chain constant region of isotype G1m17.

In some embodiments, the heavy chain constant region of the antibody, or variant antibody, contains a heavy chain constant region of isotype G1m17 that includes an amino acid sequences selected from the group heavy chain constant region 1-27 (SEQ ID NO:30-56).

In other embodiments, the heavy chain constant region of the antibody, or variant antibody, may be substantially encoded by any allotype or isoallotype of any immunoglobulin gene. In one embodiment, the heavy chain constant region variants comprise IgG1 sequences that are classified as G1m(1), G1m(2), G1m(3), G1m(17), nG1m(I), nG1m(2), and/or nG1m(17). Thus, in the context of an IgG1 isotype, the heavy chain constant region variants may comprise a Lys (G1m(17)) or Arg (G1m(3)) at position 214, an Asp356/Leu358 (G1m(1)) or Glu356/Met358 (nG1m(1), and/or a Gly (G1m(2)) or Ala (nG1m(2)) at position 431.

In an alternative embodiment, the antibody variant has a constant heavy chain region of mixed isotype, created by substituting the CH2 and CH3 domains of the parental IgG1 heavy chain constant region with the CH2 and CH3 domains from the IgG3 heavy chain contain region. In some embodiments, the IgG3 heavy chain sequences can be from IgG3 allotypes G3m5,10,11,13,14, G3m5,6,10,11,14, G3m5,6,11, 24 or G3m21,28.

In an alternative embodiment, the antibody variant has a constant heavy chain region of mixed isotype, created by substituting the CH3 domains of the parental IgG1 heavy chain constant region with the CH3 domains from IgG3 heavy chain contain region. In some embodiments, the IgG3 heavy chain sequences can be from IgG3 allotypes G3m5, 10,11,13,14, G3m5,6,10,11,14, G3m5,6,11,24 or G3m21, 28.

In some embodiments, the variant antibodies are of mixed isotype, wherein the IgG1/IgG3 fusion junction is located between amino acid residues (i.e., EU position) 236 and 237.

In some embodiments, the variant antibodies are of mixed isotype, wherein the IgG1/IgG3 fusion junction is located between amino acid residues (i.e., EU position) 340 and 341.

In some embodiments, variant antibodies of mixed isotype having the IgG1/IgG3 fusion junction located between amino acid residues (i.e., EU position) 236 and 237, have one or more amino acid from the mixed isotype heavy chain constant region selected from amino acid residues (i.e., EU position) 214, 251, 252, 253, 254, 274, 276, 311, 314, 356, 358, 380, 382, 384, 419, 422, 428, 431, 432, 433, 434, 435, 436 and 438 that is substituted with an amino acid residue different from that present in the parental mixed isotype antibody.

In some embodiments, variant antibodies of mixed isotype having the IgG1/IgG3 fusion junction located between amino acid residues (i.e., EU position) 340 and 341, have one or more amino acid from the mixed isotype heavy chain constant region selected from amino acid residues (i.e., EU position) 214, 251, 252, 253, 254, 274, 276, 311, 314, 356, 358, 380, 382, 384, 419, 422, 428, 431, 432, 433, 434, 435, 436 and 438, that is substituted with an amino acid residue different from that present in the parental mixed isotype antibody.

In some embodiments, the antibodies described herein may have a variant heavy chain variable region having attenuated non-immune binding to one or more *S. aureus* superantigens such that the antibody has low or no superantigen type binding to SpA. Such immunoglobulins and their variants can be selected so as to avoid the use of human VH3 derived sequences, which can interact with SpA at a site distinct from the Fc binding site. Alternatively, if VH3 derived sequences are used, and Fab-SpA superantigen type binding is present in the parental immunoglobulin, then modified variable heavy chains are provided in which at least one amino acid from the heavy chain variable region is substituted with an amino acid residue different from that present in the unmodified parental antibody selected from the list of VH residues including but not limited to H15, H17, H19, H57, H59, H64, H65, H66, H68, H69, H70, H80, H81 and H82 (including H82a and other H82 positions) numbered according to Kabat. In some aspects, VH region variants may reduce or abolish the superantigen type binding of the Fab region of said variant antibody to S. aureus SpA relative to the parental antibody, but do not significantly attenuate antigen binding to the antigen binding site of the variant antibody.

In certain embodiments, the antibody has a variant Fab region that attenuates non-immune binding to an S. aureus superantigen such as SpA, and also has one or more heavy chain constant region substitutions that attenuate Fc binding with one or more S. aureus FcBPs. In such embodiments, the antimicrobial antibody, or variant antibody, contains a heavy chain constant region selected from heavy chain constant regions 1-27 (SEQ ID NO: 30-56), and a heavy chain variable domain in which at least one amino acid selected from the list of VH3 residues including H15, H17, H19, H57, H59, H64, H65, H66, H68, H69, H70, H80, H81 and H82 (including H82a and other H82 positions according to Kabat numbering) is substituted with an amino acid residues different from that present in the parental IgG1 antibody.

In some embodiments, the antimicrobial variant IgG1 heavy chain is paired with a kappa light chain of allotype selected from the group Km1, Km2, Km3.

In some embodiments, the antimicrobial variant IgG1 heavy chain is paired with a lambda light chain.

In some embodiments, the antimicrobial variant IgG1 heavy chain is paired with a kappa light chain having either amino acid Val or Ala at position 153 and/or either Leu or Val at amino acid 191 (EU numbering).

To compare the effect of variant heavy chain constant region changes on the binding and effector properties of anti microbial IgG immunoglobulins, control antibodies including parental IgG immunoglobulins and a humanized anti RSV antibody having a matched variant heavy chain constant region are produced and tested. Such controls are important in distinguishing antigen binding by the variable domain of the antibody from heavy chain constant region binding to the target microbial antigen or microbe.

Additional Embodiments of Claimed Heavy Chain Constant Region Variant Immunoglobulins In some embodiments, the variant immunoglobulins of the present disclosure have enhanced antimicrobial effector function. According to the embodiments described herein, the enhanced anti-microbial effector function, may include, but is not limited to, C1q binding, C3b deposition, ADCC, ADCP, CDC, opsonophagocytic activity, antimicrobial activity, or a combination thereof.

In some embodiments, the variant immunoglobulins of the present disclosure may have altered microbial FcBP and FcRn binding to the heavy chain constant region, without significantly altering other antibody effector functions such as C1 q binding or Fc gamma receptor binding to the variant Fc domain.

The heavy chain constant region variant immunoglobulins of the present disclosure may be combined with other Fc modifications known in the art (e.g. Shields el al., J. Biol. Chem, 2001, 276, 6591-6604; Dall'Acqua et al., THE JOURNAL OF BIOLOGICAL CHEMISTRY VOL. 281, NO. 33, pp. 23514-23524, Aug. 18, 2006; reviewed in Natsume et al., Drug Design, Development and Therapy 2009:3 7-16, which are hereby incorporated by reference as if fully set forth herein). The embodiments described herein encompass combining an immunoglobulin or variant thereof, such as those described herein, with other known constant domain modifications to provide additive, synergistic, or novel properties to the modified antibody. The modifications known in the art may enhance the phenotype (anti-microbial activity) of the immunoglobulin or variant immunoglobulins with which they are combined. For example, an IgG Fc domain variant described herein with reduced Fc binding to S. aureus SpA, SSL 10 or Sbi may be combined with one or more heavy chain constant region mutations known to result in C1q binding with higher affinity than a comparable wild type constant region. Such claimed embodiments results in enhanced antimicrobial effector function.

Additionally, mutation or alternations to the hinge region of the variant heavy chain constant region, which enhances stability or the variant immunoglobulin with respect to microbial protease cleavage, are also claimed. Examples of such microbial proteases include but are not limited to IdeS, GluV8 and SpeB.

Some embodiments described herein also relate to modified variant IgG immunoglobulins that have decreased in vivo half-life by virtue of the presence of a modified human IgG1 heavy chain constant region, wherein the IgG heavy chain constant region, or fragment thereof, is modified by the introduction of one or more amino acid changes. The one or more amino acid changes may be an amino acid substitution, or by the engineering of a mixed isotype IgG constant domains, all of which have decreased affinity for one or more microbial FcBP and for the human FcRn receptor.

In some embodiments, modified variant class IgG1 antibodies are provided, wherein the in vivo half-lives are reduced by changes in one or more amino acid residues at positions which have been identified to be involved, either directly or indirectly, in the interaction of the IgG1 with the FcRn receptor. The altered half-life resulting from reduced FcRn binding will decrease the half-life of the modified variant IgG1 relative to a parental IgG1 molecule. This altered half-life will allow better control of patient exposure in the clinic.

In further embodiments, methods for modifying an antibody of class IgG1 or mixed isotype are provided, wherein said method includes substituting at least one amino acid from the heavy chain constant region with an amino acid which is different from that present in an unmodified parent antibody, thereby causing an alteration in the binding affinity of the Fc domain for a microbial FcPB and/or one or more of the following properties: effector function, FcRn binding, serum half-life, stability and/or immunogenicity.

The embodiments described herein further provide for a method of modifying an antibody of class IgG1 wherein said method includes substituting at least one amino acid from the heavy chain constant region selected from amino acid residues (i.e., EU positions) 214, 251, 252, 253, 254, 274, 276, 311, 314, 356, 358, 380, 382, 384, 419, 422, 428, 431, 432, 433, 434, 435, 436 and 438, thereby causing an alteration in the binding affinity for a microbial FcPB and/or one or more of the following properties: effector function, Additionally, present disclosure further provides for a method of producing an antibody variant having a heavy chain constant region of mixed isotype, created by substituting regions of the IgG1 heavy chain constant region with sequences from the IgG3 heavy chain constant region, or a variant IgG including a heavy chain constant region of mixed isotype. Such antibodies and their variants may also contain further modifications, in which at least one amino acid from the heavy chain constant region is substituted with an amino acid residue different from that present in the IgG1, IgG3 or mixed isotype heavy chain parental antibody. The method may include, but is not limited to steps of (a) preparing an expression vector (e.g., a replicable expression vector) that includes a suitable promoter operably linked to DNA encoding at least a constant region of an immunoglobulin heavy chain or a variant thereof, wherein at least one amino acid from the heavy chain constant region is substituted with an amino acid which is different from that present in an unmodified antibody thereby causing an alteration in FcBP binding affinity and/or one or more of the following properties: effector function, FcRn binding, serum half-life, stability, and/or immunogenicity antibodies; (b) transforming host cells with said vector; and (c) culturing said transformed host cells to produce said modified antibody. Optionally, such a method may further include preparing a second expression vector (e.g., a replicable expression vector) that includes a promoter operably linked to DNA encoding a complementary immunoglobulin light chain and further transforming said cell line with said second vector.

The embodiments described herein also include pharmaceutical compositions and methods of prophylaxis and therapy using antibodies and their variants, including modified immunoglobulins (including immunoglobulins conjugated with antimicrobial compound or radionuclides). Also included are methods of diagnosis using modified immunoglobulins and their variants. In some embodiments, the amino acid modifications of the present disclosure may be used to enhance the antimicrobial activity of the therapeutic or prophylactic antibody.

Anti-Microbial Immunoglobulins and their Heavy Chain Constant Region Variants.

According to the embodiments described herein, anti-microbial monoclonal antibodies and their variants are provided. Such anti-microbial monoclonal antibodies and their variants have variable domains which recognize one or more microbial cell surface or secreted antigens.

In some embodiments, IgG antibodies, such as a human IgG antibody, a humanized or a chimeric IgG class antibody or their variants are claimed. In such embodiments, the antigen recognition region of the antibody is directed against one or more microbial cell surface or secreted antigens.

The variant immunoglobulin IgG heavy chain constant region described herein may be combined with one or more immunoglobulin variable heavy and/or light chain regions which bind antigens produced by microbes that express one or more microbial immunoglobulin binding protein.

In some embodiments, the variable domain of the antibody binds to a microbial protein that is a microbial immunoglobulin binding protein, and the heavy chain constant region of the antibody is a variant IgG which has attenuated binding to one or more microbial Ig Binding Protein or Ig Binding Protein domain expressed by the target microbe.

In other embodiments, the variable domain of the antibody binds to a microbial protein that is not an microbial immunoglobulin binding protein, and the heavy chain constant region of the antibody is a variant IgG which has attenuated binding to one or more microbial Ig Binding Proteins or Ig Binding Protein domains expressed by the target microbe.

The anti-microbial heavy chain constant region variants IgG immunoglobulins claimed herein have enhanced anti-microbial activity relative to their parental antibodies.

In some embodiments human, humanized or chimeric anti-microbial heavy chain constant region variant immunoglobulins are claimed, which includes a heavy chain constant region amino acid sequence selected from SEQ ID NO: 31-56.

Anti-S. aureus Immunoglobulins and their Heavy Chain Constant Region Variants.

S. aureus, an important human pathogen for which there is an urgent unmet therapeutic need, a number of microbial immunoglobulin binding proteins may be expressed, including SpA, Sbi, SSL7 and SSL10.

In some embodiments, the target microbe is S. aureus, and variant IgG antibodies may be designed to have attenuated binding to one or more S. aureus IgBPs due to the introduction of one or more amino acid substitutions in the heavy chain constant region relative to the parental IgG.

In other embodiments, the target microbe is *S. aureus*, and variant antibody heavy chain constant region polypeptide sequences are combined with immunoglobulin heavy chain variable polypeptide sequences and light chains polypeptide sequences, which bind one or more cell surface or secreted *S. aureus* antigen.

In some embodiments, the *S. aureus* antigen recognized by the variable domain of immunoglobulins and there variants are cell surface or secreted antigens selected from the list which includes but is not limited to: ClfA, ClfB, Cna, Eap, Ebh, EbpS, FnBPAK, FnBPB, IsaA, IsaB, IsdA, IsdB, IsdH, SasB, SasC, SasD, SasF, SasG, SasH, SasK, SdrC, SdrD, SdrE, Spa, SraP, Coa, Ecb, Efb, Emp, EsaC, EsxA, EssC, FLIPr, FLIPr like, Sbi, SCIN-B, SCIN-C, VWbp, SpA, LTA, CP5, CP8, PNAG, dPNAG, CHIPS, PVL leukocidin, α, β and γ-hemolysins, SAK, Sea, Sep, Seb, Epa, Efb, SCIN, Exfoliatins ETB and ETA, Staphylococcal Enterotoxins SEA, SEB, SECn, SED, SEG, SHE, and SEI, Toxic-shock syndrome toxin TSST-1, Alpha Toxin, Beta toxin, Delta toxin.

Anti-SpA and Anti-Sbi Immunoglobulins and their Heavy Chain Constant Region Variants In some embodiments, the antigen recognized by the variable domain of the antibody or its variants is *S. aureus* SpA. In such embodiments, the microbial antigen recognized by the variable domain of the variant IgG antibody is an epitope found in one or more of the repeat homology IgBP domains of *S. aureus* SpA (referred to as SpA domains E, D, A, B, and C).

In some embodiments, the antigen recognized by the variable domain of the antibody or its variants is *S. aureus* Sbi. In such embodiments, the antigen epitope recognized by the variable domain of the antibody or its variants is located in one or more of the Sbi IgBP binding domains I and II.

In some embodiments, the antigen epitope recognized by the variable domain of the antibody or its variants is found in two or more of the repeat IgBP homology domains from SpA or Sbi, selected from the list SpA domains E, D, A, B, and C, and Sbi domains I and II.

In some embodiments, the antigen epitope recognized by the variable domain of the antibody or its variants is found in one or more of the repeat IgBP homology domains from both SpA and Sbi, selected from the list SpA domains E, D, A, B, and C, and Sbi domains I and II.

According to the embodiments described herein, anti-SpA monoclonal antibodies and their variants are provided. Such anti-microbial monoclonal antibodies and their variants, have variable domains which recognize *S. aureus* SpA.

In some embodiments, IgG antibodies, such as a human IgG antibody, a humanized or a chimeric IgG class antibody and their variants are claimed. In such embodiments, the antigen recognition region of the antibody is directed against *S. aureus* SpA.

In one embodiment, methods whereby monoclonal antibodies are raised or selected are provided. The disclosure also envisages the construction of chimeric antibodies from murine derived antibodies, humanization of non-human antibodies and affinity maturation of human or humanized antibodies. In certain aspects, human and/or humanized SpA antibodies and variants thereof that are described below may—in addition to affinity maturation—be subject to one or more maturation mutations that improve one or more additional properties in addition to improving affinity: avidity, stability, solubility, expression level, and/or biological activity.

In one embodiment, the murine monoclonal antibody SPA27 (described in WO 2008/140487 A2) was used for the construction of chimeric IgG immunoglobulins and their variants. The heavy chain and light chain variable domain amino acid sequence of the chimeric antibodies and their variants are shown in SEQ ID NO: 1 and 6.

In some embodiment, the murine monoclonal antibody SPA27 and its humanized versions described in WO 2008/140487 A2 can be used for the construction of chimeric IgG immunoglobulins and their variants. The heavy chain and light chain variable region amino acid sequence of the chimeric antibodies and their variants are shown SEQ ID NO: 1 and 6.

In other embodiments, anti-SpA antibodies known in the art such as monoclonal antibody 76 (described in U.S. Pat. No. 7,488,807 B2), or monoclonal antibody 107 (described in US patent application US 2010/0047252 A1) can be used for the construction of chimeric, heavy chain constant region variant IgG immunoglobulins.

In other embodiments, the CDR sequences of anti-SpA antibodies known in the art such as monoclonal antibody 3F6, 5A10 and 3D11 (Kim et al., 2012), can be used for the construction of recombinant anti-SpA antibodies (e.g., recombinant murine antibodies), chimeric anti-SpA antibodies, humanized anti-SpA antibodies, or anti-SpA Fc variant antibodies (or anti-SpA heavy chain constant region variant IgG immunoglobulins) that are derived from a parental antibody (e.g., a parental chimeric anti-SpA antibody, a parental humanized anti-SpA antibody, or a parental human anti-SpA antibody).

According to some embodiments, an anti-SpA antibody includes (i) an immunoglobulin heavy chain, which has a variable heavy chain sequence and a constant heavy chain sequence; and (ii) an immunoglobulin light chain, which has a variable light chain sequence and a constant light chain sequence. In certain aspects, the variable heavy chain includes an amino acid sequence of SEQ ID NO:182, SEQ ID NO:184, or SEQ ID NO:186. In certain aspects, the variable light chain includes an amino acid sequence of SEQ ID NO:181, SEQ ID NO:183, and SEQ ID NO:185. Said anti-SpA antibodies may be used to generate a recombinant murine antibody or a chimeric antibody. In the case of a chimeric antibody, the variable heavy chain sequence (e.g., SEQ ID NO:182, SEQ ID NO:184, or SEQ ID NO:186) may be combined with a human immunoglobulin (e.g., IgG1) heavy chain constant sequence to form the chimeric antibody's immunoglobulin heavy chain. In some aspects, the chimeric anti-SpA antibody immunoglobulin heavy chain includes an amino acid sequence of SEQ ID NO:194 or SEQ ID NO:195. In addition, the variable light chain sequence (e.g., SEQ ID NO:181, SEQ ID NO:183, or SEQ ID NO:185.) may be combined with a human immunoglobulin (e.g., IgG1) light chain constant sequence to form the chimeric antibody's immunoglobulin light chain. In some aspects, the chimeric anti-SpA antibody immunoglobulin light chain includes an amino acid sequence of SEQ ID NO:188.

In some embodiments, the chimeric antibody described above may be used as a parental anti-SpA antibody for generating an anti-SpA Fc variant antibody, which includes one or more amino acid substitutions as compared to the parental chimeric anti-SpA antibody. In such case, the anti-SpA Fc variant antibody may have a variant immunoglobulin heavy chain that includes an amino acid sequence of SEQ ID NO:196 or SEQ ID NO:197.

According to other embodiments, a humanized anti-SpA antibody may be generated. In some aspects the humanized antibody may have a variable heavy chain sequence and a variable light chain sequence which include one each of a heavy chain CDR1 sequence, a heavy chain CDR2 sequence, a heavy chain CDR3 sequence, a light chain CDR1 sequence, a light chain CDR2 sequence, a light chain CDR3 sequence, each of which may be selected from the CDR sequences in Table 1 below:

| Name of Sequence | Possible Amino Acid Sequences |
|---|---|
| Heavy chain CDR1 | GFAFSNYD (SEQ ID NO: 213)<br>GFTFNTNA (SEQ ID NO: 214)<br>GYSFTSYY (SEQ ID NO: 215) |
| Heavy chain CDR2 | ISSGGTYP (SEQ ID NO: 216)<br>IRSKSNNYAT (SEQ ID NO: 217)<br>IDPFNGGT (SEQ ID NO: 218) |
| Heavy chain CDR3 | (X)GGFLITTRDYYAMDY (SEQ ID NO: 219)*<br>(X)YGYDGTFYAMDY (SEQ ID NO: 220)*<br>(X)EHYDYDYYVMDY (SEQ ID NO: 221)* |
| Light chain CDR1 | SSVSY (SEQ ID NO: 222)<br>ESVEYSGASL (SEQ ID NO: 223) |
| Light chain CDR2 | DTS (SEQ ID NO: 224)<br>AAS (SEQ ID NO: 225)<br>EIS (SEQ ID NO: 226) |
| Light chain CDR3 | QQWSSYPPT (SEQ ID NO: 227)<br>QQSRKVPST (SEQ ID NO: 228)<br>QQWSYPFT (SEQ ID NO: 229) |

*(X) may be substituted with 0, 1, or 2 amino acids

In some embodiments the (X) of the heavy chain CDR3 sequence may be substituted with zero (0) amino acids. In other embodiments, the (X) of the heavy chain CDR3 sequence may be substituted with two (2) amino acids, and in some aspects the two amino acids may be selected from the amino acids AR or VT. In some aspects, the humanized anti-SpA antibody may have an immunoglobulin heavy chain that includes an amino acid sequence of SEQ ID NO:200, SEQ ID NO:201, SEQ ID NO:201, SEQ ID NO:202, SEQ ID NO:209, or SEQ ID NO:210. In other aspects, the humanized anti-SpA antibody may have an immunoglobulin light chain that includes an amino acid sequence of SEQ ID NO:191, SEQ ID NO:192, or SEQ ID NO:208.

In some embodiments, a humanized anti-SpA antibody (such as those described above), a human anti-SpA antibody or any chimeric anti-SpA antibody may be used as a parental anti-SpA antibody for generating an anti-SpA variant (e.g., a variant heavy chain constant region variant) or an anti-SpA Fc variant antibody. The anti-SpA Fc variant antibody may include an immunoglobulin light chain and a variant immunoglobulin heavy chain that has a variable heavy chain sequence and a (variant) constant heavy chain sequence. In such case, the variant immunoglobulin heavy chain comprises one or more amino acid substitutions in its constant heavy chain sequence as compared to that of the parental anti-SpA antibody. In some aspects, the anti-SpA Fc variant antibody includes an amino acid sequence selected from SEQ ID NOs: 31-56. In other aspects, the anti-SpA Fc variant antibody includes an amino acid sequence selected from SEQ ID NO:204, SEQ ID NO:205, SEQ ID NO:206, SEQ ID NO:207, SEQ ID NO:211, or SEQ ID NO:212.

In other embodiments, human anti-SpA antibodies can be cloned from human B cells obtained from patients recovering from a S. aureus infection, or from Patients immunized with a non-toxogenic SpA vaccine (Kim et al., 2012).

To compare the effect of variant heavy chain constant region changes on the effector properties and antimicrobial activity of variant anti-SpA IgG immunoglobulins, control antibodies including parental anti-SpA IgG immunoglobulins and humanized non-specific antibody having a matched variant heavy chain constant region are produced and tested. In one example an anti-RSV parental antibody (IgG1, allotype Gm17) having a heavy and light chain sequence shown in HC3 (SEQ ID NO: 22) and LC2 (SEQ ID NO: 24) or a matched variant heavy chain constant region antibody of HC4 (SEQ ID NO: 23) and LC2 (SEQ ID NO: 24) were produced and tested.

In some embodiments, chimeric anti-SpA heavy chain constant region variant IgG immunoglobulins can be humanized and affinity matured using a number of established methods, which are known in the art.

In some embodiments, the antigen binding portion of the anti-SpA antibody, or heavy chain constant region variant IgG antibody (i.e., the immunoglobulin heavy chain of a humanized anti-SpA antibody or variant thereof), contains at least one heavy chain variable region that includes an amino acid sequence selected from the group SEQ ID NO: 1-5 (VH Chimeric and VH1-VH4).

In some embodiments the antigen binding portion of the antibody, or heavy chain constant region variant IgG antibody (i.e., immunoglobulin light chain of a humanized anti-SpA antibody or variant thereof), contains at least one light chain variable regions that includes an amino acid sequence selected from the group SEQ ID NO 6-18 (VL chimeric and VL1-VL12).

In some embodiments, an anti-SpA antibody or heavy chain constant region variant IgG antibody, or antigen-binding portion thereof that includes a light chain variable region amino acid sequence selected form the group SEQ ID NO: 6-18 (VL chimeric and VL1-VL12), and a heavy chain variable region amino acid sequence selected from SEQ ID NO:1-5 (VH chimeric and VH1-VH4) are provided.

In one embodiment, a chimeric parental IgG1 anti-SpA antibody that includes a heavy chain region acid sequence of SEQ ID NO:19 and a light chain amino acid sequence of SEQ ID NO:21 is provided.

In one embodiment, an example chimeric variant IgG1 anti-SpA antibody that includes a variant heavy chain constant acid sequence of SEQ ID NO:20 and a light chain amino acid sequence of SEQ ID NO:21 is provided.

The embodiments described herein also include affinity matured variant anti-S. aureus antibodies in which a human, humanized, or chimeric variable domain of the antibody are derived from an anti-S. aureus antibody. Such claimed affinity matured variant antibodies have at least one amino acid substitution, deletion or insertion relative to the parental heavy or light chain variable domain sequences.

In some embodiments, the disclosure pertains to an anti-SpA antibody or variant, or antigen-binding portion thereof that includes a light chain variable region amino acid sequence selected form the group SEQ ID NO:6-18 (VL chimeric and VL1-VL12), and a heavy chain variable region amino acid sequence selected from SEQ ID NO:1-5 (VH chimeric and VH1-VH4), in which the antibody variable domain or the heavy and/or light chain has been affinity matured resulting in the introduction of variable region amino acid substitutions, insertions or deletions relative to the parental sequence. Such changes result in improved antibody affinity for its target antigen.

In some embodiments in which the antibody is directed against a S. aureus antigen, the variant immunoglobulins also have low or no superantigen type binding to SpA via the Fab region of the immunoglobulin in addition to one or more heavy chain constant region changes that attenuate Fc iterations with one or more S. aureus FcBPs. Such immunoglobulins and their variants can be selected so as to avoid the use of human VH3 derived sequences, which can interact with SpA at a site distinct from the Fc binding site. Alternatively, if VH3 derived sequences are used, and Fab-SpA superantigen type binding is present in the parental immunoglobulin, then modified variable heavy chains are provided in which at least one amino acid from the heavy chain variable FW region is substituted with an amino acid residue different from that present in the unmodified parental antibody selected from the list of VH residues including but not limited to H19 and H82a. In some aspects, VH region variants reduce or abolish the superantigen type binding of the Fab region of said variant antibody to S. aureus SpA relative to the parental antibody, but do not significantly attenuate antigen binding to the antigen binding site of the variant antibody In an additional embodiment, the modification of human or humanized VH3 family derived anti-S. aureus IgG variable heavy domain residues are claimed which abrogate superantigen type binding of SpA to anti S. aureus immunoglobulins or their heavy chain constant region variants. In one such embodiment the antigen binding portion of the antibody, or heavy chain constant region variant IgG antibody, contains at least one heavy chain variable region that includes an amino acid sequence selected from the group SEQ ID NO:1-5 (VH Chimeric and VH1-VH4), in which at least one amino acid from the heavy chain variable region is substituted with an amino acid residue different from that present in SEQ ID NO:1-5 (VH Chimeric and VH1-VH4), selected from the list of VH residues (position to Kabat numbering) selected from the list including H15, H17, H19, H57, H59, H64, H65, H66, H68, H69, H70, H80, H81 and H82 (including H82a and other H82 positions).

In an additional embodiment, the modification of human or humanized VH3 family derived anti-S. aureus IgG variable heavy domain residues are claimed which abrogate superantigen type binding of SpA to anti S. aureus immunoglobulins or their heavy chain constant region variants. In one such embodiment the antigen binding portion of the antibody, or heavy chain constant region variant IgG antibody, contains at least one heavy chain variable region that includes an amino acid sequence selected from the group SEQ ID NO:1-5 (VH Chimeric and VH1-VH4), in which at least one amino acid from the heavy chain variable FW region is substituted with an amino acid residue different from that present in SEQ ID NO:1-5 (VH Chimeric and VH1-VH4), selected from the list of VH residues including but not limited to H19 and H82a (Kabat numbering).

In an additional embodiment, the modification of human or humanized VH3 family derived anti-S. aureus IgG variable heavy domain residues are claimed which abrogate superantigen type binding of SpA to anti S. aureus immunoglobulins or their heavy chain constant region variants. In one such embodiment the antigen binding portion of the antibody, or heavy chain constant region variant IgG antibody, contains at least one heavy chain variable region that includes an amino acid sequence selected from the group SEQ ID NO:1-5 (VH Chimeric and VH1-VH4), in which at least one amino acid from the heavy chain variable FW region is substituted with an amino acid residue different from that present in SEQ ID NO:1-5 (VH Chimeric and VH1-VH4), in which Asn 82a (Kabat numbering). is either Ser or Gly.

Variant anti-SpA IgG antibodies of the embodiments described herein have amino acid changes in their heavy chain constant region relative to their parental antibodies. These amino acid substitutions result in the variant immunoglobulin having attenuated heavy chain contain domain binding to one or more microbial immunoglobulin binding protein (IgBP).

In some embodiments, in which the antibody is a variant IgG immunoglobulin, the microbial antigen recognized by the antibody is S. aureus SpA (SpA), and the antibody is a variant IgG in which amino acid substitutions have been introduced into the heavy chain constant region so as to attenuate Fc binding to one or more S. aureus IgBPs, including, but not limited to: S. aureus SpA, Sbi and SSL10.

In some embodiments, anti-SpA variant antibodies described herein block one or more function of the SpA domain to which they bind selected from, but not limited to: IgG Fc binding, VH3 Fab binding, TNFR1 binding, vWF binding, EGFR binding and osteoblast binding.

In some embodiments, the variant Fc domain of the anti-SpA antibody does not bind to SpA or Sbi, but will bind to Protein G. Protein G binding of such heavy chain constant region variant anti-microbial immunoglobulins allows for their purification using Protein G affinity chromatography using method well known in the art. In certain embodiments, the variant antibody may bind, via constant domain non-immune binding to Protein G and/or Protein L, but does not bind SpA or Sbi by interaction with the heavy chain constant domain of the variant antibody.

The disclosure also relates to the prophylactic or therapeutic use of such anti-microbial immunoglobulins and their variants, and their use in combinations with additional antimicrobial chemotherapy or anti-infective agents or in combination with one or more additional antimicrobial immunoglobulins The embodiments described herein also include pharmaceutical compositions and methods of prophylaxis and therapy using antibodies and their variants, including modified immunoglobulins (including immunoglobulins conjugated with antimicrobial compound or radionuclides). Also included are methods of diagnosis using modified immunoglobulins and their variants. In some embodiments, the amino acid modifications of the present disclosure may be used to enhance the antimicrobial activity of the therapeutic or prophylactic antibody Anti-ClfA Heavy Chain Constant Region Variant Immunoglobulins In additional embodiments, the antigen recognized by the variable domain of the claimed heavy chain constant region variant immunoglobulin is S. aureus Clumping factor A (ClfA).

In some embodiments a human, humanized or chimeric anti ClfA heavy chain constant region variant immunoglobulin are claimed.

In some embodiments variant humanized or chimeric anti-ClfA antibodies contain a heavy chain, in which at least one amino acid from the heavy chain constant region selected from, but not limited to amino acid residues (i.e., EU positions) 214, 251, 252, 253, 254, 274, 276, 311, 314, 356, 358, 380, 382, 384, 419, 422, 428, 431, 432, 433, 434, 435, 436 and 438 is substituted with an amino acid residue different from that present in the unmodified IgG1 antibody.

In some embodiments a human, humanized or chimeric anti ClfA heavy chain constant region variant immunoglobulin is claimed, including a heavy chain constant region amino acid sequence selected from, but not limited to, SEQ ID NO: 30-56 (heavy chain constant region H1-27).

In one embodiment the heavy and light chain variable domain sequences of the humanized anti-ClfA heavy chain constant region variant immunoglobulin are derived from Tefibazumab.

In one embodiment the heavy and light chain variable domain sequences of the humanized anti-ClfA parental and variants including a variable light chain amino acid sequence SEQ ID NO:29 (VL 13), and a variable heavy chain region amino acid sequence SEQ ID NO:28 (VH 5) are provided.

In one embodiments, anti-ClfA heavy chain constant region variant antibodies, including a variable light chain amino acid sequence SEQ ID NO:29 (LC 13), a variable heavy chain region amino acid sequence SEQ ID NO:28 (VH5), and a heavy chain constant region including of an amino acid sequences selected from the group SEQ ID 30-56 (heavy chain constant region 1-27) are provided.

In one embodiment, the parental anti-ClfA heavy chain and light chain of sequence shown in SEQ ID NO:25 (HC 5) and SEQ ID NO:27 (LC 3) are provided.

In another embodiment, a variant anti-ClfA heavy chain and light chain of sequence SEQ ID NO:26 (HC 6) and SEQ ID NO:27 (LC 3) are provided.

In another embodiment, the heavy and light chain variables domain sequences of the humanized anti-ClfA variant immunoglobulins, have undergone affinity maturation resulting in at least a 2 fold improvement in its affinity for its antigen.

In another embodiment, an anti-ClfA heavy chain constant region variant IgG immunoglobulin, including a light chain amino acid sequence SEQ ID NO:27 (LC 3), and a variant heavy chain sequence SEQ ID NO:26 (HC6) are provided. Also claimed are affinity matured derivative immunoglobulins having at least one amino acid substitution, deletion or insertion relative to the parental heavy or light chain variable sequences (SEQ ID NO:29 and SEQ ID NO:28). In one aspect, affinity matured variable domain variants have an affinity improvement of at lease 2 fold.

In some embodiments, the anti S. aureus activity of the anti-ClfA heavy chain constant region variant IgG immunoglobulin and their affinity-matured progeny are enhanced relative to their parental antibodies.

In some embodiments, the variant anti ClfA immunoglobulins described herein have an increase in one or more of the following Fc mediated effector functions: C1q binding, C3b deposition, complement deposition, opsonophagocytic activity, ADCC, ADCP, CDC and anti-microbial activity.

Additional Claimed Embodiments

The embodiments described herein also include heavy chain constant region variant anti-*S. aureus* antibodies in which the human, humanized, or chimeric variable domain, or variable domain CDRs of the antibody are derived from an anti-*S. aureus* antibodies selected from the list: Pagibaximab (a chimeric anti-LTA antibody; Biosynexus/Medimmune), Tefibazumab (a humanized IgG1 anti-ClfA; Aurexis, Inhibitex), CS-D7 (human anti-IsdB IgG1, Merck), Aurograb (scFv fragment anti ABC transporter; NeuTec), anti-Alpha toxin (Medimmune patent application WO/2012/109285), mAb15E11, a murine antibody recognizing Fibronectin-binding proteins A and B. Povenza et al., 2010).

The embodiments described herein also include affinity matured heavy chain constant variant anti-*S. aureus* antibodies in which the human, humanized, or chimeric variable domain of the antibody are derived from one or more anti-*S. aureus* antibodies including, but not limited to: Pagibaximab (a chimeric anti-LTA; Biosynexus/Medimmune; FIG. 37), Tefibazumab (humanized IgG1 anti-ClfA, Inhibitex/BMS), CS-D7 (a humanized anti-IsdB IgG1, Merck; FIG. 36), Aurograb (an scFv fragment anti-ABC transporter; NeuTec), and anti-Alpha toxin (Medimmune patent application WO/2012/109285, which is hereby incorporated by reference as if fully set forth herein). Such claimed affinity matured heavy chain constant region variant antibodies have at least one amino acid substitution, deletion or insertion relative to the parental heavy or light chain variable domain sequences.

The antibodies and antibody variants described herein may be of any suitable antibody structure including, but not limited to, full length antibodies, antibody fragments, monoclonal antibodies, bispecific antibodies, multispecific antibodies, peptibodies, intrabodies, minibodies, domain antibodies, synthetic antibodies (sometimes referred to herein as "antibody mimetics"), chimeric antibodies, humanized antibodies, fully human antibodies, antibody fusions or Fc fusions (sometimes referred to as "antibody conjugates"), and fragments thereof, respectively. In one embodiment, the antibodies include multispecific antibodies, such as bispecific antibodies, also sometimes referred to as "diabodies". These are antibodies that bind to two (or more) different antigens. Diabodies can be manufactured in a variety of ways known in the art (Holliger & Winter, 1993), e.g., prepared chemically or from hybrid hybridomas.

Further, the antibodies and antibody variants described herein may include one or more modifications, such as a covalent modification. Covalent modifications of antibodies that are included herein, are generally, but not always, done post-translationally. For example, several types of covalent modifications of the antibody are introduced into the molecule by reacting specific amino acid residues of the antibody with an organic derivatizing agent that is capable of reacting with selected side chains or the Nor C-terminal residues.

Another type of covalent modification is glycosylation. In another embodiment, the IgG variants disclosed herein can be modified to include one or more engineered glycoforms. An "engineered glycoform," as used herein, is a carbohydrate composition that is covalently attached to an IgG, wherein said carbohydrate composition differs chemically from that of a parent IgG.

Another type of covalent modification of the antibody includes linking the antibody to various nonproteinaceous polymers, including, but not limited to, various polyols such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337, which are hereby incorporated by reference in their entirety, as if fully set forth herein. In addition, as is known in the art, amino acid substitutions may be made in various positions within the antibody to facilitate the addition of polymers such as PEG. See for example, U.S. Publication No. 2005/0114037, which is incorporated herein by reference in its entirety.

The Fc variants of provided herein are defined according to the amino acid modifications that compose them. Thus, for example, I332E, or Ile332Glu is an Fc variant with the substitution I332E relative to the parent Fc polypeptide. Likewise, S239D/A330L/I332E defines an Fc variant with the substitutions S239D, A330L, and I332E relative to the parent Fc polypeptide. It is noted that the order in which substitutions are provided is arbitrary, that is to say that, for example, S239D/A330L/I332E is the same Fc variant as S239D/I332E/A330L, and so on. For all positions discussed herein, numbering is according to the EU index or EU numbering scheme (Kabat et al., 1991, Sequences *of Proteins of Immunological Interest*, 5th Ed., United States Public Health Service, National Institutes of Health, Bethesda, which is hereby incorporated by reference in its entirety as if fully set forth herein). The EU index or EU index as in Kabat or EU numbering scheme refers to the numbering of the EU antibody (Edelman et al., 1969, Proc Natl Acad Sci USA 63:78-85, which is hereby incorporated by reference in its entirety as if fully set forth herein).

Heavy chain constant region variants may be substantially encoded by genes from any organism, such as mammals, including but not limited to humans; rodents including, but not limited to, mice and rats; horses; lagomorpha including, but not limited to, rabbits and hares; camelidae including, but not limited to, camels, llamas, and dromedaries; and non-human primates including, but not limited to, Prosimians, Platyrrhini (New World monkeys), Cercopithecoidea (Old World monkeys), Hominoidea (including those disclosed in U.S. Patent Publication No. 2006/0235208 A1), Gibbons, and Lesser and Great Apes. In one embodiment, the heavy chain constant region variants are substantially human.

The parent heavy chain constant region polypeptide may be an antibody. Parent antibodies may be fully human, obtained for example using transgenic mice (Bruggemann et al., 1997) or human antibody libraries coupled with selection methods (Griffiths et al., 1998). The parent antibody need not be naturally occurring. For example, the parent antibody may be an engineered antibody, including but not limited to chimeric antibodies and humanized antibodies (Clark, 2000). The parent antibody may be an engineered variant of an antibody that is substantially encoded by one or more natural antibody genes. In one embodiment, the parent antibody has been or can be affinity matured, as is known in the art. Alternatively, the antibody has been modified in some other way, for example as described in U.S. patent application Ser. No. 10/339,788, filed on Mar. 3, 2003, hereby entirely incorporated by reference.

The heavy chain constant region or Fc variants described herein may be substantially encoded by immunoglobulin genes belonging to any of the antibody classes. In one embodiment, the heavy chain constant region variants find use in antibodies or Fc fusions that comprise sequences belonging to the IgG class of antibodies, including IgG1, IgG2, IgG3, or IgG4. FIG. 5 provides an alignment of these human IgG sequences. In an alternate embodiment the heavy chain constant region variants find use in antibodies or Fc fusions that comprise sequences belonging to the IgA (including subclasses IgA1 and IgA2), IgD, IgE, IgG, or IgM classes of antibodies. The heavy chain constant region variants described herein may comprise more than one protein chain. That is, the present disclosure may find use in an antibody or Fc fusion that is a monomer or an oligomer, including a homo- or hetero-oligomer.

It is well known that immunoglobulin polymorphisms exist in the human population. Gm polymorphism is determined by the IGHGI, IGHG2 and IGHG3 genes which have alleles encoding allotypic antigenic determinants referred to as G1m, G2m, and G3m allotypes for markers of the human IgG1, IgG2 and IgG3 molecules (no Gm allotypes have been found on the gamma 4 chain). Markers may be classified into 'allotypes' and 'isoallotypes'. These are distinguished on different serological bases dependent upon the strong sequence homologies between isotypes. Allotypes are antigenic determinants specified by allelic forms of the Ig genes. Allotypes represent slight differences in the amino acid sequences of heavy or light chains of different individuals. Even a single amino acid difference can give rise to an allotypic determinant, although in many cases there are several amino acid substitutions that have occurred. Allotypes are sequence differences between alleles of a subclass whereby the antisera recognize only the allelic differences. An isoallotype is an allele in one isotype which produces an epitope which is shared with a nonpolymorphic homologous region of one or more other isotypes and because of this the antisera will react with both the relevant allotypes and the relevant homologous isotypes (Clark, 1997; Gorman & Clark, 1990,).

Allelic forms of human immunoglobulins have been well-characterized (WHO Review of the notation for the allotypic and related markers of human immunoglobulins (J Immunogen 1976, 3: 357-362; WHO Review of the notation for the allotypic and related markers of human immunoglobulins. 1976, Eur. J. Immunol. 6, 599-601; Loghem, 1986, all hereby entirely incorporated by reference). Additionally, other polymorphisms have been characterized (Kim et al., 2001). At present, 18 Gm allotypes are known: G1m (1,2,3,17) or G1m (a, x, f, z), G2m (23) or G2m (n), G3m (5, 6, 10, 11, 13, 14, 15, 16, 21, 24, 26, 27, 28) or G3m (bl, c3, b5, bO, b3, b4, s, t, gl, c5, u, v, g5) (Lefranc, et al., The human IgG subclasses: molecular analysis of structure, function and regulation. Pergamon, Oxford, pp. 43-78 (1990); Lefranc, G. et al., 1979, Hum. Genet. 50, 199-211, both hereby entirely incorporated by reference). Allotypes that are inherited in fixed combinations are called Gm haplotypes.

FIG. 7 shows the allotypes of the gamma I chain of human IgG1 and the gamma 3 chain of human IgG3 showing the positions and the relevant amino acid substitutions (Gorman & Clark, 1990; Jefferis & LeFranc, 2009). For comparison, the amino acids found in the equivalent positions in human IgG2, IgG3 and IgG4 gamma chains are also shown.

The heavy chain constant region or Fc variants described herein may be substantially encoded by any allotype or isoallotype of any immunoglobulin gene. In one embodiment, the heavy chain constant region variants may find use in antibodies or Fc fusions that comprise IgG1 sequences that are classified as G1m(1), G1m(2), G1m(3), G1m(17), nG1m(I), nG1m(2), and/or nG1m(17). Thus, in the context of an IgG1 isotype, the heavy chain constant region variants may comprise a Lys (G1m(17)) or Arg (G1m(3)) at position 214, an Asp356/Leu358 (G1m(1)) or Glu356/Met358 (nG1m (1), and/or a Gly (G1m(2)) or Ala (nG1m(2)) at position 431 (FIG. 6).

In one embodiment, the heavy chain constant region variants described herein are based on human IgG1 sequences, and thus human IgG1 sequences are used as the "base" sequences against which other sequences are compared including, but not limited to, sequences from other organisms, for example, rodent and primate sequences. Heavy chain constant region variants may also comprise sequences from other immunoglobulin isotypes, such as IgG2, IgG3 or IgG4 or from different classes such as IgA, IgE, IgD, IgM, and the like. It is contemplated that, although the heavy chain constant region variants of the embodiments described herein are engineered in the context of one parent IgG, the variants may be engineered in or "transferred" to the context of another, second parent IgG. This is done by determining the "equivalent" or "corresponding" residues and substitutions between the first and second IgG, typically based on sequence or structural homology between the sequences of the first and second IgGs. In order to establish homology, the amino acid sequence of a first IgG outlined herein is directly compared to the sequence of a second IgG. After aligning the sequences, using one or more suitable homology alignment programs known in the art (e.g., using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first heavy chain constant region variant are defined. Alignment of conserved residues should conserve 100% of such residues. However, alignment of greater than 75% or as little as 50% of conserved residues is also adequate to define equivalent residues.

Equivalent residues may also be defined by determining structural homology between a first and second IgG that is at the level of tertiary structure for IgGs whose structures have been determined. In this case, equivalent residues are defined as those for which the atomic coordinates of two or more of the main chain atoms of a particular amino acid residue of the parent or precursor are within about 0.13 nm and about 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent IgG in which the IgGs are made, the heavy chain constant region variants described herein may be engineered into any second parent IgG that has significant sequence or structural homology with the heavy chain constant region variant. Thus, for example, if a variant antibody is generated wherein the parent antibody is human IgG1, by using the methods described above or other methods for determining equivalent residues, the variant antibody may be engineered in another IgG1 parent antibody that binds a different antigen, a human IgG2 parent antibody, a human IgA parent antibody, a horse IgG7 or IgG4 antibody, a mouse IgG2a or IgG2b parent antibody, and the like. Again, as described above, the context of the parent heavy chain constant region variant does not affect the ability to transfer the heavy chain constant region variants of the embodiments described herein to other parent IgGs.

The embodiments described herein provide variant antibodies that are optimized for a variety of therapeutically relevant properties. A heavy chain constant region variant that is engineered or predicted to display one or more optimized properties is herein referred to as an "optimized heavy chain constant region variant." In some embodiments, properties that may be optimized include, but are not limited to, reduced affinity for one or more microbial IgBP or FcBP. In one embodiment, the variants of the embodiments described herein may possess similar or enhanced affinity for a human activating Fcγ R, Fcγ RI, Fcγ RIIa, Fcγ RIIc, Fcγ RIIIa, and/or FcγRIIIb. In an alternate embodiment, the heavy chain constant region variants may be optimized to possess reduced affinity for the human inhibitory receptor FcγRIIb. These embodiments are anticipated to provide IgG polypeptides with enhanced therapeutic properties in humans—for example, similar or enhanced effector function relative to parental IgG and greater anti-microbial potency due to reduced microbial IgBP binding. In other embodiments, Fc of the embodiments described herein may provide enhanced affinity for one or more FcγRs, and reduced binding to FcRn and microbial IgBPs.

Heavy chain constant region variants of the embodiments described herein may comprise modifications that modulate interaction with Fc ligands other than FcγRs, including but not limited to complement proteins, FcRn, and Fc receptor homologs (FcRHs). FcRHs include but are not limited to FcRHI, FcRH2, FcRH3, FcRH4, FcRH5, and FcRH6 (Davis et al., 2002, Immunol. Reviews 190: 123-136, hereby entirely incorporated by reference).

Modifications to reduce immunogenicity may include modifications that reduce binding of processed peptides derived from the parent sequence to MHC proteins. For example, amino acid modifications may be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an heavy chain constant region variant of the embodiments described herein. See for example WO 98/52976; WO 02/079232; WO 00/3317; U.S. Ser. No. 09/903,378; U.S. Ser. No. 10/039,170; U.S. Ser. No. 60/222,697; U.S. Ser. No. 10/754,296; PCT WO 01/21823; and PCT WO 02/00165; Mallios, 1999, Bioinformatics 15: 432-439; Mallios, 2001, Bioinformatics 17: 942-948; Sturniolo et al., 1999, Nature Biotech. 17: 555-561; WO 98/59244; WO 02/069232; WO 02/77187; Marshall et al., 1995, J. Immunol. 154: 5927-5933; and Hammer et al., 1994, J. Exp. Med. 180: 2353-2358, all of which are hereby entirely incorporated by reference. Sequence-based information can be used to determine a binding score for a given peptide-MHC interaction (see for example Mallios, 1999, *Bioinformatics* 15: 432-439; Mallios, 2001, *Bioinformatics* 17: p942-948; Sturniolo et. al., 1999, *Nature Biotech.* 17: 555-561, all hereby entirely incorporated by reference).

In accordance with the embodiments described herein, conventional molecular biology, microbiology, and recombinant DNA techniques may be used within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984); all of which are hereby incorporated by reference, as if fully set forth herein.

Methods of Producing Variant Antibodies

The embodiments described herein provide methods for engineering, producing, and screening variant antibodies. The described methods are not meant to constrain the embodiments described herein to any particular application or theory of operation. Rather, the provided methods are meant to illustrate generally that one or more variant antibodies may be engineered, produced, and screened experimentally to obtain variant antibodies with optimized effector function. A variety of methods are described for designing, producing, and testing antibody and protein variants in U.S. Ser. No. 10/672,280, U.S. Ser. No. 10/822,231, U.S. Ser. No. 11/124,620, and U.S. Ser. No. 11/256,060, all hereby entirely incorporated by reference.

Described herein (see, e.g., Examples 1-4 below) are methods of producing monoclonal antibodies that recognize SpA and/or Sbi, methods for selecting antibodies that cross react with multiple SpA IgBP domains (selected from Domains E, D, A, B, C and Sbi domains I and II), methods of selecting antibodies that cross react with one or more SpA IgG binding domains and/or Sbi domains I and/or II, methods of assaying for antigen binding to SpA or Sbi using variant IgG1 antibodies, having one or more amino acid substitutions in the Fc domain which prevent Fc binding to SpA, Sbi or SSL10.

A variety of protein engineering methods may be used to design variant antibodies with optimized effector function. In one embodiment, a structure-based engineering method may be used, wherein available structural information is used to guide substitutions. An alignment of sequences may be used to guide substitutions at the identified positions. Alternatively, random or semi-random mutagenesis methods may be used to make amino acid modifications at the desired positions.

Methods for production and screening of variant antibodies are well known in the art. General methods for antibody molecular biology, expression, purification, and screening are described in Antibody Engineering, edited by Duebel & Kontermann, Springer-Verlag, Heidelberg, 2001; and Hayhurst & Georgiou, 2001; Maynard & Georgiou, 2000, which are hereby incorporated by reference in their entirety, as if fully set forth herein. Also see the methods described in U.S. Ser. No. 10/672,280, U.S. Ser. No. 10/822,231, U.S. Ser. No. 11/124,620, and U.S. Ser. No. 11/256,060, all of which are hereby entirely incorporated by reference.

In one embodiment, the heavy chain constant region variant sequences are used to create nucleic acids that encode the member sequences, and that may then be cloned into host cells, expressed and assayed, if desired. These practices are carried out using well-known procedures, and a variety of methods that may find use in the embodiments described herein are described in Molecular Cloning-A Laboratory Manual, 3rd Ed. (Maniatis, Cold Spring Harbor Laboratory Press, New York, 2001), Molecular Cloning-A Laboratory Manual, 4th Ed. (Green and Sambrook, Cold Spring Harbor Laboratory Press, New York, 2012), and Current Protocols in Molecular Biology (John Wiley & Sons), both entirely incorporated by reference. The variant antibodies of the embodiments described herein may be produced by culturing a host cell transformed with nucleic acid, such as an expression vector, containing nucleic acid encoding the variant antibodies, under the appropriate conditions to induce or cause expression of the protein. A wide variety of appropriate host cells may be used, including but not limited to mammalian cells, bacteria, insect cells, and yeast. For example, a variety of cell lines that may find use in the embodiments described herein are described in the ATCC cell line catalog, available from the American Type Culture Collection. The methods of introducing exogenous nucleic acid into host cells are well known in the art, and will vary with the host cell used.

Purification of Variant Antibodies

In one embodiment, variant antibodies are purified or isolated after expression. Antibodies may be isolated or purified in a variety of ways known to those skilled in the art. Standard purification methods include chromatographic techniques, electrophoretic, immunological, precipitation, dialysis, filtration, concentration, and chromatofocusing techniques. Purification can often be enabled by a particular fusion partner. For example, proteins may be purified using glutathione resin if a GST fusion is employed, Ni+2 affinity chromatography if a His-tag is employed, or immobilized anti-flag antibody if a flag-tag is used. For general guidance in suitable purification techniques, see Antibody Purification: Principles and Practice, 3rd Ed., Scopes, Springer-Verlag, NY, 1994, which is hereby entirely incorporated by reference.

In one embodiment, immunoglobulins and their variants are purified by affinity chromatography on Protein G, Protein L, SpA or by ion exchange chromatography.

Screening Methods

Variant antibodies may be screened using a variety of methods including, but not limited to, those that use in vitro assays, in vivo and cell-based assays, and selection technologies. Automation and high-throughput screening technologies may be utilized in the screening procedures. Screening may employ the use of a fusion partner or label, for example an immune label, isotopic label, or small molecule label such as a fluorescent or calorimetric dye.

In one embodiment, the functional and/or biophysical properties of variant antibodies are screened in an in vitro assay. In another embodiment, the protein is screened for functionality, for example its ability to bind to a microbial IgBP or FcBP, its binding affinity to its target antigen.

As is known in the art, a subset of screening methods includes those that select for favorable members of a library. The methods are herein referred to as "selection methods", and these methods find use in the embodiments described herein for screening variant antibodies. When protein libraries are screened using a selection method, only those members of a library that are favorable, that is which meet some selection criteria, are propagated, isolated, and/or observed. A variety of selection methods are known in the art that may find use in the embodiments described herein for screening protein libraries. Other selection methods that may find use in the embodiments described herein include methods that do not rely on display, such as in vivo methods. A subset of selection methods referred to as "directed evolution" methods are those that include the mating or breading of favorable sequences during selection, sometimes with the incorporation of new mutations.

In one embodiment, variant antibodies are screened using one or more cell-based or in vivo assays. For such assays, purified or unpurified proteins are typically added exogenously such that cells are exposed to individual variants or pools of variants belonging to a library. These assays are typically, but not always, based on the function of the immunoglobulin polypeptide; that is, the ability of the immunoglobulin polypeptide to bind to its target microbial antigen and mediate some biochemical event, for example effector function, ligand/receptor binding inhibition, and the like. Such assays often involve monitoring the response of target cells to the IgG, for example cell killing, change in cellular morphology, opsonophagacytosi, complement deposition, antimicrobial activity. For example, such assays may measure the ability of variant antibodies immunoglobulins to elicit antimicrobial antigen binding, microbial killing, and microbial FcBP binding, C1g and C3b deposition, opsonophagocytosis, ADCC, ADCP, or CDC. For some assays additional cells or components, that is in addition to the target cells, may need to be added, for example serum complement, IgG which binds to target microbial FcBPs, or effector cells such as peripheral blood monocytes (PBMCs), NK cells, macrophages, and the like. Such additional cells may be from any organism, such as humans, mice, rat, rabbit, and monkey. Antibodies may cause killing of certain microbes, which express the target antigen, or they may mediate attack on target microbes by immune cells, which have been added to the assay. Methods for monitoring target cell death or viability are known in the art, and include the use of dyes, immunochemical, cytochemical, and radioactive reagents.

The biological properties of the variant antibodies of the embodiments described herein may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. The animals may be referred to as disease models. Therapeutics are often tested in mice, including but not limited to nude mice, SCID mice, xenograft mice, and transgenic mice (including knockins and knock-outs). Such experimentation may provide meaningful data for determination of the potential of the protein to be used as a therapeutic. Any organism, such as mammals, may be used for testing. For example because of their genetic similarity to humans, monkeys can be suitable therapeutic models, and thus may be used to test the efficacy, toxicity, pharmacokinetics, or other property of the IgGs of the embodiments described herein. Tests in humans may be performed to obtain approval as drugs. Thus, the IgGs described in the embodiments herein may be tested in humans to determine their therapeutic efficacy, toxicity, immunogenicity, pharmacokinetics, and/or other clinical properties.

In one embodiment, methods of screening and selecting antimicrobial monoclonal antibodies are provided, the variant heavy chain constant region used for antibody selection is of human isotype IgG1 having a His to Arg substitution at position 435 and a Tyr to Phe substitution at position 436. The variant Fc domain may also be used for antibody selection is of human isotype IgG1 having a His to Arg substitution at position 435. The use of such heavy chain constant region variants is important, as they allow differentiation between antigen specific binding by the antibody from heavy chain constant region mediated binding to one of the following IgBPs, including but nor limited to SpA and Sbi In an additional embodiment of screening and selecting antimicrobial monoclonal antibodies, the variant heavy chain constant region used for antibody selection is of human isotype IgG1 and has a His to Arg substitution at position 435, a Lys to Gln substitution at position 274 and a Tyr to Phe substitution at position 436. In an additional example the variant Fc domain used for antibody selection is of human isotype IgG1 and has a His to Arg substitution at position 435 and a Lys to Gln substitution at position 274.

The uses of such heavy chain constant region variants are important so as to differentiate antigen specific variable domain binding of the antibody from heavy chain constant region mediated binding to one of the following IgBPs, including but nor limited to SpA, SSL10 and Sbi.

Therapeutic Uses of the Variant Antibodies

The variant antibodies of the embodiments described herein may find use in a wide range of products. In one embodiment an variant antibody described in the embodiments herein is a therapeutic, a diagnostic, or a research reagent. The variant may find use in an antibody composition that is monoclonal or polyclonal. In one embodiment, variant antibodies described in the embodiments herein may be used to kill target microbes that bear the target antigen, for example gram-positive bacterial cells. In an alternate embodiment, the variant antibodies are used to block, antagonize, or agonize the target antigen, for example for antagonizing a bacterial secreted virulence factor. In an alternative embodiment, variant antibodies described herein are used to block or antagonize target antigen and kill the target microbe that bear the target antigen.

The anti-microbial variant immunoglobulins described herein, which have enhanced anti-microbial activity relative to their parental antibodies, may be used for the prophylactic or therapeutic treatment of a number of important infectious diseases infections and pathological conditions caused by pathogenic microbes. For example, *Staphylococcus* and *Streptococcus* bacterial infections are responsible for several diseases, infections, and conditions, such as localized skin infections, diffuse skin infections (e.g., Impetigo), deep, localized infections, acute infective endocarditis, septicemia, necrotizing pneumonia, toxinoses (e.g., toxic shock syndrome and staphylococcal food poisoning), cystitis, meningitis, scarlet fever, Rheumatic fever, necrotizing fascitis, and pneumonia. Many of these diseases and conditions are a result of an opportunistic infection in a patient who has a compromised immune system (e.g., from chemotherapy or HIV infection) or an open wound or incision site (e.g., acute injuries or post-surgery)

Therefore, in some embodiments, methods for treating a disease, infection, or condition caused by one or more pathogenic microbes include a step of administering a therapeutically effective amount of a pharmaceutical composition that includes a variant antibody that has enhanced antimicrobial effects, such as those described herein. In some aspects, the methods for treating the patient are employed to treat the patient after the onset of the disease, infection or condition. In other aspects, the methods for treating the disease are employed to treat the patient after the onset of the disease, infection or condition as a prophylactic treatment. As such, pharmaceutical composition may include a passive vaccine composition that includes one or more variant antibodies, thereby providing passive immunization to the patient.

A "patient" or "subject" for the purposes of the embodiments described herein includes humans and other animals, e.g., mammals. The term "treatment" as used herein is meant to include therapeutic treatment, as well as prophylactic or suppressive measures for a disease, condition or disorder. Thus, for example, successful administration of a pharmaceutical composition that includes a variant antibody of the embodiments described herein prior to onset of the disease results in "treatment" of the disease. As another example, successful administration of a pharmaceutical composition that includes a variant antibody of the embodiments described herein after clinical manifestation of the disease to combat the symptoms of the disease is considered "treatment" of the disease. "Treatment" also encompasses administration of a pharmaceutical composition that includes a variant of the embodiments described herein after the appearance of the disease in order to eradicate the disease. Successful administration of a pharmaceutical composition that includes a variant of the embodiments described herein after onset and after clinical symptoms have developed, with possible abatement of clinical symptoms and perhaps amelioration of the disease, is considered "treatment" of the disease. Those "in need of treatment" as used herein, include mammals already having the disease or disorder, as well as those prone to having the disease or disorder, including those in which the disease or disorder is to be prevented.

In one embodiment, an variant antibody described herein may be administered alone (i.e., as the only therapeutically active agent in a pharmaceutical composition). In other embodiments, the variant antibody is administered in combination with one or more additional therapies. The term "in combination" or "in combination with" as used herein, means in the course of treating at least one disease or condition in a subject using two or more therapies (e.g., therapeutic agents, drugs, treatment regimens, treatment modalities or a combination thereof), in any order. This includes simultaneous administration (or "co-administration"), administration of a first therapy prior to or after administration of a second therapy, as well as in a temporally spaced order of up to several days apart. Such combination treatment may also include more than a single administration of any one or more therapies. Further, the administration of the two or more therapies may be by the same or different routes of administration.

Examples of additional therapies that may be administered in combination with the variant antibodies described herein include, but are not limited to, (1) chemotherapeutic agents (e.g., alkylating agents, antimetabolites, anti-tumor antibiotics, topoisomerase inhibitors, mitotic inhibitors hormone therapy, targeted therapeutics and immunotherapeutics), biological agents, antibodies or variant antibodies such as those described herein, antibodies unrelated to those described herein, antimicrobial agents, antibiotics (e.g., nafcillin, oxacillin, vancomycin, penicillin, ampicillin, aminoglycoside, clarithromycin, or azithromycin), antiviral agents, anti-infective agents, (2) surgery, radiation therapy, or other treatment modalities that may compromise the immune system, and (3) other suitable therapeutic agents, treatment modalities, that may be used to treat a disease, infection or condition caused by a pathogenic microbe or an underlying disease or condition that is common to patients suffering from a disease, infection or condition caused by a pathogenic microbe (e.g., cancer patients, surgery patients, HIV infected patients. In the case where a patient undergoes a surgical procedure or radiation therapy, the variant antibody may be administered before, during or soon surgery for prophylactic treatment of opportunistic infections, such as those caused a pathogenic microbe (e.g., *Staphyloccus, Streptococcus*).

In some embodiments, pharmaceutical compositions are provided wherein an variant antibody described herein and one or more therapeutically active agents are formulated as part of a composition. Formulations of the variant antibodies of the embodiments described herein are prepared for storage by mixing said IgG having the desired degree of purity with optional pharmaceutically acceptable carriers, excipients or stabilizers (Remington's Pharmaceutical Sciences 16th edition, Osol, A. Ed., 1980, which is hereby incorporated by reference in its entirety, as if fully set forth herein), in the form of lyophilized formulations or aqueous solutions.

The formulations to be used for in vivo administration are preferably sterile. This is readily accomplished by filtration through sterile filtration membranes or other methods. The variant antibody and other therapeutically active agents disclosed herein may also be formulated as immunoliposomes, and/or entrapped in microcapsules.

The concentration of the therapeutically active heavy chain constant region variant in the formulation may vary from about 0.001 to 100 weight %. In one embodiment, the concentration of the IgG is in the range of 0.003 to 1.0 molar. In order to treat a patient, a therapeutically effective dose of the variant antibody of the embodiments described herein may be administered to the patient. A "therapeutically effective dose," as used herein means a dose that produces the effects for which it is administered. The exact dose will depend on the purpose of the treatment, and will be ascertainable by one skilled in the art using known techniques. Dosages may range from 0.001 to 100 mg/kg of body weight or greater, for example 0.1, I, 10, or 50 mg/kg of body weight, with I to 10 mg/kg being a preferred range. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

Administration of the pharmaceutical composition that includes a variant antibody of the embodiments described herein, such as those in the form of a sterile aqueous solution, may be done in a variety of ways, including, but not limited to, subcutaneously, intravenously, intranasally, intraotically, transdermally, topically (e.g., gels, salves, lotions, creams, etc.), intraperitoneally, intramuscularly, intrapulmonary (e.g., AERx® inhalable technology commercially available from Aradigm, or Inhance® pulmonary delivery system commercially available from Inhale Therapeutics), vaginally, parenterally, rectally, or intraocularly. In some embodiments, the pharmaceutical composition is administered in any of the above routed using a composition in the form of a sterile aqueous solution.

Definitions

In order that for embodiments be more completely understood, several definitions are set forth below. Such definitions are meant to encompass equivalents and are not meant to be limiting.

The terms "ADCC" or "antibody dependent cell-mediated cytotoxicity," as used herein, mean a cell-mediated reaction wherein nonspecific cytotoxic cells that express FcγRs recognize bound antibody on a target cell and subsequently cause lysis of the target cell.

The terms "ADCP," or "antibody dependent cell-mediated phagocytosis," as used herein, mean a cell-mediated reaction wherein nonspecific cytotoxic cells that express FcγRs recognize bound antibody on a target cell and subsequently cause phagocytosis of the target cell.

The terms "amino acid" and "amino acid identity," as used herein, mean one of the 20 naturally occurring amino acids or any non-natural analogues that may be present at a specific, defined position. The terms "amino acid residue" or "amino acid," as used herein, refer to amino acids that are preferably in the "L" isomeric form. However, residues in the "D" isomeric form can be substituted for any L-amino acid residue, as long as the desired fictional property of immunoglobulin-binding is retained by the polypeptide. $NH_2$ refers to the free amino group present at the amino terminus of a polypeptide. COOH refers to the free carboxyl group present at the carboxyl terminus of a polypeptide. In keeping with standard polypeptide nomenclature, J. Biol. Chem., 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

The terms "amino acid modification" or "amino acid substitution" or "substitution," as used herein, mean an amino acid substitution, insertion, and/or deletion in a polypeptide sequence. An "amino acid substitution" or "substitution" as used herein, means a replacement of an amino acid at a particular position in a parent polypeptide sequence with another amino acid. For example, the substitution L328R refers to a variant polypeptide, in this case a heavy chain constant region variant, in which the leucine at position 328 is replaced with arginine. An "amino acid insertion" or "insertion" as used herein means an addition of an amino acid at a particular position in a parent polypeptide sequence. An "amino acid deletion" or "deletion," as used herein, means a removal of an amino acid at a particular position in a parent polypeptide sequence.

Amino acid substitutions can be made by mutation (for example mutation of SEQ ID NO:1-65) such that a particular codon in the DNA sequence encoding the polypeptide is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The embodiments described herein should be considered to include sequences containing conservative changes which do not significantly alter the activity or binding characteristics of the resulting protein.

The following are examples of various groupings of amino acids:

Amino acids with nonpolar R groups: Alanine, Valine, Leucine, Isoleucine, Proline, Phenylalanine, Tryptophan, Methionine Amino acids with uncharged polar R groups: Glycine, Serine, Threonine, Cysteine, Tyrosine, Asparagine, Glutamine Amino acids with charged polar R groups (negatively charged at Ph 6.0): Aspartic acid, Glutamic acid Basic amino acids (positively charged at pH 6.0): Lysine, Arginine, Histidine (at pH 6.0)

Another grouping may be those amino acids with phenyl groups: Phenylalanine, Tryptophan, Tyrosine.

Another grouping may be according to molecular weight (i.e., size of R groups) as shown below:

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

The term "antibody" or "antibodies" as used herein includes full length antibodies and antibody fragments, and includes both monoclonal and polyclonal antibodies. An antibody may also include recombinant, genetically engineered or otherwise modified forms of immunoglobulins, such as intrabodies, peptibodies, minibodies, chimeric antibodies, fully human antibodies, humanized antibodies, bispecific antibodies, and antibody fusions or heteroconjugate antibodies (e.g., diabodies, triabodies, and tetrabodies), An "antibody fragment" as used herein includes antibodies that comprise Fc regions, Fc fusions, and the constant region of the heavy chain (CH1-hinge-CH2-CH3), again also including constant heavy region fusions. Specific antibody fragments may include, but are not limited to, (i) the Fab fragment including VL, VH, CL and CH1 domains, (ii) the Fd fragment including of the VH and CH1 domains, (iii) the Fv fragment including of the VL and VH domains of a single antibody; (iv) the dAb fragment (Ward et al. 1989, Nature 341:544-546) which includes of a single variable, (v) isolated CDR regions, (vi) F (ab') 2 fragments, a bivalent fragment that includes two linked Fab fragments (vii) single chain Fv molecules (scFv), wherein a VH domain and a VL domain are linked by a peptide linker which allows the two domains to associate to form an antigen binding site (Bird et al., 1988; Huston et al., 1988), (viii) bispecific single chain Fv dimers (PCT/US92/09965) and (ix) "diabodies" or "triabodies", multivalent or multispecific fragments constructed by gene fusion (Tomlinson et. al., 2000, Methods Enzymol. 326:461-479; W094/13804; Holliger et al., 1993, Proc. Natl. Acad. Sci. U.S.A. 90:6444-6448). The antibody fragments may be modified. For example, the molecules may be stabilized by the incorporation of disulphide bridges linking the VH and VL domains (Reiter et al., 1996).

An antibody typically includes a tetrameric structure. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Thus, "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

The terms "CDC" or "complement dependent cytotoxicity," as used herein, mean a reaction wherein one or more complement protein components recognize bound antibody on a target cell and subsequently cause lysis of the target cell.

The "CH2 domain" of a human IgG Fc region (also referred to as "Cγ2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22:161-206 (1985).

The "CH3 domain" includes the stretch of residues C-terminal to a CH2 domain in an Fc region (i.e. from about amino acid residue 341 to about amino acid residue 447 of an IgG).

The terms "chimeric antibody," "chimeric antibodies," "humanized antibody," and "humanized antibodies" generally refer to antibodies that combine antibody regions (scaffold or framework regions and variable regions) from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:15341536, which are hereby incorporated by reference in their entirety, as if fully set forth herein. "Back mutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213). A humanized antibody may also comprise at least a portion of an immunoglobulin constant region, typically that of a human immunoglobulin, and thus will typically comprise a human Fc region. Humanized antibodies can also be generated using mice with a genetically engineered immune system (Roué et al., 2004). A variety techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization methods include but are not limited to methods described in Jones et al., 1986; Riechmann et al., 1988; Verhoeyen et al., 1988; Queen et al., 1989; He et al., 1998; Carter et al., 1992; Presta et al., 1997; Gorman et al., 1991; and O'Connor et al., 1998; which are hereby incorporated by reference in their entirety, as if fully set forth herein. Humanization or other methods of reducing the immunogenicity of nonhuman antibody variable regions may include resurfacing methods, as described for example in Roguska et al., 1994, Proc. Natl. Acad. Sci. USA 91:969973, which are hereby incorporated by reference in their entirety, as if fully set forth herein. In one embodiment, the parent or variant antibody has been affinity matured, as is known in the art. Structure-based methods may be employed for humanization and affinity maturation, for example as described in U.S. Ser. No. 11/004,590, which is hereby incorporated by reference in its entirety, as if fully set forth herein. Selection based methods may be employed to humanize and/or affinity mature antibody variable regions, including but not limited to methods described in Wu et al., 1999; Baca et al., 1997; Rosok et al., 1996; Rader et al., 1998 and Krauss et al., 2003, which are hereby incorporated by reference in their entirety, as if fully set forth herein. Other humanization methods may involve the grafting of only parts of the CDRs, including but not limited to methods described in U.S. Ser. No. 09/810,502; Tan et al., 2002, J. Immunol, all of which are hereby entirely incorporated by reference. Other humanization methods may involve the grafting of only parts of the CDRs, including but not limited to methods described in U.S. Ser. No. 09/810,502; Tan et al., 2002; De Pascalis et al., 2002, which are hereby incorporated by reference in their entirety, as if fully set forth herein.

The term "constant domain," as used herein, refers to the portion of an immunoglobulin molecule having a more conserved amino acid sequence relative to other portions of the immunoglobulin, the variable domain, which contains the antigen binding site. The constant domain contains the CH1, CH2 and CH3 domain of the heavy chain and the CL domain of the light chain.

The term "effector function," as used herein, is a biochemical event that results from the interaction of an antibody Fc region with an Fc receptor or ligand. Effector functions include, but are not limited to, Fcγ R-mediated effector functions such as ADCC and ADCP, and complement-mediated effector functions such as CDC.

The term "effector cell," as used herein, is a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and T cells, and may be from any organism including but not limited to humans, mice, rats, rabbits, and monkeys.

The terms "Fab" or "Fab region," as used herein, mean one or more polypeptides that comprise the VH, CH1, VL, and CL immunoglobulin domains. Because VL includes the JL region and VH includes the JH region, JL and JH also compose the Fab region. It is generally viewed in the art that the Fab region is demarcated N-terminally by the N-terminus and C-terminally by the disulfide bond that covalently links the heavy and light chains. Accordingly, for the purposes of the embodiments described herein, "Fab region" as used herein includes amino acids positions from the N-terminus to position 214 of the light chain and from the N-terminus to position 220 of the heavy chain, wherein the numbering of the C-terminal residues is according to the EU numbering scheme. Fab may refer to this region in isolation, or this region in the context of a full-length antibody or antibody fragment. Positional definitions of the regions within the Fab, including the VL, VH, JL, JH, CL, and CH1 regions, are illustrated in FIG. 1). The VL kappa and VH regions are well defined genetically and in the art, and accordingly "VL region" as used herein includes residues 1-107, and "VH region" as used herein includes residues 1-113, wherein numbering is according to the Kabat numbering scheme. The JL kappa region is made up of 5 germ line sequences of equal length, and accordingly, "JL region," as used herein, includes positions 96-107, wherein numbering is according to Kabat. There are 6 JH germ line sequences of differing length, and the exact Kabat position at which this segment combines with the VH germ line varies. For the purposes of the embodiments described herein, the JH region may comprise the residues of these sequences that are clearly defined in a Kabat sequence alignment. Based on this definition, "JH region" as used herein includes residues 100-113, wherein numbering is according to the Kabat numbering scheme. The remaining C-terminal light and heavy chain sequences of the Fab are made up of the CL and CH1 regions respectively. Thus, "CL region" as used herein includes positions 108-214, and "CH1 region" as used herein includes positions 118-220, wherein numbering is according to the EU numbering scheme. Fab may refer to this region in isolation, or this region in the context of a full-length antibody or antibody fragment.

The terms "Fc Binding protein" or "FcBP," as used herein, mean a microbial product that can bind to an immunoglobulin through interaction with the Fc region of the immunoglobulin. Examples of such proteins include SpA and Protein G which interact with the CH2-CH3 interface of the immunoglobulin Fc region, or SSL10 which interacts with IgG1 at site which is distinct from the SpA binding site.

The term "Fc fusion," as used herein, is a protein wherein one or more polypeptides are operably linked to Fc. Fc fusion is herein meant to be synonymous with the terms "immunoadhesin", "Ig fusion", "Ig chimera", and "receptor globulin" (sometimes with dashes) (Chamow et al., 1996, *Trends Biotechnol* 14:52-60; Ashkenazi et al., 1997, *Curr Opin Immunol* 9:195-200, both hereby entirely incorporated by reference). An Fc fusion combines the Fc region of an immunoglobulin with a fusion partner, which in general may be any protein, polypeptide or small molecule. The role of the non-Fc part of an Fc fusion, i.e., the fusion partner, is to mediate target binding, and thus it is functionally analogous to the variable regions of an antibody. In addition to Fc fusions, "antibody fusions" include the fusion of the constant region of the heavy chain with one or more fusion partners or conjugate partners (again including the variable region of any antibody), while other antibody fusions are substantially or completely full length antibodies with fusion partners or conjugate partners. In one embodiment, a role of the fusion or conjugate partner is to mediate target binding, and thus it is functionally analogous to the variable regions of an antibody (and in fact can be). Virtually any protein or small molecule may be linked to Fc to generate an Fc fusion or antibody fusion. Protein fusion or conjugate partners may include, but are not limited to, the target binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, such as an extracellular receptor that is implicated in disease. The fusion or conjugate partner can be proteinaceous or non-proteinaceous; the latter generally being generated using functional groups on the antibody and on the conjugate partner. For example, linkers are known in the art; for example, homo- or hetero-bifunctional linkers as are well known (see, 1994 Pierce Chemical Company catalog, technical section on cross-linkers, pages 155-200, incorporated herein by reference).

The term "Fc gamma receptor" or "Fcγ R," as used herein, is any member of the family of proteins that bind the IgG antibody Fc region and are substantially encoded by the Fcγ R genes. In humans, this family includes, but is not limited to, Fcγ RI (CD64), including isoforms FcγRIa, FcγRIb, and FcγRIc; Fcγ RII (CD32), including isoforms FcγRIIa (including allotypes H131 and R131), FcγRIIb (including FcγRIIb-1 and FcγRIIb-2), and FcγRIIc; and FcγRIII (CDl6), including isoforms FcγRIIIa (including allotypes Vl58 and F158) and FcγRIIIb (including allotypes FcγRIIIb-NAl and Fcγ RIIIb-NA2) (Jefferis et al., 2002, *Immunol Lett* 82:57-65, which is hereby entirely incorporated by reference), as well as any undiscovered human Fcγ Rs or Fcγ R isoforms or allotypes. An Fcγ R may be from any organism, including but not limited to, humans, mice, rats, rabbits, and monkeys. Mouse Fcγ Rs include but are not limited to Fcγ RI (CD64), Fcγ RII (CD32), Fcγ RIII (CDl6), and Fcγ RIII-2 (CDl6-2), as well as any undiscovered mouse Fcγ Rs or Fcγ R isoforms or allotypes.

The term "Fc ligand," as used herein, is a molecule, such as a polypeptide, from any organism that binds to the Fc region of an antibody to form an Fc/Fc ligand complex. Fc ligands include, but are not limited to, Fcγ Rs, Fcγ Rs, Fcγ Rs, FcRn, Clq, C3, mannan binding lectin, mannose receptor, staphylococcal SpA, streptococcal protein G, and viral Fcγ R. Fc ligands also include Fc receptor homologs (FcRH), which are a family of Fc receptors that are homologous to the Fcγ Rs (Davis et al., 2002, *Immunological Reviews* 190:123-136, which is hereby entirely incorporated by reference). Fc ligands may include undiscovered molecules that bind Fc.

The terms "Fc" or "Fc region," as used herein, mean a polypeptide that includes the heavy chain constant region of an antibody excluding the first heavy chain constant region immunoglobulin domain. Thus Fc refers to the last two heavy chain constant region immunoglobulin domains of IgA, IgD, and IgG, and the last three constant region immunoglobulin domains of IgE and IgM, and the flexible hinge N-terminal to these domains. For IgA and IgM, an Fc may include the J chain. For IgG, as illustrated in FIG. 1, Fc includes immunoglobulin domains Cgamma2 and Cgamma3 (Cγ2 and Cγ3) and the hinge between C gamma 1 (Cγ1) and Cgamma2 (Cγ2). Cγ1, Cγ2 and Cγ3 are also commonly referred to as CH1, CH2 and CH3. Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, as described below. The term "Fc polypeptide," as used herein, is a polypeptide that includes all or part of an Fc region. Fc polypeptides include, but are not limited to, antibodies, Fc fusions, isolated Fcs, and Fc fragments. Therefore, "outside the Fc region" as used herein means the region of an antibody that does not comprise the Fc region of the antibody. In accordance with the aforementioned definition of Fc region, "outside the Fc region" for an IgG1 antibody is herein defined to be from the N-terminus up to and including residue T225 or C229, wherein the numbering is according to the EU numbering scheme. Thus, the Fab region and part of the hinge region of an antibody are outside the Fc region.

The term "full length antibody," as used herein, is a structure that is or includes the natural biological form of an antibody, including variable and constant regions. For example, in most mammals, including humans and mice, the full length antibody of the IgG isotype is a tetramer and includes two identical pairs of two immunoglobulin chains, each pair having one light and one heavy chain, each light chain that includes immunoglobulin domains VL and CL; and each heavy chain that includes immunoglobulin domains VH, CH1, CH2, and CH3. In some mammals, for example in camels and llamas, IgG antibodies may include only two heavy chains, each heavy chain including a variable domain attached to the Fc region.

A "fully human antibody" or "complete human antibody" refers to a human antibody having the gene sequence of an antibody derived from a human chromosome with the modifications outlined herein.

The term "germline," as used herein, is the set of sequences that compose the natural genetic repertoire of a protein, and its associated alleles.

The terms "hinge" or "hinge region," as used herein, mean the flexible polypeptide that includes the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230.

An immunoglobulin Fc variant or heavy chain constant region variant includes one or more amino acid modifications relative to a parent immunoglobulin Fc polypeptide or heavy chain constant region polypeptide, wherein said amino acid modification(s) provide one or more altered properties. An Fc or heavy chain constant region variant of the embodiments described herein differ in amino acid sequence from its parent IgG by virtue of at least one amino acid modification. Thus, variants described herein have at least one amino acid modification compared to the parent. Alternatively, the variants described herein may have more than one amino acid modification as compared to the parent, for example from about one to fifty amino acid modifications, preferably from about one to ten amino acid modifications, and preferably from about one to about five amino acid modifications compared to the parent. Thus the sequences of the Fc variants or Ig heavy chain constant region variant and those of the parent Fc polypeptide are substantially homologous. For example, the variant heavy chain constant region variant sequences herein will possess about 80% homology with the parent heavy chain constant region variant sequence, preferably at least about 90% homology, and preferably at least about 95% homology. Modifications may be made genetically using molecular biology methods known in the art.

The terms "immunoglobulin BP," "IgBP" or "microbial immunoglobulin binding protein," as used herein, mean a microbial product that can bind to immunologic either through interaction with the Fc region of the immunoglobulin (e.g. SpA or Protein G), or though non-immune interaction with the Fab region (e.g. SpA-Fab binding domain), or through interaction with heavy or light chain constant regions outside the Fc region (e.g. L protein of *Peptostreptococcus magnus*).

The term "immunoglobulin (Ig)," as used herein is a protein including one or more polypeptides substantially encoded by immunoglobulin genes. Immunoglobulins include but are not limited to antibodies. Immunoglobulins may have a number of structural forms, including but not limited to full-length antibodies, antibody fragments, and individual immunoglobulin domains.

The term "IgG," as used herein, is a polypeptide belonging to the class of antibodies that are substantially encoded by a recognized immunoglobulin gamma gene. In humans, this IgG includes the subclasses or isotypes IgG1, IgG2, IgG3, and IgG4. In mice, IgG includes IgG1, IgG2a, IgG2b, IgG3.

The term "isotype," as used herein, is any of the subclasses of immunoglobulins defined by the chemical and antigenic characteristics of their constant regions. The known human immunoglobulin isotypes are IgG1, IgG2, IgG3, IgG4, IgA1, IgA2, IgM, IgD, and IgE.

The term "isotypic modification," as used herein, is an amino acid modification that converts one amino acid of one isotype to the corresponding amino acid in a different, aligned isotype. For example, because IgG1 has a tyrosine and IgG2 a phenylalanine at EU position 296, a F296Y substitution in IgG2 is considered an isotypic modification.

The term "non-immune binding," as used herein, refers to binding of an antibody to an IgBP virulence factor that does not involve antigen-dependent binding by the variable region of the antibody. In contrast, the term "immune binding," as used herein, refers to specific binding of an antigen by an antibody that involves antigen-dependent binding by the variable region of the antibody.

The term "novel modification," as used herein, is an amino acid modification that is not isotypic. For example, because none of the IgGs have a glutamic acid at position 332, the substitution I332E in IgG1, IgG2, IgG3, or IgG4 is considered a novel modification.

The terms "parent polypeptide", "parent protein", "precursor polypeptide", or "precursor protein," as used herein, mean an unmodified polypeptide that is subsequently modified to generate a variant. Said parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent Fc polypeptide" as used herein is meant an Fc polypeptide that is modified to generate a variant, and by "parent antibody" as used herein is meant an antibody that is modified to generate a variant antibody.

The terms "parental immunoglobulin," "parental antibody," or "parent antibody" as used herein, mean an unmodified immunoglobulin polypeptide that is subsequently modified to generate a variant. Said parent immunoglobulin polypeptide may be a naturally occurring polypeptide, or a variant or engineered version of a naturally occurring polypeptide. Parental immunoglobulin or antibody may refer to the polypeptide itself, compositions that comprise the parental polypeptide, or the amino acid sequence that encodes it.

The term "position" or "amino acid position," as used herein, is a location in the sequence of a protein or an antibody. Positions may be numbered sequentially, or according to established format. Several formats are known in the art including, but not limited to, EU, Kabat, Chotia, IMGT, AHo, and Abhinandan. One skilled in the art would understand the corresponding "EU position," "Kabat position," "Chotia position," IMGT position," or "AHo position." Therefore, any amino acid positions described herein are for identification purposes only, and are not meant to be limited to a particular numbering format.

The term "EU position" or "EU numbering" as used herein, is a location in the sequence of a protein. Positions may be numbered sequentially, or according to an established format, for example the EU position (Edelman, G. M. et al., Proc. Natl. Acad. USA, 63, 78-85 (1969), http://www.imgt.org/IMGTScientificChart/Numbering/IMGTIGVCsuperfamily.html). For example, position 297 is a position in the human antibody IgG1.

The term "Kabat position," or "Kabat numbering" as used herein, is a location in the sequence of a protein. Positions may be numbered sequentially, or according to an established format, for example the index as in Kabat (Kabat et al., "Sequences of Proteins of Immunological Interest", NIH Publication, 91-3242 (1991), http://www.imgt.org/IMGT-ScientificChart/Numbering/IMGTIGVCsuperfamily.html).

A "polypeptide" or "protein," as used herein, is at least two covalently attached amino acids, which includes proteins, polypeptides, oligopeptides and peptides.

The term "residue," as used herein, is an amino acid, or a position in a protein and its associated amino acid identity. For example, Asparagine 297 (also referred to as Asn297, Asn 297, N297 or 297N) is a residue in the human antibody IgG1.

A "replicon" is any genetic element (e.g., plasmid, chromosome, virus) that functions as an autonomous unit of DNA replication in vivo; i.e., capable of replication under its own control.

Two DNA sequences are "substantially homologous" when at least about 75% (preferably at least about 80%, and preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra, which are hereby incorporated in their entirety as if fully set forth herein.

The term "target cell," as used herein, is a cell that expresses a target antigen.

The term "variable region" or "variable domain" as used herein, is the region of an immunoglobulin that includes one or more Ig domains substantially encoded by any of the VK' VL and/or VH genes that make up the kappa, lambda, and heavy chain immunoglobulin genetic loci respectively.

The terms "variant polypeptide", "polypeptide variant", "variant immunoglobulin", "variant antibody" or "variant," as used herein, refer to a polypeptide sequence that differs from that of a parental polypeptide sequence by virtue of at least one amino acid modification in any part of an antibody including, but not limited to, the Fc region, the immunoglobulin heavy chain, the heavy chain constant region, the heavy chain variable region, the immunoglobulin light chain, the light chain constant region, the light chain variable region, or any fragment of combination thereof. The parent polypeptide may be a naturally occurring or wild-type (WT) polypeptide, or may be a modified version of a WT polypeptide. Variant polypeptide may refer to the polypeptide itself, a composition that includes the polypeptide, or the amino sequence that encodes it. The variant polypeptide may have at least one amino acid modification compared to the parent polypeptide, e.g. from about one to about ten amino acid modifications, or from about one to about five amino acid modifications compared to the parent. The variant polypeptide sequence herein may possess at least about 80% homology with a parent polypeptide sequence, at least about 90% homology, or at least about 95% homology.

Accordingly, the terms "Fc variant", or "variant Fc" as used herein, mean an antibody sequence that differs from that of a parent sequence by virtue of at least one amino acid modification in the Fc region. An Fc variant may only encompass an Fc region, or may exist in the context of an antibody, Fc fusion, isolated Fc, Fc fragment, or other polypeptide that is substantially encoded by Fc. Fc variant may refer to the Fc polypeptide itself, compositions including the Fc variant polypeptide, or the amino acid sequence that encodes it. The terms "Fc polypeptide variant" or "variant Fc polypeptide," as used herein, refer to an Fc polypeptide that differs from a parent Fc polypeptide by virtue of at least one amino acid modification. The terms "protein variant" or "variant protein," as used herein, mean a protein that differs from a parent protein by virtue of at least one amino acid modification. The terms "antibody variant" or "variant antibody," as used herein, mean an antibody that differs from a parent antibody by virtue of at least one amino acid modification. The terms "IgG variant" or "variant IgG," as used herein, mean an antibody that differs from a parent IgG by virtue of at least one amino acid modification. The terms "immunoglobulin variant" or "variant immunoglobulin," as used herein, mean an immunoglobulin sequence that differs from that of a parent immunoglobulin sequence by virtue of at least one amino acid modification.

Accordingly, the terms "heavy chain constant region variant", "variant heavy chain constant region," "heavy chain constant region variant," or "variant heavy chain constant region," as used herein, mean a heavy chain constant region antibody sequence that differs from that of a parent sequence by virtue of at least one amino acid modification. A heavy chain constant region variant may include an heavy chain constant region alone, or may exist in the context of an antibody, a heavy chain constant region fusion, isolated heavy chain constant region, heavy chain constant region fragment, or other polypeptide that is substantially encoded by heavy chain constant region. Heavy chain constant region variant may refer to the heavy chain constant region polypeptide itself, compositions that include the heavy chain constant region variant polypeptide, or the amino acid sequence that encodes it. The terms "heavy chain constant region polypeptide variant" or "variant heavy chain constant region polypeptide," as used herein, refer to a heavy chain constant region polypeptide that differs from a parent heavy chain constant region polypeptide by virtue of at least one amino acid modification.

Similarly, the terms "heavy chain variable region variant", "variant heavy chain variable region," "heavy chain variable region variant," "variable heavy chain sequence variant," or "variant heavy chain constant region," as used herein, mean a heavy chain variable region antibody sequence that differs from that of a parent sequence by virtue of at least one amino acid modification. A heavy chain variable region variant may include an heavy chain variable region alone, or may exist in the context of an antibody, a heavy chain variable region fusion, isolated heavy chain variable region, heavy chain variable region fragment, or other polypeptide that is substantially encoded by heavy chain variable region. Heavy chain variable region variant may refer to the heavy chain variable region polypeptide itself, compositions that include the heavy chain variable region variant polypeptide, or the amino acid sequence that encodes it. The terms "heavy chain variable region polypeptide variant" or "variant heavy chain variable region polypeptide," as used herein, refer to a heavy chain variable region polypeptide that differs from a parent heavy chain variable region polypeptide by virtue of at least one amino acid modification. The terms "protein variant" or "variant protein," as used herein, mean a protein that differs from a parent protein by virtue of at least one amino acid modification. The terms "antibody variant" or "variant antibody," as used herein, mean an antibody that differs from a parent antibody by virtue of at least one amino acid modification. The terms "IgG variant" or "variant IgG," as used herein, mean an antibody that differs from a parent IgG by virtue of at least one amino acid modification. The terms "immunoglobulin variant" or "variant immunoglobulin," as used herein, mean an immunoglobulin sequence that differs from that of a parent immunoglobulin sequence by virtue of at least one amino acid modification.

The term "wild type or WT," as used herein, is an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified antibodies. Accordingly, the present disclosure provides variant antibodies.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

The embodiments described herein is more fully understood by reference to the following examples. They should not however be construed as limiting the scope of the invention. All literature and patent citations mentioned herein are expressly incorporated by reference herein as if fully set forth herein.

The disclosure involves both the generation of antimicrobial variable domain polypeptides, which constitute the antigen-binding site of the antibody, and their combination with immunoglobulin light and heavy chain constant region sequences and their variants. The resulting variant antibodies have antimicrobial activity. The first section of the examples covers the generation of variable domain anti-microbial antibodies. In the examples profiles the antimicrobial antibodies are directed against S. aureus antigens SpA and ClfA. The second section covers the generation of heavy chain constant regions and their variants. The third section covers the construction, expression and purification of antibodies and their variants and the final section covers biological testing of example anti-microbial immunoglobulins and their heavy chain constant region variants.

Examples are provided that demonstrate the enhanced anti-microbial activity of Fc variant anti-Microbial antibodies.

Anti-Microbial Antibody Generation

Anti-*S. aureus* antibodies In some embodiments where the target microbe is *S. aureus*, heavy chain constant region variant IgG polypeptide sequences are combined with immunoglobulin heavy chain variable polypeptide sequences and light chains polypeptide sequences, which bind one or more cell surface or secreted *S. aureus* antigen. Examples of *S. aureus* antigen recognized by the variable domain of heavy chain constant region variant IgG antibodies are cell surface or secreted antigens selected from the list which includes but is not limited to: ClfA, ClfB, Cna, Eap, Ebh, EbpS, FnBPA, FnBPB, IsaA, IsaB, IsdA, IsdB, IsdH, SasB, SasC, SasD, SasF, SasG, SasH, SasK, SdrC, SdrD, SdrE, Spa, SraP, Coa, Ecb, Efb, Emp, EsaC, EsxA, EssC, FLIPr, FLIPr like, Sbi, SCIN-B, SCIN-C, VWbp, SpA, LTA, CP5, CP8, PNAG, dPNAG, alpha toxin, CHIPS, PVL leukocidin, α, β and γ-hemolysins, SAK, Sea, Sep, Seb, Epa, Efb, SCIN, Exfoliatins ETB and ETA, Staphylococcal Enterotoxins SEA, SEB, SECn, SED, SEG, SHE, and SEI, Toxic-shock syndrome toxin TSST-1, Alpha Toxin, Beta toxin, Delta toxin.

As examples of the utility, anti-SpA and anti-ClfA parental and heavy chain constant region variant IgG1 antibodies have been generated. Additionally, control heavy chain constant region variant IgG1 antibodies which target an unrelated viral antigen (anti-RSV variable domain) have been produced to enable characterization of microbial IgBP binding to the heavy chain constant region variants in the absence of microbial binding by the variable domain of the antibody. The following examples illustrate the generation of anti-*S. aureus* antibodies (including humanization of exemplar murine antibodies) and their combination with example variant heavy chain constant regions described herein.

Example 1: Epitope Discovery and Generation of Anti-SpA Monoclonal Antibodies (by In Vivo Immunization and Humanization)

In Silico Discovery of Anti-SpA Antigens and Epitopes.

The SpA amino acid sequence from 2 strains of *S. aureus* (Newman and USA 300) was initially examined (FIG. 2). Regions of high inter IgBP domain (SpA domains E, D, A, B and C) sequence homology were found which primarily mapped to region of Helices I, II and III. Models of the binding interfaces of domain B (only Helix I and II are shown for clarity) of SpA with an IgG Fc fragment (FIG. 8, derived from PDB ID: 1FC2) and the SpA domain D with a IgM VH3 Fab fragment (FIG. 9, derived from PDB ID 1DEE) were constructed from X-ray structures available within the PDB database.

The individual SpA IgBP domains (domains E, D, A, B and C) each adopt three-helix bundles (FIG. 9 represents the SpA D domain). One face, includes residues from helices I and II binds, IgG Fc (FIG. 8). Residues from helices II and III on the other face bind VH3 Ig (FIG. 9) (Deisenhofer, 1981; Graille et al., 2000).

The amino residues that vary between individual IgBP domains of SpA, referred to as inter-domain variable residues were mapped onto the model and analyzed (e.g., residues indicated by arrows in FIG. 8 and FIG. 9).

With respect to Fc binding, it was found that inter-domain variable residues mapped to the face of helix I and II that are not involved directly in interactions with the IgG Fc region. Most inter-domain variable residues are located on the non Fc interacting face of Helix I and II, the N terminus of Helix I, and the amino acid chain the connects Helix I and II (FIG. 8).

A similar strategy was taken to analyze residues that are involved in interaction between SpA IgBP domains and VH3 derived Fab sequences (FIG. 3). As shown in FIG. 9, residues involved in the interaction between SpA IgBP Helix II and III of domain D are highly conserved in Domains E, A, B and C. Inter-domain variable residues have been mapped onto the model shown in FIG. 9 (monomer of SpA domain D and a VH3 Fab fragment). Most inter-domain variable residues are located on the non-Fab interacting face of Helix II and III.

The amino acid sequence of the individual SpA IgBP domains from sequenced stains of *S. aureus* were obtained from public sequence data bases and analyzed for intra-domain strain sequence variability. The aligned sequences are shown in FIGS. 11A-E. The amino acid residues involved with binding to IgFc (FIGS. 8A-B) and VH3 Fab residues (FIGS. 9A, B, C) are highly conserved in all sequenced stains (FIGS. 11A-E). This finding demonstrates a high degree of functional (Fc and VH3 Fab binding residues) conservation of amino acid residues within SpA IgBP domains of sequenced stains.

In the stains analyzed, no substitutions were found in SpA domain C (FIG. 11C).

Within SpA domains E, D, A and B, inter-strain sequence changes within individual SpA domains were highly conservative with respect to function. In almost all cases, if a substitution occurred, it is changed to an amino acid that is found in one of the other SpA domains, and the position is not important for the interacting with either Fc or VH3 Fab (FIGS. 11A-E).

For example a number of stains have a Q to K substitution within Helix III of SpA domain E (FIGS. 11-E). K is found at the same position in all sequenced stains of *S. aureus* domains D, A, B and C that were analyzed (FIGS. 11A-D). The position of the Q to K substitution in domain E is located on the face of Helix III that does not interact with the VH3 Fab (FIG. 10).

Based on the analysis of sequence, a number of different SpA epitopes were identified that would be highly conserved in SpA domains within a *S. aureus* strain, and which are also highly conserved between *S. aureus* stains. These epitopes cover the functionally concerned Fc and Fab binding faces of SpA domains. Such epitopes, which involve SpA binding interfaces required for virulence functions, would be used when targeting anti-microbial antibodies to *S. aureus*, as they would be less prone to the selection of resistance since a) the epitopes are present in multiple SpA domains, b) mutations within such epitopes are likely to abrogate the virulence function of the SpA domain in which they occur.

Additionally, the repeat nature of the epitope in multiple SpA domains will enhance antibody avidity. Such antibodies will neutralize one or more IgBP virulence functions of SpA and target opsono-phagocytosis to SpA coated target microbes.

A number of antibody binding regions of SpA were identified. These regions are involved in functional interactions between SpA and Fc and/or Fab. Directing antibody binding to epitopes, which involve these functional binding interfaces, or selecting antibodies with such properties, is an important aspect of the embodiments described herein.

One SpA binding region that was identified is the binding interface of Helix I and II that interacts with IgFc. Epitopes, which involve this interface, will be highly conserved between SpA domains and strains. Additionally, monoclonal antibodies recognizing such epitopes will block Fc binding and may also block vWF and TNFR1 binding to SpA domains to which they bind. In the case in which the epitope to which the antibody binds involves Helix II, VH3 Fab binding to SpA is also likely to be blocked.

Another SpA binding region that was identified covers Helix II, which is involved in interacts with both IgFc and VH3 Fab. Binding of monoclonal antibodies to SpA epitopes within this highly conserved Helix, which can block both Fc and Fab binding to SpA. As Helix II is virtually invariant between SpA domains and between S. aureus stains, this region of SpA is a target of antibodies described herein.

One SpA binding region that was identified is the binding interface of Helix II and III that interacts with Ig VH3 Fab. Binding of monoclonal antibodies to SpA epitopes within this region are highly conserved between SpA domains and strains. Additionally, monoclonal antibodies recognizing such epitopes will block VH3 Fab binding and may also block Fc binding to SpA.

Immunization or selection methods for the selection of antibodies that recognize conserved SpA epitopes are provided.

Figure 12:
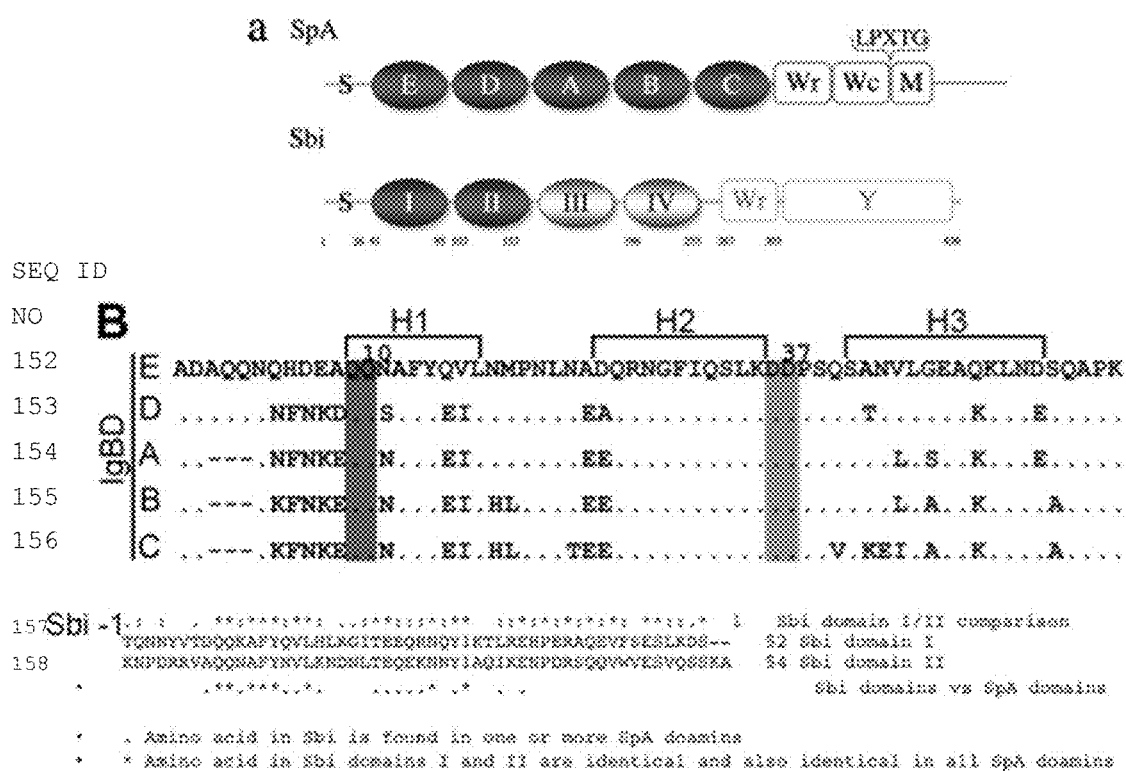
FIG. 12 illustrates the domain structure of SpA and Sbi in Panel A. Domains I and II of Sbi have homology to SpA IgBP domains. Panel B (SEQ ID NOs: 152-156) shows the amino acid sequence of domains E, D, A, B and C (Kim et al., 2010). Helix regions (see FIGS. 8 and 9) are labeled H1(Helix I), 2 (Helix II) and 3 (Helix III). The amino acid sequence of domains I and II of Sbi are shown (SEQ ID NOs: 157-158). Similarity analysis of Sbi domains I and II are shown above the Sbi sequences. Amino acids that are conserved between Sbi domains I and II and SpA IgBP domains are shown below the Sbi amino acid sequences.
Figure 13:
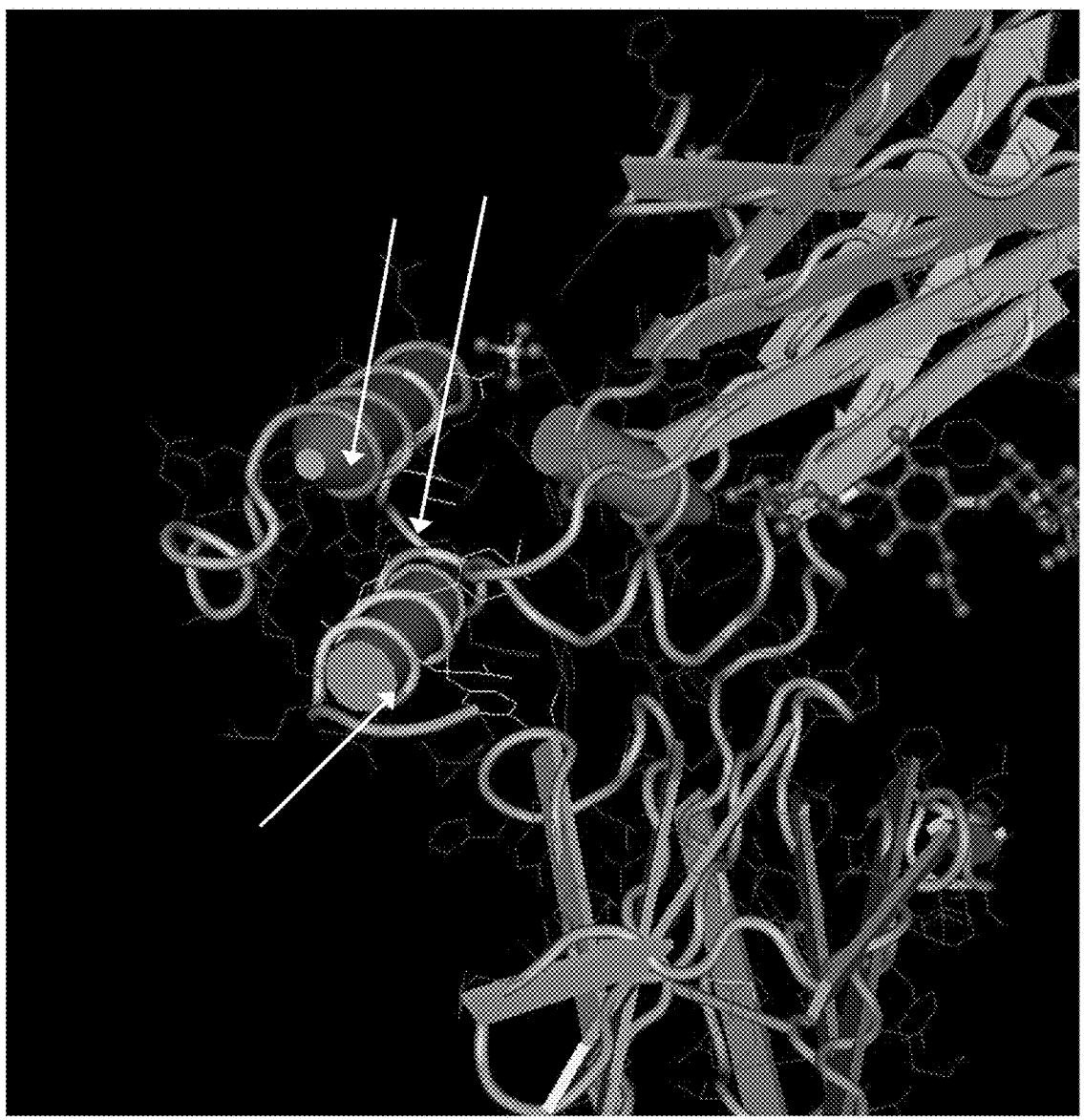
FIG. 13 The IgFc binding domains of Sbi (I and II.

The IgFc binding domains of Sbi (I and II) were also analyzed (FIGS. 12, 13 and 14). Amino acids within the predicted Helix I region are highly conserved between Sbi domains I and II (FIG. 12B) and also between Sbi domains and Spa Fc binding helix I and a number of amino acids in Helix II (FIG. 12B). Invariant residues were mapped onto the model of Spa domain D (Helix I and II) binding to the Fc region of an IgG (FIG. 13). As can be seen, residues that interact with IgFc are conserved between Spa domains and Sbi domains. In addition to these invariant residues, a number of highly conservative residues are found in Sbi that are present in some SpA domains (FIG. 12).

Figure 15:
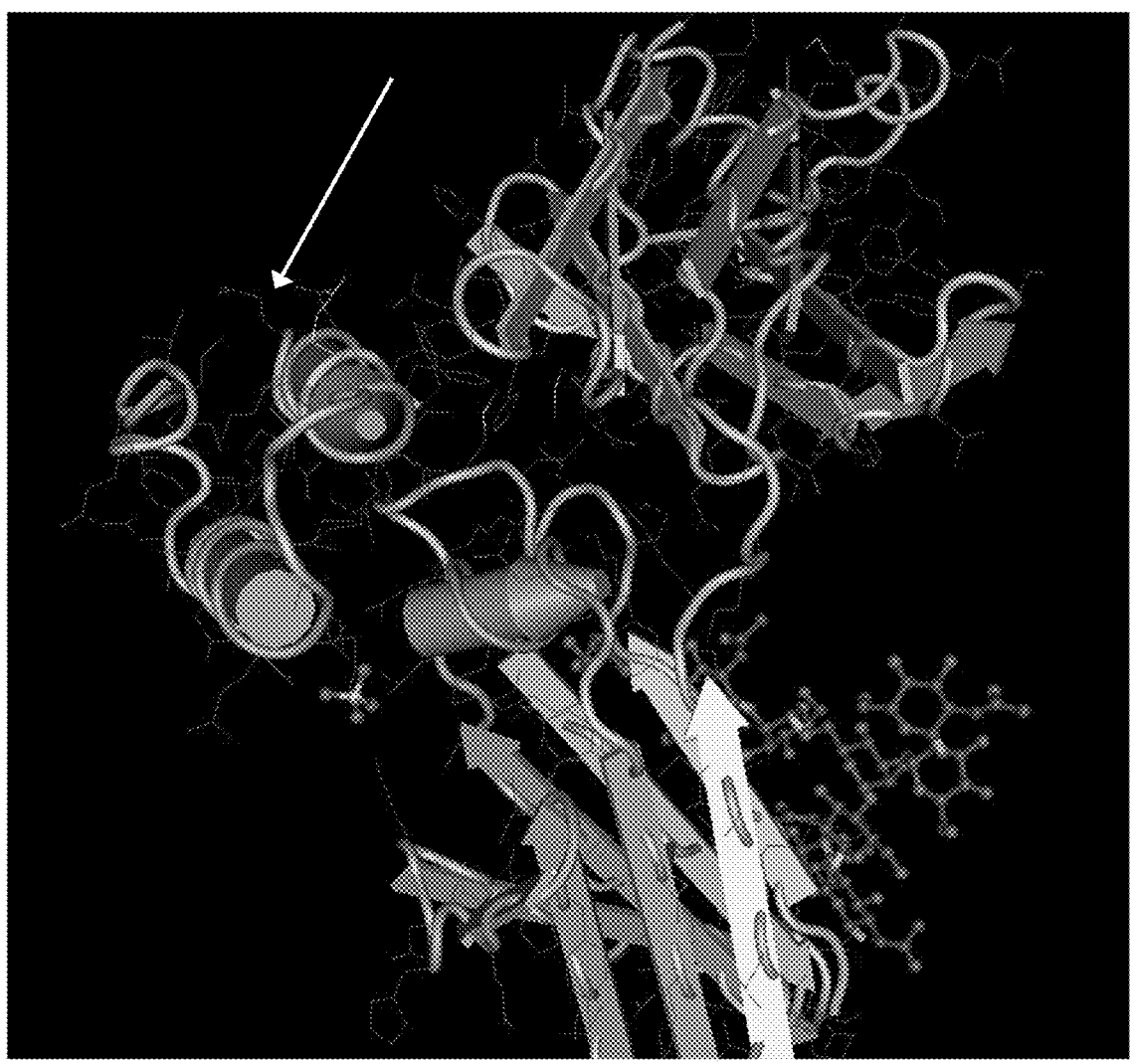
FIG. 15 models the IgFc binding domains of Sbi (Domains I and II.
Figure 18:
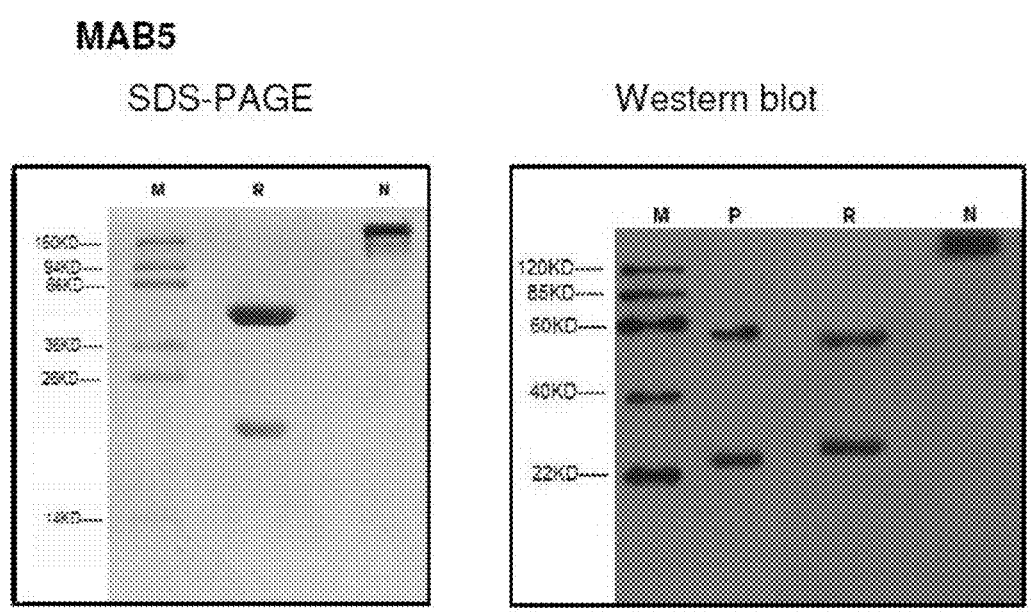
FIG. 18 is an SDS-PAGE and Western blot of anti-RSV variant antibody MAB5.
Figure 19:
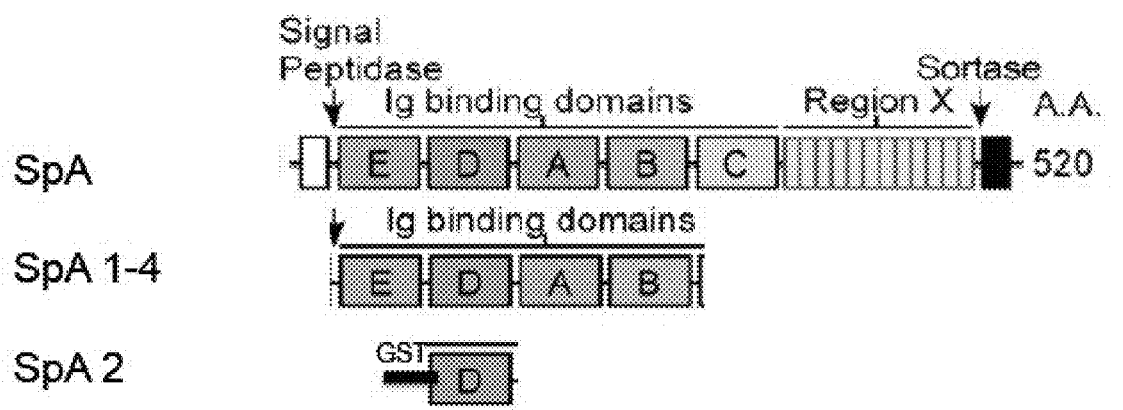
FIG. 19 shows constructs used for DLS and immunediffusion studies. The following S. aureus SpA and Sbi IgBPs proteins or their domains have been used to characterize S. aureus IgBP binding to variant and parental heavy chain constant region sequences. Purified constructs have been used for immunodiffusion and Dynamic Light Scattering experiments.
Figure 20:
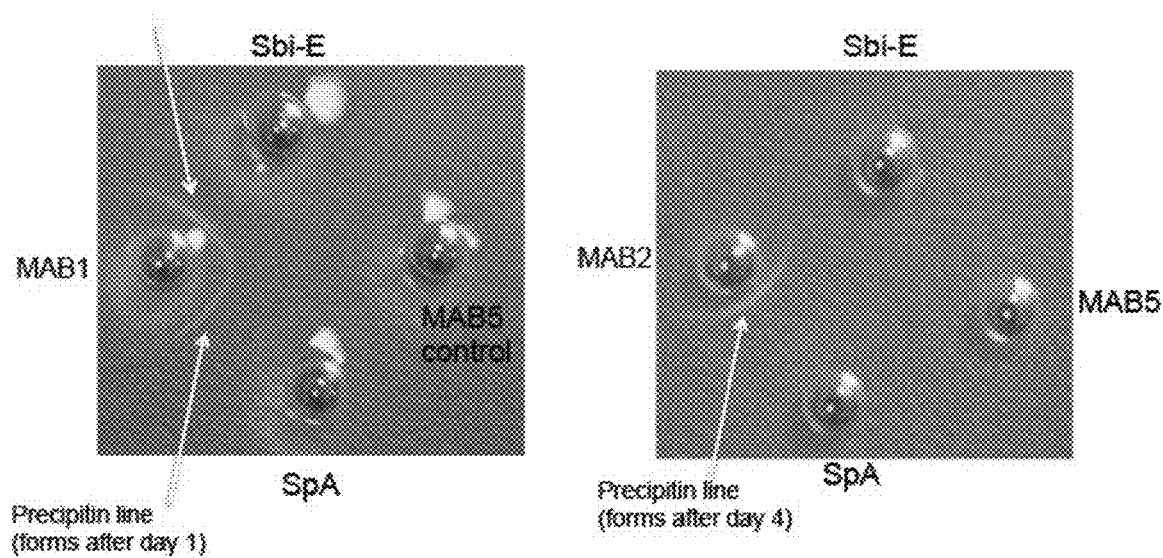
FIG. 20 shows an imuodiffusion analysis of antibodies MAB1, MAB2 and MAB5 with SpA and Sbi-E.
Figure 21:
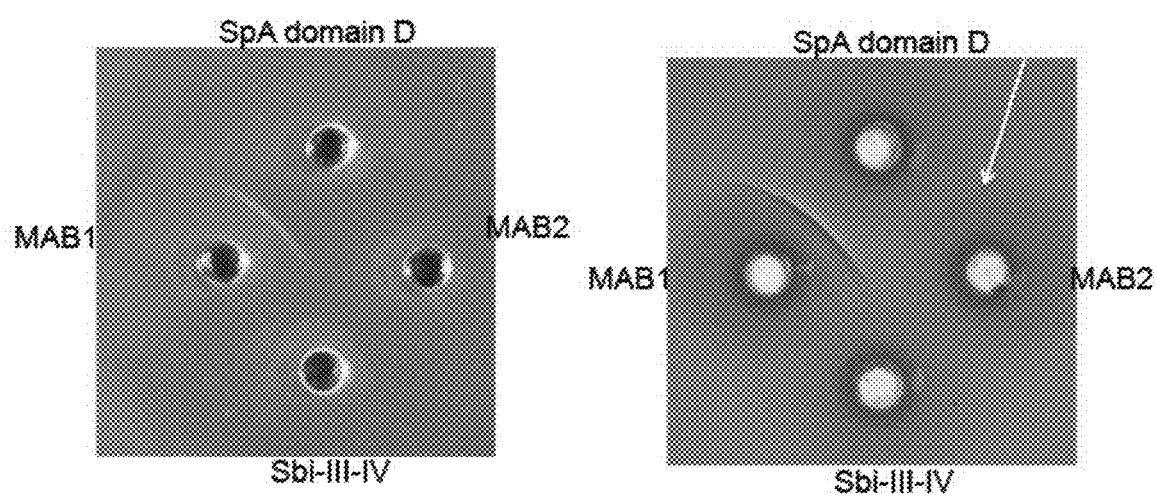
FIG. 21 shows an imuodiffusion analysis of antibodies MAB1, MAB2 with SpA domain D and Sbi-domains II/IV.
Figure 22:
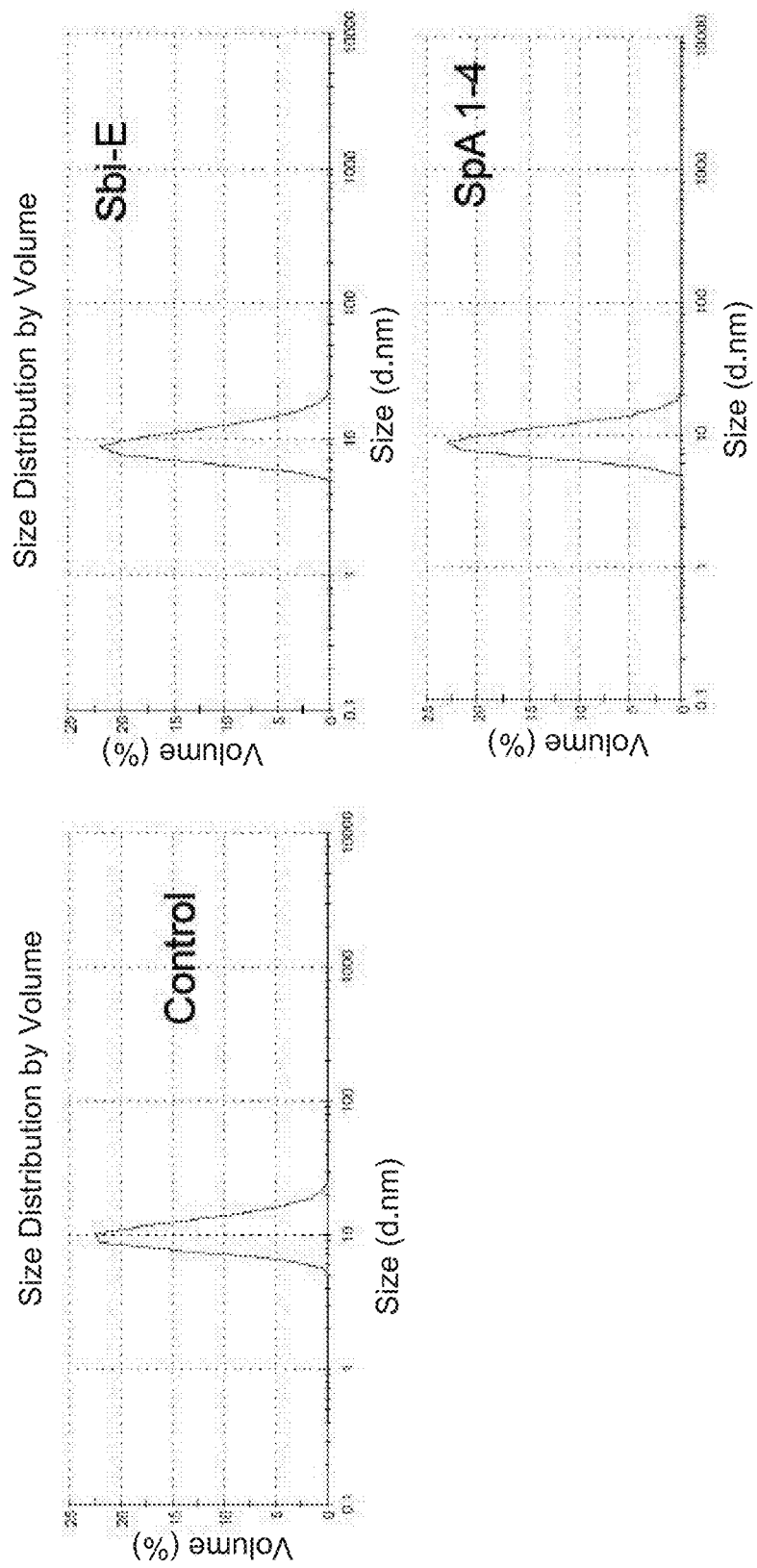
FIG. 22 shows an anti-RSV variant MAB5 analysis by DLS. The left panel shows the analysis of the control anti-RSV variant antibody alone (MAB5). The right panels show the size distribution in the presence of either Sbi-E (fragment of Sbi containing the two Ig-binding domains and two complement binding domains) or SpA1-4 (SpA IgBP domains 1-4).
Figure 23:
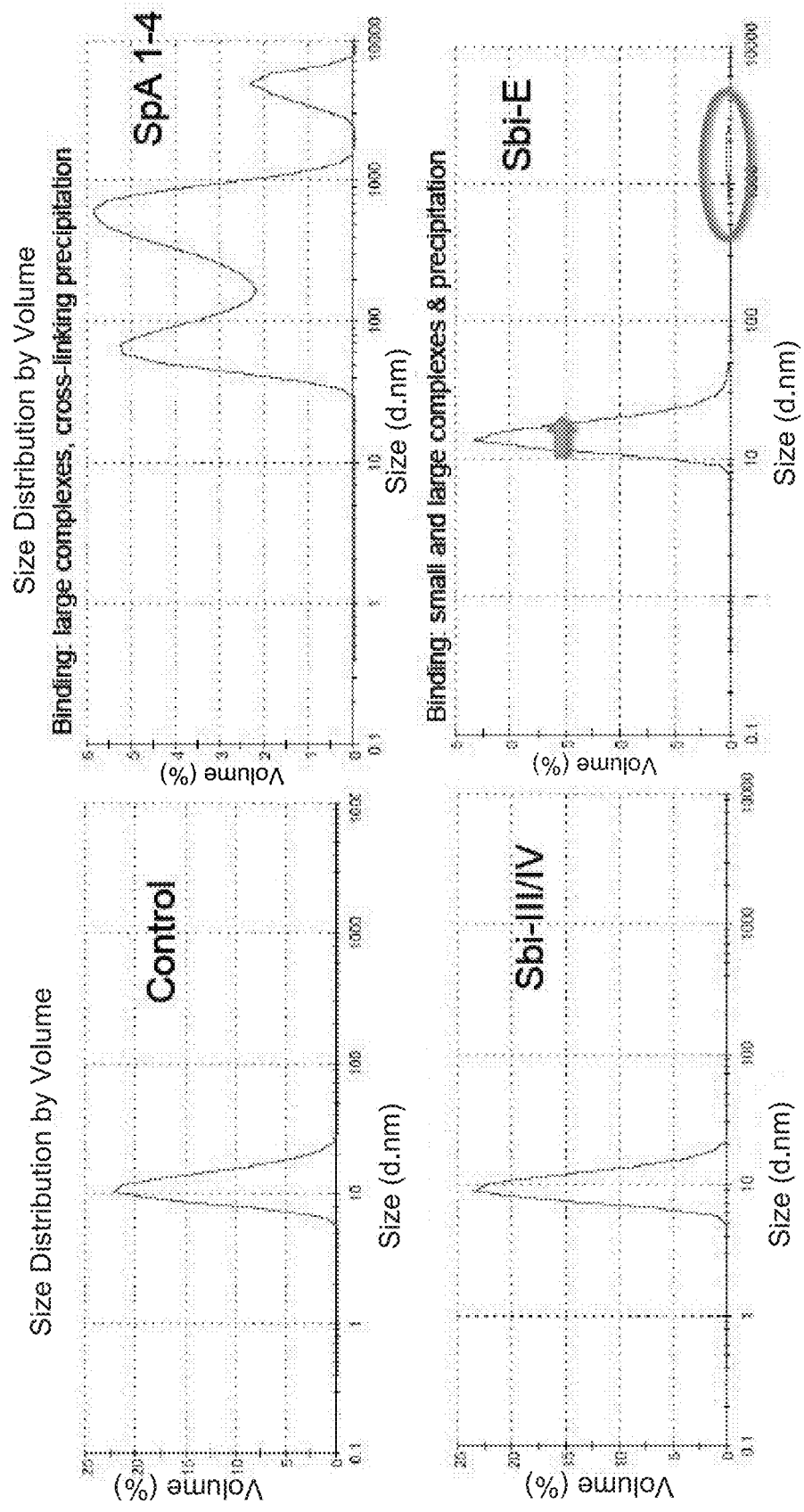
FIG. 23 shows an anti-SpA parental MAB1 analysis by DLS. The left panels shown the analysis of the parental anti-SpA antibody (MAB5) alone (upper panel) or with Sbi III/IV (fragment of Sbi containing the two complement binding domains (lower panel)). The right panels show the size distribution in the presence of either SpA 1-4 (SpA IgBP domains 1-4) or Sbi-E (fragment of Sbi containing the two Ig-binding domains and two complement binding domains).
Figure 24:
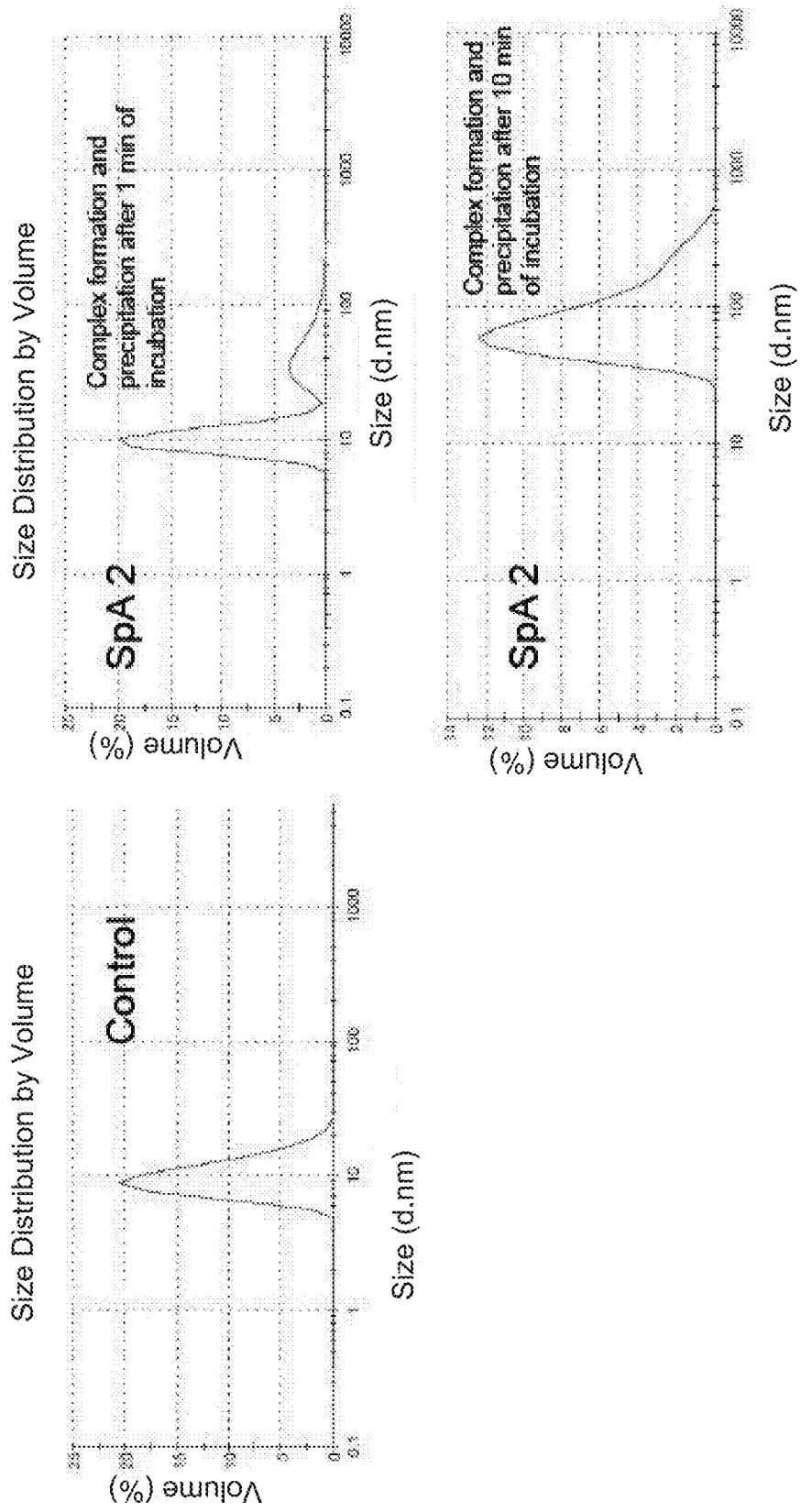
FIG. 24 illustrates a time dependent DLS peak shift with MAB1 and SpA-2. The left panel shown the analysis of the parental anti-SpA antibody alone (MAB1). The left panels show the size distribution in the presence of either SpA-2 (fragment of SpA containing domain D) after 1 min (upper panel) or 10 mins incubation (lower panel).
Figure 25:
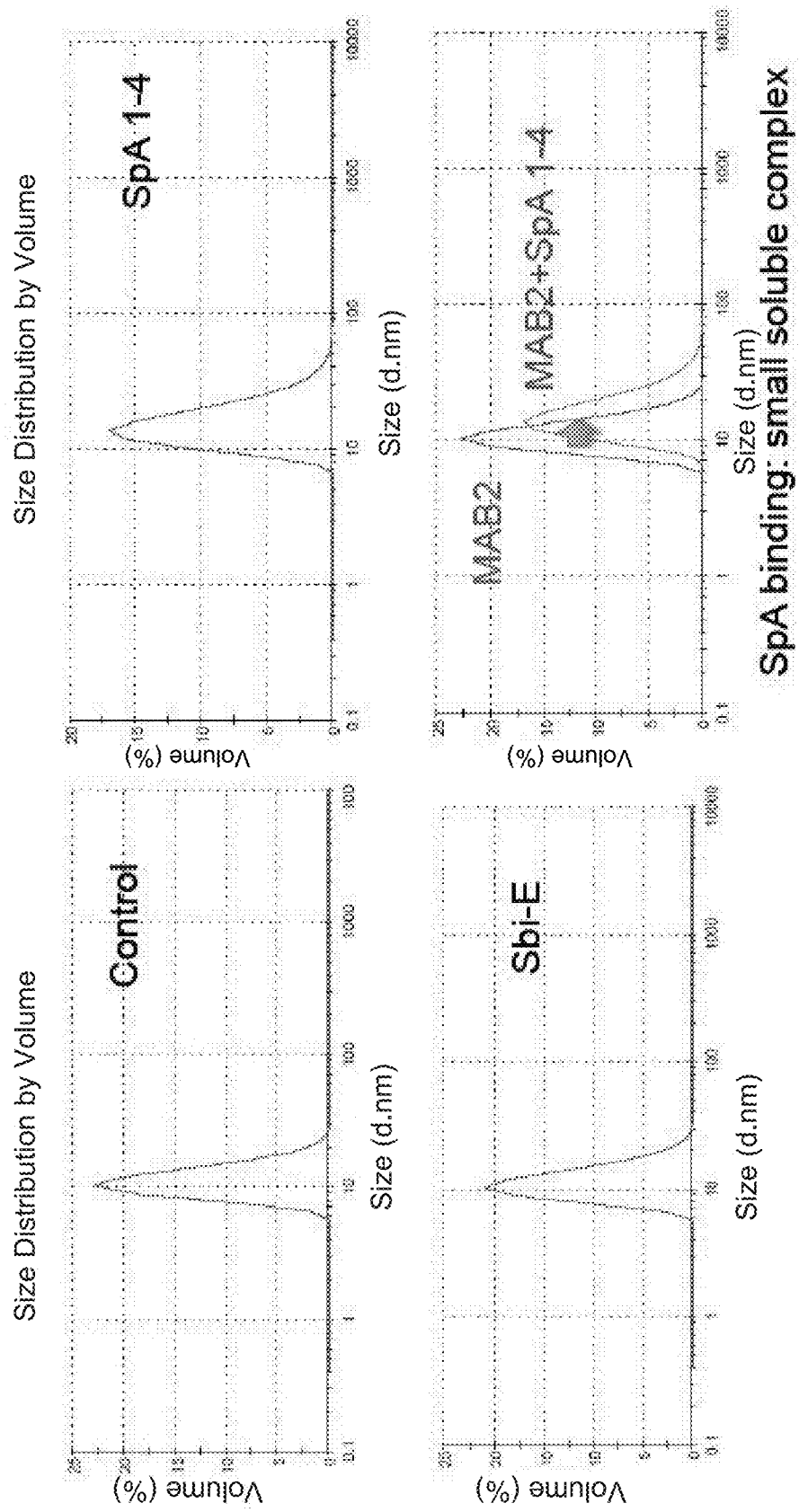
FIG. 25 shows an anti-SpA variant MAB2 analysis by DLS. The left panels shown the analysis of the variant anti-SpA antibody (MAB2) alone (upper panel) or with Sbi-E (fragment of Sbi containing the two Ig-binding domains and two complement binding domains (lower panel)). The right panels show the size distribution in the presence of SpA 1-4 (SpA IgBP domains 1-4). The lower left panel shows the overlap of the MAB2 control plot (red) and the MAB2 plot in the presence of SpA 1-4 (green).
Figure 26:
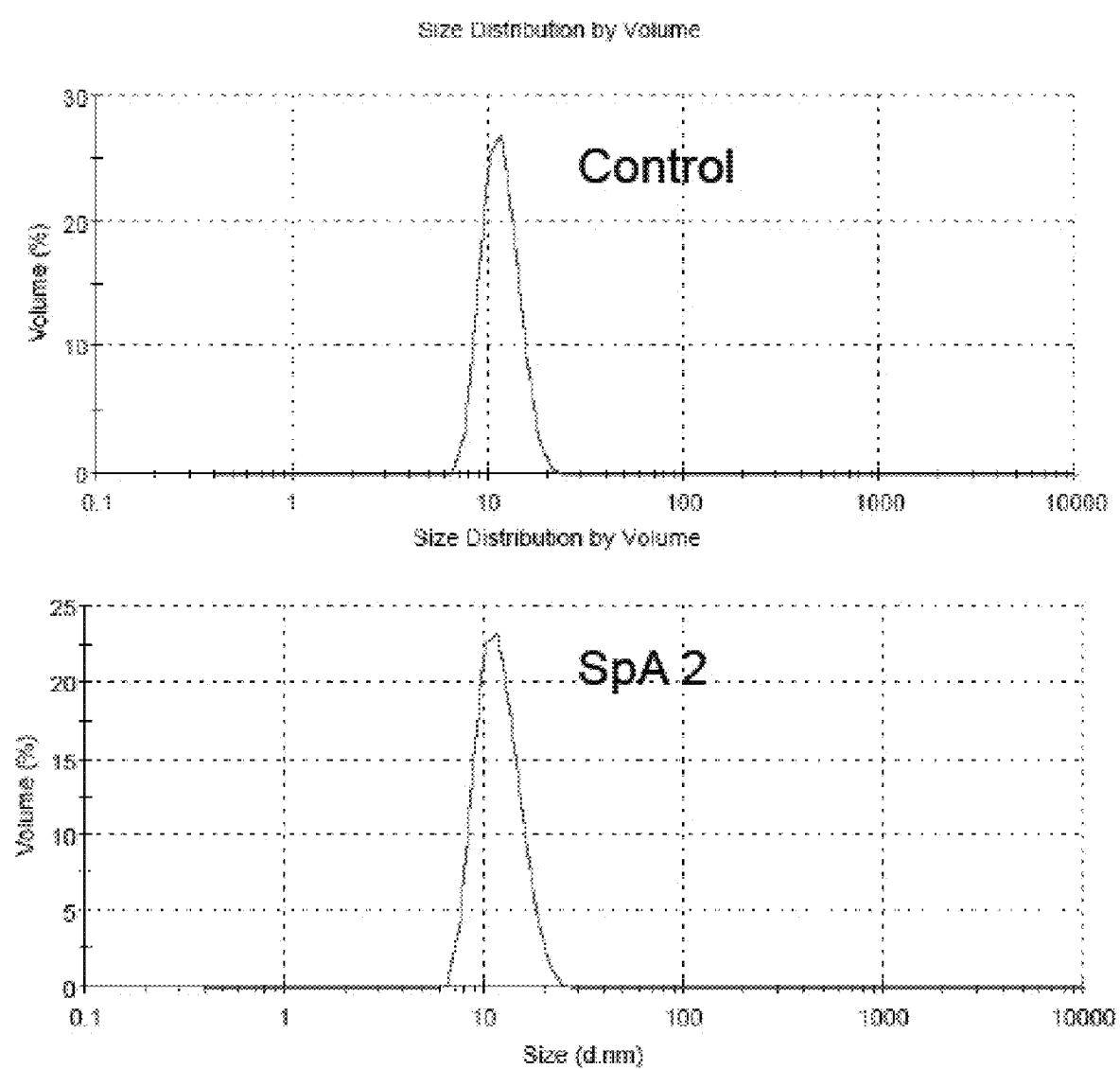
FIG. 26 shows an anti-SpA variant MAB2 analysis by DLS-Single SpA domain. The upper panels shown the analysis of the variant anti-SpA antibody (MAB2) alone or with SpA-2 (SpA domain D).—lower panel.

The amino acid sequence of the individual Sbi IgBP domains from sequenced stains of S. aureus were obtained from public sequence databases and analyzed for intra-domain strain sequence variability (FIG. 14). The aligned sequences are shown in FIG. 14 (panel A (Sbi domain I) and panel B (Sbi domain II)). In the stains analyzed, no substitutions were found in Sbi domain I (FIG. 14A). Only a single inter-strain change was found in domain II (FIG. 14B) located within Helix 1 (N to S substitution in strain CC239_JKD6009). This position is not conserved between domains I and II, and also differs between SpA domains E and the residue found in domains D, A, B and C. Mapping of the location of this residue onto the SpA model shows that this residue is not directly involved in interaction with the IgG Fc binding interface (FIG. 15).

Thus, the Fc binding interface of Sbi and SpA are conserved within and between S. aureus strains. The conserved Fc binding interfaces of Sbi and SpA domains are attractive targets for raising monoclonal antibodies. Such antibodies will neutralize one or more virulence functions of the SpA or Sbi domain to which they bind. Additionally, such antibodies will have anti S. aureus activity.

Example 2: Murine, Human or Humanized Antibodies Generation

Immunization or selection methods for the selection of cross-reactive antibodies (i.e. antibodies that recognize multiple SpA IgBP domains and/or Sbi domains) are provided.

In the case where antibodies are derived from wild type mice, such as female Swiss Webster Mice, the murine monoclonal antibodies selected may be humanized by CDR grafting using methods known in the art (Almagro and Fransson (2008)).

In an alternative method, human antibodies can be obtained directly using transgenic mice methods such as VelocImmune®. VelocImmune® is a mouse with a genetically humanized immune system, which can be used to greatly increase the speed and efficiency of in-vivo generation of fully-human therapeutic antibodies (Lonberg N (2005)).

In yet an alternative method, antibody domain fragments can be selected using Display technologies such as phage, yeast and ribosome display using methods known in the art. Following reformatting, such antibodies can be affinity matured, if required, to high affinity by methods known in the art (Hoogenboom H R (2005)).

Alternatively, human antibody variable domains can be selected from mammalian display libraries using methods known in the art. Such antibodies can be affinity matured to high affinity by methods known in the art (Bowers et al., 2011).

An alternative antibody discovery method exploits high-throughput DNA sequencing to analyze the VL and VH gene repertoires derived from the mRNA transcripts of fully differentiated mature B cells or antibody-secreting Bone Marrow Plasma Cells from SpA immunized mice as described by Reddy (Reddy et al, 2010). After a bioinformatics analysis, abundant VL and VH gene sequences are identified within the repertoire of each immunized mouse. VL and VH genes are then paired according to their relative frequencies within the repertoire. Antibody VH and VL genes are synthesized by oligonucleotide and PCR assembly. Recombinant antibodies can be expressed in bacterial and mammalian systems as single-chain variable fragments (scFv), or full-length chimeric variant IgG1 antibodies respectively. Antibodies of interest can then be humanized and affinity matured using methods know to those practicing the art (CDR grafting followed by affinity maturation).

In an alternative method, human antibodies can be isolated from patients or volunteers following recovery from a microbial infection or immunization with a vaccine against the target microbe (Wrammert et al., 2008)

Example 3: In Vivo Immunization and Selection of Anti-SpA and Anti-Sbi Antibodies Immunization Protocol:
Mice may be used in this procedure. The SpA antigen used as an antigen for immunization can be obtained from a number of commercial sources or by standard molecular biology methods known in the art. Alternatively, recombinant SpA (e.g. Thermo Fisher Scientific cat #21184) or individual Ig binding domains or combinations of SpA domains (selected from the list: SpA domain A, B, C, D or E), can be produced using standard recombinant technology. Immunization of wild type or transgenic animals (Lonberg N (2005), Almagro and Fransson (2008)) are effective method for generating antibodies to many antigens.

For antibody screening following immunization, subjects can be bled two weeks after each immunization booster and non-pooled samples can be checked for anti-SpA antibodies according to the protocol described below. Due to the interaction of murine and human isotypes with SpA via the Fc domain, murine IgG1 or human IgG3 are often used for screening to avoid interference from non-immune IgBP binding to the SpA antigen.

The ELISA format that can be used to screen for antibodies is as follows: In one example ELISA plates (e.g. Nunc MaxiSorp 96 well plates) are coated with goat anti murine IgG1 antibody and then blocked using the manufacturers recommended method. Following washing, dilutions of murine serum samples are added to wells and incubated. Following washing of the plates to remove unbound materials, peroxidase conjugated antigen, such as SpA or Sbi, is added to plates. In the case of anti-SpA murine antibodies, Mild Elution Buffer pH 6.0 (Thermo Scientific cat #21033) is used for plate washing. At this pH, binding of SpA to murine IgG1 via the Fc domain of the antibody minimal. Following washing at pH 6.0 with Mild Elution Buffer pH 6.0 (Thermo Scientific cat #21033) to remove unbound conjugate, anti-SpA murine IgG1 is detected using standard Peroxidase reagents and the absorbency signal is read.

Alternatively, engineered SpA antigens can be used which contains point mutations (Kim et al., 2010, 2102) which abolishes Fc binding to domains A, B, C, D and E of SpA (SpA KK containing the following substitutions in each SpA domain: Q9K and Q10K or SpA KKAA containing the following substitutions in each SpA domain: Q9K, Q10K, D36A and D37A (Kim et al., 2010)). To determine SpA specific serum IgG, affinity purified SpA KK or SpA KKAA can be used to coat ELISA plates (NUNC Maxisorp) at 1 µg·ml-1 in 0.1 M carbonate buffer (pH 9.5 at 4° C.) overnight. The following day, plates are blocked and incubated with dilutions of hyperimmune sera and developed using OptEIA reagent (BD Biosciences).

Fusion Protocol.

The mouse selected for fusion is boosted with the same dose of antigen used in previous immunizations. The booster regime may be administered over the four-day period prior to splenectomy and cell fusion. Alternatively, the animal can be boosted with recombinant protein consisting of individual IgBP SpA domains from the same of a different *S. aureus* strain, or combinations of domains selected from the list: SpA domain A, B, C, D or E.

In another strategy designed to identify antibodies that cross-react with multiple SpA domains, the primary immunization uses one isolated SpA domain, and the booster includes a different domain or domains than used for the primary immunization. The booster regime may be administered over the four-day period prior to splenectomy and cell fusion.

In another strategy designed to identify antibodies that cross react with SpA and Sbi, the booster can be recombinant IgBP Sbi domain I, II or I and II. Such a strategy is designed to select for antibodies that recognize a conserved interaction interface between both SpA and Sbi and Fcγ.

In yet another immunization strategy, Domain I and II of Sbi can be used for the primary immunization, and SpA, or its individual Ig binding domains selected from the list domain A, B, C, D or E, can be used as a booster. Such a strategy will select for antibodies that cross reacting with epitopes that are found on the FcBP domains of Sbi domain I or II and one or more Spa domains selected from the list: domain A,B,C,D and E. Such a strategy is designed to select for antibodies that recognize a conserved interaction interface between both SpA and Sbi and Fcγ.

On the day of fusion the selected mouse is sacrificed and the spleen is removed aseptically. The spleen may be minced using forceps and strained through a sieve. The cells may be washed twice using IMDM medium (Iscove's Modified DMEM with L-glutamine and 25 mM HEPES, Cellgro catalog number 10-016-CM; Mediatech, Inc., Herndon, Va.) and counted using a hemocytometer. The mouse myeloma cell line should be removed from static log-phase culture. The cell are washed with IMDM twice and counted using a hemocytometer.

Myeloma and spleen cells should then be mixed in a 1:5 ratio and centrifuged. The supernatant is discarded. The cell pellet is then gently resuspended by tapping the bottom of the tube. One milliliter of a 50% solution of PEG (MW 1500) is added (drop by drop) over a period of 30 seconds. The pellet is mixed gently for 30 seconds using a pipette. The resulting cell suspension is allowed to stand undisturbed for another 30 seconds. One milliliter (mL) of IMDM is then added over a period of one minute, followed by the drop wise addition of two mL of IMDM over a period of two minutes. Another five mL of IMDM is added immediately the two-minute period. The resulting cell suspension may be left undisturbed for 5 minutes.

The cell suspension may be centrifuged at room temperature for 10 minutes at 1200 rpm. The pellet is then resuspended in HAT medium (IMDM containing 10% FBS, 2 mM L-glutamine, 0.6% 2-mercaptoethanol (0.04% solution), hypoxanthine, aminopterin, thymidine, and 10% Origen growth factor). The cells are resuspended to $1 \times 10^6$ cells per milliliter. Cell suspensions are plated into 96-well plates. Two hundred microliters (or approximately $2 \times 10^5$ cells) are added to each well. The 96-well plates are incubated at 37° C. in a 7% $CO_2$ atmosphere with 100% humidity.

Seven days after the fusion, the media should be removed and replaced with IMDM containing 10% FBS, 2 mM L-glutamine, 0.6% 2-mercaptoethanol stock (0.04%), hypoxanthine and thymidine.

Hybridoma Expansion Protocol.

Fourteen days after fusion, the supernatant may be taken from wells with growing hybridoma colonies. The volume of supernatant in each well may be approximately 150-200 microliters. This supernatant may be tested for IgG1 isotype producing hybridomas with specificity for SpA using ELISA as described herein.

Positive hybridoma colonies may be transferred from the 96-well plate to a 24-well plate and 1.8 mL of IMDM containing 20% FBS, 10% Origen Cloning Factor, 2 mM L-glutamine and 0.6% 2-mercaptoethanol stock (0.04%) is added to each well. The 24-well plates are incubated as described for the 96-well plates above. Five days later, the supernatant from 24-well plate should be tested to confirm the presence of specific antibody.

Cells from positive wells may be expanded in T-25 and T-75 flasks (Corning Flasks, Corning, N.Y.). Five vials (1 mL each) of the cells from T-75 flasks are frozen in liquid nitrogen. Cells from positive wells can be cloned by limiting dilution, i.e., hybridoma cells are plated onto 96-well plates at a density of 0.25 cells per well. Growing colonies may be tested 10-14 days later using the same assay that was used to initially select the hybridomas. The subcloned cells are expanded to 24-well plates and, subsequently, T-25, T-75 and T-162 flasks. Vials of subclone cells are frozen as described above.

Sequencing of monoclonal antibodies: Total RNA samples from hybridoma cells were isolated using a standardized protocol. Briefly, 1.4×10$^7$ hybridoma cells cultured in DMEM-10 medium with 10% fetal bovine serum (FBS) were washed with PBS, sedimented by centrifugation, and lysed in TRIzol (Invitrogen). Samples were mixed with 20% chloroform and incubated at room temperature for 3 min and centrifuged at 10,000×g for 15 min at 4° C. RNAs in the aqueous layer were removed and washed with 70% isopropanol. RNA was sedimented by centrifugation and washed with 75% diethylpyrocarbonate (DEPC)-ethanol. Pellets were dried and RNA dissolved in DEPC. cDNA was synthesized with the cDNA synthesis kit (Novagen) and PCR amplified using the PCR reagent system (Stratagene), independent primers (5 pmol each), and a mouse variable heavy and light chain-specific primer set (Novagen). PCR products were sequenced and analyzed using IMGT/V-QUEST (http://www.imgt.org/IMGT_vquest/share/textes/).

Example 4: Generation of Chimeric and Humanized Anti-Microbial IgG1 Antibodies

Anti SpA antibodies: In one example, a chimeric parental version of the murine SPA27 antibody was constructed using the murine variable domain sequences as published in patent application WO 208/140487 A2. The murine variable heavy chain (VH chimeric (SEQ ID NO: 1)) was combined with a human IgG1 heavy chain constant sequence of allotype G1m17 (SEQ ID 30). IgG1 allotype G1m17,1,2 has been used as the reference. The allotypic amino acid positions that include a residue substitution relative to the reference sequence are shown Bold underlined in SEQ ID 30. The heavy chain amino acid sequence of the resulting chimeric antibody is shown in HC 1 (SEQ ID NO: 19). Likewise, the murine variable light chain sequence (VL chimeric (SEQ ID NO: 6)) was combined with a Kappa light chain constant region of allotype Km3, resulting in a chimeric light chain amino acid sequence as shown in LC 1 (SEQ ID NO:21). Heavy chain constant region variant antibodies were constructed as described above for parental antibodies. Following codon optimization for mammalian expression, DNA encoding a Kozak sequence, an N-terminal leader secretion sequence and the target polypeptides was synthesized, cloned into a mammalian expression vector pTT5, and expressed in HEK 293 cells using methods well known in the art (described later).

CDR Grafting and Humanization of Chimeric Antibodies:

CDR grafting can be used to humanize murine antibodies using standard molecular biology techniques known in the art. In one example CDR grafting was used to humanize anti-SpA murine antibody sequences using standard molecular biology techniques known in the art. Such grafted antibodies sequences (humanized) will generally require additional affinity maturation to arrive at a therapeutic humanized antibody of sufficient affinity. Standard methodology known to those practicing the art can be used for both CRD grafting and affinity maturation. One example is the mouse HC and LC CDR sequences from DNA encoding the anti-SpA monoclonal antibody SPA27.

CDRs were grafted into a human IgG1 heavy chain and a Kappa light antibody backbone sequences. The selection of the variable domain human germ line sequence used for grafting is determined by the closest homology to the mouse hybridoma variable domain sequence. In some cases, different VH germ line sequences can be used for each FW region. In the case of SPA-27, the closest heavy chain matches are VH3-49 and VH3-72. Variable heavy chain sequences were combined with constant heavy chain sequences from human IgG1 or its variants. Heavy chain constant region variants which do not bind SpA are used for screening chimeric, CDR grafted and affinity mutated antibodies so as to avoid SpA-Fc binding in ELISA assays, and to allow binding measurements using ELISA, BIACore or DLS (Dynamic Light Scattering).

Design and Construction of Humanized Antibodies Using the Murine SPA27 Anti-SpA Antibody Variable Region Sequence:

Using the anti-SPA27 murine monoclonal antibody as a reference, anti-SPA antibodies were designed using CDR grafting technology. The grafted CDR regions of the variable domains were then combined with light and heavy chain variant human IgG1 constant regions sequences.

The sequences of the heavy and light chain variable regions of SPA-27 were compared to human germline databases and homologous sequences were identified. CDR grafted human Antibody sequences (SEQ ID #1-16) were initially designed. CDR grafted antibodies comprise target variable regions derived from either VH3-49, VH3-72 or VH3-70 human germ line antibody sequences. In an alternative approach, CDR grafted antibodies can comprise a mixture of sequences derived from VH3-49, VH3-72 or VH3-70. A summary of the CDR grafted Human Antibodies derived from SPA-27 are given below.

Heavy Chain Variable Domain.

A Summary of the CDR grafted antibodies sequences are given below. The sequence for each variable heavy chain region is given:

```
VH chimeric (SEQ ID NO: 1)
EVKLVESGGGLVQPGGSRRLSCTTSGFTFTESFMTWVRQPPGKALDWLAFI

RNKANGYTTEYSASVKGRFTIARDNSQSILYLQMNALRAEDSATYYCVRGG

EYPLYVMDYWGKGTSVTVSS

VH1 (SEQ ID NO: 2):
EVQLVESGGGLVQPGRSLRLSCTASGFTFTESFMSWFRQAPGKGLEWVGFI

RNKANGYTTEYAASVKGRFTISRDDSKSIAYLQMNSLKTEDTAVYYCVRGG

EYPLYVMDYWGQGTLVTVSS

VH2 (SEQ ID NO: 3):
EVQLVESGGGLVQPGRSLRLSCTASGFTFTESFMSWIRQPPGKALEWLAFI

RNKANGYTTEYAASVKGRFTISRDDSKSIAYLQMNSLKTEDTAVYYCVRGG

EYPLYVMDYWGQGTLVTVSS

VH3 (SEQ ID NO: 4):
EVQLVESGGGLVQPGGSLRLSCAASGFTFTESFMDWVRQAPGKGLEWVGRI

RNKANGYTTEYAASVKGRFTISRDDSKNSLYLQMNSLKTEDTAVYYCVRGG

EYPLYVMDYWGQGTLVTVSS

VH4 (SEQ ID NO: 5):
EVQLVESGGGLVQPGGSLRLSCAASGFTFTESFMDWIRQPPGKALEWLAFI

RNKANGYTTEYAASVKGRFTISRDDSKNSLYLQMNSLKTEDTAVYYCVRGG

EYPLYVMDYWGQGTLVTVSS
```

Light Chains.

A Summary of the CDR grafted antibodies is given below. The sequence for each variable light chain region is given:

VL chimeric (SEQ ID NO: 6):
DIVLTQSPVSLAVSLGQRATISCRASESVEYYDTSLMQWYQQKPGQPPKLL

IYAASNVESGVPARFSGSGSGTDFSLNIHPVEEDDFATYFCQQSRKVPWTF

GGGTKLEIK

VL1 (SEQ ID NO: 7):
DIVMTQSPDSLAVSLGERATINCKSSESVEYYDTSLLAWYQQKPGQPPKLL

IYAASNVESGVPDRFSGSGSGTDFTLTISSLQAEDVAVYYCQQSRKVPWTF

GQGTKLEIK

VL2 (SEQ ID NO: 8):
DIVMTQSPDSLAVSLGERATINCKSSESVEYYDTSLLAWYQQKPGQPPKLL

IYAASNVESGVPARFSGSGSGTDFTLTISSLQEEDVAVYYCQQSRKVPWTF

GQGTKLEIK

VL3 (SEQ ID NO: 9):
DIVMTQSPDSLAVSLGERATINCKSSESVEYYDTSLLAWYQQKPGQPPKLL

IYAASNVESGVPSRFSGSGSGTDFTLTISSLQPEDVAVYYCQQSRKVPWTF

GQGTKLEIK

VL4 (SEQ ID NO: 10):
DIVMTQSPDSLAVSLGERATINCKSSESVEYYDTSLLAWYQQKPGQPPKLL

IYAASNVESGVPARFSGSGSGTDFTLTISSLQPEDVAVYYCQQSRKVPWTF

GQGTKLEIK

VL5 (SEQ ID NO: 11):
DIVMTQSPDSLAVSLGERATINCRASESVEYYDTSLMQWYQQKPGQPPKLL

IYAASNVESGVPDRFSGSGSGTDFTLTISSLQAEDVAVYYCQQSRKVPWTF

GQGTKLEIK

VL6 (SEQ ID NO: 12):
DIVMTQSPDSLAVSLGERATINCRASESVEYYDTSLMQWYQQKPGQPPKLL

IYAASNVESGVPARFSGSGSGTDFTLTISSLQEEDVAVYYCQQSRKVPWTF

GQGTKLEIK

VL7 (SEQ ID NO: 13):
DIVMTQSPDSLAVSLGERATINCRASESVEYYDTSLMQWYQQKPGQPPKLL

IYAASNVESGVPSRFSGSGSGTDFTLTISSLQEEDVAVYYCQQSRKVPWTF

GQGTKLEIK

VL8 (SEQ ID NO: 14):
DIVMTQSPDSLAVSLGERATINCRASESVEYYDTSLMQWYQQKPGQPPKLL

IYAASNVESGVPARFSGSGSGTDFTLTISSLQPEDVAVYYCQQSRKVPWTF

GQGTKLEIK

VL9 (SEQ ID NO: 15):
DIVMTQSPDSLAVSLGERATINCRASESVEYYDTSLMQWYQQKPGQPPKLL

IYAASNVESGVPDRFSGSGSGTDFTLTISSLQEEDFATYFCQQSRKVPWTF

GQGTKLEIK

VL10 (SEQ ID NO: 16):
DIVMTQSPDSLAVSLGERATINCRASESVEYYDTSLMQWYQQKPGQPPKLL

IYAASNVESGVPARFSGSGSGTDFTLTISSLQEEDFATYFCQQSRKVPWTF

GQGTKLEIK

VL11 (SEQ ID NO: 17):
DIVMTQSPDSLAVSLGERATINCRASESVEYYDTSLMQWYQQKPGQPPKLL

IYAASNVESGVPSRFSGSGSGTDFTLTISSLQEEDFATYFCQQSRKVPWTF

GQGTKLEIK

VL12 (SEQ ID NO: 18):
DIVMTQSPDSLAVSLGERATINCRASESVEYYDTSLMQWYQQKPGQPPKLL

IYAASNVESGVPARFSGSGSGTDFTLTISSLQPEDFATYFCQQSRKVPWTF

GQGTKLEIK

The humanized variable heavy chain sequences (SEQ ID NO:2-5)) were combined with a human IgG1 heavy chain constant sequence of allotype G1m17 (SEQ ID NO:30) to generate a humanized heavy chain sequence. Likewise, the humanized light chain sequences (SEQ ID NO:7-18) were combined with a Kappa light chain constant region of allotype Km3, resulting in humanized light chain amino acid sequences. Heavy chain constant region variant antibodies were designed and constructed as described above for parental antibodies. Following codon optimization for mammalian expression, DNA encoding a Kozak sequence, an N-terminal leader secretion sequence and the target polypeptides was synthesized, cloned into a mammalian expression vector pTT5, and expressed in HEK 293 cells using methods well known in the art (described later).

Anti SpA Example Antibodies:

An anti SpA chimeric parental antibody was constructed as follows. The murine variable heavy chain (VH chimeric (SEQ ID NO:1)) was combined with a human IgG1 heavy chain constant sequence of allotype G1m17 (SEQ ID NO:30). The heavy chain amino acid sequence of the resulting chimeric antibody is shown in HC 1 (SEQ ID NO:19). Likewise, the murine variable light chain sequence (VL chimeric (SEQ ID NO:6)) was combined with a Kappa light chain constant region of allotype Km3, resulting in a chimeric light chain amino acid sequence as shown in LC 1 (SEQ ID NO:21). Heavy chain constant region variant antibodies were constructed as described above for parental antibodies. In one example a heavy chain constant region variant (SEQ ID NO:40) constructed. Antibody and their variants were expressed as essentially as follows: Following codon optimization for mammalian expression, DNA encoding a Kozak sequence, an N-terminal leader secretion sequence and the target polypeptides was synthesized, cloned into a mammalian expression vector pTT5, and expressed in HEK 293 cells using methods well known in the art (described later).

Anti-ClfA Antibodies:

A humanized version of the anti-ClfA antibody T1-2 (Domanski et al., 2005) was constructed using the variable domain sequences as published in patent application U.S. 69/794,4662. A parental control antibody sequence was generated as follows: The variable heavy chain from antibody T1-2 (SEQ ID NO:28) was combined with a human IgG1 heavy chain constant sequence of allotype G1m17 (SEQ ID NO:30). The heavy chain amino acid sequence of the resulting antibody is shown in HC 5 (SEQ ID NO: 25. Likewise, the variable light chain sequence (VL chimeric (SEQ ID NO: 29)) was combined with the a Kappa light chain constant region of allotype Km3, resulting in a chimeric light chain amino acid sequence as shown in LC 2 (SEQ ID NO:24). Heavy chain constant region variant antibodies were designed and constructed as described above for parental antibodies. In one example a heavy chain constant region variant (SEQ ID NO:40) constructed. Antibody and their variants were expressed as essentially as follows: Following codon optimization for mammalian expression, DNA encoding a Kozak sequence, an N-terminal leader secretion sequence and the target polypeptides was synthesized, cloned into a mammalian expression vector pTT5, and expressed in HEK 293 cells using methods well known in the art (described later).

Anti-RSV Control Antibodies:

A parental humanized anti-RSV antibody derived from Palivizumab (Synagis, Medimmune Inc) has been used as a heavy chain constant region control antibody (parental polypeptide sequence is shown in SEQ 22). The anti-RSV parental antibody and its heavy chain constant region variants allow the effects of variants to be studies in the absence of target microbe binding by the antigen binding variable domain. The parental humanized anti-RSV heavy chain variable domain was combined with a human IgG1 heavy chain constant region of allotype G1m17 resulting in an amino acid sequence HC3 (SEQ ID NO:22). Likewise, the anti-RSV variable light chain was combined with a Kappa light chain constant region of allotype Km3, resulting in a chimeric light chain amino acid sequence of LC 2 (SEQ ID NO:24). Heavy chain constant region variant antibodies were designed and constructed as described above for parental antibodies. In one example a heavy chain constant region variant (SEQ ID NO:40) constructed. Antibody and their variants were expressed as essentially as follows: Following codon optimization for mammalian expression, DNA encoding a Kozak sequence, an N-terminal leader secretion sequence and the target polypeptides was synthesized, cloned into a mammalian expression vector pTT5, and expressed in HEK 293 cells using methods well known in the art (described later).

Generation of Heavy Chain Constant Region Antibodies and their Variants

Example 5: Anti-Microbial Heavy Chain Constant Region Variants

Parental and heavy chain constant region variant anti-SpA, anti-Clfa and anti-RSV antibodies were constructed as described above for parental antibodies. In such variant antibodies, the heavy chain constant region of the variant antibody, contains a heavy chain constant regions including an amino acid sequences selected from the group SEQ ID NO:30-56 (Heavy chain constant region 1-27).

In one example a parental chimeric anti-SpA antibody and an example heavy chain constant region variant (SEQ ID NO: 40) antibody were expressed, purified and characterized: Shown are the amino acid sequence of an anti-SpA parental heavy chain (SEQ ID NO: 19), a variant heavy chain (SEQ ID NO: 20) and a common light chain (SEQ ID NO: 21). Amino acid differences between the parental antibody of allotype G1m17 and an example variant heavy chain content chain amino acid sequence are shown in Bold underlined:

HC 1
Anti SpA Chimeric HC G1M17
(SEQ ID NO: 19)
EVKLVESGGGLVQPGGSRRLSCTTSGFTFTESFMTWVRQPPGKALDWLAFI

RNKANGYTTEYSASVKGRFTIARDNSQSILYLQMNALRAEDSATYYCVRGG

EYPLYVMDYWGKGTSVTVSSASTKGPSVFPLAPSSKSTSGGTAALGCLVKD

YFPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK

HC 2
Anti SpA Chimeric variant HC G1M17
(SEQ ID NO: 20)
EVKLVESGGGLVQPGGSRRLSCTTSGFTFTESFMTWVRQPPGKALDWLAFI

RNKANGYTTEYSASVKGRFTIARDNSQSILYLQMNALRAEDSATYYCVRGG

EYPLYVMDYWGKGTSVTVSSASTKGPSVFPLAPSSKSTSGGTAALGCLVKD

YFPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKDT

LMISRTPEVTCVVVDVSHEDPEVQFNWYVDGVEVHNAKTKPREEQYNSTYR

VVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGS

FFLYSKLTVDKSRWQQGNVFSCSVMHEALHNRFTQKSLSLSPGK

LC 1
Anti SpA Chimeric LC
(SEQ ID NO: 21)
KM3DIVLTQSPVSLAVSLGQRATISCRASESVEYYDTSLMQWYQQKPGQPP

KLLIYAASNVESGVPARFSGSGSGTDFSLNIHPVEEDDFATYFCQQSRKVP

WTFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEVT

HQGLSSPVTKSFNRGEC

As control antibodies, a humanized RSV variable domain has been used, derived from Palivizumab (Synagis, Medimmune Inc). This anti-RSV variable domain allows the effects of heavy chain constant region variants to be studies in the absence of S. aureus antigen binding by the variable domain. In one example a parental anti-RSV antibodies and an example heavy chain constant region variant (SEQ ID NO:40) were characterized: Shown are the amino acid sequence of an anti-RSV parental heavy chain (SEQ ID NO:22), an example variant heavy chain (SEQ ID NO:23) and a common light chain (SEQ ID NO:24). Amino acid differences between the parental antibody of allotype G1m17 and an example variant heavy chain content chain amino acid sequence are shown in bold underlined:

HC3
Anti RSV HC parental IgG1 of allotype G1m17
(SEQ ID NO: 22)
QVTLRESGPALVKPTQTLTLTCTFSGFSLSTAGMSVGWIRQPPGKALEWLA

DIWWDDKKHYNPSLKDRLTISKDTSKNQVVLKVTNMDPADTATYYCARDMI

FNFYFDVWGQGTTVTVSSASTKGPSVFPLAPSSKSTSGGTAALGCLVKDYF

PEPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTLM

```
ISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFF

LYSKLTVDKSRWQQGNVFSCSVMHEALHNHYTQKSLSLSPGK

HC4
Anti RSV variant HC of allotype G1m17
                                          (SEQ ID NO: 23)
QVTLRESGPALVKPTQTLTLTCTFSGFSLSTAGMSVGWIRQPPGKALEWLA

DIWWDDKKHYNPSLKDRLTISKDTSKNQVVLKVTNMDPADTATYYCARDMI

FNFYFDVWGQGTTVTVSSASTKGPSVFPLAPSSKSTSGGTAALGCLVKDYF

PEPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTLM

ISRTPEVTCVVVDVSHEDPEVQFNWYVDGVEVHNAKTKPREEQYNSTYRVV

SVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFF

LYSKLTVDKSRWQQGNVFSCSVMHEALHNRFTQKSLSLSPGK

LC 2
Anti RSV LC
                                          (SEQ ID NO: 24)
DIQMTQSPSTLSASVGDRVTITCSASSRVGYMHWYQQKPGKAPKLLIYDTS

KLASGVPSRFSGSGSGTEFTLTISSLQPDDFATYYCFQGSGYPFTFGGGTK

LEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPV

TKSFNRGEC
```

In an additional example a humanized anti-ClfA antibody and an example heavy chain constant region variant (SEQ ID NO: 40) were characterized. Shown are the amino acid sequence of an anti-ClfA parental heavy chain (SEQ ID NO: 25) an example variant heavy chain (SEQ ID NO:26) and a common light chain (SEQ ID NO:27). Also shown are the variable heavy and Light chain sequences used in parental and variant antibodies (SEQ ID NO:28 and SEQ ID NO:29). Amino acid differences between the parental antibody of allotype G1m17 and an example variant heavy chain content chain amino acid sequence are shown in Bold underlined:

```
HC 5
Humanized anti-ClfA HC in G1m17 heavy chain
background
                                          (SEQ ID NO: 25)
QVQLKESGPGLVKPSQTLSITCTISGFSLSRYSVHWVRQPPGKGLEWLGMI

WGGGNTDYNSALKSRLSISKDNSKNQVFLKMNSLTAADTAVYYCARKGEFY

YGYDGFVYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLPP

SREEMTKNQVSLTCLVKGFYPSDIAVEWESNGQPENNYKTTPPVLDSDGSF

FLYSKLTVDKSRWQQGNVFSCSVMHEALHNHYTQKSLSLSPGK

HC 6
Humanized anti-ClfA HC in variant G1M17 heavy chain
background
                                          (SEQ ID NO: 26)
QVQLKESGPGLVKPSQTLSITCTISGFSLSRYSVHWVRQPPGKGLEWLGMI

WGGGNTDYNSALKSRLSISKDNSKNQVFLKMNSLTAADTAVYYCARKGEFY

YGYDGFVYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDTL

MISRTPEVTCVVVDVSHEDPEVQFNWYVDGVEVHNAKTKPREEQYNSTYRV

VSVLTVLHQDWLNGKEYKCKVSNKALPAPIEKTISKAKGQPREPQVYTLPP

SREEMTKNQVSLTCLVKGFYPSDIAVEWESNGQPENNYKTTPPVLDSDGSF

FLYSKLTVDKSRWQQGNVFSCSVMHEALHNRFTQKSLSLSPGK

LC 3
Humanized ClfA LC KM3
                                          (SEQ ID NO: 27)
DIVMTQSPDSLAVSLGERVTMNCKSSQSVLYSSNQKNYLAWYQQKPGQSPK

LLIYWASTRESGVPDRFSGSGSGTDFTLTISSVQAEDLAVYYCHQYLSSYT

FGGGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC
```

Heavy Chain and light chain variable domain sequenced of the example humanized anti-ClfA antibody.

```
ClfA Humanized 12-9 VH sequence
VH 5 (SEQ ID NO: 28):
QVQLKESGPGLVKPSQTLSITCTISGFSLSRYSVHWVRQPPGKGLEWLGMI

WGGGNTDYNSALKSRLSISKDNSKNQVFLKMNSLTAADTAVYYCARKGEFY

YGYDGFVYWGQGTLVTVSS

ClfA Humanized 12-9 VL sequence
VL 13 (SEQ ID NO: 29):
DIVMTQSPDSLAVSLGERVTMNCKSSQSVLYSSNQKNYLAWYQQKPGQSPK

LLIYWASTRESGVPDRFSGSGSGTDFTLTISSVQAEDLAVYYCHQYLSSYT

FGGGTKLEIK
```

Example Variant IgG1 Constant Region Sequences:

Modeling was used to investigate Immunoglobulin heavy chain constant region interactions with a number of microbial IgBPs including SpA, Sbi, SSL10 and Protein G. Amino acids were selected from modeling studies for substitution in variant heavy chain constant region.

In claimed embodiments, the heavy chain constant region variant antibody is of IgG immunoglobulin, in which at least one amino acid from the heavy chain constant region selected from the group consisting of amino acid residues 214, 251, 252, 253, 254, 274, 276, 311, 314, 356, 358, 380, 382, 384, 419, 422, 428, 431, 432, 433, 434, 435, 436 and 438 (EU numbering) is substituted with an amino acid residue different from that present in the unmodified IgG1 antibody.

The amino acid sequence of example variant IgG1 heavy chains that attenuate the binding to one or more microbial IgBPs are shown below in sequences SEQ ID NO: 30-56). The Heavy chain constant region is shown using the one letter amino acid code (EU numbering 118-447). X denotes variable heavy chain residues. In different immunoglobulins described herein, the number of variable domain residues in the heavy chain variable region may vary, where the number of X residues can be greater or less than shown in HC1-HC-27. With respect to Variant Heavy Chain Fc Region Sequences, the amino acid positions that include a residue substitution relative to the reference sequence of allotype G1m17,1,2 are underlined. E356, M358 and A431 represent allotypic substitutions relative to the allotype G1m17,1,2 reference sequence (D365,L358,G431).

```
Heavy chain constant region 1
                                     (SEQ ID NO: 30)
XXXXXXXXXXXXXXXXXXXXXXXXXXXXXXXXXXXXXXXXXXXX
XXXXXXXXXXXXXXXXXXXXXXXXXXXXXXXXXXXXXXXXXXXX
XXXXXXXXXXXXXXXXXXXXXXASTKGPSVFPLAPSSKSTSGGTAALGC
LVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEAL
HNHYTQKSLSLSPGK Heavy chain constant region 2
                                     (SEQ ID NO: 31)
XXXXXXXXXXXXXXXXXXXXXXXXXXXXXXXXXXXXXXXXXXXX
XXXXXXXXXXXXXXXXXXXXXXXXXXXXXXXXXXXXXXXXXXXX
XXXXXXXXXXXXXXXXXXXXXXASTKGPSVFPLAPSSKSTSGGTAALGC
LVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEAL
HNRYTQKSLSLSPGK Heavy chain constant region 3
                                     (SEQ ID NO: 32)
XXXXXXXXXXXXXXXXXXXXXXXXXXXXXXXXXXXXXXXXXXXX
XXXXXXXXXXXXXXXXXXXXXXXXXXXXXXXXXXXXXXXXXXXX
XXXXXXXXXXXXXXXXXXXXXXASTKGPSVFPLAPSSKSTSGGTAALGC
LVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSV
FLFPPKPKDTLMISRTPEVTCVVVDVSHEDPEVQFNWYVDGVEVHNAK
TKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEAL
HNRYTQKSLSLSPGK Heavy chain constant region 4
                                     (SEQ ID NO: 33)
XXXXXXXXXXXXXXXXXXXXXXXXXXXXXXXXXXXXXXXXXXXX
XXXXXXXXXXXXXXXXXXXXXXXXXXXXXXXXXXXXXXXXXXXX
XXXXXXXXXXXXXXXXXXXXXXASTKGPSVFPLAPSSKSTSGGTAALGC
LVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESN
GQPENNYKTTPPVLDSDGSFFLYSKLTVDKSRWQQGNIFSCSVMHEAL
HNRYTQKSLSLSPGK Heavy chain constant region 5:
                                     (SEQ ID NO: 34)
XXXXXXXXXXXXXXXXXXXXXXXXXXXXXXXXXXXXXXXXXXXX
XXXXXXXXXXXXXXXXXXXXXXXXXXXXXXXXXXXXXXXXXXXX
XXXXXXXXXXXXXXXXXXXXXXASTKGPSVFPLAPSSKSTSGGTAALGC
LVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSV
FLFPPKPKDTLMISRTPEVTCVVVDVSHEDPEVQFNWYVDGVEVHNAK
TKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESN
GQPENNYKTTPPVLDSDGSFFLYSKLTVDKSRWQQGNIFSCSVMHEAL
HNRYTQKSLSLSPGK Heavy chain constant region 6:
                                     (SEQ ID NO: 35)
XXXXXXXXXXXXXXXXXXXXXXXXXXXXXXXXXXXXXXXXXXXX
XXXXXXXXXXXXXXXXXXXXXXXXXXXXXXXXXXXXXXXXXXXX
XXXXXXXXXXXXXXXXXXXXXXASTKGPSVFPLAPSSKSTSGGTAALGC
LVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESN
GQPENNYKTTPPVLDSDGSFFLYSKLTVDKSRWQEGNVFSCSVMHEAL
HNRYTQKSLSLSPGK Heavy chain constant region 7
                                     (SEQ ID NO: 36)
XXXXXXXXXXXXXXXXXXXXXXXXXXXXXXXXXXXXXXXXXXXX
XXXXXXXXXXXXXXXXXXXXXXXXXXXXXXXXXXXXXXXXXXXX
XXXXXXXXXXXXXXXXXXXXXXASTKGPSVFPLAPSSKSTSGGTAALGC
LVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSV
FLFPPKPKDTLMISRTPEVTCVVVDVSHEDPEVQFNWYVDGVEVHNAK
```

-continued

TKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESN

GQPENNYKTTPPVLDSDGSFFLYSKLTVDKSRWQEGNVFSCSVMHEAA

LHNRYTQKSLSLSPGK

Heavy chain constant region 8:

(SEQ ID NO: 37)
XXXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXX

XXXXXXXXXXXXXXXXXXXXXXXASTKGPSVFPLAPSSKSTSGGTAALGC

LVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESN

GQPENNYKTTPPVLDSDGSFFLYSKLTVDKSRWQEGNIFSCSVMHEAL

HNRYTQKSLSLSPGK

Heavy chain constant region 9:

(SEQ ID NO: 38)
XXXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXX

XXXXXXXXXXXXXXXXXXXXXXXASTKGPSVFPLAPSSKSTSGGTAALGC

LVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSV

FLFPPKPKDTLMISRTPEVTCVVVDVSHEDPEVQFNWYVDGVEVHNAK

TKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESN

GQPENNYKTTPPVLDSDGSFFLYSKLTVDKSRWQEGNIFSCSVMHEAL

HNRYTQKSLSLSPGK

Heavy chain constant region 10:

(SEQ ID NO: 39)
XXXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXX

XXXXXXXXXXXXXXXXXXXXXXXASTKGPSVFPLAPSSKSTSGGTAALGC

LVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEAL

HNRFTQKSLSLSPGK

Heavy chain constant region 11:

(SEQ ID NO: 40)
XXXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXX

XXXXXXXXXXXXXXXXXXXXXXXASTKGPSVFPLAPSSKSTSGGTAALGC

LVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSV

FLFPPKPKDTLMISRTPEVTCVVVDVSHEDPEVQFNWYVDGVEVHNAK

TKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEAL

HNRFTQKSLSLSPGK

Heavy chain constant region 12:

(SEQ ID NO: 41)
XXXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXX

XXXXXXXXXXXXXXXXXXXXXXXASTKGPSVFPLAPSSKSTSGGTAALGC

LVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESN

GQPENNYKTTPPVLDSDGSFFLYSKLTVDKSRWQQGNIFSCSVMHEAL

HNRFTQKSLSLSPGK

Heavy chain constant region 13:

(SEQ ID NO: 42)
XXXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXX

XXXXXXXXXXXXXXXXXXXXXXXASTKGPSVFPLAPSSKSTSGGTAALGC

LVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSV

FLFPPKPKDTLMISRTPEVTCVVVDVSHEDPEVQFNWYVDGVEVHNAK

TKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESN

GQPENNYKTTPPVLDSDGSFFLYSKLTVDKSRWQQGNIFSCSVMHEAL

HNRFTQKSLSLSPGK

Heavy chain constant region 14:

(SEQ ID NO: 43)
XXXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXX

XXXXXXXXXXXXXXXXXXXXXXXASTKGPSVFPLAPSSKSTSGGTAALGC

LVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESN

GQPENNYKTTPPVLDSDGSFFLYSKLTVDKSRWQEGNVFSCSVMHEAL

HNRFTQKSLSLSPGK

Heavy chain constant region 15:
(SEQ ID NO: 44)
XXXXXXXXXXXXXXXXXXXXXXXXXXXXXXXXXXXXXXXXXXXXXX
XXXXXXXXXXXXXXXXXXXXXXXXXXXXXXXXXXXXXXXXXXXXX
XXXXXXXXXXXXXXXXXXXXXXASTKGPSVFPLAPSSKSTSGGTAALGC
LVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSV
FLFPPKPKDTLMISRTPEVTCVVVDVSHEDPEVQFNWYVDGVEVHNAK
TKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESN
GQPENNYKTTPPVLDSDGSFFLYSKLTVDKSRWQEGNVFSCSVMHEAL
HNRFTQKSLSLSPGK Heavy chain constant region 16:
(SEQ ID NO: 45)
XXXXXXXXXXXXXXXXXXXXXXXXXXXXXXXXXXXXXXXXXXXXXX
XXXXXXXXXXXXXXXXXXXXXXXXXXXXXXXXXXXXXXXXXXXXX
XXXXXXXXXXXXXXXXXXXXXXASTKGPSVFPLAPSSKSTSGGTAALGC
LVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESN
GQPENNYKTTPPVLDSDGSFFLYSKLTVDKSRWQEGNIFSCSVMHEAL
HNRFTQKSLSLSPGK Heavy chain constant region 17:
(SEQ ID NO: 46)
XXXXXXXXXXXXXXXXXXXXXXXXXXXXXXXXXXXXXXXXXXXXXX
XXXXXXXXXXXXXXXXXXXXXXXXXXXXXXXXXXXXXXXXXXXXX
XXXXXXXXXXXXXXXXXXXXXXASTKGPSVFPLAPSSKSTSGGTAALGC
LVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSV
FLFPPKPKDTLMISRTPEVTCVVVDVSHEDPEVQFNWYVDGVEVHNAK
TKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESN
GQPENNYKTTPPVLDSDGSFFLYSKLTVDKSRWQEGNIFSCSVMHEAL
HNRFTQKSLSLSPGK Heavy chain constant region 18:
(SEQ ID NO: 47)
XXXXXXXXXXXXXXXXXXXXXXXXXXXXXXXXXXXXXXXXXXXXXX
XXXXXXXXXXXXXXXXXXXXXXXXXXXXXXXXXXXXXXXXXXXXX
XXXXXXXXXXXXXXXXXXXXXXASTKGPSVFPLAPSSKSTSGGTAALGC
LVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEAL
HNHFTQKSLSLSPGK Heavy chain constant region 19:
(SEQ ID NO: 48)
XXXXXXXXXXXXXXXXXXXXXXXXXXXXXXXXXXXXXXXXXXXXXX
XXXXXXXXXXXXXXXXXXXXXXXXXXXXXXXXXXXXXXXXXXXXX
XXXXXXXXXXXXXXXXXXXXXXASTKGPSVFPLAPSSKSTSGGTAALGC
LVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSV
FLFPPKPKDTLMISRTPEVTCVVVDVSHEDPEVQFNWYVDGVEVHNAK
TKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEAL
HNHFTQKSLSLSPGK Heavy chain constant region 20:
(SEQ ID NO: 49)
XXXXXXXXXXXXXXXXXXXXXXXXXXXXXXXXXXXXXXXXXXXXXX
XXXXXXXXXXXXXXXXXXXXXXXXXXXXXXXXXXXXXXXXXXXXX
XXXXXXXXXXXXXXXXXXXXXXASTKGPSVFPLAPSSKSTSGGTAALGC
LVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSV
FLFPPKPKDTLMITRTPEVTCVVVDVSHEDPEVKFNWYVDGVEVHNAK
TKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEAL
HNHYTQKSLSLSPGK Heavy chain constant region 21:
(SEQ ID NO: 50)
XXXXXXXXXXXXXXXXXXXXXXXXXXXXXXXXXXXXXXXXXXXXXX
XXXXXXXXXXXXXXXXXXXXXXXXXXXXXXXXXXXXXXXXXXXXX
XXXXXXXXXXXXXXXXXXXXXXASTKGPSVFPLAPSSKSTSGGTAALGC
LVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSV
FLFPPKPKDTLMITRTPEVTCVVVDVSHEDPEVQFNWYVDGVEVHNAK
TKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEAL
HNHYTQKSLSLSPGK Heavy chain constant region 22:
(SEQ ID NO: 51)
XXXXXXXXXXXXXXXXXXXXXXXXXXXXXXXXXXXXXXXXXXXXXX
XXXXXXXXXXXXXXXXXXXXXXXXXXXXXXXXXXXXXXXXXXXXX
XXXXXXXXXXXXXXXXXXXXXXASTKGPSVFPLAPSSKSTSGGTAALGC -continued
LVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSV

FLFPPKPKDTLTITRTPEVTCVVVDVSHEDPEVKFNWYVDGVEVHNAK

TKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEAL

HNHYTQKSLSLSPGK

Heavy chain constant region 23:
(SEQ ID NO: 52)
XXXXXXXXXXXXXXXXXXXXXXXXXXXXXXXXXXXXXXXXXXXXX

XXXXXXXXXXXXXXXXXXXXXXXXXXXXXXXXXXXXXXXXXXXXX

XXXXXXXXXXXXXXXXXXXXASTKGPSVFPLAPSSKSTSGGTAALGC

LVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSV

FLFPPKPKDTLTITRTPEVTCVVVDVSHEDPEVQFNWYVDGVEVHNAK

TKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEAL

HNHYTQKSLSLSPGK

Heavy chain constant region 24:
(SEQ ID NO: 53)
XXXXXXXXXXXXXXXXXXXXXXXXXXXXXXXXXXXXXXXXXXXXX

XXXXXXXXXXXXXXXXXXXXXXXXXXXXXXXXXXXXXXXXXXXXX

XXXXXXXXXXXXXXXXXXXXASTKGPSVFPLAPSSKSTSGGTAALGC

LVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSV

FLFPPKPKDTLMITRTPEVTCVVVDVSHEDPEVKFNWYVDGVEVHNAK

TKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEAL

HNHFTQKSLSLSPGK

Heavy chain constant region 25:
(SEQ ID NO: 54)
XXXXXXXXXXXXXXXXXXXXXXXXXXXXXXXXXXXXXXXXXXXXX

XXXXXXXXXXXXXXXXXXXXXXXXXXXXXXXXXXXXXXXXXXXXX

XXXXXXXXXXXXXXXXXXXXASTKGPSVFPLAPSSKSTSGGTAALGC

LVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSV

FLFPPKPKDTLMITRTPEVTCVVVDVSHEDPEVQFNWYVDGVEVHNAK

TKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEA

LHNHFTQKSLSLSPGK

Heavy chain constant region 26:
(SEQ ID NO: 55)
XXXXXXXXXXXXXXXXXXXXXXXXXXXXXXXXXXXXXXXXXXXXX

XXXXXXXXXXXXXXXXXXXXXXXXXXXXXXXXXXXXXXXXXXXXX

XXXXXXXXXXXXXXXXXXXXASTKGPSVFPLAPSSKSTSGGTAALGC

LVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSV

FLFPPKPKDTLTITRTPEVTCVVVDVSHEDPEVKFNWYVDGVEVHNAK

TKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEAL

HNHFTQKSLSLSPGK

Heavy chain constant region 27:
(SEQ ID NO: 56)
XXXXXXXXXXXXXXXXXXXXXXXXXXXXXXXXXXXXXXXXXXXXX

XXXXXXXXXXXXXXXXXXXXXXXXXXXXXXXXXXXXXXXXXXXXX

XXXXXXXXXXXXXXXXXXXXASTKGPSVFPLAPSSKSTSGGTAALGC

LVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSV

FLFPPKPKDTLTITRTPEVTCVVVDVSHEDPEVQFNWYVDGVEVHNAK

TKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEAL

HNHFTQKSLSLSPGK

Example parental and heavy chain constant region variants have amino acid sequences shown in SEQ ID 30-56.

In examples, parental heavy chain variable domains were combined with a human IgG1 heavy chain constant region of allotype G1m17 resulting in an heavy chain constant region amino acid sequence of SEQ ID NO:30. Likewise, variable light chains were combined with a Kappa light chain constant region of allotype Km3). Following codon optimization for mammalian expression, DNA encoding a Kozak sequence, an N-terminal leader secretion sequence and the target polypeptides was synthesized, cloned into a mammalian expression vector pTT5, and expressed in HEK 293 cells using methods well known in the art (described later).

Construction, Expression, Purification of Antibodies and their Variants

Example 6: Expression and Purification of Antibodies and their Variants

Antibodies and their heavy chain constant region variants were produced as follows: Codon optimization for antibody expression in 293 cells was performed using the Optimum-Gene™ Gene Design Technology (GenScript USA Inc). DNA was synthesized including a 5' EcoR1 cloning site, a Kozak sequence, and a leader signal sequence, followed by the IgG heavy or light chain DNA sequence. The 3' end of the Ig DNA sequences are followed by a stop codon and HindIII cloning site. One Synthetic DNA examples is given in SEQ ID: 57, where XXXXXXXXXXXX represents the codon optimized heavy or light chain DNA sequence). Oligonucleotide synthesis was performed using methods that are well known in the art. Antibody heavy and light chain synthetic DNA sequences were cloned into the pUC57 vector using EcoR1 and Hind III cleavage sites. Plasmid preparations were made of each plasmid and the immunoglobulin sequence inserts were sub-cloned into the expression vector pTT5 (National Research Council of Canada (NRCC)). Plasmid preparations of immunoglobulin expression vectors were made to provide transfection grade expression plasmids.

chromatography. This finding was surprising as Tyr436 makes important interactions with Protein G. This finding is important for the efficient purification of variant antibodies having a variant heavy chain constant region containing Arg 435 and Phe 436 (all amino acids are according to EU numbering).

Both the parental anti-SpA antibody and its variant were purified by affinity chromatography on a HiTrap™ rProtein A FF column. Although the anti-SpA variant (MAB2) does not bind to SpA via its Fc domain (see later; FIG. 22-26 and text), the antibody does bind SpA via its variable domain.

```
                                                          SEQ ID: 57
EcoR1  Kozak Sequence       Leader signal peptide
GAATTCGCCGCCACCATGGGATGGAGCTGTATCATCCTCTTCTTGGTAGCAACAG CTACAGGTGTCCACTCC XXXXXXXXXXXXTGATAAGCTT
                                        Stop codon   Hind III
```

Expression and Purification of Antibodies by Protein A or Protein G Chromatography:

Recombinant plasmids encoding the heavy chain and light chain of anti-microbial antibodies, or their heavy chain constant region variants, were transiently co-transfected into 100 mL of suspension HEK293 cell cultures, respectively. Following confirmation of antibody expression, large scale HEK293 expression of antibodies was performed in bioreactors to provide 50 mg quantities of test antibodies.

HEK 293-6E cells were grown in serum free Freestyle 293 expression medium (Invitrogen, Carlsbad, Calif., USA). The cells were maintained in Erlenmeyer Flasks at 37° C. with 5% CO2 (Corning Inc., Acton, Mass.) on an orbital shaker (VWR Scientific, Chester, Penna.). One day before transfection, the cells were seeded at an appropriate density in Corning Erlenmeyer Flasks. On the day of transfection, DNA and PEI (Polysciences, Eppelheim, Germany) were mixed at an optimal ratio and then added into the flask with cells ready for transfection. The supernatant collected on day 6 was used for purification.

Cell culture broth was centrifuged and followed by filtration. Filtered supernatant was loaded onto a 5 mL HiTrap™ Protein G HP or HiTrap™ rProtein A FF column (GE Healthcare, Uppsala, Sweden) at 1.0 mL/min. After washing and elution with appropriate buffer (The following buffers were used affinity chromatography: Binding buffer: 20 mM PB, 150 mM NaCl, pH 7.2; Elution buffer: 50 mM citrate (pH 3.0) or 0.1M Gly-HCl (pH 3.0); Neutral buffer: 1 M Tris-HCl, pH 9.0.), the fractions were collected and neutralized with 1M Tris-HCl, pH 9.0. The purified protein was analyzed by SDS-PAGE Western blot by using standard protocols for molecular weight, yield and purity measurements.

Results of Expression and Purification:

As expected the anti-RSV heavy chain constant region variant (MAB5) was not bound by HiTrap™ rProtein A FF column. This finding confirms that SpA no longer binds to the variant heavy chain constant region sequence (SEQ ID: 40). MAB5 was bound by the HiTrap™ Protein G HP column, demonstrating that although SpA and G both bind the CH2-CH3 interface of IgG1, their binding involves different amino acids. Therefore, His 435 and Tyr 436 are not required for binding to Protein G, as they have been mutated to Arg 435 and Phe 436 In the variant antibody MAB5. Thus, variant antibodies having a heavy chain constant region amino acid sequence of SEQ ID: 40 do not bind to SpA via their Fc domain, but do bind to Protein G. Such antibodies can be affinity purified by Protein G affinity The purification of antibody MAB2 thus represents SpA binding via the variable domain of the antibody. The anti-SpA parental antibody (MAB1) can bind SpA via its Fc and variable domains.

Both the anti-ClfA parental antibody and its variant were purified by affinity chromatography on Protein G. As was demonstrated for the anti-RSV variant antibody (MAB5), the anti-ClfA variant antibody (MAB4) also bind via its Fc domain to Protein G but not SpA. The parental anti-ClfA was bound by both SpA and Protein G and was purified by Protein G affinity chromatography.

Characterization of example antibodies: Purified antibodies were analyzed by SDS-PAGE and Western blotting. For western blotting, the primary antibody was Goat-anti-Human IgG-HRP (GenScript, Cat. No: A00166).

SDS-PAGE and Western Blotting of Anti-SpA Parental Antibody MA81 and Variant Antibody MA82.

Anti-SpA parental antibody MAB1 (HC amino acid SEQ ID NO:19 and LC amino acid SEQ ID NO: 21) and an example anti-SpA variant antibody MAB2 (HC amino acid SEQ ID NO:20 and LC amino acid SEQ ID NO: 21) were expressed in HEK293 cell, purified on HiTrap™ rProtein A FF, and analyzed by SDS-PAFGE and western blotting (FIG. 16).

SDS-PAGE and Western blotting of anti-Clfa parental antibody MAB3 and variant antibody MAB4.

Anti-ClfA parental antibody MAB3 (HC amino acid SEQ ID NO:25 and LC amino acid SEQ ID NO: 27) and an example anti-ClfA variant antibody MAB4 (HC amino acid SEQ ID NO:26 and LC amino acid SEQ ID NO: 27) were expressed in HEK293 cell, purified on Protein G, analyzed by SDS-PAGE and western blotting (FIG. 17).

Anti-RSV Control Variant Antibody (MAB5)

Anti-RSV variant antibody MAB5 (HC amino acid SEQ ID NO:23 and LC amino acid SEQ ID NO: 24) were expressed in HEK293 cell, purified on Protein G and analyzed by SDS-PAFG (FIG. 18). MAB5 does not bind SpA and was purified on Protein G.

Biological Testing of Example Anti-Microbial Immunoglobulins and their Heavy Chain Constant Region Variants

Example 7: Antibody Characterization for Binding to *S. aureus* IgBP by Immunodiffusion Binding to IgBPs: All procedures should be performed at room temperature unless specified otherwise. Goat anti-mouse antibody (gamma-chain specific, conjugated to horseradish peroxidase (HRP)) can be obtained from Zymed Laboratories (Invitrogen, Inc., Carlsbad, Calif.). TMB (3,3', 5,5'-tetramethylbenzidene), a chromogenic substrate for horseradish peroxidase enzyme activity, may be obtained from Neogen Corporation (Lansing, Mich.). The described procedures can be used for any IgBP. SpA and Sbi are used as illustrative examples. SpA may be purchased from commercial sources or produced using standard molecular Biology methods as previously described. For example, SpA domains A, B, C, D and/or E, or their variants (Kim et al., 2010) can be PCR amplified using two primers. Alternatively, the sequence of the SpA or Sbi domain or domains of interest can be synthesized and expressed using molecular biology techniques well known in the art. PCR products can be cloned into pET-15b to generating N-terminal His6-tagged recombinant fusion proteins. Polyhistidine-tagged fusion proteins can be purified by affinity chromatography. Alternatively, other fusion tags such as GST can be used for expression and purification. Sbi or its IgFc binding domains were produced using standard molecular biology methods as previously described (Haupt et al., 2008; Zhang et al., 1999).

The following IgBPs or their domains have been used to characterize S. aureus IgBP binding to variant and parental heavy chain constant region sequences (immune binding by the variable domain vs Fc binding by the heavy chain constant region).

Expression and Purification of SpA.

Cloning, expression and purification of recombinant Sbi and SpA: Recombinant fragments of the N-terminal region of Sbi (adjacent to the poly-proline region) are engineered, expressed and purified as His Tagged fusions as described previously by (Burman et al. 2008, THE JOURNAL OF BIOLOGICAL CHEMISTRY VOL. 283, NO. 25, pp. 17579-17593, Jun. 20, 2008). The following Sbi constructs were used in this study: Sbi-E (amino acids 28-266) containing IgG-binding domains I and II and C3 interacting domains III and IV; Sbi-III/IV (amino acids 150-266). Sbi fragments were purified by nickel ion-chelating chromatography. Recombinant SpA can be purchased of produced as described previously (O'Seaghdha et al., 2006).

GST-SPA-D expression: *E. coli* strain BL21 (DE3) was used for the GST-SpA domain D fusion protein expression (construct provided by Prof Timothy Foster, Trinity College Dublin). Bacteria containing pGEX-KG plasmid was grown overnight in LB medium supplemented with 100 μg/ml ampicillin at 37° C. The 15 ml primary culture was incubated with 1 L LB medium containing 100 μg/ml ampicillin. Cells were grown at 37° C. with shaking at 180 rpm. The expression of the GST-SpA domain fusion protein was induced during the exponential phase of growth (OD600=0.75) by adding isopropyl thiogalactoside (IPTG) to a final concentration of 0.5 mM in the culture. *E. coli* cells were collected by centrifugation (8000 g, 20 min) 3 h after induction. Cell pellet was suspended in 20 ml of PBS. The re-suspended cells were sonicated on ice for 6 times at 80% amplitude for 10 s separated by 10 min interval. The resulting extract was clarified by centrifugation (60,000 g, 30 min, 4° C.). The supernatant was collected and purified through affinity chromatography. The supernatant sample was split equally and loaded on a 1 ml GSTrap column (GE healthcare) using AKTA with a flow rate of 1 ml/min. The loaded column was washed with 10 column volumes of PBS buffer and the bound GST-SpA domain D fusion protein was eluted with GST Elution buffer (10 mM glutathione, 50 mM Tris, pH8.0). The peak fractions of the GST-SpA domain D fusion protein was then buffer exchange into PBS buffer for further use.

SSL10 from *S. aureus* NCTC8325, kind gift from Prof Jos van Strijp and Dr Carla de Haas.

Sbi-E and Sbi-III-IV Expression:

Sbi constructs were expressed in *Escherichia coli* strains BL21(DE3), BL21(DE3)-Star, or Rosetta (see also Burman et al. JBC 283; 17579-17593, 2008). Freshly transformed *E. coli* cells were grown in a shaker at 37° C. in Luria Bertani broth (LB), containing ampicillin, until they reached an extinction of 0.6 at 600 nm. Isopropyl-D-thiogalactopyranoside (Melford) was added to a final concentration of 0.2 mM, and the cells were incubated at 28° C. for an additional 4 h. Cells from a 1-liter culture were harvested by centrifugation, resuspended in 10 ml of binding buffer (20 mM Tris-HCl, 0.5 M NaCl, 20 mM imidazole, pH 8.0), and lysed by sonication. The lysate was centrifuged at 40,000 g for 15 min and the supernatant filtered through a 0.45 μm filter. The proteins were purified using nickel-ion chelating chromatography by either applying the filtered supernatant to a Sartobind membrane (Sartorius) or a 1-ml HiTrap column attached to an AKTA purifier (Amersham Biosciences). Next, the column was washed with binding buffer, and the bound proteins were eluted with a buffer containing 1M imidazole, for the Sartobind purification, or a 0.05-1 M imidazole gradient for the HiTrap purification. Purified protein was dialyzed into a buffer solution, typically 20 mM Tris, pH 8.0, 100 mMNaCl, and stored at 80° C. until use.

Double Immunodiffusion Assay:

Double immunodiffusion experiments were performed on Petri dishes containing a 1% agarose gel. Wells were punched in the agar and individual wells filled with 50 μl of sample at 1 mg/ml in PBS (anti-SpA monoclonals; Recombinant SpA (Biovision) GST-SpA-D; Sbi-E, Sbi III-IV or SSL10), and left to incubate for 72 h at 4° C. Insoluble protein complexes formed precipitin lines at the zone of equivalence. Large soluble protein complexes were vizualised by Coomassie staining.

Results: MAB1 (Parental anti-SpA antibody) formed a precipitin Line (after day 1) with SpA and (after day 2) with Sbi-E (fragment of Sbi containing the two Ig-binding domains and two complement binding domains). In contract the anti-RSV variant antibody did not form a precipitin line with either SpA or Sbi-E. As the variable domain of MAB1 recognizes SpA, this result shows that binding to Sbi-E is mediated by Fc binding to the parental antibody, whereas binding to SpA is likely a combination of variable domain and Fc binding. MAB2 (anti-SpA variant example) forms a precipitin line (after day 4) only with SpA. This demonstrated that MAB2, like the control variant antibody MAB5 (anti-RSV variant antibody), does not bind via its Fc domain to Sbi-E or to SpA. The precipitin line formed with SpA represents variable domain binding to SpA.

In a second series of immune-precipitation experiments, MAB1 (parental anti-SpA antibody) formed a precipitin Line with SpA domain D, but not with Sbi III/IV domains, which do not have Fc binding function. In contact no precipitin lines are seen with variant MAB2 (panel A). Following Coomassie staining, a week precipitin line is seen with MAB2 (anti-SpA variant example antibody), which represents variable domain binding to SpA domain D. This indicates that MAB2 forms a small soluble complex with SpA domain D, which is only visible with Coomassie staining of the ID plate. The data show that MAB2, in contract to MAB1, does not precipitate in the presence of the single SpA domain, but forms a soluble complex as evidenced by coomassie staining of the immunodiffusion gel. This data is consistent with the design objective of the variant antibody, which has abolished the SpA and Sbi Fc binding sites from the heavy chain constant region of the anti-SpA variant antibody (MAB2) and the anti-RSV variant antibody (MAB5).

Example 8: Antibody Characterization for Binding to *S. aureus* IgBP by Dynamic Light Scattering (DLS)

Dynamic light scattering is a technique for measuring the size of molecules and nanoparticles. Scattering intensity is proportional to the square of the protein molecular weight, making the technique ideal for identifying the presence of antibody antigen complexes and aggregates. DLS was used to investigate antibody antigen complex formation.

Immune complex formation was characterised by dynamic light scattering (Nano-S Zetasizer, Malvern). All readings were taken at 25° C. over a three consecutive 40-second periods in a low-volume, sealed quartz cuvette containing 50 μl samples of the anti-SPA monoclonal antibodies (1 mg/ml) and mixtures with (1 mg/ml) recombinant 4-domain SpA (Biovision); GST-SpA-D; Sbi-E, Sbi III-IV or SSL10.

FIG. 22 shows the DLS results for the control anti-RSV antibody (MAB5). The left panel shown the analysis of the control anti-RSV variant antibody alone (MAB5). The right panels show the size distribution in the presence of either Sbi-E (fragment of Sbi containing the two Ig-binding domains and two complement binding domains) or SpA1-4 (SpA IgBP domains 1-4). There is no peak shift seen by DLS, indicate no immune complexes have been formed between the variant antibody and the Sbi or SpA IgBP domains. These results are in agreement with the lack of precipitin lines in ID experiments.

In contract to the variant anti-RSV antibody, the parental anti-SpA antibody (MAB1) shows a large complex pattern of peak shifts in the presence of SpA 1-4, indicating large antibody-SpA complexes and cross-linking (FIG. 23—upper right panel)). This also occurs with Sbi-E, although the major peak shift appears relatively homogeneous, and large complexes are less apparent (Lower right panel-blue circle). No peak shifts were seen with SbiIII/IV (lower right panel), demonstrating that the interaction with Sbi is via antibody Fc interactions with the Sbi FcBP domains present in Sbi-E. This result is in agreement with the results generated by ID studies (FIGS. 20 and 21).

FIG. 24 shows the DLS analysis of the parental anti-SpA antibody (MAB1) with SpA-2 (SpA domain D alone). Peak shift DLS analysis was performed after incubation of antibody and SpA-2 for 1 min (upper right panel) and 10 mins (lower right panel). Complex formation and precipitation are seen to increase rapidly with time (FIG. 24). The results found with MAB1 are in agreement with the results generated by ID studies (FIGS. 20 and 21).

In contract to the parental anti-SpA antibody, the anti-SpA variant antibody (MAB2) shows no peak shift in the presence of Sbi-E, and a small homogeneous peak shift in the presence of SpA 1-4 (FIG. 25). The overlap of the MAB2 control and MAB2 in the presence of SpA 1-4 is shown in the lower left panel of FIG. 25. This result demonstrates that the variant heavy chain constant region of MAB2 does not bind to Sbi or SpA. The complex formation seen with SpA 1-4 represents binding via the variable domain of the anti-SpA variant antibody. Analysis of the single SpA domain D construct (FIG. 26), did not indicate any measurable peak shift due to the small size of the single SpA domain D, and the absence of any cross linking (FIG. 26, lower panel). The ant-SpA variant antibody (MAB2) shows a peak shift with DLS in the presence of SpA that is consistent with a soluble complex formed via the variable domain of the antibody. No cross-linking or precipitation peaks can be observed. The results found with MAB2 are in agreement with the results generated by ID studies (FIGS. 20 and 21).

Example 9: ELISA Binding to Isolated Microbial IgBPs

Such IgBP domains, variants, and IgBP domains from different *S. aureus* stains having a variety of amino acid substitutions within their IgBP can be used to determine the binding to IgBP domains and full length proteins from different microbial stains. For example, in the case of *S. aureus* SpA, different domains (for example, the amino acid sequence of SpA from clinical stains shown in FIG. 11 for domains A, D, C, D and E), can be used for binding and epitope mapping of antibodies described herein. The antibodies that may be used in accordance with the embodiments described herein are able to bind to epitopes that block one or more virulence functions of SpA, including Fc binding, VH3 Fab binding vWF binding, TNFR binding, EGFR binding and osteoblast binding. Additional antibodies are able to recognize conserved functional epitopes on SpA domains that allows the antibody to binds to multiple stains of SpA and multiple domains within such stains.

The target antigen (100 μL of 1 μg/mL SpA or Sbi antigens suspension in carbonate buffer, pH 9.2) may be coated in each well of the ELISA plates (Immulon 2; Dynex Technologies, Inc., Chantilly, Va.) for 1 hour at 37° C. After the coating step, the wells are washed twice with PBST (phosphate buffered saline (150 mM NaCl in 10 mM sodium phosphate buffer, pH 7.4) containing 0.05% w/v Tween 20).

After discarding the last wash, coating the wells with the target antigen, nonspecific protein-binding sites in the ELISA plates may be blocked. Two hundred microliters of PBST containing 2% (w/v) dehydrated skim milk (blotto solution) are added to each well. The plates are incubated at 37° C. for 1 hour. The blotto solution should then be discarded. Murine IgG1 antibody or chimeric/humanized antibodies in which H435 of the Fc region has been mutated to R to abolish Fc binding to SpA, (100 μL/well, diluted in wash buffer) may be added to each well. The plates are incubated for 1-2 hours at 37° C. After incubation, wells are washed 3 times with Mild Elution Buffer pH 6.0 (Thermo Scientific cat #21033).

One hundred microliters of an appropriate dilution of Goat anti-mouse or anti-human antibody-HRP conjugate in the blotto solution may be added to each well and incubated at 37° C. for 1-2 hours. After this incubation period, the conjugate solution should be removed and the wells washed 3 times with PBST. After removing the last wash, 100 μL of TMB (Kblue, Neogen Cat No. 300199) can be added to each well and the plates are held at room temperature for 1-10 minutes to observe the development of blue color. The relative HRP enzyme activity in each well is measured in a plate reader by absorbance of a 650-nm wavelength light source.

Example 10: Inhibition of Virulence Functions of SpA by Antibodies and their Variants Inhibition of *S. aureus* SpA-Fc binding by anti SpA antibodies: inhibition of binding of human IgG to SpA can be tested by ELISA. ELISA plates are coated with recombinant SpA or individual domains of SpA. Purified SpA or its domains are coated onto ELISA plates in 0.1 M carbonate buffer, pH 9.5. Plates are incubated with peroxidase-conjugated human IgG, (The Jackson Laboratory), or purified labeled human IgG1 Fc and developed using OptEIA reagent. Alternatively, S. aureus cells can be used (see later method for cell ELISA). For inhibition of labeled IgG-Fc binding, plates are incubated with anti SpA antibodies (heavy chain constant region variants are used, which do not bind to SpA via the Fc domain) before ligand binding.

Inhibition of S. aureus SpA-vWF binding by anti SpA antibodies: inhibition of binding of human IgG to SpA can be tested by ELISA. ELISA plates are coated with recombinant SpA or individual domains of SpA. Purified SpA or its variants are coated onto ELISA plates in 0.1 M carbonate buffer, pH 9.5. Plates are incubated with peroxidase-conjugated human vWF, (Thermo Fisher Scientific) and developed using OptEIA reagent. For inhibition of labeled vWF binding, plates are incubated with anti SpA antibodies (heavy chain constant region variants are used, which do not bind to SpA via the Fc domain) before ligand binding.

Inhibition of S. aureus SpA-VH3 binding by anti SpA antibodies: inhibition of binding of human VH3 IgG to SpA can be tested by ELISA. ELISA plates are coated with recombinant SpA or individual domains of SpA. Purified SpA or its variants were coated onto ELISA plates in 0.1 M carbonate buffer, pH 9.5. Plates are incubated with peroxidase-conjugated human Fab VH3, (Graille et al., 2000) and developed using OptEIA reagent. For inhibition of labeled VH3 Fab binding, plates were incubated with anti SpA antibodies (heavy chain constant region variants are used, which do not bind to SpA via the Fc domain) before ligand binding.

Example 11: ELISA Binding to Target Microbes

Binding to S. aureus Cells. Antibodies and their Fc variants may be tested for their ability to bind to intact cells of S. aureus. The bacterial strains used in this example, S. aureus can be obtained from the American Type Culture Collection (Manassass, Va.).

Bacterial cultures used for antigen preparation may be grown overnight at 37° C. in Tryptic Soy Broth. The cell suspensions are washed three times by centrifuging the suspension at 10,600×g for 10 minutes at 4° C., decanting the supernatant, and resuspending the pellet in 100 mM sodium bicarbonate, pH 9.5. After the final wash, the cells are suspended in the sodium bicarbonate buffer to approximate cell densities of $10^7$ $10^6$ and $10^5$ colony-forming units per milliliter. These suspensions can be used as antigen to coat 96-well plates. Control solutions, containing 1.0, 0.1, and 0.01 mg/mL, respectively, purified SpA are coated into several wells of each plate.

Streptavidin-conjugated alkaline phosphatase can be obtained from Jackson Immunoresearch (West Grove, Pa.) and may be diluted to a working concentration of 0.5 μg/mL prior to use. The alkaline phosphatase chromogenic substrate, pNPP, can be obtained from KPL (Gaithersberg, Md.). Anti-SpA monoclonal antibody SPA-27 and its corresponding biotin-conjugated derivative may be obtained from Sigma Chemical Company (St. Louis, Mo.).

Bacterial suspensions and SpA controls may be added to a 96-well plate (100 μg/well) and the plates may be incubated at 37° C. for 1 hour. The wells are then washed five times with PBS. Nonspecific protein-binding sites re blocked by adding 200 L of a blotto solution (PBST with 2% w/v nonfat dehydrated milk) and the plates are held overnight at 4° C. The plates are subsequently washed with PBST.

Unlabeled test antibody solutions may be diluted to 50 μg protein/mL in acetate buffer (500 μM NaCL/100 μM Sodium acetate, pH 3.5). These solutions may be used to prepare serial 2-fold dilutions (to 0.78 μg protein/mL) of the antibodies in acetate buffer. SPA-27 antibody is use as a positive control.

One hundred microliters of each dilution of the murine IgG1 antibodies or chimeric/humanized antibodies of IgG1 isotype (with one or more Fc region mutations designed to block non specific antibody binding to SpA and Sbi) are then transferred into duplicate wells and the plates are incubated at 37° C. for 1 hour. The plates may then be subsequently washed five times with Mild Elution Buffer pH 6.0 (Thermo Scientific cat #21033).

One hundred microliters of the diluted, biotin-conjugated anti mouse or anti human antibody may be added to the wells and the plates are incubated at 37° C. The wells may then be washed with PBST.

After washing the wells, 100 μL of streptavidin-alkaline phosphatase conjugate, diluted in blotto solution, may be added to each well and the plates may be incubated at 37° C. for 1 hour. After washing the wells, 100 μL of the pNPP substrate solution is added to each well and the plates may be held at room temperature for 10 minutes. The alkaline phosphatase reaction may be stopped by adding 100 μL of 5% (w/v) disodium EDTA and the plates may be placed in a plate reader, where the absorbance at 405-nm wavelength is read.

The IgG1 hybridoma supernatants may be diluted in sodium acetate buffer (500 μM NaCL/100 μM Sodium acetate, pH 3.5) for the binding assay. After the binding reaction, the amount of antibody bound to the immobilized bacteria is measured using the alkaline phosphatase-conjugated antibody and detection reagents.

In an alternative method, an ELISA based screen was used to investigate anti-SpA and anti-ClfA antibody binding to S. aureus (Newman stain) and a SpA deficient S. aurues stain (ΔSpA) in the presence and absence of human IgG1-Fc used to block non-specific binding and IgBP medicated Fc binding.

ΔSpA strains of S. aureus can be generated by deletion of the spa gene on the chromosome of S. aureus Newman by allelic replacement, as described previously (Bae T., and Schneewind O. (2005)).

One day before the experiment, 100 μl/well of a Staph aureus overnight culture diluted to an OD600 of 1.0 was added to a 96 well plate and incubated at 4° C. overnight. On the day of the experiment, plates were washed with 150 μl/well PBS-T (PBS with 0.05% Tween 20) 2× then blocked with 150 μl/well PBS-T w/0.5% BSA. The plates were agitated for 1 hour after blocking. The plates were then washed with 150 μl/well PBS-T (2×) then 100 μl/well of primary mAb at various dilutions were added to each ELISA plate. The plate was shaken at room temp for 12 hour, washed with 150 μl/well PBS-T (2×) then 100 μl/well secondary antibody (goat antihuman IgG (HRP) @ 1:5,000 in PBS-T—Thermo #31413) was added. The plates were shaken at room temp for 1 hour, washed with 150 μl/well PBS-T (2×) then 100 μl/well TMB was added and the plates incubated until sufficient color change has been reached (usually around 5 minutes). 100 μl/well 2M sulfuric acid was then added to stop the reaction and the plate read at OD450 on a Spectramax. In some cases, Human IgG Fc (Jackson ImmunoResearch #009-000-008) was added at 100 µg/ml to both the blocking agent and the primary antibody.

In a representative S. aureus Cell ELISA (FIG. 27), a number of antibodies were tested for binding to S. aureus (Newman stain) and a SpA deficient S. aureus strain (ΔSpA) in the presence and absence of human IgG1-Fc used to block non-specific binding and IgBP medicated Fc binding. Test Antibodies include anti-SpA MAB1 and anti-SpA variant MAB2, anti-ClfA Parental MAB, anti-RSV variant MAB5 and a non-specific anti-KLH antibody.

Figure 27:
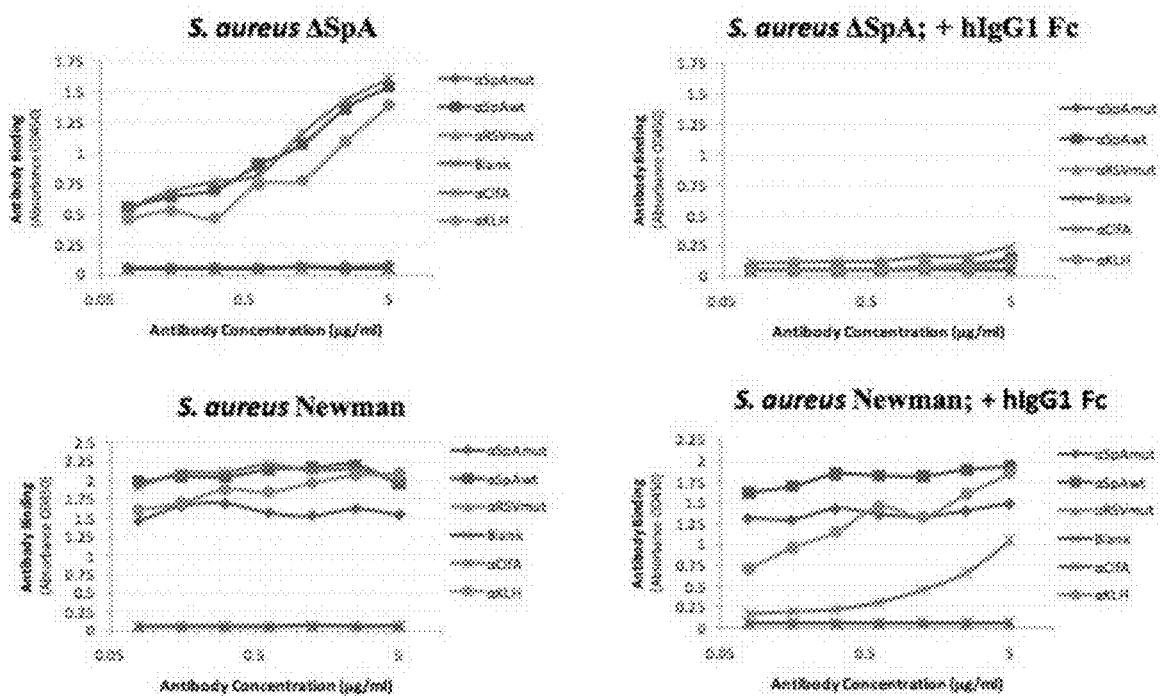
FIG. 27 shows an analysis of binding of antibodies to S. aureus Newman and a S. aureus SpA delation stain in the absence and presence of blocking human IgG1Fc. Antibodies tested include anti-SpA MAB1, anti-SpA variant MAB2, anti-ClfA Parental MAB, anti-RSV MAB5 and a non-specific anti-KLH antibody. In the left panels, antibodies are tested in the absence of hIgG1 Fc. The upper panels represent binding to a S. aureus stain lacking expression of SpA (delta SpA=ΔSpA). The lower panels represent binding to S. aureus Newman stain. Blank contains no primary antibody.
Figure 28:
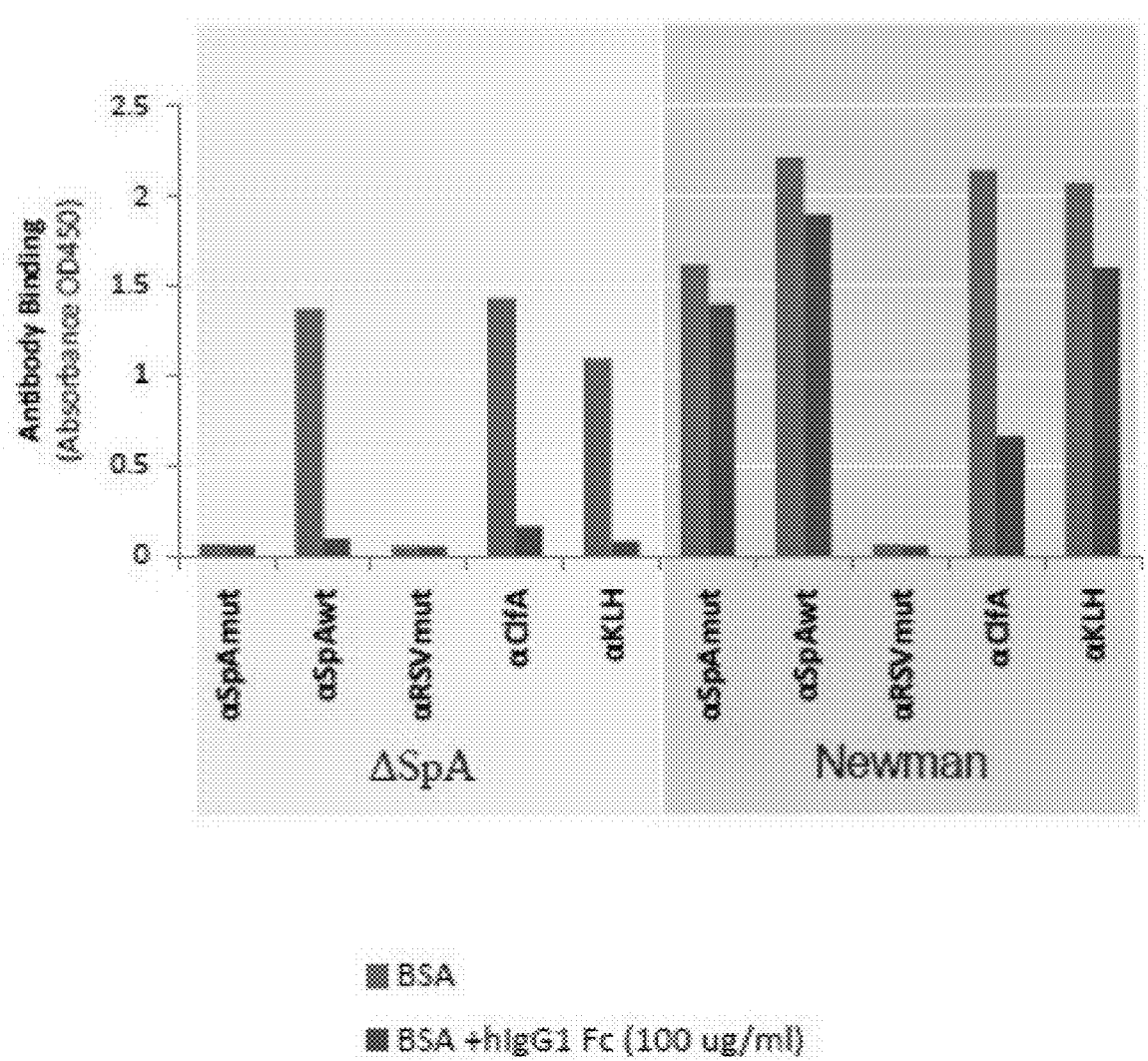
FIG. 28 shows tabulated results of ELISA binding of antibodies and their variants to a S. aureus stain lacking expression of SpA (Yellow panel: ΔspA) and to S. aureus Newman stain (Pink Panel: Newman) in the presence (Red bars) or absence (Blue bars) of human IgG1-Fc.
Figure 29:
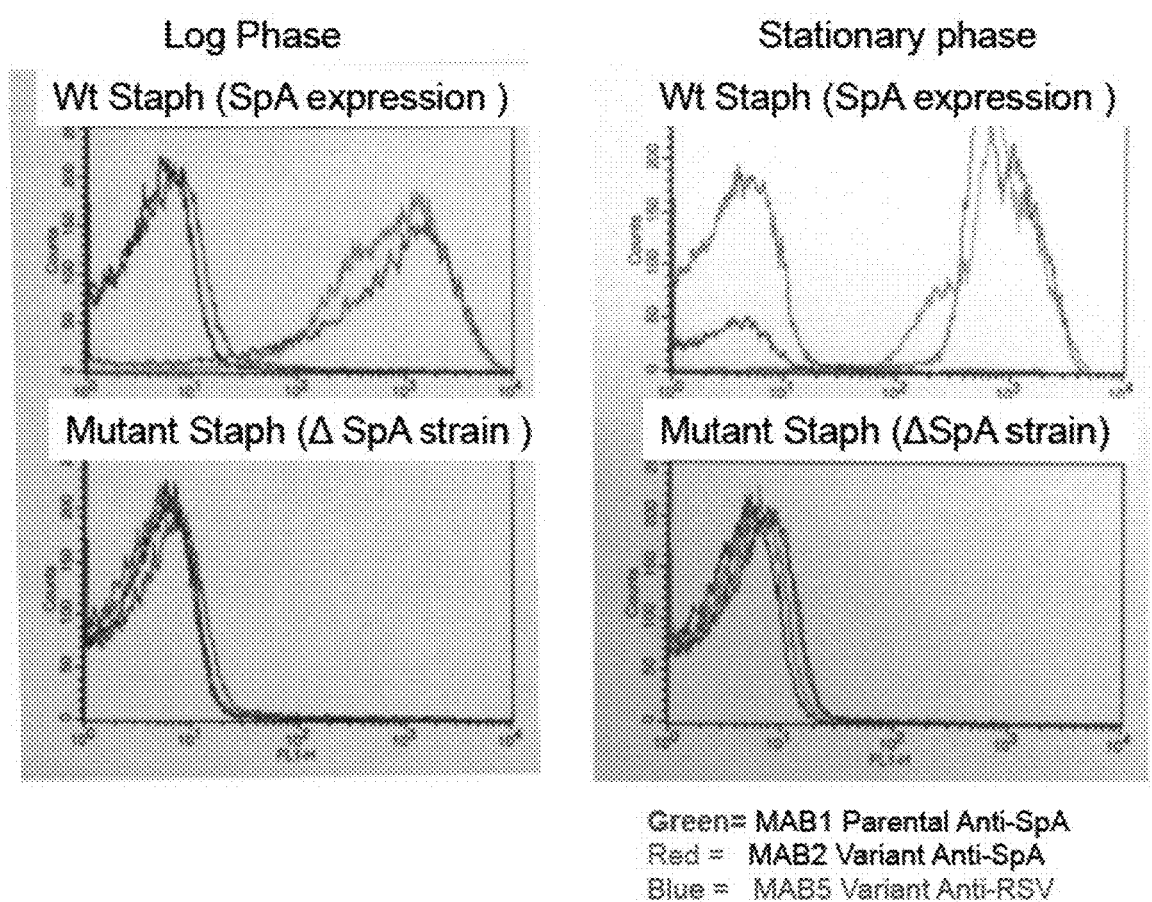
FIG. 29 shows a FACS analysis of antibody Binding to S. aureus: Binding of the parental anti-SpA antibody (MAB1), an example anti-SpA variant antibody (MAB2) and a heavy chain constant region matched anti-RSV variant control antibody (MAB6) were investigated by FACS, using S. aureus Newman strain (upper panels) or a ΔSpA strain (lower panels)) grown to log phase (left panels) or from stationary phase cultures (right panels).

Discussion of ELISA Results:

The ELISA results are shown in FIG. 27. These results indicate that the control (anti-KLH) and parental antibodies (non-variant antibodies) have high non-specific binding to S. aureus Newman stain (lower panels). This non-immune binding is reduced by include human IgG1-Fc as a blocker (FIG. 27, right panels) (for example see anti-KLH and anti-ClfA antibodies). This is presumably due to blockage of IgBP Fc binding sites on the S. aureus Newman stain (FIG. 27 right panels). This is supported by the finding that the anti-RSV variant antibody (MAB5) does not bind to S. aureus Newman stain in the absence or presence of blocking human IgG1-Fc FIG. 27; lower panels). Thus, mutations introduced into the heavy chain constant region of variant MAB2 and MAB5 eliminate Fc binding of the variant antibodies to S. aureus cell surface IgBPs. In contrast, both the anti-SpA parental and anti-SpA variant antibodies bind strongly to S. aureus Newman stain in the absence or presence of blocking human IgG1-Fc (FIG. 27, lower panels), demonstrating variable domain binding by the anti-SpA antibodies. The variant anti-RSV antibody had minimal background binding whereas the variant anti-SpA antibody had significant binding.

The variant anti-SpA and anti-RSV antibodies (MAB2 and MAB5) have no binding to SpA deficient Staph (FIG. 27, upper panels). However, Fc mediated binding of the parental anti-SpA, anti-ClfA and anti-KLH antibodies are seen that can be blocked by human IgG1-Fc (FIG. 27, Upper left panel). This may be due to binding by alternative IgBPs expressed by the ΔSpA strain, such as *S. aureus* Sbi.

The results shown in FIG. 27 are tabulated in FIG. 28. These results indicate that the heavy chain constant region mutations in MAB2 and MAB5 eliminated non-specific binding and SpA Fc medicated binding. The specific binding of the anti-SpA heavy chain constant region variant demonstrated variable domain binding of this antibody to SpA. Additionally, IgG1Fc did not compete with anti-SpA antibody binding to SpA, demonstrating that the region of SpA recognized by the variable domain of anti-SpA antibodies MAB1 and MAB2 do not overlap with the SpA-Fc binding sites.

Example 12: FACS Analysis of Antibody Binding to *S. aureus*

Binding of the parental anti-SpA antibody (MAB1), an example anti-SpA variant antibody (MAB2) and a heavy chain constant region matched anti-RSV variant control antibody (MAB6) were investigated by FACS, using *Staphylococcus aureus* Newman stain (FIG. 29; upper panels) or a ΔSpA strain (FIG. 29, Lower panels)) grown in log phase (FIG. 29, left panels), or from stationary phase cultures (FIG. 29; right panels). Standard FACS methods known in the art were used for the analysis. The second antibody used in the study was Alexa Fluor 488 conjugated Fab goat anti-human IgG. As can be see in FIG. 29, the control anti-RSV variant antibody did not bind to *S. aureus* under all conditions tested, confirming that the heavy chain constant region variant chain does not bind to *S. aureus* FcBPs via its Fc domain. This confirms the data seen in cellular ELISA assays. In contrast, the parental and variant anti-SpA antibodies (MAB1 and MAB2) bound strongly to *S. aureus* from stationary or log phase cultures, but not to the ΔSpA strain of *S. aureus*. This result confirms that antibody binding by the variant anti-SpA antibody (MAB2) is mediated by the variable domain of the antibody.

Effector Function Testing of Variant Antibodies

In a variety of in vivo and in vitro settings, antibody coating of targets has been shown to mediate potent killing mechanisms such as complement-dependent cytotoxicity (CDC), antibody-dependent cellular cytotoxicity (ADCC), antibody-dependent cellular phagocytosis (ADCP) and opsonophagocytosis. These effector functions are mediated by the antibody heavy chain constant region. To verify that variant antibodies described herein do not have attenuated effector function, due to the introduction of mutations that attenuate bacterial IgBP binding, antibodies can be tested in a number of binding assays (FcγRs and C1q binding) and effector function assays (Complement deposition opsonophagocytosis, CDC, ADCC, ADCP, anti-microbial activity), Construction, Expression, and Purification of FcγRs: FcγR binding of Fc variant antibodies: FcγRs can be constructed as C-terminal-6×His-GST fusions, expressed in 293T (human FcγRs) cells, and purified by using nickel affinity chromatography. Detailed methods are provided in Lazar et al., 2006.

FcγR binding of parental and Fc variant antibodies: Variants are constructed, expressed and purified, and can be screened for FcγR affinity by using an AlphaScreen assay. AlphaScreen assays can use untagged variant IgG1 to compete the interaction between biotinylated IgG bound to streptavidin donor beads and FcγR-His-GST bound to anti-GST acceptor beads.

True binding constants can be obtained by a competition surface plasmon resonance (SPR) experiment. Competition SPR experiments measured capture of free Ab from a preequilibrated Ab/receptor analyte mixture to V158 FcγRIIIa-His-GST bound to an immobilized anti-GST surface. Equilibrium dissociation constants ($K_D$ values) are calculated by using the proportionality of initial binding rate on free Ab concentration in the Ab/receptor equilibrium. Detailed description of AlphaScreen and SPR assays is provided in Lazar et al., 2006 and references therein. SPR measurements were performed using a BIACore 3000 instrument (GE Healthcare). Fcγ R affinity can be determined as described in Nieba et al., 1996.

C1q binding of parent and variant antibodies: Surface plasmon resonance determination of binding affinities. SPR measurements can be performed in HBS-EP running buffer (10 mM HEPES pH 7.4, 0.15 M NaCl, 3 mM EDTA, 0.005% v/v surfactant P20, GE Healthcare) using a BIACore 3000 instrument (GE Healthcare).

For determining C1q affinity of IgG1K antibodies and their variants, a Protein L CM5 biosensor chip (GE Healthcare) can be generated using a standard primary amine coupling protocol. The chip's reference channel can be coupled to bovine serum albumin (BSA) to minimize non-specific binding of C1q. Antibodies at 50 nM can be immobilized on the protein L surface for 0.5 or 1 min at 10 μL/min. C1q in 2-fold serial dilutions (starting at 100 or 25 nM, 5 concentrations total) is injected over antibody-bound surface for 3 min at 30 μL/min followed by a 4.5 min dissociation phase. C1q molarity can be calculated using the molecular weight of the C1q hexameric bundle, 410 kDa. After each cycle, the surface can be regenerated by injecting glycine buffer (10 mM, pH 1.5). In order to subtract non-specific C1q binding to antibody-coated protein L surface, an Fc variant with greatly ablated CDC activity can be included. Sensorgrams can be processed by zeroing time and response before the injection of C1q and by subtracting appropriate nonspecific signals (response of BSA-blocked reference channel, response of an Fc variant with ablated CDC, and response of running buffer). Kinetic parameters can be determined by global fitting of association and dissociation phase data with a two-state binding model (A+B AB AB*). $K_d$ was calculated as $K_{d1}/(1+1/K_{d2})$.

ADCC of Parent and Fc Variant Antibodies.

ADCC can be measured by using either the DELFIA EuTDA-based cytotoxicity assay (PerkinElmer) or the LDH Cytotoxicity Detection Kit (Roche Diagnostics). Human PBMCs can be purified from leukopacks by using a Ficoll gradient and allotyped for V/F158 FcγRIIIa by using PCR. NK cells can be isolated from human PBMCs by using negative selection and magnetic beads (Miltenyi Biotec, Auburn, Calif.). Target cell lines can be obtained from American Type Culture Collection. For Eu-based detection, target cells are first loaded with BATDA [Bis(acetoxymethyl)-2,2':6',2"-terpyridine-6,6"-dicarboxylate] at $1\times10^6$ cells per ml and washed 4×. For both Eu- and LDH-based detection, target cells can be seeded into 96-well plates at 10,000 cells per well and opsonized by using Fc variant or WT Abs at the indicated final concentration. Triton X-100 and PBMCs alone can be run as controls. Effector cells can be added at 25:1 PBMCs:target cells or 4:1 NK cells:target cells, and the plate are incubated at 37° C. for 4 h. Cells are incubated with either $Eu^{3+}$ solution or LDH reaction mixture, and fluorescence can be measured by using a Fusion Alpha-FP (PerkinElmer). Data can be normalized to maximal (Triton) and minimal (PBMCs alone) lysis and fit to a sigmoidal dose-response model.

ADCP of Parent and Fc Variant Antibodies.

For phagocytosis experiments, monocytes can be isolated from human V/F158 FcγRIIIa PBMCs by using a Percoll gradient and differentiated into macrophages by culture with 0.1 ng/ml granulocyte/macrophage colony-stimulating factor for 1 week. For quantitative ADCP, target cells (e.g. WIL2-S for anti CD20 antibody Fc variants) can be labeled with PKH67, seeded in a 96-well plate at 20,000 cells per well, and treated with WT or variant Ab at the designated final concentrations. Macrophages are labeled with PKH26 (Sigma) and added to the opsonized labeled target cells at 20,000 cells per well, and the cells are co-cultured for 18 hours. Fluorescence is measured by using dual-label flow cytometry.

CDC of parental and Fc variant antibodies can be tested initially in the context of an anti CD20 antibody as described in Moore et al., 2010. For CDC assays, target Ramos or Raji cells can be washed 2× in RHB Buffer (RPMI Medium 1640 containing 20 mM HEPES, 2 mM glutamine, 0.1% BSA, pH 7.2) by centrifugation and resuspension and seeded at 40,000 cells per well. Native IgG1 or variant antibody is added at the indicated final concentrations. Human serum complement (Quidel, San Diego, Calif.) are diluted with RHB buffer and added to opsonized target cells. Plates can be incubated for 2 hr at 37° C., Alamar Blue is added, cells are cultured overnight, and fluorescence is measured in relative fluorescence units. Data is normalized to maximal (Triton X-100) and minimal (complement alone) lysis and fitted to a sigmoidal dose-response curve.

FcRn binding of variant anti-SpA antibodies: FcRn binding can be measured as described previously (Dall'Acqua et al., 2006; Datta-Mannan et al., 2006).

Anti-S. aureus effector function can be tested in a number of in vitro assays. These assays may include a C1q deposition, C3 deposition, bacterial opsonophagocytic assays and bactericidal assay, which are described below.

Example 13: Anti-S. aureus C1q Deposition Assays of Selected Antibodies and their Fc Variants C1q deposition assay: This assays tests for the ability of antibodies to deposit complement on bacteria. Add 100 µl of bacteria (@ OD600 1.0) to microtubes washing 1× with 1 ml HBSS+, Centrifuge at ~7000×g (9000 rpm), for 5 minutes at 4° C. Next, add 50 µl l of a 2× concentration of test antibody or isotype control diluted in GV buffer. Add 50 µl of human complement @ 20% diluted in GV buffer for a 10% final concentration. Incubate samples at 37° C. in shaking water bath for 60 minutes, then wash 2× with 1 ml HBSS+, ~7000×g (9000 rpm), for 5 minutes at 4° C. Add 100 µl of a mouse anti-human C1q mAb, or C1q isotype control for a final concentration of 3 µg/ml in GV buffer, incubate for 30 minutes @ 4° C. Next, wash 2× with 1 ml of HBSS+].

FACS detection of complement on bacteria: Add 100 µl of anti-mouse IgG-PE at a 1:50 dilution in HBSS+ at 4° C. Incubate for 30 minutes, in the dark, on ice with shaking. Wash 2× with 1 ml HBSS, ~7000×g (9000 rpms), for 5 minutes at 4° C. Resuspend in 0.5 ml of HBSS+, at 4° C. Transfer samples to FACS tubes. Analyze samples by Accuri gating on bacteria, 10,000 events, FL2.

Reagents: HBSS+: w/Mg Ca. #14025-092, Gibco; Gelatin veronal buffer (GV), #G6514, Sigma; Human Serum Complement #A113, Quidel—(thaw rapidly in 37° C. water bath to ~90% leaving small pellet, mix and put on ice, aliquot and store at −80° C.); Mouse-IgG1 anti-human C1q antibody (1.1 mg/ml), #A201, Quidel; Negative control for anti-human C1q Mab: Anti-TNP mouse IgG1 (isotype control for C1q mAb), NA/LE, clone 107.3, stock=1.0 mg/ml, #554721, BD Pharmingen; PE-conjugated F(ab')2 fragment donkey anti-mouse IgG (H+L) antibody, #715-116-150, Jackson Immuno Research—(rehydrate with 1.0 ml distilled water and add 20 µl of stock per 980 µl of HBSS+=1:50 dilution); Distilled water, #15230, Gibco.

Figure 30A:
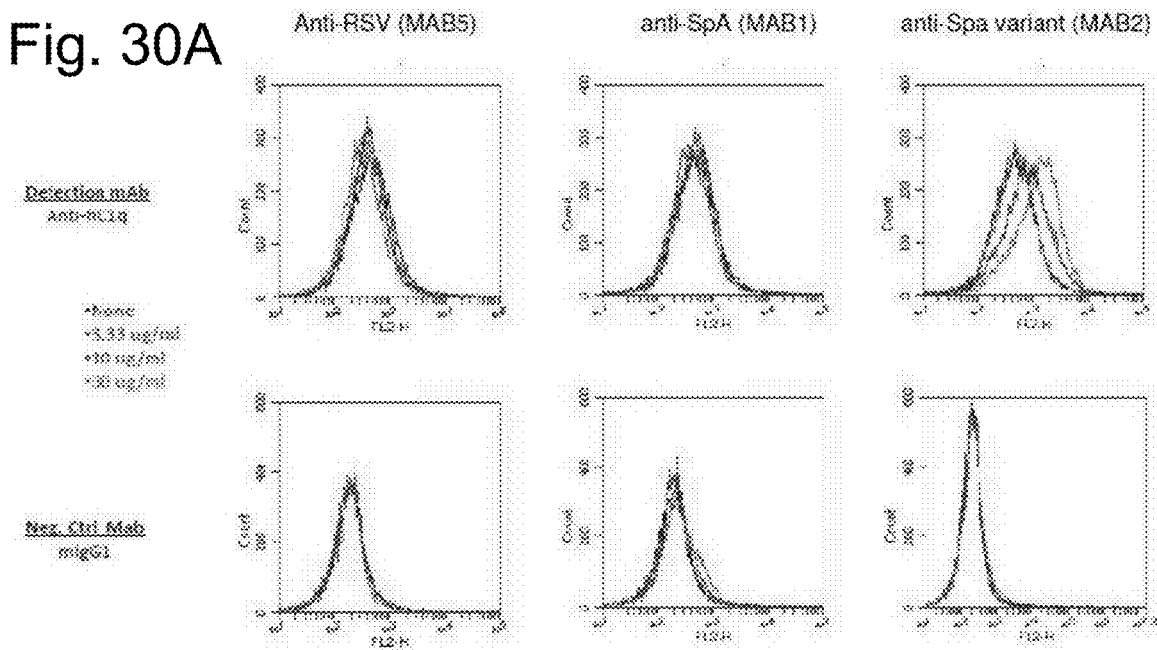
FIGS. 30A and 30B show antibody mediated C1q deposition: FACS analysis was performed to test whether the parental anti-SpA antibody MAB1 (center panel), its variant anti-SpA antibody MAB2 (right panel), or the control anti-RSV variant antibody MAB5 (left panel) antibodies are able to deposit C1q on wild type S. aureus Newman (FIG. 30A) or a S. aureus ΔSpA stain (FIG. 30B). The upper panel of FIGS. 30(a) and (b) use an anti-hC1q detection antibody, while the lower panels use a negative control detection antibody. Three concentrations of each antibody are shown for each Histogram: 3.33 μg/ml (red), 10 μg/ml (blue) and 30 μg/ml (green).
Figure 30B:
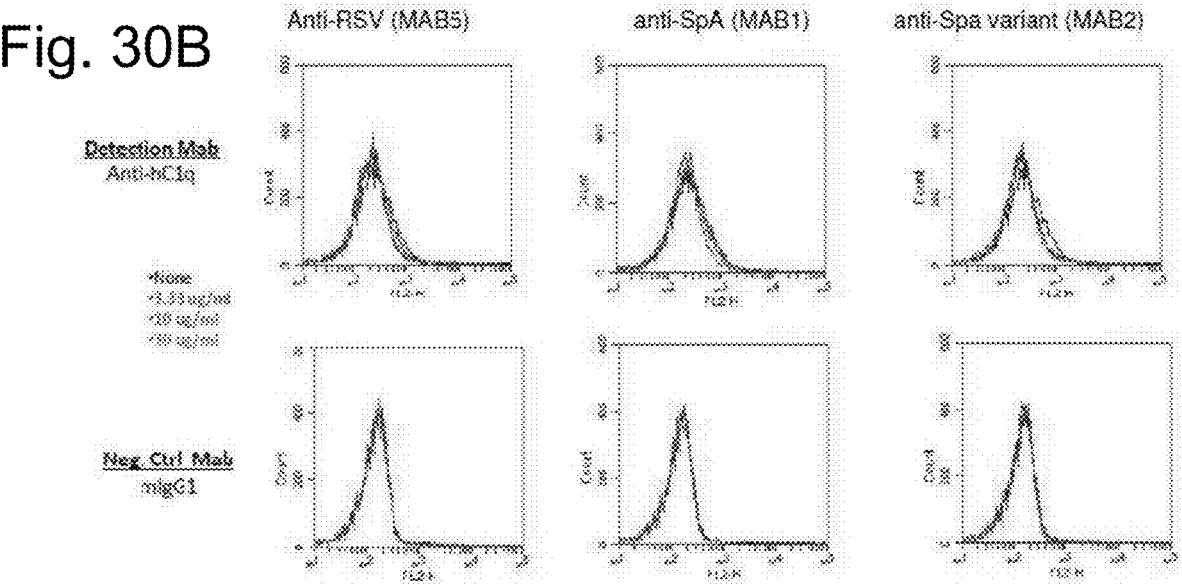
Figure 31:
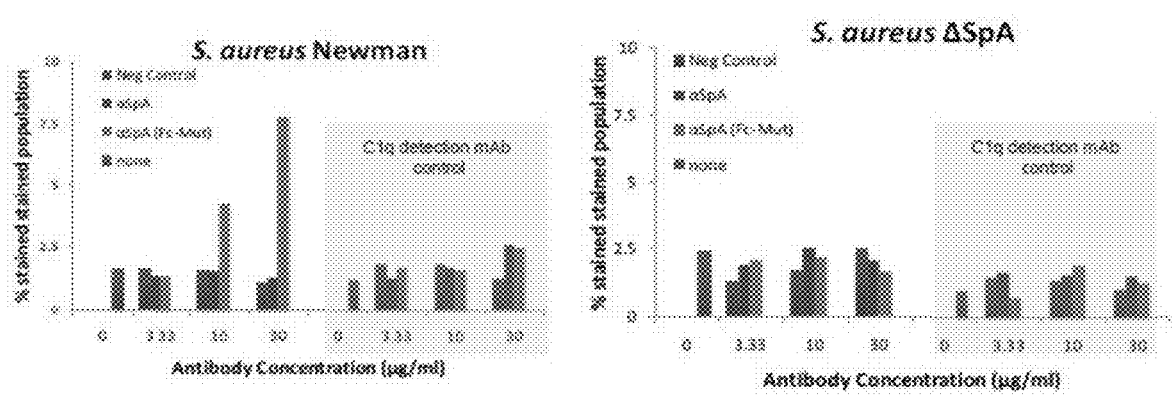
FIG. 31 shows a tabulation of antibody mediated C1q deposition data. The data from the FACS Histograms in FIG. 30 are tabulated. The Y axis shows % stained bacterial population.

Results: C1q deposition assays were performed to test whether the parental anti-SpA (MAB1), its variant anti-SpA (MAB2), and the control anti-RSV variant (MAB5) antibodies are able to can deposit C1q on wild type S. aureus Newman and a S. aureus ΔSpA strain (FIG. 30). A dose titration of the test antibodies was performed using S. aureus WT and ΔSpA Newman strain in the presence of pooled human serum as a source of complement. As shown in FIG. 30a, the variant anti-SpA antibody (MAB2), deposits C1q on the surface of the wild type S. aureus Newman strain in a dose dependent manner, while the parental anti-SpA antibody (MAB1) and negative control anti-RSV variant antibodies (MAB5) lack this function (FIG. 30a, upper panel). The ability of the anti-SpA variant antibody (MAB2) to deposit C1q on S. aureus is lost in assays using the ΔSpA S. aureus stain, which has no SpA expression (FIG. 30b). This result demonstrates that the anti-SpA variant antibody shows antigen dependent deposition of complement on the S. aureus Newman strain. This demonstrates that FcBPs expressed by S. aureus are able to neutralize the C1q effector function of the parental IgG1 antibodies, but not that of its variants such as MAB2. The FACS data from FIG. 30 is tabulated in FIG. 31.

Example 14: C3 Complement Deposition Assay

C3 deposition was determined using *S. aureus* stain JE2 and measured by FACS. The following methods were used. Staph JE2 was grown overnight in THB at 37° C. with shaking. Next day, stationary phase culture were washed and resuspended in PBS to OD600 nm=0.4. Aliquot 1 ml of bacterial culture into eppendorf tubes and spin at max speed for 2 min, then resuspend the pellet in 50 µl of HEPES buffer (120 mM HEPES, 140 mM NaCl, 5 mM $CaCl_2$) and 25 mM $MgCl_2$). Dilute pooled human serum to 10% in HEPES buffer. Add 50 µl of 10% serum to the bacteria.

Figure 32:
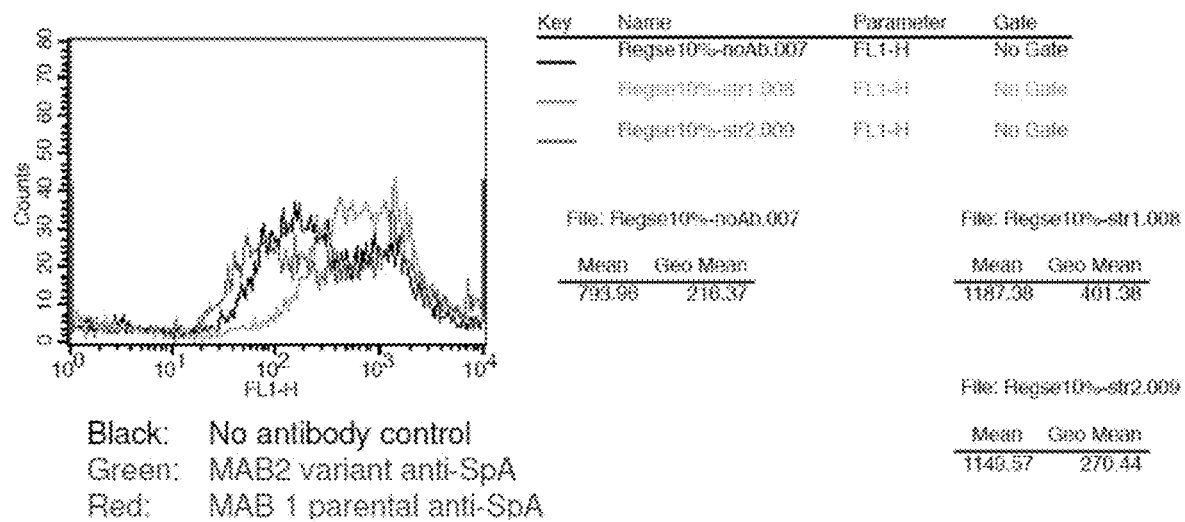
FIG. 32 shows a C3 complement deposition assay on Staph JE2 using FACS. C3 deposition on the surface of S. aureus stain JE2 was tested using the anti-SpA parental antibody (MAB1: Red plot) and an example anti-SpA variant antibody (MAB2; Green Plot).

Add anti-SpA parental (MAB1) or variant antibodies (MAB2) at a final concentration of 2 µg/ml. Incubate for 30 min at 37° C. Spin max/2 min, Wash 1× with 1 ml of 0.1% BSA+PBS, then resuspend in 100 ul of αC3b (diluted 1:200 in 0.1% BSA+PBS (Protos Immuno Research)). Incubate for 20 min at 4° C. and then wash as described above. Resuspend in 500 µl of PBS and analyse using FACS (FIG. 32).

Results: As can be seen in FIG. 32, the anti-SpA parental antibody was unable to deposited C3 on the surface of *S. aureus* JE2 (Control-black vs MAB1-Red). In contract, the anti-SpA variant antibody resulted in strong C3 deposition of the surface of *S. aureus* JE2 (MAB2-green). This result reinforces that data seen for C1q deposition, and demonstrates that *S. aureus* interacts with the heavy chain constant region of parental antibodies, blocking their effector function. This interaction is presumably mediated by *S. aureus* IgBPs including SpA. In contract, variant antibody MAB2 maintains its effector function as demonstrated by robust C1q and C3 deposition on the surface of *S. aureus* SpA expressing stains.

Example 15: Neutrophil-Mediated Opsonophagocytic Assay

An opsonization assay may be a colorimetric assay, a chemiluminescent assay, a fluorescent or radiolabel uptake assay, a cell-mediated bactericidal assay, or any other appropriate assay known in the art which measures the opsonic potential of a substance and thereby identifies reactive immunoglobulin. In an opsonization assay, an infectious agent, a cell, and the opsonizing substance to be tested are incubated together.

In certain embodiments, the opsonization assay is a cell-mediated bactericidal assay. In this in vitro assay, an infectious agent such as a bacterium, a phagocytic cell, and an opsonizing substance such as immunoglobulin, may be incubated together. Any eukaryotic cell with phagocytic or binding ability may be used in a cell-mediated bactericidal assay. In certain embodiments, phagocytic cells are macrophages, monocytes, neutrophils, or any combination of these cells. Complement proteins may be included to promote opsonization by both the classical and alternate pathways.

In one method, the ability of parental and variant anti-SpA antibodies and control antibodies were evaluated for the ability of example test antibodies to mediate the phagocytosis of opsonized bacteria labeled with FITC.

Figure 33:
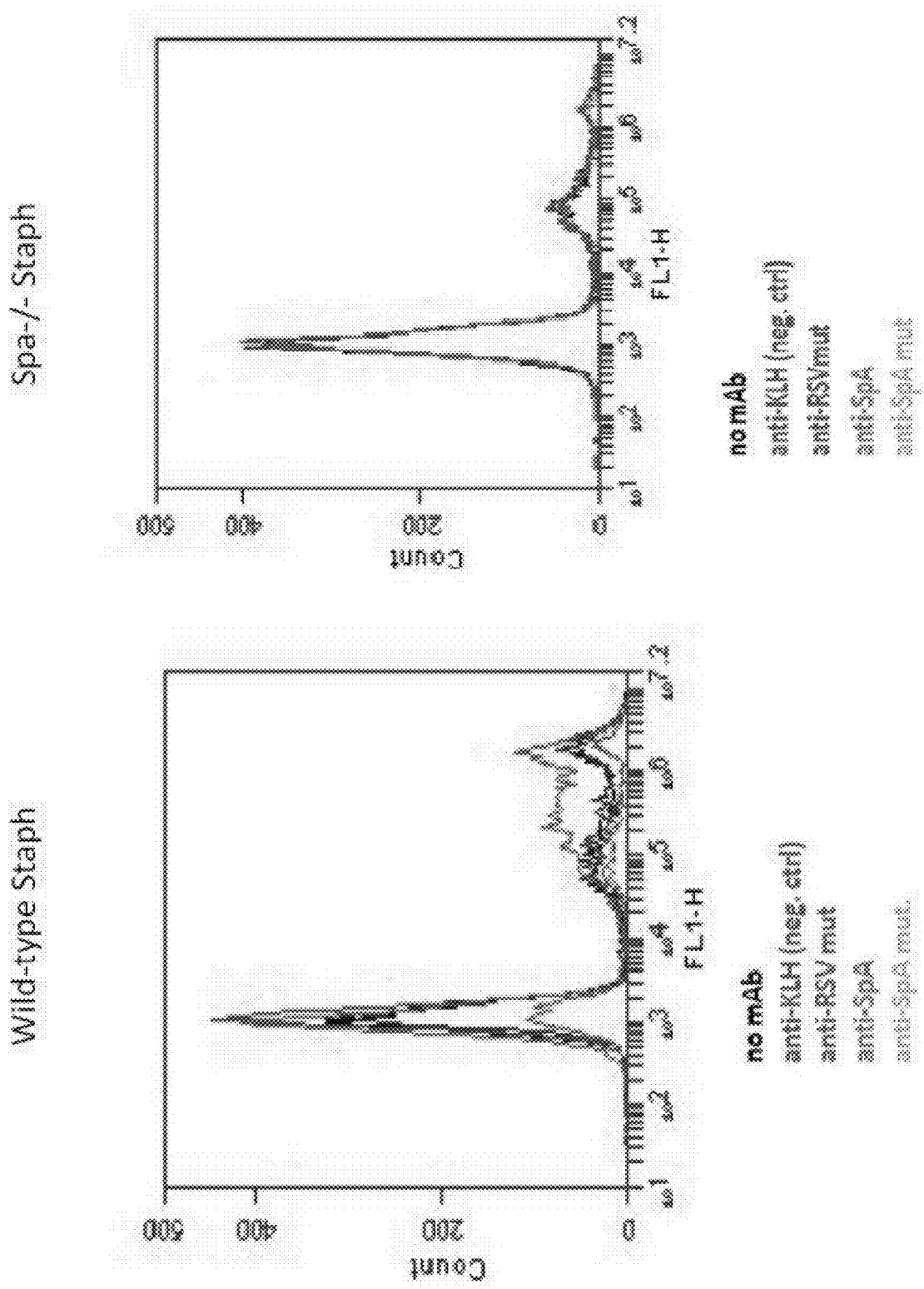
FIG. 33 illustrates neutrophil-mediated opsonophagocytic activity of anti-SpA antibodies. The anti-SpA parental antibody (MAB1—Green plot) and an example variant anti-SpA antibody (MAB2—pink plot) were tested in phagocytosis assay using S. aureus Newman stain (left panel) and a ΔSpA strain lacking SpA expression (right panel). Control anti-RSV variant (MAB5—Blue plot) and anti-KLH antibodies (Red Plot) are used as negative controls. Phagocytosis of FITC labeled S. aureus was analyzed by FACS.
Figure 34:
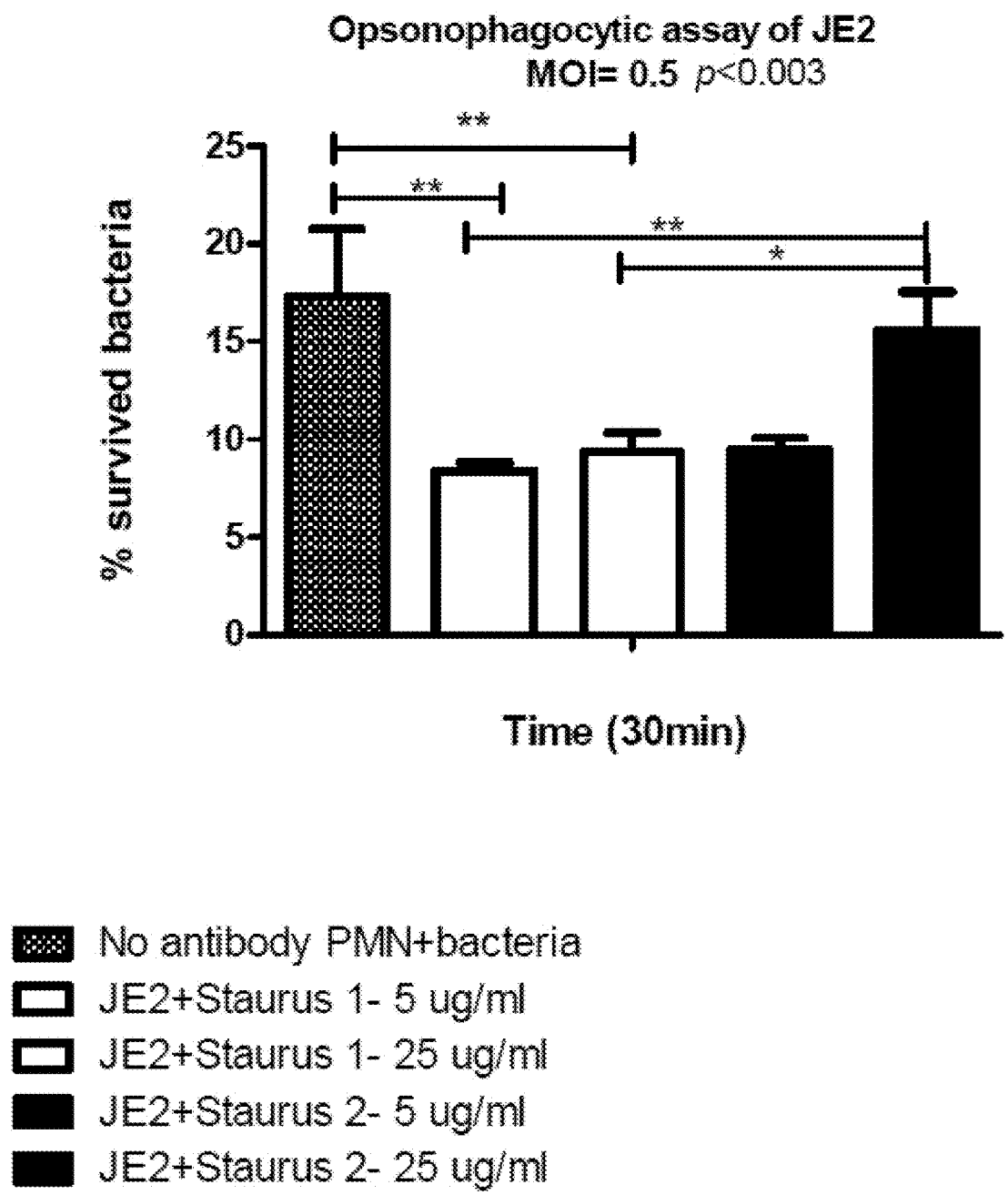
FIG. 34 shows an opsonophagocytic assay of anti-SpA antibodies. Opsonophagocytic assay of MAB1 and MAB2 using S. aureus JE2 was determined in a second Opsinophagocytic assay. % Bacterial survival (Y axis) was measured for S. aureus JE2 following treatment with MAB1 (dark bars) and MAB 2 (light bars) using 5 ug/ml and 25 ug/ml of test antibody. A control (no antibody) is shown on the left side (grey bar)
Figure 35:
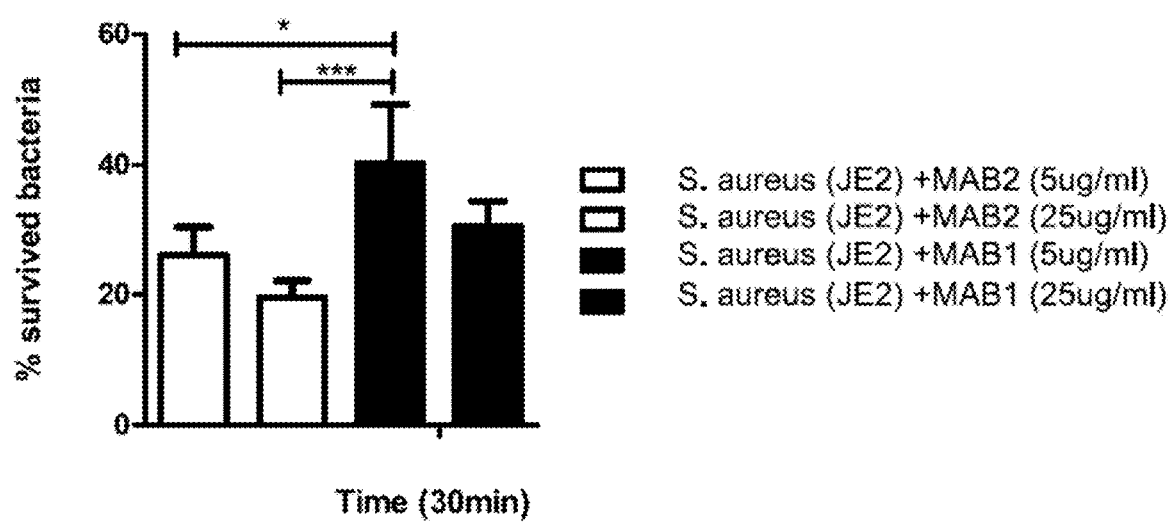
FIG. 35 shows a neutrophil-mediated opsonophagocytic bactericidal assay. Opsonophagocytic killing of S. aureus JE2 using pooled human serum. Parental anti-SpA MAB1 (Dark Bars) and an example variant anti-SpA MAB2 (light bars) were tested for their effect on the opsonophagocytic killing of S. aureus JE2 using 5 μg/ml (left bar of pair) and 25 μg/ml (right bar of pair) of test antibody.

The following method was performed: Resuspend FITC labeled bacteria in 1 ml cold OPA buffer (HBSS Ca++ & Mg+++ 0.2% BSA) at ~4.0E+08 CFU/ml. Opsonize with specific antibodies or control. Add 100 µl of Mab in OPA buffer to bacteria-FITC pellet (see above) for 30 minutes, 37 C shaking water bath. Aspirate dry, keep on ice in dark until phagocytosis assay set up. Add 100 µl of washed PMNs at 10E+06/ml (1.0E+06/tube) to opsonized bacterial cell pellet in mirotube, transfer to 12×75 mm polypropylene FACS tube. Incubate in 37° C. shaking H2O bath for 30 minutes. Next, add 100 µl of cold quench/tube (to quench the staining of any externally bound bacteria) vortex, add 2 ml of cold AB. Spin for 5 minutes at 1,200 rpm, 4° C. Decant supernatant and wash again with 2 ml of AB, 4° C. Add 0.5 ml of AB/tube (4° C.) read on Accuri, collect 5000 events, FL1. Reagents: OPA buffer: HBSS Ca++ & Mg+++ 0.2% BSA; AB: Dulbecco's DPBS–+2% FBS: Quench: Trypan blue (Gibco #15250-061) diluted 1:3 in DPBS– (1 ml trypan blue and 2 ml PBS): HBSS: Mg++ Ca++, Gibco, #14025-092; DPBS: no Mg++ Ca++, Sigma #D8537 or Lonza/BioWhittaker #17-512Q Phagocytosis Results: The anti-SpA parental antibody (MAB1) and an example variant anti-SpA antibody (MAB2) were tested in two phagocytosis assay (FIG. 33 and FIG. 34). In the first assay (FIG. 33), two control antibodies were used (an anti-RSV variant (MAB5) and a non-specific parental anti-KLH antibody). *S. aureus* Newman stain and a ΔSpA strain lacking SpA expression were used at the target bacteria. As shown in FIG. 33, the anti-SpA variant antibody was able to enhance the phagocytosis of the *S. aureus* wild type Newman strain as compared to control antibodies. The control antibodies were able to induce some non-specific uptake. The parental anti-SpA antibody gave a similar results as the control antibodies, demonstrating that *S. aureus* is able to suppress the effector function of the parental ant-SpA antibody (MAB1), but not that of its variant (MAB2). No enhancement of phagocytosis was seen using the ΔSpA *S. aureus* strain, demonstrating variable domain specificity of the enhanced effector function of the anti-SpA variant antibody MAB2.

In a second opsono-phagocytosis assay format, anti-SpA MAB 1 and 2 (variant) were tested (FIG. 34). The opsonic ability of an antibody is determined by the amount or number of infectious agents remaining after incubation. The fewer the number of infectious agents that remain after incubation, the greater the opsonic activity of the antibody tested. In a cell-mediated bactericidal assay, opsonic activity is measured by comparing the number of surviving bacteria between two similar assays, only one of which contains the antibody being tested. Alternatively, opsonic activity is determined by measuring the number of viable organisms before and after incubation with a sample antibody. A reduced number of bacteria after incubation in the presence of antibody indicates a positive opsonizing activity. In the cell-mediated bactericidal assay, positive opsonization is determined by culturing the incubation mixture under appropriate bacterial growth conditions. Any reduction in the number of viable bacteria comparing pre-incubation and post-incubation samples, or between samples, which contain immunoglobulin, and those that do not, is a positive reaction. As can be seen (FIG. 34) the variant anti-SpA antibody (MAB2) resulted in significant enhanced opssonphagocytic activity as measured by bacterial survival when compared to the Parental MAB1. The control represents bacterial survival in the absence of added antibody.

Example 16: Neutrophil-Mediated Opsonophagocytic Bactericidal Assay

Opsono-phagocytic killing of *S. aureus* JE2 using pooled human serum. The following assay was used to test parental and variant anti-SpA antibodies for their effect on the opsonophagocytic killing of *S. aureus* JE2

Bacteria were grown overnight in THB. In the morning dilute cultures 1:40 in fresh THB and grow to OD600 nm=0.4. Pellet *S. aureus* at @ 4000 rpm for 10 min then wash in 10 ml of PBS. Centrifuge as above and resuspend in 300 ul of PBS. Adjust to the OD600 nm=0.4 in 3 ml of PBS. Dilute bacteria 1:5 in pooled human serum using siliconized tube. Test antibodies (MAB1 and MAB2) were added to tubes at a final concentration of 5 μg/ml and 25 μg/ml. Tubes were incubated at 37° C. for 30 min, then diluted 1:40 in RPMI. 100 μl of bacteria were added to 100 ul of neutrophils (MOI=0.5) in 96 well tissue culture plates, spun at 1600 rpm for 5 min and incubate at 37° C.+$CO_2$ for 30 min. After 30 min, serial dilutions were made in molecular grade water and then plated on THA plates.

Results: It can be seen from FIG. 35 that there was a significant increase in opsonophagocytic killing of *S. aureus* JE2 by the variant anti-SpA antibody as compared to the parental anti-Spa antibody.

Example 17: Generation of Additional Humanized Anti-SpA IgG1 Antibodies and their Variants Additional Anti SpA Antibodies:

In additional examples of anti-SpA Fc variant antibody design, CDR sequences from murine antibodies were used for the design of additional preferred anti-SpA humanized antibodies. These parental humanized antibodies were then used for the design of Fc variant antibodies as previously described in Example 5. The heavy and light chain CDR amino acid sequences from antibodies 3F6, 5A10 and 3D11 (Kim et al., 2012) were obtained from Patent Application WO 2013/142349 A1. In one embodiment, 3F6 is selected for generating an anti-SpA antibody because it was able to bind to all 5 domains of SpA and to Sbi (Kim et al., 2012). In another embodiment, antibody 5A10 is selected for generating an anti-SpA antibody because it was able to recognize all 5 SpA domains, but not Sbi. To design chimeric and humanized antibodies using the limited sequence data available, CDR sequences from each antibody were first used to design murine heavy and light chain variable domain sequences based on CDR amino acid sequence alignment. Designed sequences are shown in SEQ ID NOs: 181-186 below. In SEQ ID Nos: 182, 184 and 186, (X) represents an insertion of 0, 1 or 2 amino acids.

```
SEQ ID NO: 181 (LC CDR murine graft-GKV4-55*01-
IGKJ1):
QIVLTQSPAIMSASPGEKVTMTCSASSSVSYMYWYQQKPGSSPRLLIY

DTSNLASGVPVRFSGSGSGTSYSLTISRMEAEDAATYYCQQWSSYPPT

FGGGTKLEIK

SEQ ID NO: 182 (HC CDR murine graf-IGHV5-9-4*01-
IGHJ4):
EVQLVESGGGLVKPGGSLKLSCAASGFAFSNYDMSWVRQSPEKRLEWV

AEISSGGTYPYPDTVTGRFTISRDNAKNTLYLEMSSLRSEDTAMYYCA

R(X)GGFLITTRDYYAMDYWGQGTSVTVSS

SEQ ID NO: 183 (LC CDR murine graft-IGKV3-1*01-
IGKJ1):
DIVLTQSPASLAVSLGQRATISCRASESVEYSGASLMQWYQQKPGQPP
```

-continued

```
KLLIYAASNVESGVPARFSGSGSGTDFSLNIHPVEEDDIAMYFCQQSR

KVPSTFGGGTKLEIK

SEQ ID NO: 184 (HC CDR murine graft-IGHV10S3*01-
IGHJ4):
EVQLVETGGGLVQPKGSLKLSCAASGFTFNTNAMNWVRQAPGKGLEWV

ARIRSKSNNYATYYADSVKDRFTISRDDSQSMLYLQMNNLKTEDTAMY

YC(X)VTEHYDYDYYVMDYWGQGTSVTVSS

SEQ ID NO: 185 (LC CDR murine graft-IGKV4-86*01-
IGKJ1):
EIVLTQSPAITAASLGQKVTITCSASSSVSYMHWYQQKSGTSPKPWIY

EISKLASGVPARFSGSGSGTSYSLTISSMEAEDAAIYYCQQWSYPFTF

GSGTKLEIK

SEQ ID NO: 186 (HC CDR murine graft-IGHV1S30*01-
IGHJ4):
EVQLQQSGPELVKLGPSVKISCKASGYSFTSYYMHWVKQSHGKSLEWI

GEIDPFNGGTSYNQKFKGKATLTVDTSSSTAYMELHSLTSEDSLVYYC

AR(X)YGYDGTFYAMDYWGQGTSVTVSS
```

The murine heavy (SEQ ID NOs: 182, 184 and 186) and light chain variable sequences (SEQ ID NOs: 181, 183 and 185) were then used for the design of chimeric antibodies (containing murine variable domain sequences and human constant domain sequences). Such methods can be used for any heavy and light chain combination selected from SEQ ID NOs: 181-186. Examples of the construction of a chimeric antibodies and their Fc variants are provided, using the CDR grafted murine variable region sequences SEQ ID NO:183 (light chain variable domain) and SEQ ID NO:184 (heavy chain variable domain). The murine IGHV10-1 gene (SEQ ID NO: 193) was used to generate the CDR grafted murine heavy chain (SEQ ID NO: 184). This is then combined with a human IgG1 heavy chain constant sequence of allotype G1m17 (SEQ ID NO:30). As described previously, any IgG1 allotype can also be used for the IgG heavy chain construction.

The heavy chain amino acid sequence of the resulting Fc chimeric antibodies are provided as SEQ ID NOs: 194 and 195. Likewise, the murine variable light chain sequence mIGKV3-1 (SEQ ID NO: 187) was used to generate a CDR grafted variable murine Kappa light chain and full length light chain (SEQ ID NOs: 183 and 188).

Fc variant antibodies can be constructed as described previously using Fc variants provided in SEQ ID NOS: 31-56. For example, variant heavy chains incorporating the Fc region of SEQ ID NO: 40 are provided (SEQ ID NOs: 196-197).

Following codon optimization of the target polypeptides for mammalian expression, DNA encoding a Kozak sequence, an N-terminal leader secretion sequence can be synthesized, cloned into a mammalian expression vector such as pTT5, and expressed in HEK 293 cells using methods well known in the art (for example, as described previously herein).

```
SEQ ID NO: 187 murine VL sequence mIGKV3-1:
DIVLTQSPASLAVSLGQRATISCRASESVEYYGTSLMQWYQQKPGQPP

KLLIYAASNVESGVPARFSGSGSGTDFSLNIHPVEEDDIAMY

SEQ ID NO: 188 Chimeric light chain amino acid
sequence mIGKV3-cdr graft:
DIVLTQSPASLAVSLGQRATISCRASESVEYSGASLMQWYQQKPGQPP
```

KLLIYAASNVESGVPARFSGSGSGTDFSLNIHPVEEDDIAMYFCQQSR

KVPSTFGGGTKVEIKRTVAAPSVFIFPPSDEQLKSGTASVVCLLNNFY

PREAKVQWKVDNALQSGNSQESVTEQDSKDSTYSLSSTLTLSKADYEK

HKVYACEVTHQGLSSPVTKSFNRGEC

SEQ ID NO: 189 Human VL sequence IGKV1D-39*1:
DIQMTQSPSSLSASVGDRVTITCRASQSISSYLNWYQQKPGKAPKLLI

YAASSLQSGVPSRFSGSGSGTDFTLTISSLQPEDFATYYCQQSYSTP

SEQ ID NO: 190 Human VL sequence IGKV4-1*1:
DIVMTQSPDSLAVSLGERATINCKSSQSVLYSSNNKNYLAWYQQKPGQ

PPKLLIYWASTRESGVPDRFSGSGSGTDFTLTISSLQAEDVAVYYCQQ

YYSTP

SEQ ID NO: 191 Humanized light chain amino acid
sequence hIGKV1D-39-cdr graft-IGKJ1-hIgKC:
DIQMTQSPSSLSASVGDRVTITCRASESVEYSGASLMQWYQQKPGKAP

KLLIYAASNVESGVPSRFSGSGSGTDFTLTISSLQPEDFATYYCQQSR

KVPSTFGGGTKVEIKRTVAAPSVFIFPPSDEQLKSGTASVVCLLNNFY

PREAKVQWKVDNALQSGNSQESVTEQDSKDSTYSLSSTLTLSKADYEK

HKVYACEVTHQGLSSPVTKSFNRGEC

SEQ ID NO: 192 Humanized light chain amino acid
sequence hIGKV4-1-cdr graft-IGKJ1-hIgKC:
DIVMTQSPDSLAVSLGERATINCRASESVEYSGASLMQWYQQKPGQPP

KLLIYAASNVESGVPDRFSGSGSGTDFTLTISSLQAEDVAVYYCQQSR

KVPSTFGGGTKVEIKRTVAAPSVFIFPPSDEQLKSGTASVVCLLNNFY

PREAKVQWKVDNALQSGNSQESVTEQDSKDSTYSLSSTLTLSKADYEK

HKVYACEVTHQGLSSPVTKSFNRGEC

SEQ ID NO: 193 murine VH sequence IGHV10-1:
EVQLVESGGGLVQPKGSLKLSCAASGFSFNTYAMNWVRQAPGKGLEWV

ARIRSKSNNYATYYADSVKDRFTISRDDSESMLYLQMNNLKTEDTAMY

YCVR

SEQ ID NO: 194 Chimeric heavy chain amino acid
sequence mIGHV10-IGHJ4-hIgG1
EVQLVESGGGLVQPKGSLKLSCAASGFTFNTNAMNWVRQAPGKGLEWV

ARIRSKSNNYATYYADSVKDRFTISRDDSESMLYLQMNNLKTEDTAMY

YCVTEHYDYDYYVMDYWGQGTSVTVSSASTKGPSVFPLAPSSKSTSGG

TAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCS

VMHEALHNHYTQKSLSLSPGK

SEQ ID NO: 195 Chimeric heavy chain amino acid
sequence mIGHV10-IGHJ4-hIgG1
EVQLVESGGGLVQPKGSLKLSCAASGFTFNTNAMNWVRQAPGKGLEWV

ARIRSKSNNYATYYADSVKDRFTISRDDSESMLYLQMNNLKTEDTAMY

YCARVTEHYDYDYYVMDYWGQGTSVTVSSASTKGPSVFPLAPSSKSTS

GGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKAL

PAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFS

CSVMHEALHNHYTQKSLSLSPGK

SEQ ID NO: 196 Chimeric heavy chain variant
amino acid sequence mIGHV10-IGHJ4-hIgG1
EVQLVESGGGLVQPKGSLKLSCAASGFTFNTNAMNWVRQAPGKGLEWV

ARIRSKSNNYATYYADSVKDRFTISRDDSESMLYLQMNNLKTEDTAMY

YCVTEHYDYDYYVMDYWGQGTSVTVSSASTKGPSVFPLAPSSKSTSGG

TAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEL

LGGPSVFLFPPKPKDTLMISRTPEVTCVVVDVSHEDPEVQFNWYVDGV

EVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCS

VMHEALHNRFTQKSLSLSPGK

SEQ ID NO: 197 Chimeric heavy chain variant
amino acid sequence mIGHV10-IGHJ4-hIgG1
EVQLVESGGGLVQPKGSLKLSCAASGFTFNTNAMNWVRQAPGKGLEWV

ARIRSKSNNYATYYADSVKDRFTISRDDSESMLYLQMNNLKTEDTAMY

YCARVTEHYDYDYYVMDYWGQGTSVTVSSASTKGPSVFPLAPSSKSTS

GGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAP

ELLGGPSVFLFPPKPKDTLMISRTPEVTCVVVDVSHEDPEVQFNWYVD

GVEVHNAKTKPREEQYNSTYRVVSVLTVLHQDWLNGKEYKCKVSNKAL

PAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFS

CSVMHEALHNRFTQKSLSLSPGK

SEQ ID NO: 198 Human VH sequence IGHV3-73
EVQLVESGGGLVQPGGSLKLSCAASGFTFSGSAMHWVRQAPGKGLEWV

GRIRSKANSYATAYAASVKGRFTISRDDSKNTLYLQMNSLKTEDTAVY

YCTR

SEQ ID NO: 199 Human VH sequence IGHV3-23_1
EVQLLESGGGLVQPGGSLRLSCAASGFTFSSYAMSWVRQAPGKGLEWV

SAISGSGGSTYYADSVKGRFTISRDNSKNTLYLQMNSLRAEDTAVYYC

AK

SEQ ID NO: 200 Humanized heavy chain amino acid
sequence: hIGHV3-73graft-IGHJ4-hIgG1
EVQLVESGGGLVQPGGSLRLSCAASGFTFNTNAMNWVRQAPGKGLEWV

GRIRSKSNNYATYYADSVKDRFTISRDDSKNSLYLQMNSLKTEDTAVY

YCAREHYDYDYYVMDYWGQGTSVTVSSASTKGPSVFPLAPSSKSTSGG

TAALGCLVKDYFPEPVTVSWNSGALTSGVHTFPAVLQSSGLYSLSSVV

-continued

TVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCS

VMHEALHNHYTQKSLSLSPGK

SEQ ID NO: 201 Humanized heavy chain amino acid
sequence: hIGHV3-73graft-IGHJ4-hIgG1
EVQLVESGGGLVQPGGSLRLSCAASGFTFNTNAMNWVRQAPGKGLEWV

GRIRSKSNNYATYYADSVKDRFTISRDDSKNSLYLQMNSLKTEDTAVY

YCARVTEHYDYDYYVMDYWGQGTSVTVSSASTKGPSVFPLAPSSKSTS

GGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKAL

PAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFS

CSVMHEALHNHYTQKSLSLSPGK

SEQ ID NO: 202 Humanized heavy chain amino acid
sequence: hIGHV3-23graft-IGHJ4-hIgG1
EVQLLESGGGLVQPGGSLRLSCAASGFTFNTNAMNWVRQAPGKGLEWV

SRIRSKSNNYATYYADSVKDRFTISRDNSKNTLYLQMNSLRAEDTAVY

YCAKEHYDYDYYVMDYWGQGTSVTVSSASTKGPSVFPLAPSSKSTSGG

TAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCS

VMHEALHNHYTQKSLSLSPGK

SEQ ID NO: 203 Humanized heavy chain amino acid
sequence: hIGHV3-23graft-IGHJ4-hIgG1
EVQLLESGGGLVQPGGSLRLSCAASGFTFNTNAMNWVRQAPGKGLEWV

SRIRSKSNNYATYYADSVKDRFTISRDNSKNTLYLQMNSLRAEDTAVY

YCAKVTEHYDYDYYVMDYWGQGTSVTVSSASTKGPSVFPLAPSSKSTS

GGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKAL

PAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFS

CSVMHEALHNHYTQKSLSLSPGK

CDR Grafting and Humanization of Anti-SpA Antibodies:
CDR grafting can be used to humanize murine antibodies sequences. Designed murine variable domain sequences SEQ ID NOs:181-186 were used to BLAST human IGHV and IGKV germline sequences using methods known in the art. The closest human V-gene alignments to sequences SEQ ID NOs:181-186 were used for the design of CDR grafted humanized heavy and light chains. A number of V genes with varying degrees of amino acid identity to the search sequence can be used for humanization. Examples of human germ line IGLV and IGHV gene sequences selected following alignment to murine SEQ ID NO: 181-186 are as follows: SEQ ID NO: 181: IGKV3-111; SEQ ID NO: 182: IGHV3-66*4; SEQ ID NO: 183: IGKV4-11 and IGKV1D-391; SEQ ID NO: 184: IGHV3-73*2, IGHV 3-731 and IGHV 3-231; SEQ ID NO: 185: IGKV3-111; SEQ ID NO: 186: IGHV1-46*3. In addition to the above examples, any other human V gene sequence or allotype can be used for CDR grafting.

Examples of the construction of CDR grafted, humanized anti-SpA antibodies and their Fc variants are provided. Such grafted humanized antibodies sequences, in addition to an affinity maturation process may require an additional maturation process, resulting in one or more maturation mutations to arrive at a therapeutic humanized antibody having optimal affinity and other improved physicochemical properties such as affinity, avidity, stability, solubility, expression level, and/or biological activity. Standard methodology known to those practicing the art can be used for both CRD grafting, affinity maturation or physicochemical optimization. In one illustrative example, CDR grafting was used to humanize the sequence of an anti-SpA murine antibody using the HC and LC CDR sequences from DNA encoding the antibody 3F6. The same methods can be used for the humanization of antibodies derived from the murine CDR grafted sequences SEQ ID NOS: 181, 182, 185 and 186. As a non-limiting example of the humanization method, designed murine variable LC and HC sequences SEQ ID NOS: 183 and 184 are shown. The closest human germ line V-gene alignments to the murine VL SEQ ID NO: 183 and VH sequence SEQ ID NO: 184 were used for the design of CDR grafted humanized heavy and light chains. For the construction of CDR grafted light and heavy chains, the following human germ line sequences were selected for grafting IGKV4-11 (SEQ ID NO:190), IGKV1D-391 (SEQ ID NO:189), IGHV3-73, (SEQ ID NO:198) and IGHV 3-231 (SEQ ID NO:199).

CDRs sequences were grafted into human IgG1 heavy chain and Kappa light antibody backbone sequences. The resulting humanized parental heavy (SEQ ID NOs:200-203) and light chain (SEQ ID NOS:191 and 192) sequences are provided. The IgG1 allotype of the example provided it that on G1m17 (SEQ ID NO:30). As described previously, any IgG1 allotype can also be used for the IgG heavy chain construction.

Following codon optimization of the target polypeptides for mammalian expression, DNA encoding a Kozak sequence, an N-terminal leader secretion sequence can be synthesized, cloned into a mammalian expression vector such as pTT5, and expressed in HEK 293 cells using methods well known in the art (as described herein). Heavy chains (SEQ ID NOs: 200-203) can be expressed with either light chain (SEQ ID NOs: 191 or 192). The resulting secreted antibody can be purified from culture media using methods described previously or known in the art, examples of which are described herein.

For the construction of humanized Fc variants derived from the described parental heavy chains (SEQ ID NOs: 200-203), Fc domain variant sequences can be used as described for Example 5. Examples of such substitute variant heavy chain constant sequences are provided in SEQ ID NOs: 31-56, and anti-SpA humanized Fc variant heavy chains using one substitute variant heavy chain constant sequence (SEQ ID NO:40) are shown in SEQ ID NOs:204-207 below.

```
SEQ ID NO: 204 Humanized variant heavy chain
amino acid sequence: hIGHV3-73graft-IGHJ4-hIgG1:
EVQLVESGGGLVQPGGSLRLSCAASGFTFNTNAMNWVRQAPGKGLEWV

GRIRSKSNNYATYYADSVKDRFTISRDDSKNSLYLQMNSLKTEDTAVY

YCAREHYDYDYYVMDYWGQGTSVTVSSASTKGPSVFPLAPSSKSTSGG

TAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEL

LGGPSVFLFPPKPKDTLMISRTPEVTCVVVDVSHEDPEVQFNWYVDGV

EVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCS

VMHEALHNRFTQKSLSLSPGK

SEQ ID NO: 205 Humanized variant heavy chain
amino acid sequence: hIGHV3-73graft-IGHJ4-hIgG1:
EVQLVESGGGLVQPGGSLRLSCAASGFTFNTNAMNWVRQAPGKGLEWV

GRIRSKSNNYATYYADSVKDRFTISRDDSKNSLYLQMNSLKTEDTAVY

YCARVTEHYDYDYYVMDYWGQGTSVTVSSASTKGPSVFPLAPSSKSTS

GGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAP

ELLGGPSVFLFPPKPKDTLMISRTPEVTCVVVDVSHEDPEVQFNWYVD

GVEVHNAKTKPREEQYNSTYRVVSVLTVLHQDWLNGKEYKCKVSNKAL

PAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFS

CSVMHEALHNRFTQKSLSLSPGK

SEQ ID NO: 206 Humanized variant heavy chain
amino acid sequence: hIGHV3-23graft-IGHJ4-hIgG1:
EVQLLESGGGLVQPGGSLRLSCAASGFTFNTNAMNWVRQAPGKGLEWV

SRIRSKSNNYATYYADSVKDRFTISRDNSKNTLYLQMNSLRAEDTAVY

YCAKEHYDYDYYVMDYWGQGTSVTVSSASTKGPSVFPLAPSSKSTSGG

TAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEL

LGGPSVFLFPPKPKDTLMISRTPEVTCVVVDVSHEDPEVQFNWYVDGV

EVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCS

VMHEALHNRFTQKSLSLSPGK

SEQ ID NO: 207 Humanized variant heavy chain
amino acid sequence: hIGHV3-23graft-IGHJ4-hIgG1:
EVQLLESGGGLVQPGGSLRLSCAASGFTFNTNAMNWVRQAPGKGLEWV

SRIRSKSNNYATYYADSVKDRFTISRDNSKNTLYLQMNSLRAEDTAVY

YCAKVTEHYDYDYYVMDYWGQGTSVTVSSASTKGPSVFPLAPSSKSTS

GGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAP

ELLGGPSVFLFPPKPKDTLMISRTPEVTCVVVDVSHEDPEVQFNWYVD

GVEVHNAKTKPREEQYNSTYRVVSVLTVLHQDWLNGKEYKCKVSNKAL

PAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFS

CSVMHEALHNRFTQKSLSLSPGK
```

Fc variant antibodies derived from SEQ ID NOs:200-203 can be constructed as described previously using Fc variants provided in SEQ ID NOs:31-56. For example variant heavy chains incorporating the Fc region of SEQ ID NO:40 are provided (SEQ ID NOs:204-207). Following codon optimization of the target polypeptides (i.e. heavy chain, or its variant and light chain) for mammalian expression, DNA encoding a Kozak sequence, an N-terminal leader secretion sequence can be synthesized, cloned into a mammalian expression vector such as pTT5, and expressed in HEK 293 cells using methods well known in the art (examples of which are described herein). Heavy chains (SEQ ID NO: 204-207) can be expressed with either described light chain (SEQ ID NO: 191 or 192). The resulting secreted antibody can be purified from culture media using methods described previously or known in the art.

Heavy chain constant region Fc variants which do not bind SpA are preferred for used in screening chimeric, CDR grafted and affinity mutated antibodies so as to avoid SpA-Fc binding in ELISA assays, and to allow accurate binding measurements to be made with full length antibodies using ELISA, BIACore or DLS (Dynamic Light Scattering).

Following codon optimization for mammalian expression, DNA encoding a Kozak sequence, an N-terminal leader secretion sequence and the target polypeptides are synthesized, cloned into a mammalian expression vector pTT5, and expressed in HEK 293 cells using methods well known in the art (described previously). Methods previously described in Examples 5 to 16 can be used for expression, purification and biological analysis of parental or variant anti-SpA antibodies.

In another example of the generation of a humanized anti-SpA antibodies and their variants, the CDRs from murine antibody 5A10 was used for the generation of chimeric and humanized antibodies as described above. Designed murine variable LC and HC sequences are shown in SEQ ID NOs:181 and 182. The closest human germ line V-gene alignments to the murine VL SEQ ID NO: 181 and VH sequence SEQ ID NO 182 were IGKV3-111 and IGHV3-66*4. These germ line VL and LH sequences were used for the design of CDR grafted humanized heavy and light chains.

CDRs sequences were grafted into human IgG1 heavy chain and Kappa light antibody backbone sequences. The resulting humanized parental heavy (SEQ ID NO: 209-210) and light chain (SEQ ID NO:208) sequences are provided. The IgG1 allotype of the example provided it that on G1m17 (SEQ ID NO:30). As described previously, any IgG1 allotype can also be used for the IgG heavy chain construction. Additionally, other germ line human VH and VL sequences can be used for CDR grafting.

SEQ ID NO: 208 Humanized light chain amino acid
sequence IGKV3-11*-1-cdr graft-IGKJ1-hIgKC:
EIVLTQSPATLSLSPGERATLSCRASQSVSYLAWYQQKPGQAPRLLI

YDTSNRATGIPARFSGSGSGTDFTLTISSLEPEDFAVYYCQQWSSYPP

TFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

SEQ ID NO: 209 Humanized heavy chain amino acid
sequence: hIGHV3-66*4 graft-IGHJ4-hIgG1:
EVQLVESGGGLVQPGGSLRLSCAASGFAFSNYDMSWVRQAPGKGLEWV

SVISSGGTYPYADSVKGRFTISRDNSKNTLYLQMNSLRAEDTAVYYCA

RARGGFLITTRDYYAMDYWGQGTSVTVSSASTKGPSVFPLAPSSKSTS

GGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKAL

PAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFS

CSVMHEALHNHYTQKSLSLSPGK

SEQ ID NO: 210 Humanized heavy chain amino acid
sequence: hIGHV3-66*4 graft-IGHJ4-hIgG1:
EVQLVESGGGLVQPGGSLRLSCAASGFAFSNYDMSWVRQAPGKGLEWV

SVISSGGTYPYADSVKGRFTISRDNSKNTLYLQMNSLRAEDTAVYYCA

RGGFLITTRDYYAMDYWGQGTSVTVSSASTKGPSVFPLAPSSKSTSGG

TAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCS

VMHEALHNHYTQKSLSLSPGK

For the construction of humanized Fc variants derived from the described parental heavy chains (SEQ ID NO: 209-210), Fc domain variant sequences can be used as described for Example 5. Examples of such substitute variant heavy chain constant sequences are provided in SEQ ID NO: 211-212.

SEQ ID NO: 211 Humanized variant heavy chain
amino acid sequence: hIGHV3-66*4-23graft-
IGHJ4-hIgG1:
EVQLVESGGGLVQPGGSLRLSCAASGFAFSNYDMSWVRQAPGKGLEWV

SVISSGGTYPYADSVKGRFTISRDNSKNTLYLQMNSLRAEDTAVYYCA

RARGGFLITTRDYYAMDYWGQGTSVTVSSASTKGPSVFPLAPSSKSTS

GGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAP

ELLGGPSVFLFPPKPKDTLMISRTPEVTCVVVDVSHEDPEVQFNWYVD

GVEVHNAKTKPREEQYNSTYRVVSVLTVLHQDWLNGKEYKCKVSNKAL

PAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFS

CSVMHEALHNRFTQKSLSLSPGK

SEQ ID NO: 212 Humanized variant heavy chain
amino acid sequence: hIGHV3-66*4 graft-
IGHJ4-hIgG1:
EVQLVESGGGLVQPGGSLRLSCAASGFAFSNYDMSWVRQAPGKGLEWV

SVISSGGTYPYADSVKGRFTISRDNSKNTLYLQMNSLRAEDTAVYYCA

RGGFLITTRDYYAMDYWGQGTSVTVSSASTKGPSVFPLAPSSKSTSGG

TAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEL

LGGPSVFLFPPKPKDTLMISRTPEVTCVVVDVSHEDPEVQFNWYVDGV

EVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCS

VMHEALHNRFTQKSLSLSPGK

Following codon optimization of the target polypeptides for mammalian expression, DNA encoding a Kozak sequence, an N-terminal leader secretion sequence can be synthesized, cloned into a mammalian expression vector such as pTT5, and expressed in HEK 293 cells using methods well known in the art (as described herein). Heavy chains (SEQ ID NOs: 209-212) can be expressed with light chain (SEQ ID No: 208). The resulting secreted antibody can be purified from culture media using methods described previously or known in the art, examples of which are described herein.

Example 18: Attenuation of Superantigen Type Binding of VH3 Derived Humanized Antibodies to SpA Some of the claimed humanized antibodies of the current invention utilize heavy chain variable sequences derived from the IGHV-3 family of germ line V gene sequences. Antibodies using such IGHV-3 gene sequences have the potential to bind SpA in a superantigen like manner (as described in Graille et al., 2000). The IGHV amino acids responsive for such non-immune binding have been defined from the crystal structure of *S. aureus* Protein A complexed with the Fab fragment of a human VH3 derived antibody.

Interactions involve the following heavy chain amino acids: H15, H17, H19, H57, H59, H64, H65, H66, H68, H69, H70, H80, H81, H82a and H82b (FIGS. 3*a* and *b*). To attenuate superantigen binding to IGHV-3 sequences present in the variable region of the heavy chains of any of the antibodies of the invention described herein, one or more amino acid changes can be introduced at contact residues (i.e. one or more changes can be introduced at positions selected from the list including but not limited to H15 G, H17 S, H19 R, H57 X (X can be K, I or T), H59 Y, H64 K, H65 G, H66 R, H68 T, H70 S, H81 Q, H82a N and H82b S) such that the resulting amino acid is different from that of the original parental IGHV-3 derived VH gene sequence. In other words, according to some embodiments, a variant immunoglobulin heavy chain that is part of an anti-*Staphylococcus aureus* (e.g., anti-SpA) variable heavy chain sequence variant antibody includes one or more amino acid substitutions in its variable heavy chain sequence as compared to a parental anti-SpA antibody, wherein the one or more amino acid substitutions include one or more Kabat positions selected from heavy chain positions H15, H17, H19, H57, H59, H64, H65, H66, H68, H69, H70, H80, H81 and, H82a, H82b. The parental antibody may be any suitable anti-*Staphylococcus aureus* or anti-SpA antibody including, but not limited to, an anti-SpA humanized antibody, an anti-SpA Fc variant antibody, an anti-SpA matured antibody, or an anti-SpA matured Fc variant antibody Using the X-ray structure (FIG. 3), which defines IGHV-3 SpA interactions, and the IMGT, NCBI and VBASE databases of germ line IGHV3 alleles/polymorphisms, the following amino acid substitutions were designed to attenuate SpA IGHVH3 interactions:

H19R to K (found in 3-73)
H82a N to I (found in 3-15*08)
H82a N to S (found in 3-30*15)
H80/N82a to L to V/N to S (found in 3-64*3 and *5)
H81 Q to H ((found in 3-47*01)
H68 T to A ((found in 3-30*09)
H68/H69 TI to NT ((found in 3-251 to *5)
H68 Y to H ((found in 3-631 and *2)
H17 S to A ((found in 3-13*02)

The above amino acid changes can be introduced either alone or in any combination so as to attenuate SpA-VH3 binding.

In a second approach to selection of amino acid substitutions at positions including but not limited to H15 G, H17 S, H19 R, H57 X (X can be K, I or T), H59 Y, H64 K, H65 G, H66 R, H68 T, H70 S, H81 Q, H82a N and H82b S, analysis of in vivo somatic hyper mutation events were analyzed using data in the NCBI archive of antibody sequences. IGHV mutations are aligned to IGHV-3 germ line sequences as described in Bowers et al 2013, (THE JOURNAL OF BIOLOGICAL CHEMISTRY VOL. 288, NO. 11, pp. 7688-7696, Mar. 15, 2013). Mutations were then modeled onto the x-ray crystal structure of the SpA IGHV-3 interface (FIG. 3) and mutations predicted to disrupt SpA finding to IGHV-3 germ line sequences include, but are not limited to:

H17S to P
H19R to G. K or T
H57K, I or T to A, P, R, or S
H59Y to F, H, N, or S
H68 T to A, I or S
H70S to F
H81Q to E, H or R
H82a N or G to D, H, K, S, T
H82b S to G, N, or T

Such amino acid changes can be introduced either alone or in any combination so as to attenuate SpA-VH3 binding. Such mutations can be introduced into antibodies VH domains of the invention by methods known in the art.

Alternatively, the antibody can be modified by in vitro or in vivo SHM so as to introduce mutations into the variable domain, including framework regions, that attenuates IGHV-3 superantigen binding to SpA, but are neutral, or enhance affinity of the variable domain for antigen specific binding to Spa or Sbi.

REFERENCES

The references, patents and published patent applications listed below, and all references cited in the specification above are hereby incorporated by reference in their entirety, as if fully set forth herein.

Acharya K R, Passalacqua E F, Jones E Y, Harlos K, Staurt D I, Brehm R D. Structural basis of superantigen action inferred from crystal structure of toxic-shock syndrome toxin-1. Nature 1994; 367: 94-7;

Almagro J C, Fransson J (2008) Humanization of antibodies. Front Biosci 13:1619-1633

Al-Shangiti A M, Nair S P, Chain B M (2005) Clin Exp Immunol 140:461-469

ANDERS LARSSON* AND JOHN SJOQUIST, JOURNAL OF CLINICAL MICROBIOLOGY, December 1989, p. 2856-2857 Vol. 27

Arcus V L, Langley R, Proft T, Fraser J D, Baker E N (2002a) J Biol Chem 277:32274-32281.

Arcus V (2002b) Curr Opin Struct Biol 12:794-801

Ashkenazi et al., 1997, Curr Opin Irnrnunol 9: 195-200,

Baba T, Takeuchi F, Kuroda M, Yuzawa H, Aoki K, Oguchi A, Nagai Y, Iwama N, Asano K, Naimi T, et al. (2002) Lancet 359:1819-1827

Baca et al., 1997, J. Biol. Chern. 272(16):10678-10684;

Barnes. N, and P. Mark Hogarth Bruce D. Wines, Maree S. Powell, Paul, *The Journal of Immunology*, 2000, 164: 5313-5318.

Bassler, B. L. (1999) Curr. Opin. Microbiol. 2, 582-587

J, G., Beavis, R. C. & Novick, R. P. (1995) Proc. Natl. Acad. Sci. USA 92, 12055-12059

Benito, Y., Kolb, F. A., Romby, P., Lina, G., Etienne, J. & Vandenesch, F. (2000) RNA 6, 668-679

Bird et al., 1988, Science 242:423-426, Huston et al., 1988, Proc. Natl. Acad. Sci. U.S.A. 85:58795883

Bjorck (1988) Protein L. A novel bacterial cell wall protein with affinity for Ig L chains. The Journal of Immunology, Vol 140, Issue 4: 1194-1197

Bjorck, L., and Kronvall, G. (1984) J. Immunol. 133, 969-974,

Bohach, G. A., Fast, D. J., Nelson, R. D. & Schlievert, P. M. (1990) Crit. Rev. Microbiol. 17, 251-272.

Bouma, B., de Groot, P. G., van den Elsen, J. M., Ravelli, R. B., Schouten, A., Simmelink, M. J., Derksen, R. H., Kroon, J., and Gros, P. (1999) EMBO J. 18, 5166-5174

Bowers et al., PNAS Dec. 20, 2011 vol. 108 no. 51 20455-20460

Boyle, M. D. P. (1990) in Bacterial Immunoglobulin-Binding Proteins, ed. Boyle, M. P. D. (Academic, San Diego), Vol. 1, pp. 17-28, Bruggemann et al., 1997, Curr Opin Biotechnol 8:455-458, Burman et al., JBC. 283, 25, 17579-17593, 2008, Itoh et al., Mol Immunol 2010 January; 47(4):932-8.

Burman, J. D., Leung, E., Atkins, K. L., O'Sheaghdha, M. N., Lango, L., Bernardo, P., Bagby, S., Svergun, D. I., Foster, T. J., Isenman, D. E., and van den Elsen, J. M. H. (2008) J. Biol. Chem. 283, 17579-17593

Burmeister W P, Huber A H, Bjorkman P J (1994) Nature 372:379-383)

Burton, D. R. (1985) Mol. Immunol. 22, 161-206;

Cary, S., Krishnan, M. R., Marion, T. & Silverman, G. J. (1999) Mol. Immunol. 36, 769-776)

Casadevall A E, Dadachova E, Pirofski L A. Passive antibody therapy for infectious diseases. Nat Rev Microbiol 2004; 2(9): 695-703

Cary, S., Lee, J., Wagenknecht, R. & Silverman, G. J. (2000) J. Immunol. 164, 4730-4741)

Chamow et al., 1996, Trends Biotechnol 14:52-60;

Cheng, A. G., H. K. Kim, M. L. Burts, T. Krausz, O. Schneewind, and D. M. Missiakas. 2009. Genetic requirements for *Staphylococcus aureus* abscess formation and persistence in host tissues. FASEB J. 23:3393-3404. doi: 10.1096/fj.09-135467

Cheung, A. L. & Projan, S. J. (1994) J. Bacteriol. 176, 4168-4172;

Chien, Y. & Cheung, A. L. (1998) J. Biol. Chem. 273, 2645-2652

Clark, 2000, Immunol Today 21:397-402,

Clark, 1997, IgG effector mechanisms, Chern Immunol. 14 Oct. 19, 2006 65:88-110;

Clark, E., Upadhyay, A., Bagby, S., and van den Elsen, J. (2009) Mol. Immunol., 46, 2834-2835.

Claro T, Widaa A, O'Seaghdha M, Miajlovic H, Foster T J, et al. (2011) Staphylococcus aureus Protein A Binds to Osteoblasts and Triggers Signals That Weaken Bone in Osteomyelitis. PLoS ONE 6(4): e18748, 2011

Dall'acqua, W., Johnson, L. S., Ward, E. S.: US20070122403A1 (2007)

Davies et al., 2001, Bioteehnol Bioeng 74:288-294

Datta-Mannan et al (2006) Drug Metabolism and Disposition 35, 86-94

Deisenhofer, 1981, Biochemistry 20:2361-2370

De Jonge M, Burchfield D, Bloom B, et al. Clinical trial of safety and efficacy of inh-a21 for the prevention of nosocomial Staphylococcal bloodstream infection in premature infants. J. Pediatr 2007; 151(3): 260-265

De Lano, W. L., Ultsch, M. H., De Vos, A. M., and Wells, J. A. (2000) Science 287, 1279-1283

De Pascalis et al., 2002, J. Immnnol. 169:3076-3084

Derrick, J. P. and Wigley, D. B. (1992) Nature (London) 359, 752-754;

Domanski et al., INFECTION AND IMMUNITY, August 2005, p. 5229-5232

Emsley J., Cruz M., Handin R. et. al. Crystal structure of the von Willebrand Factor A1 domain and implications for the binding of platelet glycoprotein Ib. J Biol. Chem. 273: 10396-10401, 24 Apr. 2098.

Fagan et al., INFECT. IMMUN 1991, 69, 851-4857

Firan et al., Int Immunol. 2001 13:993-1002,

Forsgren & Sjouist, J Immunol. 1966; 97:822-7

Foster T, J., Nature Rev. Immunol, 3, 2005, 948-958 and references cited therein.

Foster, T. J., O'Reilly, M., Patel, A. H. & Bramley, A. J. (1988) Antonie Van Leeuwenhoek, 54-475-482. 17. Patel, A. H., Nowlan, P., Weavers, E. D. & Foster, T. (1987) Infect. Immun. 55, 3103-3110.

Furatawa et al., 1975, Keller et al., J Immunol. 1976:772-7; Sprague et al., J. Virol., Apr. 1, 2008; 82: 3490-3499, Lilley et al., J Virol 2001-75, 11218

Garman et al., 2000, Nature 406:259-266

Gemmell et al., J. Med. Microbiol.—Vol. 46 (1997), 208-2-13;

Gemmell et al., 1991 Zentralbl Bakteriol (Suppl.), 273-277

Ghetie et al., 2000, Annu Rev Immunol 18:739-766;

Gorman & Clark, 1990, Semin Immunol 2(6):457-66

Gomez, M. I., et al. 2004. Nat. Med. 10:842-848

Gomez, M. I., Seaghdha, M. O., and Prince, A. S. 2007. EMBO J. 26:701-709.

Gomez M I, O'Seaghdha M, Magargee M, Foster T J, Prince A S (2006) Staphylococcus aureus protein A activates TNFR1 signaling through conserved IgG binding domains. J Biol Chem 281: 20190-20196.

Gorman et al., 1991, Proc. Natl. Acad. Sci. USA 88:4181-4185;

Gouda, H., Torigoe, H., Saito, A., Sato, M., Arata, Y., and Shimada, I. (1992) Biochemistry 31, 9665-9672

Gouda, H., Shiraishi, M., Takahashi, H., Kato, K., Torigoe, H., Arata, Y., and Goward, C., Scawen, M., Murphy, J. and Atkinson, T. (1993) Trends Biochem. Sci. 18, 136-140, Goodyear, C. S., and Silverman, G. J. (2004) Proc. Natl. Acad. Sci. U.S.A. 101, 11392-11397

Griffiths et al., 1998, Curr Opin Biotechnol 9: !O2108,

Graille et al., Proc Natl Acad Sci USA. 2000 May 9; 97(10): 5399-5404

Hall et al., INFECTION AND IMMUNITY, December 2003, p. 6864-6870

Haupt K, Reuter M, van den Elsen J, Burman J, Halbich S, et al. (2008) The Staphylococcus aureus Protein Sbi Acts as a Complement Inhibitor and Forms aTripartite Complex with Host Complement Factor H and C3b. PLoS Pathog 4(12): e1000250. doi:10.1371/journal.p-pat.1000250

Hayhurst & Georgiou, 2001, Curr Opin Chern Biol 5:683-689;

Haynes B F, Fauci A S. Introduction to immune system. In: Braunwald E, Fauci A S, Kasper D L, Hauser S L, Longo D L, Jameson J L, editors. Harrison's principles of internal medicine. New York: McGraw Hill; 2005. pp. 1907-30)

He et al., 1998, J. Immunol. 160: 1029-1035;

Herr A B, Ballister E R, Bjorkman P J (2003) Nature 423:614-620

Heden, L.-O., Frithz, E., and Lindahl, G. (1991) Eur. J. Immunol. 21, 1481-149

Hillson, J. L., Karr, N. S., Oppliger, I. R., Mannik, M. & Sasso, E. H. (1993) J. Exp. Med. 178, 331-336.)

Hoogenboom H R (2005) Selecting and screening recombinant antibody libraries. Nat Biotechnol 23:1105-1116.

Holliger and Winter, 1993, Current Opinion Biotechnol. 4:446-449 domain. Science. 297: 1176-1179, 16 Aug. 2002.

Herr A B, Ballister E R, Bjorkman P J (2003) Nature 423:614-620 (2000) Infect Immun 68:4407-4415

Huizinga E. G., Tsuji S., Romijn R. A. et. al. Structures of glycoprotein lbalpha and its complex with von Willebrand factor A1 domain. Science. 297: 1176-1179, 16 Aug. 2002

Hulstein J. J., de Groot P. G., Silence K. et. al. A novel nanobody that detects the gain-of-function phenotype of von Willebrand factor in ADAMTS13 deficiency and von Willebrand disease type 2B. Blood. 106: 3035-3042, 1 Nov. 2005.

Huizinga E. G., Tsuji S., Romijn R. A. et. al. Structures of glycoprotein lbalpha and its complex with von Willebrand factor A1

Idusogie et al., 2000, J Immunol 164:4178-4184

James L C, Keeble A H, Khan Z, Rhodes D A, Trowsdale J (2007) Proc Natl Acad Sci USA 104:6200-6205)

Jansson, B., Uhlen, M., and Nygren, P. A. (1998) FEMS Immunol. Med. Microbiol. 20, 69-78

Jefferis, R and LeFranc, M-P, 2009, mABs 1: 1-6,

Jefferis et al., 2002, Immunol Lett 82:57-65

Jerlstro et al., (1991) Mol. Microbiol. 5, 843-849;

Jones et al., 1986, Nature 321:522-525;

Kazeeval T. N. and A. B. Shevelev, Biochemistry (Moscow), 2009, Vol. 74, pp. 12-21;

Kim et al., 2001, J. Mol. Evol. 54:1-9, hereby entirely incorporated by reference Kim H et al. JEM 2010; 207:1863-1870

Kim H. K, Emolo, C., DeDent, A. C, Falugi, F., Dominique M. Missiakas, D. M., and Schneewind, O. (2012) Infect Immun. 80, 3460-70

Kotzin, B. L., Leung, D. Y., Kappler, J. & Marrack, P. (1993) Adv. Immunol. 54, 99-166.

Kozlowski, L. M., Kunning, S. R., Zheng, Y., Wheatley, L. M. & Levinson, A. I. (1995) J. Clin. Immunol. 15, 145-151

Krapp et al., 2003, J Mol Biol 325:979-989

Kristiansen, S. V., Pascual, V. & Lipsky, P. E. (1994) J. Immunol. 153, 2974-2982.

Kroll M. H., Hellums J. D., McIntire L. V. et. al. Platelets and shear stress. Blood. 88: 1525-1541, 1 Sep. 1996.

Krauss et al., 2003, Protein Engineering 16(10):753-759.

Kronvall, J Immunol. 1973 November; 111(5):1401-6; Schroder et al., 1986 Immunology, 57, 305

Langley R, Wines B, Willoughby N, Basu I, Proft T, Fraser J D (2005) JMonteiro R C, Van De Winkel J G (2003) Annu Rev Immunol 21:177-204)

Lazar G A, Dang W, Karki S, et al. Engineered antibody immunoglobulin variants with enhanced effector function. Proc Natl Acad Sci USA 2006; 103(11): 4005-4010.

Lehner, T, Monoclonal antibodies against microorganisms. Curr Opin Immunol 1989; 1(3): 462-466;

Levinson, A. I., L. Kozlowski, Y. Zheng, and L. M. Wheatley. 1995. B cell superantigens: definition and potential impact on the immune response. J. Clin. Immunol. 15:26S-36S;

Levinson, A. I., and L. Kozlowski. 1996. Staphylococcal protein A: functional properties of a model B-cell superantigen, p. 99-106. In M. Zouali (ed.), Human B-cell superantigens. Landes Bioscience Publishers, Austin, Ill.

Lewis M J, Pleass R J, Batten M R, Atkin J D, Woof J M (2005) J Immunol 175:6694-670)

Lewis, M. J., Meehan, M., Owen, P., and Woof, J. M. JBC. 283, 17615-17623, 2008;

Meehan, M., Lynagh, Y., Woods, C., and Owen, P. (2001) Microbiology 147, 3311-3322

Li, H., Llera, A., Malchiodi, E. L. & Mariuzza, R. A. (1999) Annu. Rev Immunol. 17, 435-466.

Little et al., 2000, Immunol Today 21:364-370

Lina G, Bohach G A, Nair S P, Hiramatsu K, Jouvin-Marche E, Mariuzza R (2004) J Infect Dis 189:2334-2336;

Llewely, M and Cohen, J Lancet Infectious Diseases 2, Issue 3-156-162, 2002;

Loghem, E., Frangione, B., Recht, B., and Franklin, E. C. (1982) Scand. J. Immunol. 15, 275-278, 21

Loghem Evan, 1986, Allotypic markers, Monogr Allergy 19: 40-51

Lonberg N (2005) Human antibodies from transgenic animals. Nat Biotechnol 23:1117-1125

Maillard et al., JBC, 2004, 279, pp. 2430-2437, 2004

Marasco W A, Sui J, The growth and potential of human antiviral monoclonal antibody therapeutics. Nat Biotechnol 2007-25(12): 1421-1434;

Mascari L. M. and Ross J. M. Quantification of staphylococcal-collagen binding interactions in whole blood by use of a confocal microscopy shear-adhesion assay. J Infect. Dis. 188: 98-107, 1 Jul. 2003.

Martin et al., 2001, Mol Cell 7:867-877

Martin et al., J. C J. Clin. Invest. 119:1931-1939 (2009)

Maynard & Georgiou, 2000, Annu Rev Biorned Eng 2:33976,

Maxwell et al., 1999, Nat Struct Bioi 6:437-442

Mimura et al., 2001, J Bioi Chern 276:45539-45547

Moks, T., Abrahmsen, L., Nilsson, B., Hellman, U., Sjoquist, J., and Uhlen, M. (1986) Eur. J. Biochem. 156, 637-643

Moore, G. L., Chen, H., Karki S., and Lazar, G. A. mAbs (2010) 2, 181-189

Morea et al., 1997, Biophys Chem 68:9-16;

Morea et al., 2000, Methods 20:267279

Morfeldt, E., Taylor, D., von Gabain, A & Arvidson, S. (1995) EMBO J. 14, 4569-4577.

Nardella et al., Mol Immunol. 1985 June; 22(6):705-713

Nardella F A, et al., J Immunol. 1987 Feb. 1; 138(3):922-92

Nieba, L., Krebber, A. & Pluckthun, A. (1996) Anal. Biochem. 234, 155-165.

Nilson, B. H., et al. (1993). J. Immunol. Methods 164, 33-40

Nizet, J Allergy Clin Immunol 2007; 120:13-22

Novak L., Deckmyn H., Damjanovich S. et. al. Shear-dependent morphology of von Willebrand factor bound to immobilized collagen. Blood. 99: 2070-2076, 15 Mar. 2002.

Novick R. P. Mol Microbiol. 2003 June; 48(6):1429-49

Novick, R. P., Ross, H. F., Projan, S. J., Kornblum, J., Kreiswirth, B. & Moghazeh, S. (1993) EMBO J. 12, 3967-3975;

O'Connor et al., 1998, Protein Eng 11:321-8.

Ogata & Shigeta, Infect Immun. 1979; 770-4.

O'Seaghdha M, van Schooten C J, Kerrigan S W, Emsley J, Silverman G J, et al. (2006) Staphylococcus aureus protein A binding to von Willebrand factor A1 domain is mediated by conserved IgG binding regions. FEBS J 273: 4831-4841

O'Toole, P., L. Stenberg, M. Rissler, and G. Lindahl. Proc Natl Acad Sci USA. 1992 89: 8661-8665;

Palmqvist N, Foster T, Tarkowski A, Josefsson E. Protein A is a virulence factor in S. aureus arthritis and septic death. Microb Pathog 2002; 33: 239-49

Papageorgiou A C, Acharya K R. Microbial superantigens: from structure to function. Trends Microbiol 2000; 8: 369-75;

Papageorgiou, A. C., Tranter, H. S. & Acharya, K. R. (1998) J. Mol. Biol. 277, 61-79

Para, Goldstein & Spear, J Virol. 1982; 41, 137-44

Patel et al., J. Immunol. 2010; 184; 6283-6292

Pawar P., Shin P. K., Mousa S. A. et. al. Fluid shear regulates the kinetics and receptor specificity of Staphylococcus aureus binding to activated platelets. J Immunol. 173: 1258-1265, 15 Jul. 2004.

Peng, H. L., Novick, R. P., Kreiswirth, B., Kornblum, J. & Schlievert, P. (1988) J. Bacteriol. 170, 4365-4372)

Pleass R J, Dunlop J I, Anderson C M, Woof J M (1999) J Biol Chem 274:23508-23514, Carayannopoulos L, Hexham J M, Capra J D (1996) J Exp Med 183:1579-1586)

Pleass R J, Areschoug T, Lindahl G, Woof J M (2001) J Biol Chem 276:8197-8204.)

Presta L G. Molecular engineering and design of therapeutic antibodies. Curr Opin Immunol 2008; 20(4): 460-470]

Presta et al., 1997, Cancer Res. 57(20):4593-9;

Provenza G, Provenzano M, Visai L, Burke F M, Geoghegan J A, Stravalaci M, Gobbi M, Mazzini G, Arciola C R, Foster T J, Speziale P. FEBS J. 2010 November; 277(21): 4490-505.

Queen et al., 1989, Proc Natl Acad Sci, USA 86:10029-33;

Radaev et al., 2001, J Bioi Chem 276:16469-16477

Rader et al., 1998, Proc. Natl. Acad. Sci. USA 95: 8910-8915;

Raghavan et al., 1996, Annu Rev Cell Dev Bioi 12:181-220

Ramsland, P. A., Willoughby, N., Trist, H. M., Farrugia, W., Hogarth, P. M., Fraser, J. D., and Wines, B. D. (2007) Proc. Natl. Aacd. Sci. U.S.A. 104, 15051-15056;

Ravetch et al., 2001, Annu Rev Immunol 19:275-290

Recht, B., Frangione, B., Franklin, E., and van Loghem, E. (1982) J. Immunol. 127

Recsei, P., Kreiswirth, B., O'Reilly, M., Schlievert, P., Gruss A. & Novick, R. P. (1986) Mol. Gen Genet. 202, 58-61;

Reddy S. T et al., Nature Biotechnology 28, 965-969 (2010)

Reiter et al., 1996, Nature Biotech. 14:12391245

Reis, K. J, Ayouh, E. M, and Boyle, M. D. P. (1984) J. Immunol. 132-3091-3097

Riechmann et al., 1988; Nature 332:323-329;

Roben, P. W., Salem, A. N., and Silverman, G. J. (1995) J. Immunol. 154, 6437-6445

Roque et al., 2004, Biotechnol. Prog. 20:639-654

Roguska et al., 1994, Proc. Natl. Acad. Sci. USA 91:969973

Romagnani, S., Giudizi, M. G., del Prete, G., Maggi, E., Biagiotti, R., Almerigogna, F. & Ricci, M (1982) J. Immunol. 129, 596-602)

Rosok et al., 1996, J. Biol. Chern. 271(37): 22611-22618;

Rupp M E, Holley H P, Lutz J, et al. Phase ii, randomized, multicenter, double-blind, placebo-controlled trial of a polyclonal anti-S. aureus capsular polysaccharide immune globulin in treatment of S. aureus bacteremia. Antimicrob Agents Chemother 2007; 51(12): 4249-4254.

Sadler J. E. Biochemistry and genetics of von Willebrand factor. Annu. Rev Biochem. 67: 395-424, 1998.

Sasso, E. H., Silverman, G. J. & Mannik, M. (1989) J. Immunol. 142, 2778-2783.

Sasano, M., Burton, D. R. & Silverman, G. J. (1993) J. Immunol. 151, 5822-5839.

Sauer-Eriksson et al., 1995, Structure 3:265-278

Seppala, I., Kaartinen, M., Ibrahim, S. & Makela, O. (1990) J. Immunol. 145, 2989-2993.

Shields et al., 2001, J Bioi Chern 276:6591-6604

Shields et al., 2002, J Bioi Chern 277:26733-26740

Shimada, I. (1998) Biochemistry 37, 129-136

Sidorin, E. V. and Solov'eva, T. F. Biochemistry (Moscow), 2011, Vol. 76, 295-308

Silverman et al., J Exp Med. 2000 Jul. 3; 192(1):87-98;

Siedlecki C. A., Lestini B. J., Kottke-Marchant K. K. et. al. Shear-dependent changes in the three-dimensional structure of humanvon Willebrand factor. Blood. 88: 2939-2950, 15 Oct. 1996.

Silverman, G. J. 1997. B cell superantigens. Immunol. Today 18:379-386.

Silverman, G. J., Nayak, J. V., Warnatz, K., Najjar, F. F., Cary, S., Tighe, H. & Curtiss, V. E. (1998) J. Immunol. 161, 5720-5732.

Simmons et al., 2002, J Irnrnunol Methods 263:133-147

Sondermann et al., 2001, J Mol Biol 309:737749

Sondermann et al., 1999, Embo J 18:1095-1103

Sondermann et al., 2000, Nature 406:267-273

Sprague E R, Wang C, Baker D, Bjorkman P J (2006) PLoS Biol 4:e148.)

Starovasnik, M. A., O'Connell, M. P., Fairbrother, W. J. & Kelley, R. F. (1999) Protein Sci. 8, 1423-1431)

Starovasnik, M. A., Skelton, N. J., O'Connell, M. P., Kelley, R. F., Reilly, D., and Fairbrother, W. J. (1996) Biochemistry 35, 15558-15569

Tan et al., 2002, J. Immunol. 169:1119-1125;

Tashiro, M. & Montelione, G. T. (1995) Curr. Opin. Struct. Biol. 5, 471-481

Tashiro et al., 1995, Curr Struet Bioi 5:471-481

Torpier, Capron & Ouaissi, Nature 1979 278, 447-9

Tsurushita & Vasquez, 2004, Humanization of Monoclonal Antibodies, Molecular Biology of B Cells, 533-545, Elsevier Science (USA)

Uhlen et al., 1984, J Biol Chem 259, 1695-1702

Uff S., Clemetson J. M., Harrison T. et. al. Crystal structure of the platelet glycoprotein Ib(alpha) N-terminal domain reveals an unmasking mechanism for receptor activation. J Biol. Chem. 277: 35657-35663, 20 Sep. 2002.

Umaiia et al., 1999, Nat Bioteehnol 17:176-180

Viau, M., Longo, N. S., Lipsky, P. E., and Zouali, M. (2005) J. Immunol. 175, 7719-7727

Vaccaro C, Zhou J, Ober R J, Ward E S. Engineering the fc region of immunoglobulin g to modulate in vivo antibody levels. Nat Biotechnol 2005; 23(10): 1283-1238;

van Egmond M, van Garderen E, van Spriel A B, Damen C A, van Amersfoort E S, van Zandbergen G, van Hattum J, Kuiper J, van de Winkel J G (2000) Nat Med 6:680-685 van Egmond M, Damen C A, van Spriel A B, Vidarsson G, van Garderen E, van de Winkel J G (2001) Trends Immunol 22:205-211. 43.

Verhoeyen et al., 1988, Science, 239:1534-1536;

Vidarsson, et al., BLOOD, 15 Nov. 2006 VOLUME 108, NUMBER 10). Relative to the wild-type antibody, the H435A mutant is deficient in transfer across the placenta Weems J J, Steinberg J P, Filler S, et al. Phase ii, randomized, double-blind, multicenter study comparing the safety and pharmacokinetics of tefibazumab to placebo for treatment of S. aureus bacteremia. Antimicrob Agents Chemother 2006; 50(8): 2751-2755.

Watkins J. F. (1964) Nature, 202, 1364; Chapman T. L. et al., JBC 1999, 274, 6911

Williams R J, Ward J M, Henderson B, Poole S, O'Hara B P, Wilson M, Nair S P (2000) Infect Immun 68:4407-4415

Wines, B. D., Willoughby, N., Fraser, J. D., and Hogarth, P. M. (2006) J. Biol. Chem. 281, 1389-1393

Wines B D, Willoughby N, Fraser J D, Hogarth P M (2006) J Biol Chem 281:1389-1393. 24.

Wrammert. J, Smith. K, Miller. J, Langley. W. A, Kokko. K, Larsen, C, Zheng, N. Y., Mays. I, Garma. L, Helms. C, James. J, Air. G. M, Capra. J. D, Ahme. R, & Wilson P. C. Nature. 2008 May 29; 453(7195): 667-671.

Woof J M (2002) Biochem Soc Trans 30:491-494.,

Wu et al., 1999, J. Mol. Biol. 294:151-162;

Xiong J. P., Stehle T., Goodman S. L. et. al. New insights into the structural basis of integrin activation. Blood. 102: 1155-1159, 2003

Yee et al., Virology. 1982; 120:376-82

Zhang, L., Jacobsson, K., Vasi, J., Lindberg, M., and Frykberg, L. (1998) Microbiology 144, 985-991)

Zeitlin L, Cone R A, Moench T R, Whaley K J. Preventing infectious disease with passive immunization. Microbes Infect 2000; 2(6): 701-708

What is claimed is:

1. A variant Fc polypeptide comprising:
   an amino acid sequence that differs from a parent Fc polypeptide by amino acid substitutions, wherein the parent Fc polypeptide comprises a CH2 sequence comprising SEQ ID NO:76 and a CH3 sequence comprising SEQ ID NO:80; and
   wherein the amino acid substitutions comprise:
   (i) a substitution of H435R and Y436F; and
   (ii) an amino acid substitution that attenuates binding of S. aureus Fc binding protein SSL10 to the variant Fc polypeptide, wherein the amino acid substitution that attenuates binding of S. aureus Fc binding protein SSL10 to the variant Fc polypeptide is a substitution of K at EU position 274 with a Q (K274Q); a substitution of N at EU position 276 with a K (N276K); or a substitution of K274Q and N276K.

2. The variant Fc polypeptide of claim 1, wherein the one or more amino acid substitutions further comprise a substitution that occurs at EU position 214, 251, 252, 253, 254, 256, 311, 314, 356, 358, 380, 382, 384, 419, 422, 428, 431, 432, 433, 434, 438, or a combination thereof.

3. The variant Fc polypeptide of claim 1, wherein the variant Fc polypeptide is part of an antibody or an Fc fusion.

4. The variant Fc polypeptide of claim 3, wherein the variable domain of the antibody recognizes and binds an IgBP.

5. The variant Fc polypeptide of claim 1, wherein the IgG1 molecule of any allotype or isoallotype comprises (i) a K or an R at EU position 214; (ii) a D or an E at EU position 356; (iii) an M or an L at EU position 358; and (iv) an A or a G at EU position 431.

6. The variant Fc polypeptide of claim 1, wherein the CH3 domain, or a portion of the CH3 domain of the parent Fc polypeptide is replaced with a homologous sequence from an IgG3 of any allotype or isoallotype, resulting in a variant Fc polypeptide of mixed isotype.

* * * * *